(12) United States Patent
Cowman et al.

(10) Patent No.: US 9,134,311 B2
(45) Date of Patent: Sep. 15, 2015

(54) **METHODS AND COMPOSITIONS FOR TREATING AND PREVENTING MALARIA USING AN INVASION LIGAND DIRECTED TO A P

(56) References Cited

OTHER PUBLICATIONS

Alonso, et al., "A trial of the synthetic malaria vaccine SPf66 in Tanzania: rationale and design," Vaccine 1994, vol. 12, No. 2, pp. 181-186.
D'Alessandro, et al., "Efficacy trial of malaria vaccine SPf66 in Gambian infants," The Lancet, London, Aug. 19, 1994, vol. 346, Issue 8973, pp. 462-467.
Leach, et al., "A pilot safety and immunogenicity study of the malaria vaccine SPf66 in Gambian infants," Parasite Immunology 1995; 17: pp. 441-444.
Masinde, et al., "Immunization With SPf66 and Subsequent Infection With Homologous and Heterologous *Plasmodium falciparum* Parasites," American Journal of Tropical Medicine and Hygiene, 59(4), 1998, pp. 600-605.
Acosta, et al., "Evaluation of the SPf66 vaccine for malaria control when delivered through the EPI scheme in Tanzania," Tropical Medicine and International Health, May 1999, vol. 4, No. 5, pp. 368-376.
Nosten, et al., "Randomised double-blind placebo-controlled trial of SPf66 malaria vaccine in children in northwestern Thailand," The Lancet, Sep. 14, 1996; 348, 9029; Research Library, pp. 701-707.
Guiguemede, et al., "Immunisation against malaria: a first of a sporozoite vaccine," Bulletin de la Societe de Pathologies Exotique; 83(2): 1990, pp. 217-227.
Brown, et al., "Safety, immunogenicity and limited efficacy study of a recombinant *Plasmodium falciparum* circumporozolte vaccine in Thai soldiers," Vaccine, 1994, vol. 12, No. 2, pp. 102-107.
Sherwood, et al., "*Plasmodium falciparum* circumsporozoite vaccine immunogenicity and efficacy trial natural challenge quantitation in an area of endemic human malaria of Kenya," Vaccine, 1996, vol. 14, No. 8, pp. 817-827.
Genton, et al., (2005) Acta Tropica Suppl 95:84.
Kester, et al., "Efficacy of Recombinant Circumsporozoite Protein Vaccine Regimens against Experimental *Plasmodium falciparum* Malaria," The Journal of Infectious Diseases, 2001; 183: pp. 640-647.
Bojang, et al., "Efficacy of RTS,S/AS02 malaria vaccine against *Plasmodium falciparum* infection in semi-immune adult men in The Gambia: a randomised trial," The Lancet, vol. 358, 9297, Dec. 8, 2001; pp. 1927-1934.
Alonso, et al., "Duration of protection with RTS,S/AS02A malaria vaccine in prevention of *Plasmodium falciparum* disease in Mozambican children: single-blind extended follow-up of a randomised controlled trial," The Lancent, Dec. 10-Dec. 16, 2005, vol. 366, No. 9502, Research Library, p. 2012.
Bojang, et al., "Safety and immunogenicty of RTS,S/AS02A candidate malaria vaccine in Gambian children," Vaccine 23 (2005) pp. 4148-4157.
Graves, et al., Vaccines for preventing malaria (pre-erythrocytic) (Review); The Cochrane Collaboration Library, 2009, Issue 1; Cochrane Database of Systematic Review 4: CD006199.
Aponte, et al., "Safety of the RTS,S/AS02D candidate malaria vaccine in infants living in a highly endemic area of Mozambique: a double blind randomised controlled phase I/IIb trial," The Lancent, Nov. 3, 2007, vol. 370, Issue 9598; pp. 1543-1551.
Moorthy, et al., "A Randomised, Double-Blind, Controlled Vaccine Efficacy Trial of DNA/MVA ME-TRAP Against Malaria Infection in Gambian Adults," Nature, Nov. 2004, vol. 1, Issue 2, pp. 128-136.
Lawrence, et al., "Effect of vaccination with 3 recombinant asexual-stage malaria antigens on initial growth rates of *Plasmodium falciparum* in non-immune volunteers," Vaccine, 18 (2000) pp. 1925-1931.
Genton, et al., "A Recombinant Blood-Stage Malaria Vaccine Reduces *Plasmodium falciparum* Density and Exerts Selective Pressure on Parasite Populations in a Phase 1-2b Trial in Papua New Guinea," The Journal of Infectious Diseass, 2002, 185, pp. 820-827.
Moran, et al., "The Malaria Product Pipeline: Planning for the Future," The George Institute for International Health, Sep. 2007.
Makobongo, et al., "Immunization of AOTUS Monkeys with Recombinant Cysteine-Rich Interdomain Region 1a Protects against Severe Disease During *Plasmodium falciparum* Reinfection," The Journal of Infectious Diseases, Mar. 1, 2006; 193; pp. 731-740.
Good, et al., "'Original antigenic sin', T cell memory, and malaria sporozoite immunity: an hypothesis for immune evasion," Parasite Immunology, 1993, 15: pp. 187-193.
Taylor, et al., "Selective recognition of malaria antigens by human serum antibodies is not genetically determined but demonstrates some features of clonal imprinting," International Immunology, vol. 8, No. 6, pp. 905-915.
Riley, E.M., "The role of MHC- and Non-MHC-associated genes in determining the human immune response to malaria antigens" Parasitology (1996), 112, S39-S51, Cambridge University Press.
Struik, et al., "Does malaria suffer from lack of memory?," Immunological Reviews 2004, vol. 201: pp. 268-290, Blackwell Munksgoard 2004.
Urban, et al., "A role for CD36 in the regulation of dendritic cell function," PNAS, Jul. 17, 2001, vol. 98, No. 15, pp. 8750-8755.
Balde, et al., "Apoptosis modulation in mononuclear cells recovered from individuals exposed to *Plasmodium falciparum* infection," Parasite *Immunology, Feb. 8, 2000, 22: pp. 307-318.
Toure-Balde, et al., "*Plasmodium falciparum* induces apoptosis in human mononucelar cells," Infection and Immunity, 1996, 64(3): pp. 744-750.
Holder, et al., "Merozoite surface protein 1, immune evasion, and vaccines against asexual blood stage malaria," Parassitologia 41: 1999, pp. 441-414.
Tian, et al., "Genetic Regulation of Protective Immune Response in Congenic Strains of Mice Vaccinated with a Subunit Malaria Vaccine," The Journal of Immunology, 1996, 157: pp. 1176-1183.
Hirunpetcharat, et al., "Delection of *Plasmodium berghei*-specific CD4+ T cells adoptively transferred into recipient mice after challenge with homologous parasite," PNAS, vol. 95, Feb. 1998, pp. 1715-1720.
Deans, et al., "Invasion Pathways and Malaria Severeity in Kenyan *Plasmodium falciparum* Clinical Isolates," Infection and Immunity, Jun. 2007, vol. 75(6), pp. 3014-3020.
Persson, et al., "Variation in the use of erthrocyte invasion pathways by *Plasmodium falciparum* mediates evasion of human inhibitory antibodies," Journal of Clinical Investigation, Jan. 2008, vol. 118 (1), pp. 342-351.

\* cited by examiner

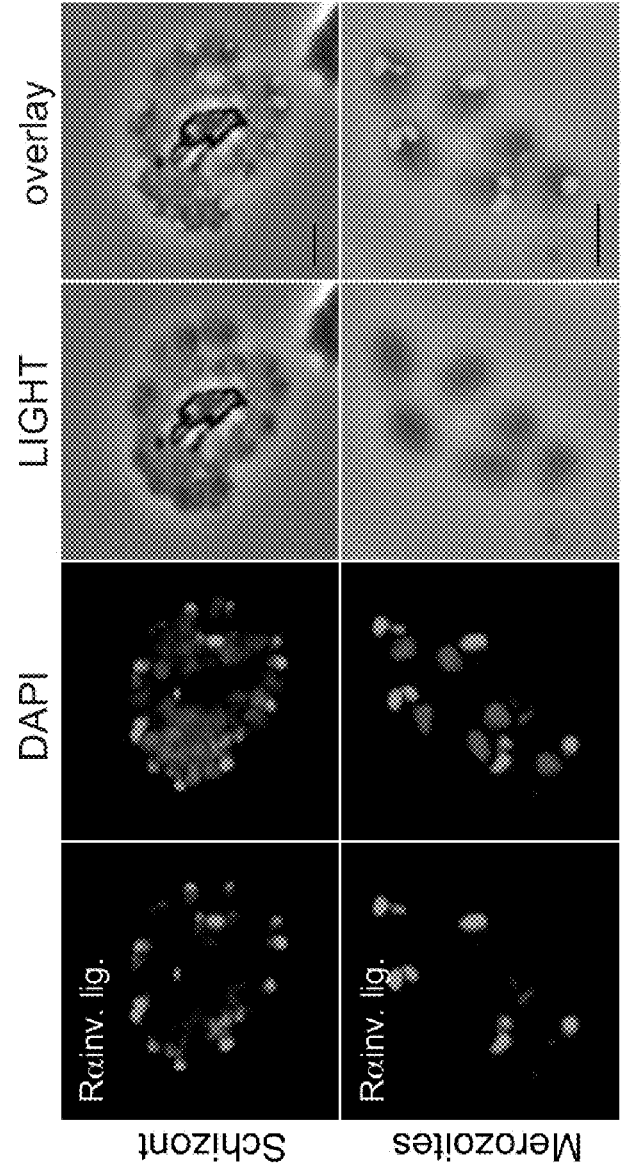
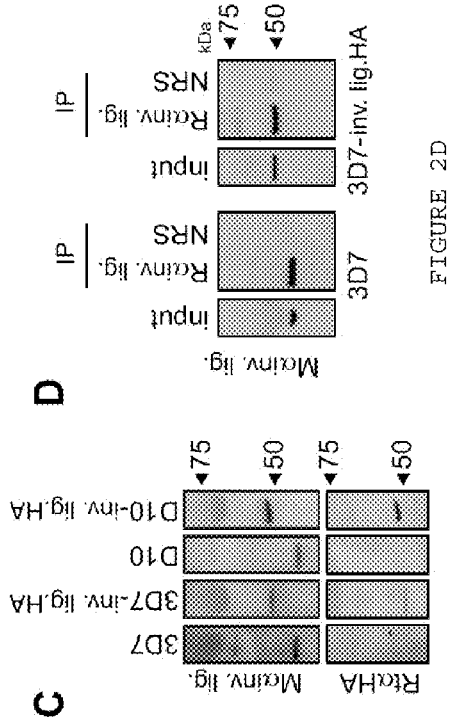
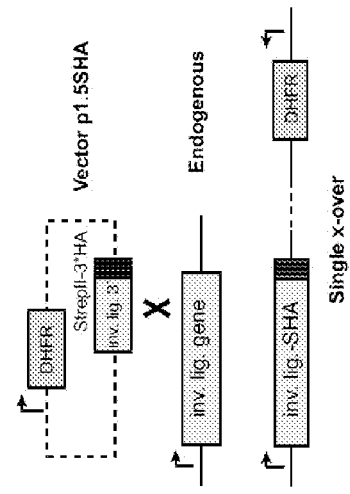
FIGURE 2A
FIGURE 2B
FIGURE 2C
FIGURE 2D

FIGURE 4A
FIGURE 4B
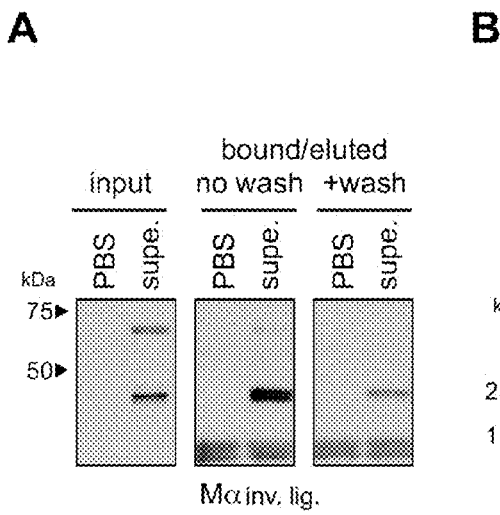
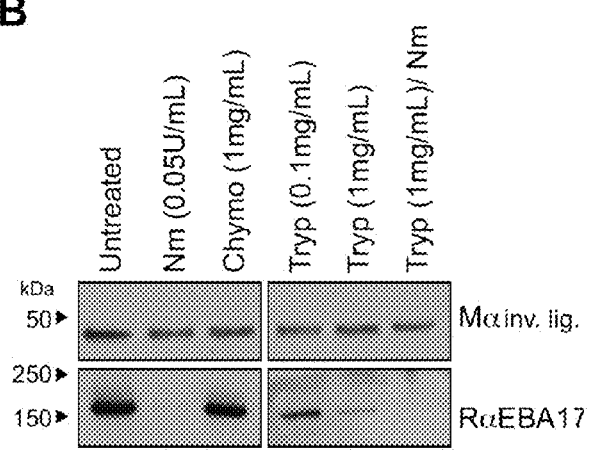
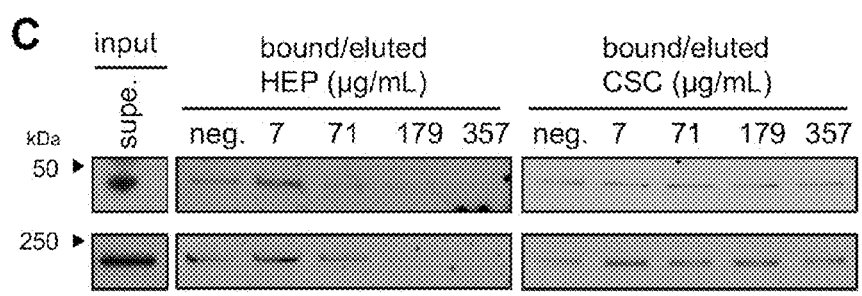
FIGURE 4C
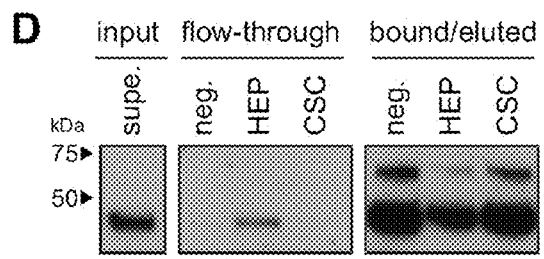
FIGURE 4D FIGURE 5A
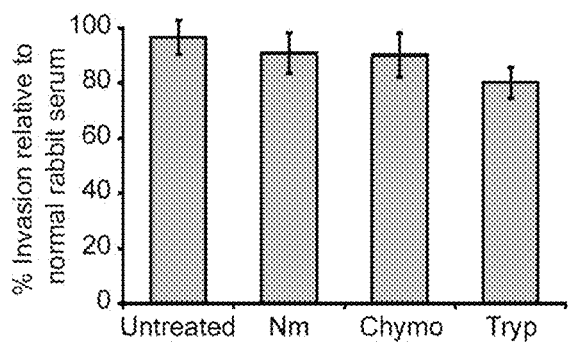
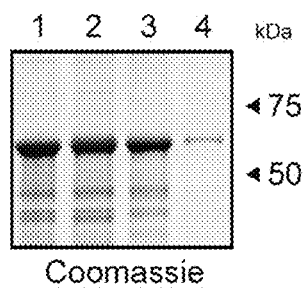
FIGURE 5B
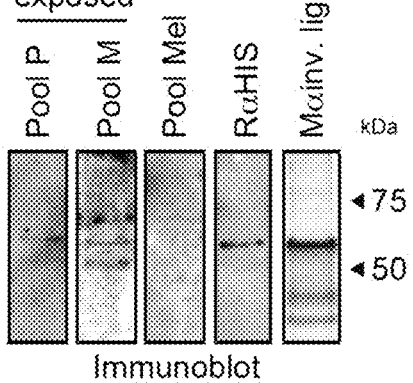
FIGURE 5C

FIGURE 6

FIGURE 7A
FIGURE 7B
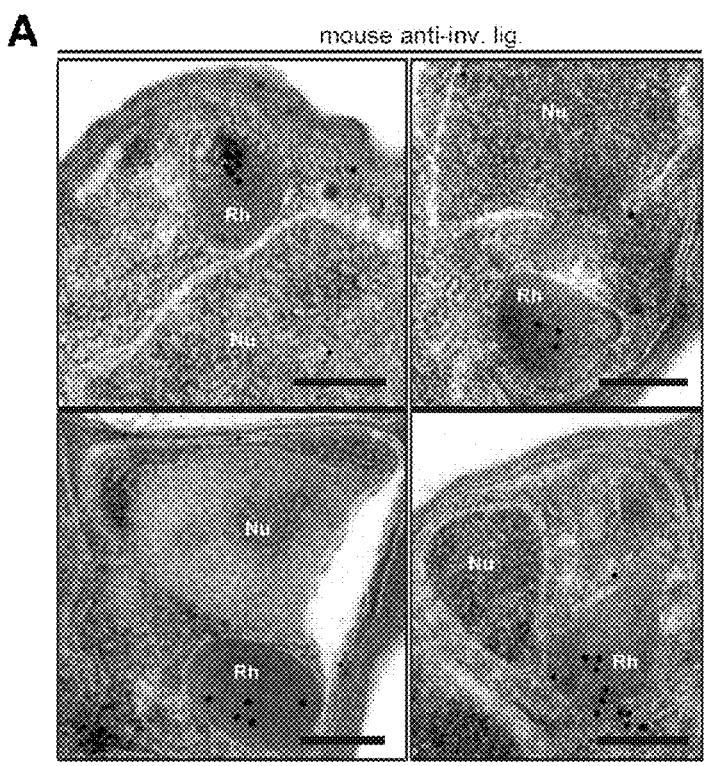
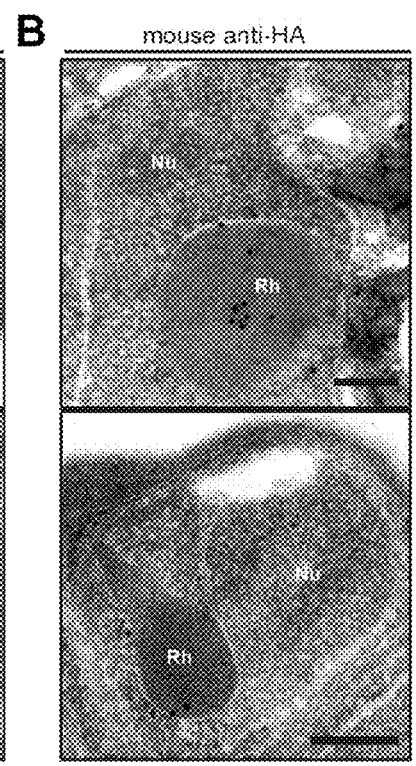

FIGURE 8A
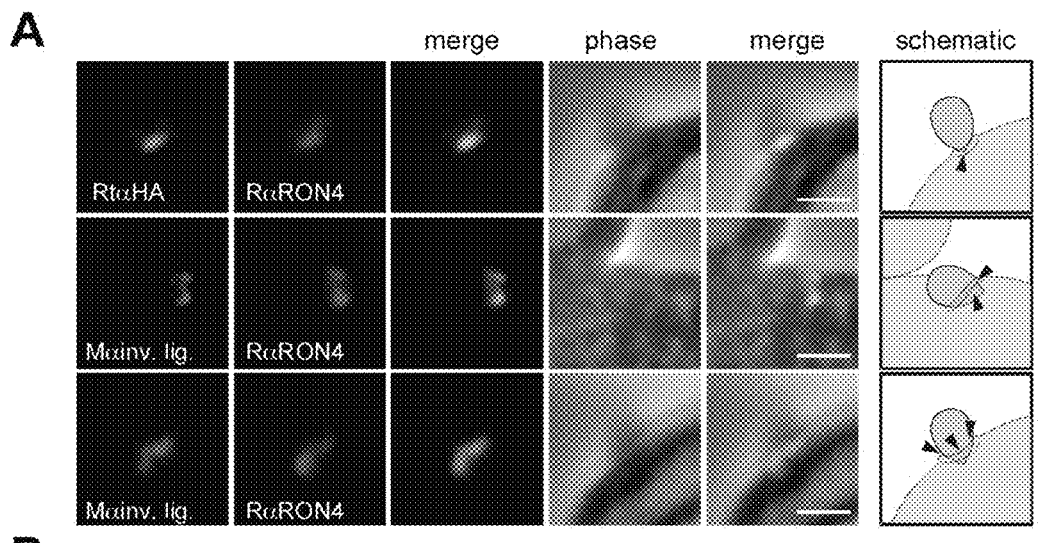
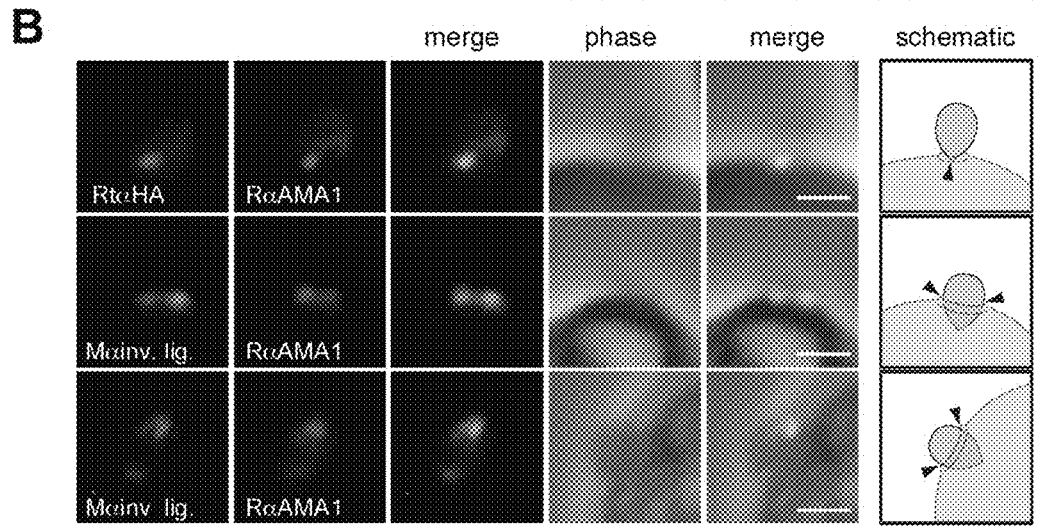
FIGURE 8B

METHODS AND COMPOSITIONS FOR TREATING AND PREVENTING MALARIA USING AN INVASION LIGAND DIRECTED TO A PROTEASE-RESISTANT RECEPTOR

CROSS REFERENCE TO RELATED APPLICATIONS

The present application is a National Stage Application claiming the priority of co-pending PCT Application No. PCT/AU2009/001099 filed Aug. 27, 2009, which in turn, claims priority from U.S. Provisional Application No. 61/092,323, filed Aug. 27, 2008. Applicants claim the benefits of 35 U.S.C. §120 as to the PCT application and priority under 35 U.S.C. §119 as to the said United States Provisional application, and the entire disclosures of both applications are incorporated herein by reference in their entireties.

FIELD OF THE INVENTION

The present invention relates to vaccines for the treatment and prevention of malaria. In particular the invention provides antigens capable of eliciting antibodies capable of preventing invasion of *Plasmodium* parasite into erythrocytes.

BACKGROUND

Human malaria is caused by infection with protozoan parasites of the genus *Plasmodium*. Four species are known to cause human disease: *Plasmodium falciparum, Plasmodium malariae, Plasmodium ovale* and *Plasmodium vivax*. However, *Plasmodium falciparum* is responsible for the majority of severe disease and death. Recent estimates of the annual number of clinical malaria cases worldwide range from 214 to 397 million (World Health Organization. The world health report 2002: reducing risks, promoting healthy life. Geneva: World Health Organization, 2002; Breman et al (2004) American Journal of Tropical Medicine and Hygiene 71 Suppl 2:1-15), although a higher estimate of 515 million (range 300 to 660 million) clinical cases of *Plasmodium falciparum* in 2002 has been proposed (Snow et al. (2004) American Journal of Tropical Medicine and Hygiene 71(Suppl 2):16-24). Annual mortality (nearly all from *Plasmodium falciparum* malaria) is thought to be around 1.1 million (World Health Organization. The world health report 2002: reducing risks, promoting healthy life. Geneva: World Health Organization, 2002; Breman et al (2004) American Journal of Tropical Medicine and Hygiene 71 Suppl 2:1-15). Malaria also significantly increases the risk of childhood death from other causes (Snow et al. (2004) American Journal of Tropical Medicine and Hygiene 71 Suppl 2:16-24). Almost half of the world's population lives in areas where they are exposed to risk of malaria (Hay et al (2004) Lancet Infectious Diseases 4(6):327-36), and the increasing numbers of visitors to endemic areas are also at risk. Despite continued efforts to control malaria, it remains a major health problem in many regions of the world, and new ways to prevent and/or treat the disease are urgently needed.

Early optimism for vaccines based on malarial proteins (so called subunit vaccines) has been tempered over the last two decades as the problems caused by allelic polymorphism and antigenic variation, original antigenic sin, and the difficulty of generating high levels of durable immunity emerged, and with the notable failures of many promising subunit vaccines (such as SPf66) have led to calls for a change in approach towards a malaria vaccine. Consequently, this growing sense of frustration has lead to the pursuit of different approaches that focus on attenuated strains of malaria parasite or irradiated *Plasmodium falciparum* sporozoites (Hoffmann et al. (2002) J Infect Dis 185(8):1155-64). Similarly, both the limited success achieved to date with protein-based vaccines and the recognition that cell mediated immunity may be critical to protection against hepatic and perhaps blood stages of the parasite has led to a push for DNA and vectored vaccines, which generate relatively strong cell mediated immunity. To date DNA vaccines have demonstrated poor efficacy in humans with respect to antibody induction (Wang et al. (2001) PNAS 98: 10817-10822).

To be effective, a malaria vaccine could prevent infection altogether or mitigate against severe disease and death in those who become infected despite vaccination. Four stages of the malaria parasite's life cycle have been the targets of vaccine development efforts. The first two stages are often grouped as 'pre-erythrocytic stages' (i.e. before the parasite invades the human red blood cells): these are the sporozoites inoculated by the mosquito into the human bloodstream, and the parasites developing inside human liver cells (hepatocytes). The other two targets are the stage when the parasite is invading or growing in the red blood cells (the asexual stage); and the gametocyte stage, when the parasites emerge from red blood cells and fuse to form a zygote inside the mosquito vector (gametocyte, gamete, or sexual stage). Vaccines based on the pre-erythrocytic stages usually aim to completely prevent infection. For asexual, blood stage vaccines, because the level of parasitaemia is in general proportional to the severity of disease (Miller, et al. (1994) Science 264, 1878-1883), vaccines aim to reduce or eliminate (e.g. induce stertile immunity) the parasite load once a person has been infected. However, most adults in malaria-endemic settings are clinically immune (e.g. do not suffer symptoms associated with malaria), but have parasites at low density in their blood. Gametocyte vaccines aim towards preventing the parasite being transmitted to others through mosquitoes. Ideally, a vaccine effective at all these parasite stages is desirable (Richie and Saul, Nature. (2002) 415(6872):694-701).

The SPf66 vaccine (Patorroyo et al. (1988) Nature 332: 158-161) is a synthetic hybrid peptide polymer containing amino acid sequences derived from three *Plasmodium falciparum* asexual blood stage proteins (83, 55, and 35 kilodaltons; the 83 kD protein corresponding to merozoite surface protein (MSP)-1) linked by repeat sequences from a protein found on the *Plasmodium falciparum* sporozoite surface (circumsporozoite protein). Therefore it is technically a multistage vaccine. SPf66 was one of the first types of vaccine to be tested in randomized controlled trials in endemic areas and is the vaccine that has undergone the most extensive field testing to date. While having marginal efficacy in four trials in South America (Valero et al. (1993) Lancet 341(8847):705-10. Valero et al. (1996) Lancet 348(9029):701-7; Sempertegui et al. (1994) Vaccine 12(4):337-42; Urdaneta et al. (1998) American Journal of Tropical Medicine and Hygiene 58(3): 378-85), these trials suggested a slightly elevated incidence of *Plasmodium vivax* in the vaccine groups. The vaccine has also been demonstrated to be ineffective for reducing new malaria episodes, malaria prevalence, or serious outcomes (severe morbidity and mortality) in Africa (Alonso et al. Lancet 1994; 344(8931):1175-81 and Alonso et al Vaccine 12(2):181-6); D'Alessandro et al. (1995) Lancet 346(8973):462-7.; Leach et al. (1995) Parasite Immunology 1995; 17(8): 441-4.; Masinde et al. (1998) American Journal of Tropical Medicine and Hygiene 59(4):600-5; Acosta 1999 Tropical Medicine and International Health 1999; 4(5):368-76) and Asia (Nosten et al. (1996) Lancet; 348(9029):701-7), and is consequently no longer being tested.

Four types of pre-erythrocytic vaccines (CS-NANP; CS102; RTS,S; and ME-TRAP) have been trialed. The CS-NANP-based pre-erythrocytic vaccines were the first to be tested, beginning in the 1980s. The vaccines used in the first trials comprised three different formulations of the four amino acid B cell epitope NANP, which is present as multiple repeats in the circumsporozoite protein covering the surface of the sporozoites of *Plasmodium falciparum*. The number of NANP repeats in these vaccines varied from three to 19, and three different carrier proteins were used. The CS-NAN P epitope alone appears to be ineffective in a vaccine, with no evidence for effectiveness of CS-NANP vaccines in three trials (Guiguemde et al. (1990) Bulletin de la Societe de Pathologie Exotique 83(2):217-27; Brown et al. (1994) Vaccine 12(2):102-7; Sherwood et al. (1996) Vaccine 14(8):817-27).

The CS102 vaccine is also based on the sporozoite CS protein, but it does not include the NANP epitope. It is a synthetic peptide consisting of a stretch of 102 amino acids containing T-cell epitopes from the C-terminal end of the molecule. All 14 participants in this small trial of non-immune individuals had malaria infection as detectable by PCR (Genton et al. (2005) Acta Tropica Suppl 95:84).

The RTS,S recombinant vaccine also includes the NANP epitope. It contains 19 NANP repeats plus the C terminus of the CS protein fused to hepatitis B surface antigen (HBsAg), expressed together with un-fused HBsAg in yeast. The resulting construct is formulated with the adjuvant ASO2/A. Thus the vaccine contains a large portion of the CS protein in addition to the NANP region, as well as the hepatitis B carrier. The RTS,S pre-erythrocytic vaccine has shown some modest efficacy, in particular with regard to prevention of severe malaria in children and duration of protection of 18 months (Kester et al. (2001) Journal of Infectious Diseases 2001; 183(4):640-7.1; Bojang et al. (2001) Lancet 358(9297):1927-34; Alonso et al. (2005) Lancet 366(9502):2012 Alonso et al. (2005) Lancet 366(9502):2012-8), Bojang et al. (2005) Vaccine 23(32):4148-57). In four trials, it was effective in preventing a significant number of clinical malaria episodes, including good protection against severe malaria in children, with no serious adverse effects (Graves et al. (2006) Cochrane Database of Systematic Reviews 4: CD006199). The RTS,S vaccine has shown significant efficacy against both experimental challenge (in non-immunes) and natural challenge (in participants living in endemic areas) with malaria. Although no evidence was found for efficacy of RTS,S against clinical malaria in adults in The Gambia in the first year of follow up, efficacy was observed in the second year after immunization, after a booster dose. However, there was no reduction in parasite densities (which positively associate with pathology). Nonetheless, in a recent study in Mozambique, the vaccine appeared to have efficacy in infants (Aponte et al. (2007) 370(9598) 1543-1551).

The ME-TRAP pre-erythrocytic vaccine is a DNA vaccine that uses the prime boost approach to immunization. It uses a malaria DNA sequence known as ME (multiple epitope)-TRAP (thrombospondin-related protein). The ME string contains 15 T-cell epitopes, 14 of which stimulate CD8 T-cells and the other of which stimulates CD4 T-cells, plus two B-cell epitopes from six pre-erythrocytic antigens of *Plasmodium falciparum*. It also contains two non-malarial CD4 T-cell epitopes and is fused in frame to the TRAP sequence. This sequence is given first as DNA (two doses) followed by one dose of the same DNA sequence in the viral vector MVA (modified vaccinia virus Ankara). There was no evidence for effectiveness of ME-TRAP vaccine in preventing new infections or clinical malaria episodes, and the vaccine did not reduce the density of parasites or increase mean packed cell volume (a measure of anaemia) in semi-immune adult males (Moorthy et al. (2004) Nature 363(9403):150-6).

The first blood-stage vaccine to be tested in challenge trials is Combination B, which is a mixture of three recombinant asexual blood-stage antigens: parts of two merozoite surface proteins (MSP-1 and MSP-2) together with a part of the ring-infected erythrocyte surface antigen (RESA), which is found on the inner surface of the infected red cell membrane. The MSP-1 antigen is a 175 amino acid fragment of the relatively conserved blocks 3 and 4 of the K1 parasite line; it also includes a T-cell epitope from the *Plasmodium falciparum* circumsporozoite (CS) protein as part of the MSP1 fusion protein. The MSP2 protein includes the nearly complete sequence from one allelic form (3D7) of the polymorphic MSP-2 protein. The RESA antigen consists of 70% of the native protein from the C-terminal end of the molecule. A small efficacy trial of Combination B in non-immune adults with experimental challenge showed no effect (Lawrence (2000) Vaccine 18(18):1925-31). In the single natural-challenge efficacy trial of in semi-immune children (Genton (2002) Journal of Infectious Diseases 185(6):820-7), no effect on clinical malaria infections was detected. In this trial, significant efficacy (measure by reduction in parasite density) was only observable in the group who were not pretreated with sulfadoxine-pyrimethamine. Also, in these children there was a reduction in the proportion of children with medium and high parasitaemia levels. Vaccines in the Genton et al. (2002) trial had a lower incidence and prevalence of parasites with the 3D7 type of MSP2 (the type included in the vaccine) than the placebo group, and a higher incidence of malaria episodes were associated with the FC27 type of MSP2, suggesting specific immunity. Importantly, there was no statistically significant change in prevalence of parasitemia, nor was there evidence for an effect of combination B against episodes of clinical malaria in either the group pretreated with the antimalarial or the group with no antimalarial, in fact the results for these subgroups tended in the opposite direction. Furthermore, the relative role of the three vaccine constituents cannot be assessed when based on the trials that have been carried out to date.

In addition to the asexual-stage components of Combination B, many other potential asexual stage vaccines have been under preclinical evaluation, such as regions of apical membrane antigen 1 (AMA1), the merozoite surface proteins MSP1, MSP2, MSP3, MSP4, and MSP5: glutamate-rich protein (GLURP), rhoptry associated protein-2 (RAP2), EBA-175, EBP2, MAEBL, and DBP, and *Plasmodium falciparum* (erythrocyte membrane protein-1 (PfEMP1). Importantly however, a recent examination of the vaccine candidate still under consideration (Moran et al. (2007) The Malaria Product Pipeline, The George Institute for International Health, September 2007) has shown that many preclinical vaccine projects are inactive; in particular vaccine projects using the F1 domain of EBA-175 (e.g. by ICGEB), EBA-140 (also known as BAEBL), and RAP-2 are inactive. The inactivity of these projects highlights that much work is needed to find blood stage antigens that will afford a protective immune response.

There are many problems faced in the selection of antigens for malaria vaccine development, including antigenic variation, antigen polymorphism, and original antigenic sin, and further problems such as MHC-limited non-responsiveness to malarial antigens, inhibition of antigen presentation, and the influence of maternal antibodies on the development of the immune system in infants.

Many blood stage vaccine candidates, such as MSP-1, MSP-2, MSP-3 and AMA-1, have substantial polymorphisms that may have an impact on both immunogenicity and protective effects, and in the case of MSP-1, and MSP-2, immune responses to particular allelic forms has been observed in vaccine trials (and also for MSP-3 and AMA-1 in mice). Molecular epidemiological studies can guide antigen selection and vaccine design as well as provide information that is needed to measure and interpret population responses to vaccines, both during efficacy trials and after introduction of vaccines into the population. They also may provide insight into the selective forces acting on antigen genes and potential implications of allele specific immunity. Consequently the different allelic forms would need to be included in any vaccine to counter the affect of antigenic polymorphism at immunogenic residues.

The cyclical recrudescences of malaria parasites in humans is thought to be due to the selective pressure placed upon parasitized red cells by antibodies to variant antigens, such as PfEMP1. *Plasmodium falciparum* possesses about 50 variant copies of PfEMP1 which are expressed clonally such that only one is expressed at a time, and the development of antibodies against the expanding clonal type then reduce this clone from the affected individual, and subsequently a different variant, not recognized by antibodies, emerges and cycling continues. This antigenic variation also poses a problem for vaccines containing clonally expressed antigens, and immunization studies with recombinant conserved CD36-binding portion of PfEMP1 failed to confer protection in Aotus monkeys (Makobongo et al. (2006) JID 193:731-740.

A third problem confounding malaria vaccine initiatives is original antigenic sin; a phenomenon in which individuals tend to make antibodies only to epitopes expressed on antigenic types to which they have been exposed (or cross-reactive antigens), even in subsequent infections carrying additional, highly immunogenic epitopes (Good, et al. (1993) Parasite Immunol. 15, 187-193. Taylor et al. (1996) Int. Immunol. 8, 905-915, Riley, (1996) Parasitology 112, S39-S51 (1996))

It has also been proposed that immunity to malaria relies on maintaining high levels of immune effector cells, rather than in the generation of effectors from resting memory cells (Struck and Riley (2004) Immunological Reviews 201: 268-290). Consequently, the time taken to generate sufficient levels of effector cells may be crucial in determining whether a protective memory response can be mounted to prevent disease. Also, malaria parasites may interfere directly with memory responses by interfering with antigen presentation by dendritic cells (Urban et al. (1999) Nature 400:73-77, Urban et al. (2001) PNAS 98:8750-8755), and premature apoptosis of memory cells (Toure-Balde et al. (1996) Infection and Immunity 64: 744-750, Balde et al. (2000) Parasite Immunology 22:307-318).

Furthermore, it has been demonstrated that antibodies to particular malarial antigens (such as MSP-1) may inhibit the activity of malaria-protective antibodies (Holder et al (1999) Parassitologica 41:409-14), and that there may be MHC-limited non-responsiveness to malarial antigens (Tian et al (1996) J Immunol 157:1176-1183, Stanisic et al. (2003) Infection and Immunity 71: 5700-5713). Maternally derived antibodies have also been shown to interfere with the development of antibody responses in infants, and has been implicated for malaria in mice (Hirunpetcharat and Good (1998) PNAS 95:1715-1720), consequently these problems need to be addressed for vaccination of children against malaria.

As will be apparent from the foregoing review of the prior art, there remained significant problems to be overcome in the design of an efficacious vaccine against malaria. It is an aspect of the present invention to overcome or ameliorate a problem of the prior art by providing antigens, and combinations of antigens capable of eliciting antibodies that can treat or prevent malaria.

A reference herein to a patent document or other matter which is given as prior art is not to be taken as an admission that that document or matter was known or that the information it contains was part of the common general knowledge as at the priority date of any of the claims.

SUMMARY OF THE INVENTION

In a first aspect, the present invention provides an immunogenic molecule comprising a contiguous amino acid sequence of an invasion ligand of a strain of *Plasmodium falciparum*, the invasion ligand capable of binding to an erythrocyte receptor, the receptor function being resistant to trypsin and neuraminidase and chymotrypsin, wherein when administered to a subject the molecule is capable of inducing an immune response to the strain. Applicant has discovered a new invasion ligand/receptor pathway in the invasion of erythrocytes by *Plasmodium falciparum*. The ligand is proposed to be useful as a vaccine (or as a component of a vaccine) whereby administration of the vaccine to a subject elicits antibodies capable of binding to the natural parasite. Binding of the antibodies to the parasite is proposed to inhibit invasion of erythroctyes thereby interrupting the life cycle of the parasite. In one embodiment, the invasion ligand is devoid of a transmembrane domain and/or a cytosolic domain normally present in other invasion ligands of *Plasmodium falciparum*. These domains are typically found at the C-terminus of other invasion ligands. The absence of one or both of these domains distinguishes the invasion ligands described herein with those of the prior art. In one embodiment, the invasion ligand has a molecular weight of about 62.5 kDa. This is significant smaller than other invasion ligands of *Plasmodium falciparum*, and again highlights the atypical nature of the invasion ligand described herein.

In one embodiment of the immunogenic molecule, the invasion ligand comprises a sequence selected from the group consisting of SEQ ID NOS:1, 2, 3, 4, 5, 6, 7, 8, 9, 10, 11 and 12 or variants thereof. The contiguous amino acid sequence may comprise at least about 5, 8, 10, 20, 50 or 100 or more amino acids of SEQ ID NO: 1 or 2, or variant thereof. In one embodiment, the invasion ligand comprises the entirety of SEQ ID NO:1 or 2 or variant thereof.

In one embodiment of the invention, the immune response is an invasion inhibitory response. Invasion of erythrocytes is an important step in the life history of the malaria parasite. Without wishing to be limited by theory in any way, it is proposed that the invasion ligands of the present invention play an important role in erythrocyte selection and commitment to invasion.

The strain of *Plasmodium falciparum* may be a wild type strain.

In a second aspect, the present invention provides a composition comprising an immunogenic molecule as described herein and a pharmaceutically acceptable excipient, and optionally a vaccine adjuvant.

The composition may comprise further invasion ligands of *Plasmodium falciparum*, thereby providing an improvement in vaccine efficacy. Accordingly, in one embodiment, the composition comprises an immunogenic molecule comprising a contiguous amino acid sequence of a reticulocyte-binding protein homologue (Rh) protein of a strain of *Plasmodium*

*falciparum*, wherein the Rh protein is selected from the group consisting of Rh1, Rh2a, Rh2b, and Rh4.

Where the Rh protein is Rh1 the contiguous amino acid sequence may be found in the region between about residue 1 to about the transmembrane domain of Rh1, or the region from about residue 1 to about residue 2897.

Where the Rh protein is Rh2a the contiguous amino acid sequence may be found in the region between about 31 amino acids N-terminal of the Prodom PD006364 homology region to about the transmembrane domain of Rh2a. In certain embodiments, the contiguous amino acid sequence is found in the region from about residue 2027 to 3115 of Rh2a, or the region from about residue 2027 to about residue 2533 of Rh2a, or the region from about residue 2098 to about residue 2597 of Rh2a, or the region from about residue 2616 to about residue 3115 of Rh2a.

Where the Rh protein is Rh2b the contiguous amino acid sequence may be found in the region between about 31 amino acids N-terminal of the Prodom PD006364 homology region to about the transmembrane domain of Rh2b. In certain embodiments, the contiguous amino acid sequence is found in the region from about residue 2027 to 3115 of Rh2b, or the region from about residue 2027 to about residue 2533 of Rh2b, or the region from about residue 2098 to about residue 2597 of Rh2b, or the region from about residue 2616 to about residue 3115 of Rh2b.

Where the Rh protein is Rh4 the contiguous amino acid sequence may found in the region from about the MTH1187/YkoF-like superfamily domain to about the transmembrane domain of Rh4, or in the region from about residue 1160 to about residue 1370 of Rh4.

In certain embodiments, the composition comprises an immunogenic molecule comprising a contiguous amino acid sequence of an erythrocyte binding antigen (EBA) protein of a strain of *Plasmodium falciparum*. The contiguous amino acid sequence may be found in the region between the F2 domain and the transmembrane domain of the EBA protein. The contiguous amino acid sequence may be found in the region from about residue 746 to about residue 1339 of the EBA protein.

The EBA may be selected from the group consisting of EBA140, EBA175 and EBA181.

Where the EBA is EBA140, the contiguous amino acid sequence may be found in the region between the F2 domain and the transmembrane domain of EBA140, or in the region from about residue 746 to about residue 1045 of EBA140.

Where the EBA is EBA175 the contiguous amino acid sequence may be found in the region between the F2 domain and the transmembrane domain of EBA175. The contiguous amino acid sequence may be found in the region from about residue 761 to about residue 1271 of EBA175.

Where the EBA is EBA181 the contiguous amino acid sequence may be found in the region between the F2 domain and the transmembrane domain of EBA181. In one embodiment the contiguous amino acid sequence is found in the region from about residue 755 to about residue 1339 of EBA181.

In a third aspect, the present invention provides a method of treating or preventing a condition caused by or associated with infection by *Plasmodium falciparum* comprising administering to a subject in need thereof an effective amount of a composition as described herein.

A fourth aspect of the invention provides use of an immunogenic molecule or a composition as described herein in the manufacture of a medicament for the treatment or prevention of a condition caused by or associated with infection by *Plasmodium falciparum*.

A fifth aspect of the present invention provides a method of screening for the presence of a *Plasmodium falciparum* invasion-inhibitory antibody directed against an invasion ligand described herein, comprising obtaining a biological sample from a subject and identifying the presence or absence of an antibody capable of binding to an invasion ligand as described herein.

Throughout the description and the claims of this specification the word "comprise" and variations of the word, such as "comprising" and "comprises" is not intended to exclude other additives, components, integers or steps.

BRIEF DESCRIPTION OF THE FIGURES

FIG. 1. Characterization of invasion ligand of *Plasmodium falciparum*.

FIG. 2. An invasion ligand according to SEQ ID NO: 1 is expressed in schizonts and merozoites and is refractory to knock-out but not C-terminal tagging.

FIG. 2A) Indirect immunofluorescence and phase contrast micrographs of late segmented schizonts and free merozoites using rabbit polyclonal serum raised the invasion ligand. The panels from left to right are rabbit anti-invasion ligand, DAPI nuclear stain, phase contrast image and an overlay of all three images. Scale bars=1 µM. FIG. 2B) The scheme for plasmid integration by single homologous crossover recombination to add a single Strep-tag II and triple Hemagluttinin (HA) tag to the invasion ligand C terminus. FIG. 2C) Immunoblot with anti-the invasion ligand monoclonal (clone 6H2) against culture supernatant from wild type 3D7 and D10, and HA tagged parasite lines in both to detect invasion ligand. The reactivity at ~70 kDa is cross-reactivity of antibody with serum albumin which is present at high concentration in the supernatant medium. FIG. 2D) Immunoprecipitation of invasion ligand with rabbit polyclonal serum against invasion ligand (or pre-immune normal rabbit serum control) probed with invasion ligand monoclonal.

FIG. 3. Invasion ligand localizes to the apical pole of merozoites and follows the tight junction during invasion.

FIG. 4. Invasion ligand binds to the erythrocyte surface.

(FIG. 4A) Immunoblot of invasion ligand from culture supernatant (input) bound to erythrocytes and eluted using high salt from the host cell surface with and without a PBS wash. (FIG. 4B) Immunoblot of invasion ligand from culture supernatant bound to erythrocytes in the presence of different enzymes that modify surface receptors (Nm, neuraminidase; Chymo, chymotrypsin; Tryp, trypsin). EBA175 binding control (sensitive to Nm and Tryp treatment). (FIG. 4C) Immunoblot of invasion ligand from culture supernatant bound to erythrocytes in the presence of increasing concentrations of heparin (HEP) or chondroitin sulfate C (CSC). EBA175, binding control. (FIG. 4D) Immunoblot of unbound and bound/eluted fractions from culture supernatant incubated with heparin-agarose beads, showing selective depletion of invasion ligand (negative lane). The presence of soluble HEP but not CSC out-competes invasion ligand binding, increasing the amount in the unbound fractions and decreasing that which can be bound and then eluted.

FIG. 5. Antibodies against the invasion ligand inhibit merozoite invasion in vitro and recombinant full length invasion ligand is recognized by human malaria-immune sera.

FIG. 5A) Bar chart showing inhibition of invasion into untreated, neuraminidase (Nm)-, chymotrypsin (Chymo)- or trypsin (Tryp)-treated erythrocytes in the presence of rabbit antiserum raised against invasion ligand. Each data point represents the % invasion with respect to invasion into the same treated cells but for normal rabbit serum and is the average of at least four replicate assays (carried out in triplicate) with errors bars showing the 95% CI. FIG. 5B) Generation of soluble recombinant full length invasion ligand: Lane 1, purified inclusion body; Lane 2, guanidine-HCl solubilized sample; Lane 3, Ni-resin purified invasion ligand; Lane 4, refolded invasion ligand. FIG. 5C) Reactivity of pooled sera from different malaria hyperendemic regions of Papua New Guinea (Pool P and M) and pooled Melbourne control sera with refolded full length invasion ligand. Rabbit anti-His and mouse invasion ligand monoclonal are included as positive controls.

Figure 6:
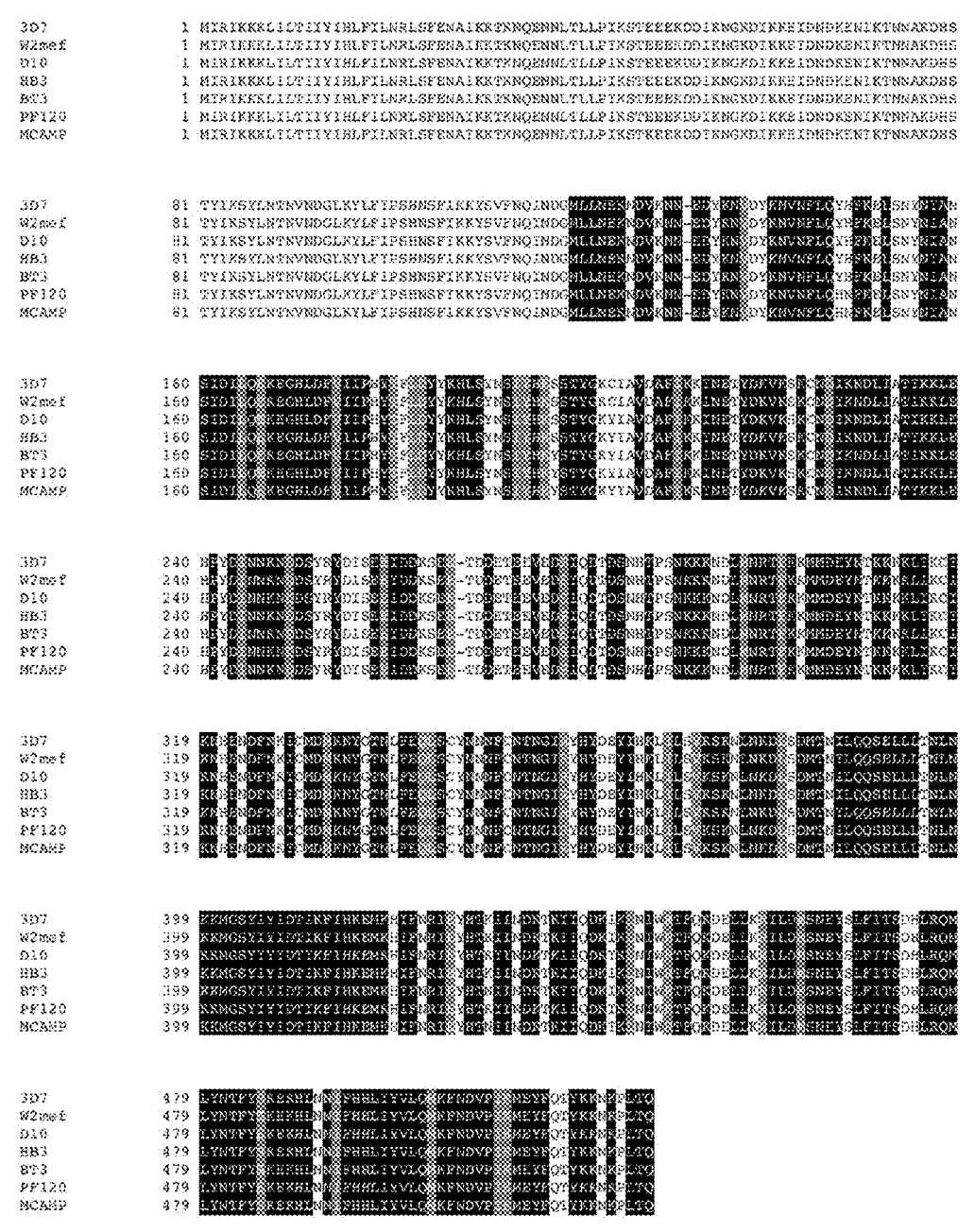

FIG. 6. Alignment of invasion ligand proteins from seven different *P. falciparum* strains and the partial sequence of the *P. reichenowi* invasion ligand orthologue.

FIG. 7. The invasion ligand localises to the rhoptry body.

(FIG. 7A) Immuno-electron microscopy of late schizonts localising invasion ligand (using anti-invasion ligand antibody) to the merozoite rhoptries. (FIG. 7B) Immuno-electron microscopy of late schizonts localising invasion ligand (using anti-HA in the tagged line) to the merozoite rhoptries. Scale bars=0.2 μM.

FIG. 8. The invasion ligand follows the tight junction during invasion.

Figure 1A:
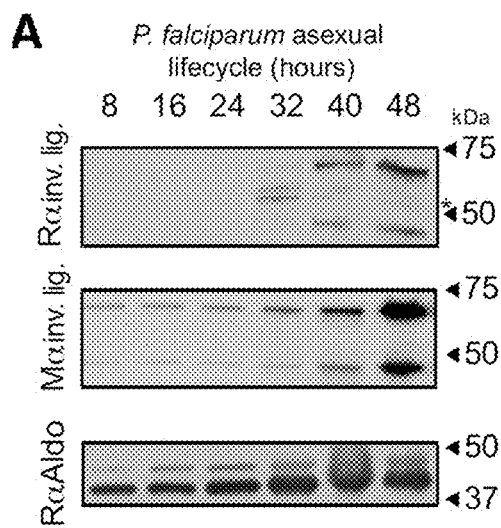
FIG. 1A) Immunoblot of whole *P. falciparum* parasite lysate at 8 hour intervals across the 48hour lifecycle (0 hour=invasion) probed with rabbit polyclonal and mouse monoclonal serum raised against a recombinant portion of an invasion ligand according to SEQ ID NO:1. The bottom panel corresponds to a loading control using antibodies to aldolase.
Figure 1B:
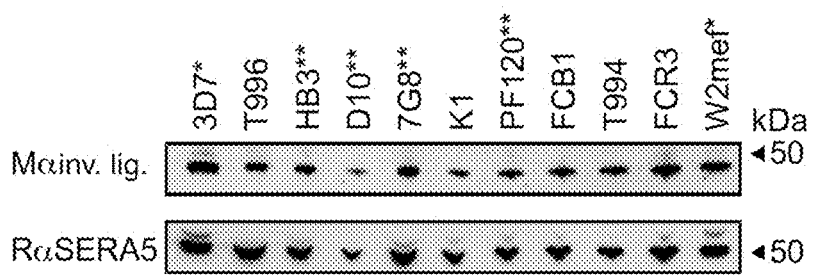
FIG. 1B) Immunoblot of proteins from post-schizont rupture supernatants released from the parasite lines 3D7, T996, HB3, D10, 7G8, K1, PF120, FCB1, T994 and W2mef. An asterisk marks those with known sequence. Double asterisk marks those that have a cysteine to tyrosine substitution at position 203.

Co-localisation of invasion ligand with rabbit antisera against two markers of the tight junction (FIG. 8A) RON4 and (FIG. 8B) AMA1 in invading merozoites arrested using cytochalasin D. Cartoon schematic is shown on the right, with black arrows marking tight junction. DAPI nuclear stain. Scale bars=1 μM.

DETAILED DESCRIPTION OF THE INVENTION

The present invention is predicated at least in part on the identification of a novel ligand/receptor mechanism facilitating invasion of the malaria parasite into erythrocytes. The invasion ligand is significantly smaller than the other invasion ligands of the parasite, and lacks transmembrane and cytosolic domains. The cognate receptor is distinguished by its' resistance to proteases that typically adversely affect the function of other receptors used for invasion by *Plasmodium falciparum*. Applicant has also characterized the role of the invasion ligand in invasion of the parasite into human red blood cells. The invasion of red blood cells is a key event in the infection of a subject with the malaria parasite, and it is therefore proposed that the invasion ligand described herein is useful as an antigen in the formulation of a vaccine against malaria. Accordingly, the present invention provides an immunogenic molecule comprising a contiguous amino acid sequence of an invasion ligand of a strain of *Plasmodium falciparum*, the invasion ligand capable of binding to an erythrocyte receptor, the receptor function being resistant to trypsin and neuraminidase and chymotrypsin, wherein when administered to a subject the molecule is capable of inducing an immune response to the strain.

This approach to formulating a vaccine for malaria is distinguished from approaches of the prior art, and is indeed contrary to the general teaching of the prior art prior to the present invention. Previous work characterizing the function of Rh proteins (and also erythrocyte binding antigen (EBA) proteins) in human red cell (erythrocyte) invasion by *Plasmodium falciparum* has demonstrated that these molecules are not essential for red cell invasion. Experiments have demonstrated that the genes encoding these molecules (e.g. EBA175, EBA140, EBA181, Rh1, Rh2a, Rh2b and Rh4) can be disrupted in different *Plasmodium falciparum* lines without an obvious effect on blood stage growth rates.

In contrast to other invasion ligands of *Plasmodium falciparum* which are each very large (220-350 kDa), type I transmembrane proteins localising to the rhoptries, the invasion ligands described herein uniquely lack a transmembrane domain and are significantly smaller in size. The absence of the transmembrane domain in the invasion ligand suggests that the protein is not accessible to the human immune system. Other invasion ligands (and their orthologues in *P. vivax* and *P. yoelii*) are large type-I integral membrane proteins with a putative transmembrane region close to the C-terminus.

In complete contrast to the teachings of the prior art, the present invention demonstrates that the invasion ligands described herein are involved in invasion of human erythrocytes, are subject to host mediated selection, binds human erythrocytes and are the target of human antibodies in natural infection. Applicant proposes that the present invasion ligands elicit an immune response in human infections.

To investigate whether the present invasion ligands are targets for host-mediated positive selection, Applicant sequenced the entire gene encoding the ligands in seven different strains of *Plasmodium falciparum*. The sequences, along with variants from sequenced genomes, show the presence of thirteen non-synonymous (but no silent) polymorphisms, predominantly in the N-terminal half of the gene. The imbalance in substitutions that alter amino acid residues indicates selection favouring diversity in the present invasion ligands, indicating the ligands elicit an immune response. This limited level of diversity may arise from the ability of the ligands to mediate phenotypic variation by differential expression (although this does not appear to be the case for the present invasion ligands) or alternatively may result from the localization of the ligands to the moving tight junction (as discussed infra), a location that results in a degree of immune exposure given the recognition of by recombinant invasion ligand by malaria immune-sera.

In one embodiment, the invasion ligand may have an amino acid sequence according to SEQ ID NO: 1. However, it will be understood that other strain-specific variants are also included in the scope of the invention. While the invasion ligand gene from different *P. falciparum* strains does reveal a small number of polymorphisms no predicted differences in molecular weight are seen. To experimentally determine if the protein showed any marked differences in the level of expression or unexpected size diversity, Applicant performed immunoblots with culture supernatants from a diverse panel of parasite lines. The 45 kDa processed product was detected in all parasite strains tested and shows no expression level variation (FIG. 1D) consistent with it having an important function across all strains.

Applicant has further demonstrated that the subject invasion ligands localise to the apical end of the merozoite. In order to determine the temporal expression pattern and subcellular localisation of invasion ligand, Applicant raised polyclonal and monoclonal antibodies against a central fragment that incorporated six cysteine residues from 3D7 (FIG. 1C). Immunoblots using both the polyclonal and monoclonal antibodies identified a protein band of ~63 kDa, the predicted molecular weight of the invasion ligands, expressed predominantly in mature schizont stages (40-48 h) (FIG. 1C). Also observed was a smaller product of 45 kDa that likely corresponds to a processed fragment of full length the invasion ligand (FIG. 1C). Accordingly, in one embodiment, the invasion ligand is expressed in merozoite stages, and/or localizes to the apical complex (FIGS. 2, 3, 7 and 8).

The absence of a transmembrane region in the invasion ligand means that it cannot be processed by a rhomboid protease. While not definitive, this suggests that the ligand may form a complex with other merozoite proteins, at least one of which may be an integral membrane protein anchoring the ligand to the surface and, following processing, releasing the ligand into the culture supernatant. It is possible that the invasion ligand is dependent on an interaction with another *Plasmodium* protein for successful organelle targeting. Transmembrane proteins can act as an escort for soluble microneme proteins in the related apicomplexan parasite *Toxoplasma gondii*. Additionally, *P. falciparum* rhoptry proteins RAP2 and RAP3 which both lack transmembrane regions are escorted to the body of the rhoptries by RAP1 and the trafficking of the full complex appears to be dependent on interaction with the GPI-anchored protein RAMA.

Applicant has demonstrated that the invasion ligand is capable of binding to erythrocytes (FIG. 4). Demonstration of this ability is indicative that the ligand plays a key role in merozoite invasion. Enzyme treatment of red cells allows examination of the receptors to which the *Plasmodium falciparum* proteins bind. In particular, neuraminidase removes sialic acid residues from the erythrocyte surface and blocks invasion pathways dependent on sialic acid present on both glycophorin A and other receptors, trypsin treatment cleaves proteins such as glycophorin A and C, but does not affect glycophorin B, and chymotrypsin cleaves a non-overlapping set of proteins including glycophorin B and band 3 on the erythrocyte surface. Using this approach, invasion phenotypes can be broadly classified into two main groups: i) sialic acid (SA)-dependent invasion, demonstrated by poor invasion of neuraminidase-treated erythrocytes (neuraminidase cleaves SA on the erythrocyte surface), and ii) SA-independent invasion, demonstrated by efficient invasion of neuraminidase-treated erythrocytes. Applicant demonstrates binding of the invasion ligand described herein to erythrocytes is insensitive to neuraminidase, trypsin and chymotrypsin treatment but is substantially reduced in the presence of heparin, suggesting carbohydrate moieties are involved in the binding of the invasion ligand. Furthermore, binding may also involve a proteoglycan. Resistance to neuraminidase and all proteases tested indicates the erythrocyte receptor for the invasion ligand is distinct from the receptors that have been characterized for the other immunogens.

Demonstration that the present invasion ligands are involved in trypsin-, neuraminidase- and chymotrypsin-independent invasion of red cells, indicates that the interaction of the invasion ligand with a trypsin-, neuraminidase- and chymotrypsin-independent erythrocyte receptor is important for *Plasmodium falciparum* infection.

Applicant has further demonstrated that the invasion ligands appear important for parasite survival in all strains of *P. falciparum* tested, covering a range of preferred alternative invasion pathways. The adaptability of *P. falciparum* in its use of alternative receptors during erythrocyte invasion occurs by differential expression of proteins, as discussed supra, and in some cases silencing and activation of some genes following selection under specific conditions. In contrast, the invasion ligands described herein may play a conserved role across all parasite strains, including those that invade using alternate receptors or invasion pathways. Accordingly, in one embodiment the invasion ligands are expressed across all parasite lines. In another embodiment the ligands are refractory to genetic disruption in all parasite lines. This indicates a key role in invasion.

An immunoblot using a soluble recombinant invasion ligand (generated from refolding of ligand from *E. coli* inclusion bodies) demonstrates that the ligands are recognized in natural malaria infections, indicating it elicits immune responses in humans. Accordingly, in one embodiment the ligand is recognized to a greater level by pooled human sera from a malaria-endemic community as compared with pooled malaria-non-exposed immune sera (FIG. 5). This indicates that the ligand is recognized in natural malaria infections. This unexpected recognition of the invasion ligand by the human immune system, and its role of binding to and in invasion of human erythrocytes indicates that invasion using ligands of the present invention are targeted by immune responses in humans in natural malaria infection.

The targeting of the invasion ligands described herein by immune responses in humans in natural malaria infection may inhibit an interaction of the ligand with a trypsin-, neuraminidase- and chymotrypsin-independent erythrocyte receptor.

Antibodies that inhibit the growth of blood stage *Plasmodium falciparum* parasites in vitro are found in the sera of some, but not all, individuals living in malaria endemic regions (Marsh, et al (1989) Trans. R. Soc. Trop. Med. Hyg. 83:293, Brown, et al (1982) Nature. 297:591, Brown, et al. (1983) Infect. Immun. 39:1228, Bouharoun-Tayoun, et al. (1990) J. Exp. Med. 172:1633-1641). Inhibitory antibodies are likely to contribute to the clinical immunity observed in highly exposed individuals. Inhibitory antibodies may act in a manner involving direct anti-microbial activity, activation of compliment, opsonisation, the generation of antioxidants, or antibody-dependent cell cytotoxicity. Alternatively, inhibitory antibodies may act in a manner that is independent of complement or other cellular mediators and function by preventing invasion of erythrocytes by the extracellular merozoite form of the parasite.

The present invention requires that the immunogenic molecule is capable of inducing an immune response in the subject. Furthermore, the immunogenic molecule may be capable of inducing an immune response in the subject that is capable of inhibiting the interaction of *Plasmodium falciparum* with a host erythrocyte. Applicant has demonstrated that antibodies to invasion ligand inhibit invasion in vitro (FIG. 5). Accordingly, the immunogenic molecule may be further capable of inducing an invasion-inhibitory immune response in the subject. As used herein, the term "invasion-inhibitory" is intended to include the complete prevention of invasion of an invasion-competent erythrocyte for the life-span of the subject. The term is also intended to include the partial prevention of invasion, as measured by for example, the proportion of a population of invasion-competent erythrocytes that are invaded, the number of attempts by which it is necessary for a given parasite to invade an erythrocyte, the time taken for a parasite to invade an erythrocyte, and the number of parasites required to ensure that a single erythrocyte is invaded. The complete or partial inhibition of invasion may be for a short period of time (such as several hours), an intermediate period of time (such as weeks, or months), or a protracted period of time (such as years or decades). The inhibition of invasion may be measured in vivo or in vitro.

For the avoidance of doubt, the term "invasion" is intended to include the entire invasion process such that the complete parasite enters the cytoplasm, and is completely encircled by the cytoplasm. The term also includes components of the entire invasion process such as the binding of the parasite to the surface of the erythrocyte, the reorientation of the apical end of the parasite to contact the erythrocyte surface, entry of the parasite into a parasitophorous vacuole, release of protein from apical organelles, and the shedding of parasite surface protein by proteases. Furthermore, the term "invasion" includes both SA dependent and SA-independent invasion pathways. Immune responses to these pathways are known as type-A and type-B inhibitory responses, respectively.

The present invention includes immunogenic molecules capable of eliciting an immune response against a wild-type strain of *P. falciparum*, or any of the following strains: 3D7, W2MEF, GHANA1, V1_S, RO-33, PREICH, HB3, SANTA-LUCIA, 7G8, SENEGAL3404, FCC-2, K1, RO-33, D6, DD2, or D10, or any other known or newly isolated strain of *Plasmodium falciparum*. An isolate or strain of *Plasmodium falciparum* is a sample of parasites taken from an infected individual on a unique occasion. Typically, an isolate is uncloned, and may therefore contain more than one genetically distinct parasite clone. A *Plasmodium falciparum* line is a lineage of parasites derived from a single isolate, not necessarily cloned, which have some common phenotype (e.g. drug-resistance, ability to invade enzyme treated red cells etc.). A *Plasmodium falciparum* clone is the progeny of a single parasite, normally obtained by manipulation or serial dilution of uncloned parasites and then maintained in the laboratory. All the members of a clone have been classically defined as genetically identical, but this is not necessarily the case, since members of the clone may undergo mutations, chromosomal rearrangements, etc, which may survive in in vitro culture conditions. While the immunogenic molecule will typically include amino acid sequences found in an invasion ligand of the strain for which protection is desired, this is not necessarily required.

Typically, the immunogenic molecule is a polypeptide, or includes a polypeptide region. As used herein, the term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included are, for example, polypeptides containing one or more analogs of an amino acid (including, for example, unnatural amino acids, etc.), as well as other modifications known in the art. Polypeptides can occur as single chains or associated chains.

In one form of the immunogenic molecule, the invasion ligand comprises an amino acid sequence as described in SEQ ID NO: 1, or a variant thereof.

```
Amino acid sequence of invasion ligand, with leader sequence.
                                                      SEQ ID NO: 1
MIRIKKKLILTIIYIHLFILNRLSFENAIKKTKNQENNLTLLPIKSTEEEKDDIKNGKDI

KKEIDNDKENIKTNNAKDHSTYIKSYLNTNVNDGLKYLFIPSHNSFIKKYSVFNQINDGM

LLNEKNDVKNNEDYKNVDYKNVNFLQYHFKELSNYNIANSIDILQEKEGHLDFVIIPHYT

FLDYYKHLSYNSIYHKSSTYGKCIAVDAFIKKINETYDKVKSKCNDIKNDLIATIKKLEH

PYDINNKNDDSYRYDISEEIDDKSEETDDETEEVEDSIQDTDSNHTPSNKKKNDLMNRTF

KKMMDEYNTKKKKLIKCIKNHENDFNKICMDMKNYGTNLFEQLSCYNNNFCNTNGIRYHY

DEYIHKLILSVKSKNLNKDLSDMTNILQQSELLLTNLNKKMGSYIYIDTIKFIHKEMKHI

FNRIEYHTKIINDKTKIIQDKIKLNIWRTFQKDELLKRILDMSNEYSLFITSDHLRQMLY

NTFYSKEKHLNNIFHHLIYVLQMKFNDVPIKMEYFQTYKKNKPLTQ
```

The underlined residues comprise the leader sequence, and it will be understood that the leader sequence is not essential to the invention, and in some circumstances it may even be preferable to remove one or all of the residues comprising the leader sequence.

Variants of any of the sequences disclosed herein are included in the scope of this invention and include embodiments whereby E at amino acid 48 is replaced with K, Y at amino acid 147 is replaced with H, H at amino acid 148 is replaced with N, S at amino acid 197 is replaced with Y, C at amino acid 203 is replaced with Y, I at amino acid 204 is replaced with K or R, N at amino acid 347 is replaced with Y or D, Y at amino acid 358 is replaced with F, E at amino acid 362 is replaced with D, V at amino acid 371 is replaced with I, I at amino acid 407 is replaced with V, I at amino acid 410 is replaced with M, and K at amino acid 429 is replaced with N. These latter variable residues are indicated in bold typeface.

The present invention includes immunogenic molecules that are truncated or extended forms of the molecules described herein. It will be understood that these alternative forms of the sequences may be aligned at the amino acid level, and that the point mutations listed in the preceding paragraph may apply to the corresponding residues in any of SEQ ID NOs: 2 to 12, as described infra For example, the immunogenic molecule may be devoid of any one or all of the residues that comprise a leader sequence of the immunogenic molecule as described in SEQ ID NO:1 (underlined). In one form of the molecule, the molecule is completely devoid of all leader residues, as described by SEQ ID NO:2, or variant thereof.

```
                                                    SEQ ID NO: 2
SFENAIKKTKNQENNLTLLPIKSTEEEKDDIKNGKDIKKEIDNDKENIKTNNAKDHSTYI

KSYLNTNVNDGLKYLFIPSHNSFIKKYSVFNQINDGMLLNEKNDVKNNEDYKNVDYKNVN

FLQYHFKELSNYNIANSIDILQEKEGHLDFVIIPHYTFLDYYKHLSYNSIYHKSSTYGKC

IAVDAFIKKINETYDKVKSKCNDIKNDLIATIKKLEHPYDINNKNDDSYRYDISEEIDDK

SEETDDETEEVEDSIQDTDSNHTPSNKKKNDLMNRTFKKMMDEYNTKKKKLIKCIKNHEN

DFNKICMDMKNYGTNLFEQLSCYNNNFCNTNGIRYHYDEYIHKLILSVKSKNLNKDLSDM

TNILQQSELLLTNLNKKMGSYIYIDTIKFIHKEMKHIFNRIEYHTKIINDKTKIIQDKIK

LNIWRTFQKDELLKRILDMSNEYSLFITSDHLRQMLYNTFYSKEKHLNNIFHHLIYVLQM

KFNDVPIKMEYFQTYKKNKPLTQ
```

In another form of the molecule SEQ ID NO: 2 possess an N-terminal methionine residue.

In another form of the invention the immunogenic molecule is yet further truncated, and comprises a sequence according to SEQ ID NO: 3, or variant thereof.

```
                                                    SEQ ID NO: 3
HFKELSNYNIANSIDILQEKEGHLDFVIIPHYTFLDYYKHLSYNSIYHKSSTYGKCIAV

DAFIKKINETYDKVKSKCNDIKNDLIATIKKLEHPYDINNKNDDSYRYDISEEIDDKSE

ETDDETEEVEDSIQDTDSNHTPSNKKKNDLMNRTFKKMMDEYNTKKKKLIKCIKNHEND

FNKICMDMKNYGTNLFEQLSCYNNNFCNTNGIRYHYDEYIHKLILSVKSKNLNKDLSDM

TNILQQSELLLTNLNKKMGSYIYIDTIKFIHKEMKHIFNRIEYHTKIINDKTKIIQDKI

KLNIWRTFQKDELLKRILDMSNEYSLFITSDHLRQMLYNTFYSKEKHLNNIFHHLIYVL

QMKFNDVPIKMEYFQTYKKNKPLTQ
```

In another form of the invention the immunogenic molecule comprises a sequence with 1, 2, 3, 4, 5, 6, 7, 8, 9, or 10 residues added to the N-terminus of the molecule described by SEQ ID NO: 3. For example, the molecule may be that described by to SEQ ID NO: 4, or variant thereof.

```
                                                    SEQ ID NO: 4
NFLQYHFKELSNYNIANSIDILQEKEGHLDFVIIPHYTFLDYYKHLSYNS

IYHKSSTYGKCIAVDAFIKKINETYDKVKSKCNDIKNDLIATIKKLEHPY

DINNKNDDSYRYDISEEIDDKSEETDDETEEVEDSIQDTDSNHTPSNKKK

NDLMNRTFKKMMDEYNTKKKKLIKCIKNHENDFNKICMDMKNYGTNLFEQ

LSCYNNNFCNTNGIRYHYDEYIHKLILSVKSKNLNKDLSDMTNILQQSEL

LLTNLNKKMGSYIYIDTIKFIHKEMKHIFNRIEYHTKIINDKTKIIQDKI

KLNIWRTFQKDELLKRILDMSNEYSLFITSDHLRQMLYNTFYSKEKHLNN

IFHHLIYVLQMKFNDVPIKMEYFQTYKKNKPLTQ.
```

In another form of the invention the immunogenic molecule comprises a sequence according to SEQ ID NO: 5, or variant thereof.

```
                                                    SEQ ID NO: 5
DYKNVNFLQYHFKELSNYNIANSIDILQEKEGHLDFVIIPHYTFLDYYKH

LSYNSIYHKSSTYGKCIAVDAFIKKINETYDKVKSKCNDIKNDLIATIKK

-continued
LEHPYDINNKNDDSYRYDISEEIDDKSEETDDETEEVEDSIQDTDSNHTP

SNKKKNDLMNRTFKKMMDEYNTKKKKLIKCIKNHENDFNKICMDMKNYGT

-continued
NLFEQLSCYNNNFCNTNGIRYHYDEYIHKLILSVKSKNLNKDLSDMTNIL

QQSELLLTNLNKKMGSYIYIDTIKFIHKEMKHIFNRIEYHTKIINDKTKI

IQDKIKLNIWRTFQKDELLKRILDMSNEYSLFITSDHLRQMLYNTFYSKE

KHLNNIFHHLIYVLQMKFNDVPIKMEYFQTYKKNKPLTQ
```

Alternatively, the immunogenic molecule may be a truncated form of the molecule described by SEQ ID NO:3. For example, the molecule may be truncated by 1, 2, 3, 4, 5, 6, 7, 8, 9, or 10 amino acid residues at the N-terminus. In one form of the invention the immunogenic molecule comprises a sequence according to SEQ ID NO: 6, or variant thereof.

```
                                                    SEQ ID NO: 6
SNYNIANSIDILQEKEGHLDFVIIPHYTFLDYYKHLSYNSIYHKSSTYGK

CIAVDAFIKKINETYDKVKSKCNDIKNDLIATIKKLEHPYDINNKNDDSY
```

-continued

RYDISEEIDDKSEETDDETEEVEDSIQDTDSNHTPSNKKKNDLMNRTFKK

MMDEYNTKKKKLIKCIKNHENDFNKICMDMKNYGTNLFEQLSCYNNNFCN

TNGIRYHYDEYIHKLILSVKSKNLNKDLSDMTNILQQSELLLTNLNKKMG

SYIYIDTIKFIHKEMKHIFNRIEYHTKIINDKTKIIQDKIKLNIWRTFQK

DELLKRILDMSNEYSLFITSDHLRQMLYNTFYSKEKHLNNIFHHLIYVLQ

MKFNDVPIKMEYFQTYKKNKPLTQ

In another form of the invention the immunogenic molecule comprises a sequence according to SEQ ID NO: 7, or variant thereof.

SEQ ID NO: 7
ANSIDILQEKEGHLDFVIIPHYTFLDYYKHLSYNSIYHKSSTYGKCIAVD

AFIKKINETYDKVKSKCNDIKNDLIATIKKLEHPYDINNKNDDSYRYDIS

EEIDDKSEETDDETEEVEDSIQDTDSNHTPSNKKKNDLMNRTFKKMMDEY

NTKKKKLIKCIKNHENDFNKICMDMKNYGTNLFEQLSCYNNNFCNTNGIR

YHYDEYIHKLILSVKSKNLNKDLSDMTNILQQSELLLTNLNKKMGSYIYI

DTIKFIHKEMKHIFNRIEYHTKIINDKTKIIQDKIKLNIWRTFQKDELLK

RILDMSNEYSLFITSDHLRQMLYNTFYSKEKHLNNIFHHLIYVLQMKFND

VPIKMEYFQTYKKNKPLTQ

In one form of the invention the immunogenic molecule is yet further truncated. In one form of the invention the immunogen molecule comprises SEQ ID NO: 8

SEQ ID NO: 8
NSIYHKSSTYGKCIAVDAFIKKINETYDKVKSKCNDIKNDLIATIKKLEH

PYDINNKNDDSYRYDISEEIDDKSEETDDETEEVEDSIQDTDSNHTPSNK

KKNDLMNRTFKKMMDEYNTKKKKLIKCIKNHENDFNKICMDMKNYGTNLF

EQLSCYNNNFCNTNGIRYHY

Fragments of any of SEQ ID NOS: 1 to 8 are included in the scope of the invention. Exemplary fragments include that described by SEQ ID NO:9 or variant thereof.

SEQ ID NO: 9
IAVDAFIKKINETYDKVKSKCNDIKNDLIATIKKLEHPYDINNKNDDSYR

YDISEEIDDKSEETDDETEEVEDSIQDTDSNHTPSNKKKNDLMNRTFKKM

MDEYNTKKKKLIKCIKNHENDFNKICMDMKNYGTNLFEQLSCYNNNFCNT

NGIRYHY

Alternatively, the fragment may comprise from about residue 204 to about residue 360 of SEQ ID NO:2. In one form of the invention, the immunogenic molecule is described by SEQ ID NO:10 or variant thereof.

SEQ ID NO: 10
IAVDAFIKKINETYDKVKSKCNDIKNDLIATIKKLEHPYDINNKNDDSYR

YDISEEIDDKSEETDDETEEVEDSIQDTDSNHTPSNKKKNDLMNRTFKKM

MDEYNTKKKKLIKCIKNHENDFNKICMDMKNYGTNLFEQLSCYNNNF

Alternatively, the fragment may comprise from about residue 204 to about residue 344 of SEQ ID NO:2. In one form of the invention, the immunogenic molecule is described by SEQ ID NO:11

IAVDAFIKKINETYDKVKSKCNDIKNDLIATIKKLEHPYDINNKNDDSYR

YDISEEIDDKSEETDDETEEVEDSIQDTDSNHTPSNKKKNDLMNRTFKKM

MDEYNTKKKKLIKCIKNHENDFNKICMDMKNYGTNLFEQLS

Alternatively, the fragment may comprise from about residue 204 to about residue 328 of SEQ ID NO:2. In one form of the invention, the immunogenic molecule is described by SEQ ID NO:12, or variant thereof.

SEQ ID NO: 12.
IAVDAFIKKINETYDKVKSKCNDIKNDLIATIKKLEHPYDINNKNDDSYR

YDISEEIDDKSEETDDETEEVEDSIQDTDSNHTPSNKKKNDLMNRTFKKM

MDEYNTKKKKLIKCIKNHENDFNKI

It is understood that the present invention is not limited to immunogenic molecules having any of the specific amino acid sequences as described herein. Shorter molecules may exhibit immunogenicity sufficient for the inducement of an immune response, or possibly a protective immune response. For example, and without wishing to be limited by theory, it is thought that inclusion of 1, 2, or 3 of any of the 6 cysteine residues (found at positions 203, 224, 317, 329, 345, and 351 may be preferable for maintenance of disulfide bonding in the immunogenic molecule. Thus, in one embodiment the immunogenic molecule comprises residues from about residue 203 to about residue 224, 317, 329, 345, or 351; or residues from about residue 224 to about residue 317, 329, 345, or 351; or residues from about residue 329 to about residue 345 or 351, or residues from about residue 345 to about residue 351. In one embodiment, cysteines 203 (polymorphic in *Plasmodium falciparum*) and 329 (absent in *Plasmodium* reichenowi) pair in the molecule by way of disulfide bridge to form a loop. Accordingly, in one form of the invention the immunogenic molecule comprises amino acid residues from about residue 203 to about residue 329. It is further proposed that cysteines 224 and 317 pair with either cysteine 345 or cysteine 351, such that the immunogenic molecule comprise residues from about residue 224 to about residue 345 or 351; or from about residue 317 to about residue 345 or 351.

The contiguous amino acid sequence may comprise at least about 5, 8, 10, 20, 50 or 100 or more amino acids. The strain of *Plasmodium falciparum* may be a wild type strain. The immune response to the strain may be an invasion-inhibitory immune response. The skilled person is capable of routine experimentation designed to identify the shortest efficacious sequence, or the length of sequence that provides the greatest or most effective immune response or invasion-inhibitory response in the subject.

Similarly, the skilled person understands that strict compliance with any amino acid sequence described herein is not necessarily required, and he or she could decide by a matter of routine whether any further mutation is deleterious or preferred. Thus, the immunogenic molecules of the present invention include sequences having 50% or more identity (e.g. 60%, 65%, 70%, 75%, 80%, 85%, 90%, 91%, 92%, 93%, 94%, 95%, 96%, 97%, 98%, 99%, 99.5% or more) to any protein described herein. The immunogenic molecules also include variants (e.g. allelic variants, homologs, orthologs, paralogs, mutants, etc.). The molecules may lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus.

Expression of the immunogenic molecules of the invention may take place in *Plasmodium*, however other heterologous hosts may be utilised. The heterologous host may be prokaryotic (e.g. a bacterium) or eukaryotic. It is preferably *E. coli*, but other suitable hosts include *Bacillus subtilis, Vibrio cholerae, Salmonella typhi, Salmonella typhimurium, Neisseria lactamica, Neisseria cinerea, Mycobacteria* (e.g. *M. tuberculosis*), yeasts, etc. The immunogenic molecules of the present invention may be present in the composition as individual separate polypeptides. Generally, the recombinant fusion proteins of the present invention are prepared as a GST-fusion protein and/or a His-tagged fusion protein.

Polypeptides of the invention can be prepared by various means (e.g. recombinant expression, purification from cell culture, chemical synthesis, etc.) and in various forms (e.g. native, fusions, non-glycosylated, lipidated, etc.). They are preferably prepared in substantially pure form (i.e. substantially free from other Plasmodial or host cell proteins).

While the immunogenic molecule may comprise a single antigenic region, by the use of well-known recombinant DNA methods, more than one antigenic region may be included in a single immunogenic molecule. At least two (i.e. 2, 3, 4, 5, 6, 7, 8, 9, 10, 11, 12, 13, 14, 15, 16, 17, 18, 19, 20 or more) antigens can be expressed as a single polypeptide chain (a 'hybrid' polypeptide). Hybrid polypeptides offer two principal advantages: first, a polypeptide that may be unstable or poorly expressed on its own can be assisted by adding a suitable hybrid partner that overcomes the problem; second, commercial manufacture is simplified as only one expression and purification need be employed in order to produce two polypeptides which are both antigenically useful.

Hybrid polypeptides can be represented by the formula $NH_2$-A-(-X-L-)$_n$-B—COOH, wherein: X is an amino acid sequence of a *Plasmodium falciparum* antigen as defined herein; L is an optional linker amino acid sequence; A is an optional N-terminal amino acid sequence; B is an optional C-terminal amino acid sequence; and n is 2, 3, 4, 5, 6, 7, 8, 9, 10, 11, 12, 13, 14 or 15.

If a -X- moiety has a leader peptide sequence in its wild-type form, this may be included or omitted in the hybrid protein. In some embodiments, leader peptides (if present) will be deleted except for that of the -X- moiety located at the N-terminus of the hybrid protein i.e. a leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of (-X-L-), linker amino acid sequence -L- may be present or absent. For instance, when n=2 the hybrid may be $NH_2$-$X_1$-$L_1$-$X_2$-$L_2$-COOH, $NH_2$-$X_1$-$X_2$-$COOH_5$ $NH_2$-$X_1$-$L_1$-$X_2$-COOH, $NH_2$-X1-X2-L2-COOH, etc. Linker amino acid sequence(s) -L- will typically be short (e.g. 20 or fewer amino acids i.e. 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising $Gly_n$ where n=2, 3, 4, 5, 6, 7, 8, 9, 10 or more), and histidine tags (i.e. $His_n$ where n=3, 4, 5, 6, 7, 8, 9, 10 or more). Other suitable linker amino acid sequences will be apparent to those skilled in the art. A useful linker is GSGGGG, with the Gly-Ser dipeptide being formed from a BamHI restriction site, thus aiding cloning and manipulation, and the $(Gly)_4$ tetrapeptide being a typical poly-glycine linker. The same variants apply to (-Y-L-). Therefore, for each m instances of (-Y-L-), linker amino acid sequence -L- may be present or absent.

-A- is an optional N-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. $His_n$ where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides an N-terminus methionine.

-B- is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. $His_n$, where n=3, 4, 5, 6, 7, 8, 9, 10 or more), or sequences which enhance protein stability. Other suitable C-terminal amino acid sequences will be apparent to those skilled in the art. Most preferably, n is 2 or 3.

The invention provides a process for producing an immunogenic molecule of the invention, comprising the step of synthesising at least part of the immunogenic molecule by chemical means.

Polypeptides used with the invention can be prepared by various means (e.g. recombinant expression, purification from cell culture, chemical synthesis, etc.). Recombinantly-expressed proteins are preferred, particularly for hybrid polypeptides.

Polypeptides used with the invention are preferably provided in purified or substantially purified form i.e. substantially free from other polypeptides (e.g. free from naturally-occurring polypeptides), particularly from other *Plasmodium* or host cell polypeptides, and are generally at least about 50% pure (by weight), and usually at least about 90% pure i.e. less than about 50%, and more preferably less than about 10% (e.g. 5%) of a composition is made up of other expressed polypeptides. Thus the antigens in the compositions are separated from the whole organism with which the molecule is expressed.

Another aspect of the present invention provides a composition comprising an immunogenic molecule as described herein and a pharmaceutically acceptable excipient and optionally a vaccine adjuvant. Such excipients include any excipient that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier.

The pH of the composition is preferably between 6 and 8, preferably about 7. The pH may be maintained by the use of a buffer. A phosphate buffer is typical. The composition may be sterile and/or pyrogen-free. The composition may be isotonic with respect to humans. Compositions may include sodium salts (e.g. sodium chloride) to give tonicity.

A concentration of 10+/−2 mg/ml NaCl is typical. Compositions may also comprise a detergent e.g. a Tween (polysorbate), such as Tween 80. Detergents are generally present at low levels e.g. <0.01%.

Compositions may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilised material. The pH of a composition for lyophilisation may be adjusted to around 6.1 prior to lyophilisation.

The composition may further comprise an antimalarial that is useful for the treatment of Plasmodial infection. Preferred antimalarials for use in the compositions include the chloroquine phosphate, proguanil, primaquine, doxycycline, mefloquine, clindamycin, halofantrine, quinine sulphate, quinine dihydrochloride, gluconate, primaquine phosphate and sulfadoxine.

The compositions of the invention may also comprise one or more immunoregulatory agents. Preferably, one or more of the immunoregulatory agents include(s) an adjuvant. The adjuvant may be selected from one or more of the group consisting of a TH1 adjuvant and TH2 adjuvant, further discussed below.

Adjuvants which may be used in compositions of the invention include, but are not limited to those described in the following passages.

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. (e.g. see chapters 8 & 9 of Powell & Newman (eds.) Vaccine Design (1995) Plenum), or mixtures of different mineral compounds, with the compounds taking any suitable form (e.g. gel, crystalline, amorphous, etc.), and with adsorption being preferred. The mineral containing compositions may also be formulated as a particle of metal salt (WO00/23105).

A typical aluminium phosphate adjuvant is amorphous aluminium hydroxyphosphate with $PO_4/Al$ molar ratio between 0.84 and 0.92, included at 0.6 mg $Al^{3+}$/ml. Adsorption with a low dose of aluminium phosphate may be used e.g. between 50 and 100 µg $Al^{3+}$ per conjugate per dose. Where an aluminium phosphate it used and it is desired not to adsorb an antigen to the adjuvant, this is favoured by including free phosphate ions in solution (e.g. by the use of a phosphate buffer).

Oil emulsion compositions suitable for use as adjuvants in the invention include oil-in-water emulsions and water-in-oil emulsions.

A submicron oil-in-water emulsion may include squalene, Tween 80, and Span 85 e.g. with a composition by volume of about 5% squalene, about 0.5% polysorbate 80 and about 0.5% Span 85 (in weight terms, 4.3% squalene, 0.5% polysorbate 80 and 0.48% Span 85), known as 'MF595' (57-59 chapter 10 of Powell & Newman (eds.) Vaccine Design (1995) Plenum; chapter 12 of 'Hagen (ed.) Vaccine Adjuvants: Preparation Methods and Research Protocols (Volume 42 of Methods in Molecular Medicine series)). The MF59 emulsion advantageously includes citrate ions e.g. 10 mM sodium citrate buffer.

An emulsion of squalene, a tocopherol, and Tween 80 can be used. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene tocopherol is preferably <1 as this provides a more stable emulsion. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.

An emulsion of squalene, a tocopherol, and a Triton detergent (e.g. Triton X-100) can be used.

An emulsion of squalane, polysorbate 80 and poloxamer 401 ("Pluronic™ L 121") can be used. The emulsion can be formulated in phosphate buffered saline, pH 7.4. This emulsion is a useful delivery vehicle for muramyl dipeptides, and has been used with threonyl-MDP in the "SAF-I" adjuvant, (0.05-1% Thr-MDP, 5% squalane, 2.5% Pluronic L121 and 0.2% polysorbate 80). It can also be used without the Thr-MDP, as in the "AF" adjuvant (Hariharan et al. (1995) Cancer Res 55:3486-9) (5% squalane, 1.25% Pluronic L121 and 0.2% polysorbate 80). Microfluidisation is preferred.

Complete Freund's adjuvant (CFA) and incomplete Freund's adjuvant (IFA) may also be used.

Saponin formulations may also be used as adjuvants in the invention (see for example Chapter 22 of Powell & Newman (eds.) Vaccine Design (1995) Plenum). Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS1 8, QS21, QH-A, QH-B and QH-C. Preferably, the saponin is QS21. A method of production of QS21 is disclosed in ref. 63. Saponin formulations may also comprise a sterol, such as cholesterol (WO96/33739).

As discussed supra, combinations of saponins and cholesterols can be used to form unique particles called immunostimulating complexes (ISCOMs) (see for example Chapter 23 of Powell & Newman (eds.) Vaccine Design (1995) Plenum). ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in WO96/33739, EP-A-0109942, WO96/11711). Optionally, the ISCOMS may be devoid of additional detergent WO00/07621.

A review of the development of saponin based adjuvants can be found in Barr et al. (1998) Advanced Drug Delivery Reviews 32:247-271 and Sjolanderet al. (1998) Advanced Drug Delivery Reviews 32:321-338.

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein pi). VLPs are discussed further in (Niikura et al. (2002) Virology 293:273-280, Lenz et al. (2001) J Immunol 166:5346-5355, Pinto et al. (2003) J Infect Dis 188:327-338, Gerber et al. (2001) Virol 75:4752-4760, WO03/024480 and WO03/024481). Virosomes are discussed further in, for example, Gluck et al. (2002) Vaccine 20:610-B16.

Adjuvants suitable for use in the invention include bacterial or microbial derivatives such as non-toxic derivatives of enterobacterial lipopolysaccharide (LPS), Lipid A derivatives, immunostiinulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 77. Such "small particles" of 3dMPL are small enough to be sterile filtered through a 0.22 μm membrane (EP-A-0689454v). Other non-toxic LPS derivatives include monophosphoryl lipid A mimics, such as aminoalkyl glucosamine de phosphate derivatives e.g. RC-529 (Johnson et al (1999) Bioorg Med Chem Lett 9:2273-2278, Evans et al. (2003) Expert Rev Vaccines 2:219-229).

Lipid A derivatives include derivatives of lipid A from *Escherichia coli* such as OM-174. OM-174 is described for example in Meraldi et al. (2003) Vaccine 21:2485-2491, Pajak et al. (2003) Vaccine 21:836-842.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. Kandimalla et al (2003) Nucleic Acids Research 31: 2393-2400, WO02/26757 and WO99/62923 disclose possible analog substitutions e.g. replacement of guanosine with 2'-deoxy-7-deazaguanosine. The adjuvant effect of CpG oligonucleotides is further discussed in Krieg (2003) Nature Medicine 9:831-835, McCluskie et al. (2002) FEMS Immunology and Medical Microbiology 32:179-185, WO98/40100, U.S. Pat. Nos. 6,207,646, 6,239,116 and 6,429,199.

The CpG sequence may be directed to TLR9, such as the motif GTCGTT or TTCGTT (Kandimalla et al. (2003) Biochemical Society Transactions 31 (part 3):654-658). The CpG sequence may be specific for inducing a TH1 immune response, such as a CpG-A ODN, or it may be more specific for inducing a B cell response, such a CpG-B ODN. CpG-A and CpG-B ODNs are discussed in refs. Blackwell et al. (2003) J Immunol 170:4061-4068, Krieg (2002) Trends Immunol 23:64-65. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla et al. (2003) Biochemical Society Transactions 31 (part 3):654-658, Kandimalla et al (2003), BBRC 306:948-953, Bhagat et al. (2003) BBRC 300:853-861 and WO03/035836.

Other immunostimulatory oligonucleotides include a double-stranded RNA or an oligonucleotide containing a palindromic sequence, or an oligonucleotide containing a poly (dG) sequence.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in WO95/17211 and as parenteral adjuvants in WO98/42375. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in Beignon et al. (2002) Infect Immun 70:3012-3019, Pizza et al. (2001) Vaccine 19:2534-2541, Pizza et al. (2000) Int J Med Microbiol 290:455-461, Scharton-Kersten et al. (2000) Infect Immun 68:5306-5313, Ryan et al. (1999) Infect Immun 67:6270-6280, Partidos et al. (1999) Immunol Lett 67:209-216, Peppoloni et al. (2003) Expert Rev Vaccines 2:285-293, Pine et al. (2002) J Control Release 85:263-270. Numerical reference for amino acid substitutions is preferably based on the alignments of the A and B subunits of ADP-ribosylating toxins set forth in Domenighini et al. (1995) Mol Microbiol 15:1165-1167, specifically incorporated herein by reference in its entirety.

Human immunomodulators suitable for use as adjuvants in the invention include cytokines, such as interleukins (e.g. IL-15 IL-2, IL-4, IL-5, IL-6, IL-7, IL-12, IL-17, IL-18 (WO99/40936), IL-23, IL27 (Matsui M. et al. (2004) J. Virol 78: 9093) etc.) (WO99/44636), interferons (e.g. interferon-γ), macrophage colony stimulating factor, tumor necrosis factor and macrophage inflammatory protein-1 alpha (MIP-1 alpha) and MIP-1 beta (Lillard J W et al, (2003) Blood 101(3):807-14).

Bioadhesives and mucoadhesives may also be used as adjuvants in the invention. Suitable bioadhesives include esterified hyaluronic acid microspheres (Singh et al) (2001) JCont Release 70:267-276) or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention (WO99/27960).

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

Examples of liposome formulations suitable for use as adjuvants are described in U.S. Pat. Nos. 6,090,406, 5,916, 588, EP-A-0626169.

Adjuvants suitable for use in the invention include polyoxyethylene ethers and polyoxyethylene esters (WO99/52549). Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152). Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

Phosphazene adjuvants include poly(di(carboxylatophenoxy)phosphazene) ("PCPP") as described, for example, in references Andrianov et al. (1998) Biomaterials 19:109-115 and Payne et al. (1998) Adv Drug Delivery Review 31:185-196.

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

Imidazoquinoline adjuvants include Imiquimod ("R-837") (U.S. Pat. Nos. 4,680,338 and 4,988,815), Resiquimod ("R-848") (WO92/15582), and their analogs; and salts thereof (e.g. the hydrochloride salts). Further details about immunostimulatory imidazoquinolines can be found in references Stanley (2002) Clin Exp Dermatol 27:571-577, Wu et al. (2004) Antiviral Res. 64(2):79-83, Vasilakos et al. (2000) Cell Immunol. 204(I):64-74, U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293 and Jones (2003) Curr Opin Investig Drugs 4:214-218.

Thiosemicarbazone adjuvants include those disclosed in WO2004/060308. Methods of formulating, manufacturing, and screening for active compounds are also described in WO2004/060308. The thiosemicarbazones are particularly effective in the stimulation of human peripheral blood mononuclear cells for the production of cytokines, such as TNF-α.

Tryptanthrin adjuvants include those disclosed in WO2004/064759. Methods of formulating, manufacturing, and screening for active compounds are also described in WO2004/064759. The thiosemicarbazones are particularly effective in the stimulation of human peripheral blood mononuclear cells for the production of cytokines, such as TNF-α.

Various nucleoside analogs can be used as adjuvants, such as (a) Isatorabine (ANA-245; 7-thia-8-oxoguanosine) and prodrugs thereof; (b) ANA975; (c) ANA-025-1; (d) ANA380; (e) the compounds disclosed in U.S. Pat. No. 6,924,271, US2005/0070556 and U.S. Pat. No. 5,658,731, or (f) a pharmaceutically acceptable salt of any of (a) to (g), a tautomer of any of (a) to (g), or a pharmaceutically acceptable salt of the tautomer.

Q. Lipids linked to a phosphate-containing acyclic backbone Adjuvants containing lipids linked to a phosphate-containing acyclic backbone include the TLR4 antagonist E5564 (Wong et al. (2003) J Clin Pharmacol 43(7):735-42 and US2005/0215517).

Small molecule immunopotentiators useful ad adjuvants include N2-methyl-1-(2-methylpropyl)-1H-imidazo(4,5-c)quinoline-2,4-diamine; N2,N2-dimethyl-1-(2-methylpropyl)-1H-imidazo(4,5-c)quinoline-2,4-diamine; N2-ethyl-N2-methyl-1-(2-methylpropyl)-1H-imidazo(4,5-c)quinoline-2,4-diamine; N2-methyl-1-(2-methylpropyl)-N2-propyl-1H-imidazo(4,5-c)quinoline-2,4-diamine; 1-(2-methylpropyl)-N2-propyl-1H-imidazo(4,5-c)quinoline-2,4-diamine; N2-butyl-1-(2-methylpropyl)-1H-imidazo(4,5-c)quinoline-2,4-diamine; N2-butyl-N2-methyl-1-(2-methylpropyl)-1H-imidazo(4,5-c)quinoline-2,4-diamine; N2-methyl-1-(2-methylpropyl)-N2-pentyl-1H-imidazo(4,5-c)quinoline-2,4-diamine; N2-methyl-1-(2-methylpropyl)-N2-prop-2-enyl-1H-imidazo(4,5-c)quinoline-2,4-diamine; 1-(2-methylpropyl)-2-((phenylmethyl)thio)-1H-imidazo (4,5-c)quinolin-4-amine; 1-(2-methylpropyl)-2-(propylthio)-1H-imidazo(4,5-c)quinolin-4-amine; 2-((4-amino-1-(2-methylpropyl)-1H-imidazo(4,5-c)quinolin-2-yl)(methyl)amino)ethanol; 2-((4-amino-1-(2-methylpropyl)-1H-imidazo(455-c)quinolin-2-yl)(methyl)amino)ethyl acetate; 4-amino-1-(2-methylpropyl)-1,3-dihydro-2H-imidazo(4,5-c)quinolin-2-one; N2-butyl-1-(2-methylpropyl)-N4,N4-bis (phenylmethyl)-1H-imidazo(4,5-c)quinoline-2,4-diamine; N2-butyl-N2-methyl-1-(2-methylpropyl)-N4,N4-bis(phenylmethyl)-1H-imidazo(4,5-c)quinoline-2,4-diamine; N2-methyl-1-(2-methylpropyl)-N4,N4-bis(phenylmethyl)-1H-imidazo(4,5-c)quinolne-2,4-diamine; N2,N2-dimethyl-1-(2-methylpropyl)-N4,N4-bis(phenylmethyl)-1H-imidazo (4,5-c)quinoline-2,4-diamine; 1-(4-amino-2-(methyl (propyl)amino)-1H-imidazo(4,5-c)quinolin-1-yl}-2-methylpropan-2-ol; 1-(4-amino-2-(propylamino)-1H-imidazo(4,5-c)quinolin-1-yl)-2-methylpropan-2-ol; N43N4-dibenzyl-1-(2-methoxy-2-methylpropyl)-N2propyl-1H-imidazo(4,5-c)quinoline-2,4-diamine.

One potentially useful adjuvant is an outer membrane protein proteosome preparation prepared from a first Gram-negative bacterium in combination with a liposaccharide preparation derived from a second Gram-negative bacterium, wherein the outer membrane protein proteosome and liposaccharide preparations form a stable non-covalent adjuvant complex. Such complexes include "IVX-908", a complex comprised of *Neisseria meningitidis* outer membrane and lipopolysaccharides. They have been used as adjuvants for influenza vaccines (WO02/072012).

Other substances that act as immunostimulating agents are disclosed in Vaccine Design ((1995) eds. Powell & Newman. ISBN: 030644867X. Plenum) and Vaccine Adjuvants: Preparation Methods and Research Protocols (Volume 42 of Methods in Molecular Medicine series) (ISBN: 1-59259-083-7. Ed. O'Hagan). Further useful adjuvant substances include: Methyl inosine 5'-monophosphate ("MIMP") Signorelli & Hadden (2003) Int Immunopharmacol 3(8):1177); a polyhydroxlated pyrrolizidine compound (WO2004/064715), examples include, but are not limited to: casuarine, casuarine-6-α-D-glucopyranose, 3-epz-casuarine, 7-epz-casuarine, 3,7-diepz-casuarine, etc; a gamma inulin (Cooper (1995) Phar Biotechnol 6:559) or derivative thereof, such as algammulin; compounds disclosed in PCT/US2005/022769; compounds disclosed in WO2004/87153, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds (U.S. Pat. No. 6,606,617, WO02/018383), Hydrapthalamide compounds, Benzophenone compounds, Isoxazole compounds, Sterol compounds, Quinazilinone compounds, Pyrrole compounds (WO/04/018455), Anthraquinone compounds, Quinoxaline compounds, Triazine compounds, Pyrazalopyrimidine compounds, and Benzazole compounds (WO03/082272); loxoribine (7-allyl-8-oxoguanosine) (U.S. Pat. No. 5,011,828); a formulation of a cationic lipid and a (usually neutral) co-lipid, such as aminopropyl-dimethyl-myristoleyloxy-propanaminium bromide-diphytanoylphosphatidyl-ethanolamine (Vaxfectin™) or aminopropyl-dimethyl-bis-dodecyloxy-propanaminium bromide-dioleoylphosphatidyl-ethanolamine ("GAP-DLRIE:DOPE"). Formulations containing (±)-N-(3-aminopropyl)-N,N-dimethyl-2,3-bis(syn-9-tetradeceneyloxy)-1-propanaminium salts are preferred (U.S. Pat. No. 6,586,409).

The invention may also comprise combinations of aspects of one or more of the adjuvants identified above. For example, the following adjuvant compositions may be used in the invention: (1) a saponin and an oil-in-water emulsion (WO99/11241); (2) a saponin (e.g. QS21)+a nontoxic LPS derivative (e.g. 3dMPL) (WO94/00153); (3) a saponin (e.g. QS21)+a non-toxic LPS derivative (e.g. 3dMPL)+a cholesterol; (4) a saponin (e.g. QS21)+3dMPL+IL-12 (optionally+a sterol) (WO98/57659); (5) combinations of 3dMPL with, for example, QS21 and/or oil-in-water emulsions (EP0835318, EP0735898, EP0761231); (6) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (7) one or more mineral salts (such as an aluminum salt)+a non-toxic derivative of LPS (such as 3dMPL).

In some forms of the composition, the immunogenic molecule is present in combination with a contiguous amino acid sequence of one or more further invasion ligands relevant to the treatment or prevention of a condition caused by or associated with infection by *Plasmodium falciparum*. In one embodiment of the composition the further invasion ligand is a reticulocyte-binding protein homologue (Rh) protein of a strain of *Plasmodium falciparum*. The Rh protein may be Rh1, Rh2a, Rh2b, or Rh4. The contiguous amino acid sequence may comprise at least about 5, 8, 10, 20, 50 or 100 or more amino acids.

The Duffy-binding like (DBL) proteins include erythrocyte-binding antigen (EBA)175, EBA140 (also known as BAEBL) and EBA181 (also known as JSEBL). Another DBL gene family member, eba165 (also known as PEBL) of *Plasmodium falciparum*, appears not to be expressed as a functional protein. These proteins are orthologs of DBL proteins identified in *Plasmodium vivax*. The cysteine-rich dual DBL domains found toward the N-terminus of EBA175 (called F1 and F2 domains) mediates binding to its cognate receptor, and it is likely that similar domains in EBA140 and EBA181 also play receptor-binding roles. C-terminal of a transmembrane domain, is a cytoplasmic tail of the DBL proteins that does not appear to be directly linked to the actin-myosin motor. The sequence of *Plasmodium falciparum* EBA175 is described herein as SEQ ID NO; 6. The F1 and F2 domains of EBA175 are at amino acids 158 to 397, and 462 to 710, respectively. The transmembrane domain of EBA175 is located at amino acids 1425 to 1442. The sequence of *Plasmodium falciparum* EBA181 is described herein as SEQ ID NO; 7. The F1 and F2 domains of EBA181 are at amino acids 129 to 371, and 433 to 697, respectively. The transmembrane domain of EBA181 is located at amino acids 1488 to 1510. The sequence of *Plasmodium falciparum* EBA140 is described herein as SEQ ID NO; 8. The F1 and F2 domains of EBA140 are at amino acids 154 to 405, and 456 to 706, respectively. The transmembrane domain of EBA140 is located at amino acids 1134 to 1153.

As discussed supra, enzyme treatment of red blood cells has allowed examination of the receptors to which the *Plasmodium falciparum* proteins bind. In particular, DBL proteins bind erythrocytes in a sialic-acid-dependent manner as neuraminidase treatment of the host cell ablates binding. EBA175 and EBA140 bind to glycophorin A and C, respectively, and while sialic acid on these receptors is essential for binding, the protein backbone is also important for specificity. EBA181 and Rh1 also bind to glycosylated erythrocyte receptors, although their identity is currently unknown. In contrast, there is no evidence that Rh2a directly binds to erythrocytes. Rh2b and Rh4 have been implicated in merozoite invasion since disruption of the corresponding gene causes these parasites to change the receptor they use for invasion on enzyme-treated red cells.

In one embodiment the invasion ligand is Rh2a or Rh2b. Rh2a and Rh2b have a putative signal sequence at the N terminus and a potential transmembrane domain followed by a short cytoplasmic tail at the C terminus, similar to the structures of Py235, PvRBP-1, and PvRBP-2. Analysis of Rh2a and Rh2b has identified a region showing homology to the "0045457 Spectrin repeat" domain (SUPERFAMILY Accession: SSF46966) at amino acids 1735 to 1833, and a region showing homology to the "UPF0103 YJR008W C21ORF19-LIKE CEREVISIAE P47085 SACCHAROMYCES CHROMOSOME C2ORF4 PA5G0009 IPF893" domain (PRODOM Accession: PD006364) at amino acids 2133 to 2259 of Rh2a and amino acids 2058 to 2184 of Rh2b. The transmembrane domain of Rh2a is located at amino acids 3066 to 3088.

Where the further invasion ligand is Rh2b the contiguous amino acid sequence is found in SEQ ID NO: 13 as described below, or a variant thereof.

SEQ ID NO: 13
Amino acid sequence of Rh2b (PlasmoDB
Accession No: MAL13P1.176)
MKRSLINLENDLFRLEPISYIQRYYKKNINRSDIFHNKKERGSKVYSNVS

SFHSFIQEGKEEVEVFSIWGSNSVLDHIDVLRDNGTVVFSVQPYYLDIYT

CKEAILFTTSFYKDLDKSSITKINEDIEKFNEEIIKNEEQCLVGGKTDFD

NLLIVLENAEKANVRKTLFDNTFNDYKNKKSSFYNCLKNKKNDYDKKIKN

IKNEITKLLKNIESTGNMCKTESYVMNNNLYLLRVNEVKSTPIDLYLNRA

KELLESSSKLVNPIKMKLGDNKNMYSIGYIHDEIKDIIKRYNFHLKHIEK

GKEYIKRITQANNIADKMKKDELIKKIFESSKHFASFKYSNEMISKLDSL

FIKNEEILNNLFNNIFNIFKKKYETYVDMKTIESKYTTVMTLSEHLLEYA

MDVLKANPQKPIDPKANLDSEVVKLQIKINEKSNELDNAISQVKTLIIIM

KSFYDIIISEKASMDEMEKKELSLNNYIEKTDYILQTYNIFKSKSNIINN

NSKNISSKYITIEGLKNDIDELNSLISYFKDSQETLIKDDELKKNMKTDY

LNNVKYIEENVTHINEIILLKDSITQRIADIDELNSLNLININDFINEKN

ISQEKVSYNLNKLYKGSFEELESELSHFLDTKYLFHEKKSVNELQTILNT

SNNECAKLNFMKSDNNNNNNNSNIINLLKTELSHLLSLKENIIKKLLNHI

EQNIQNSSNKYTITYTDINNRMEDYKEEIESLEVYKHTIGNIQKEYILHL

YENDKNALAVHNTSMQILQYKDAIQNIKNKISDDIKILKKYKEMNQDLLN

YYEILDKKLKDNTYIKEMHTASLVQITQYIPYEDKTISELEQEFNNNNQK

LDNILQDINAMNLNINILQTLNIGINACNTNNKNVEHLLNKKIELKNILN

DQMKIIKNDDIIQDNEKENFSNVLKKEEEKLEKELDDIKFNNLKMDIHKL

LNSYDHTKQNIESNLKINLDSFEKEKDSWVHFKSTIDSLYVEYNICNQKT

HNTIKQQKNDIIELIYKRIKDINQEIIEKVDNYYSLSDKALTKLKSIHFN

IDKEKYKNPKSQENIKLLEDRVMILEKKIKEDKDALIQIKNLSHDHFVNA

DNEKKKQKEKEEDDEQTHYSKKRKVMGDIYKDIKKNLDELNNKNLIDITL

-continued

NEANKIESEYEKILIDDICEQITNEAKKSDTIKEKIESYKKDIDYVDVDV
SKTRNDHHLNGDKIHDSFFYEDTLNYKAYFDKLKDLYENINKLTNESNGL
KSDAHNNNTQVDKLKEINLQVFSNLGNIIKYVEKLENTLHELKDMYEFLE
TIDINKILKSIHNSMKKSEEYSNETKKIFEQSVNITNQFIEDVEILKTSI
NPNYESLNDDQIDDNIKSLVLKKEEISEKRKQVNKYITDIESNKEQSDLH
LRYASRSIYVIDLFIKHEIINPSDGKNFDIIKVKEMINKTKQVSNEAMEY
ANKMDEKNKDIIKIENELYNLINNNIRSLKGVKYEKVRKQARNAIDDINN
IHSNIKTILTKSKERLDEIKKQPNIKREGDVLNNDKTKIAYITIQINNGR
IESNLLNILNMKHNIDTILNKAMDYMNDVSKSDQIVINIDSLNMNDIYNK
DKDLLINILKEKQNMEAEYKKMNEMYNYVNETEKEIIKHKKNYEIRIMEH
IKKETNEKKKKFMESNNKSLTTLMDSFRSMFYNEYINDYNINENFEKHQN
ILNEIYNGFNESYNIINTKMTEIINDNLDYNEIKEIKEVAQTEYDKLNKK
VDELKNYLNNIKEQEGHRLIDYIKEKIFNLYIKCSEQQNIIDDSYNYITV
KKQYIKTIEDVKFLLDSLNTIEEKNKSVANLEICTNKEDIKNLLKHVIKL
ANFSGIIVMSDTNTEITPENPLEDNDLLNLQLYFERKHEITSTLENDSDL

ELDHLGSNSDESIDNLKVYNDIIELHTYSTQILKYLDNIQKLKGDCNDLV

KDCKELRELSTALYDLKIQITSVINRENDISNNIDIVSNKLNEIDAIQYN

FEKYKEIFDNVEEYKTLDDTKNAYIVKKAEILKNVDINKTKEDLDIYFND

LDELEKSLTLSSNEMEIKTIVQNSYNSFSDINKNINDIDKEMKTLIPMLD

ELLNEGHNIDISLYNFIIRNIQIKIGNDIKNIREQENDTNICFEYIQNNY

NFIKSDISIFNKYDDHIKVDNYISNNIDVVNKHNSLLSEHVINATNIIEN

IMTSIVEINEDTEMNSLEETQDKLLELYENFKKEKNIINNNYKIVHFNKL

KEIENSLETYNSISTNFNKINETQNIDILKNEFNNIKTKINDKVKELVHV

DSTLTLESIQTFNNLYGDLMSNIQDVYKYEDINNVELKKVKLYIENITNL

LGRINTFIKELDKYQDENNGIDKYIEINKENNSYIIKLKEKANNLKENFS

KLLQNIKRNETELYNINNIKDDIMNTGKSVNNIKQKFSSNLPLKEKLFQM

EEMLLNINNIMNETKRISNTDAYTNITLQDIENNKNKENNNMNIETIDKL

IDHIKIHNEKIQAEILIIDDAKRKVKEITDNINKAFNEITENYNNENNGV

IKSAKNIVDKATYLNNELDKFLLKLNELLSHNNNDIKDLGDEKLILKEEE

ERKERERLEKAKQEEERKERERIEKEKQEKERLEREKQEQLKKEALKKQE

QERQEQQQKEEALKRQEQERLQKEEELKRQEQERLEREKQEQLQKEEELR

KKEQEKQQQRNIQELEEQKKPEIINEALVKGDKILEGSDQRNMELSKPNV

SMDNTNNSPISNSEITESDDIDNSENIHTSHMSDIESTQTSHRSNTHGQQ

ISDIVEDQITHPSNIGGEKITHNDEISITGERNNISDVNDYSESSNIFEN

GDSTINTSTRNTSSTHDESHISPISNAYDHVVSDNKKSMDENIKDKLKID

ESITTDEQIRLDDNSNIVRIDSTDQRDASSHGSSNRDDDEISHVGSDIHM

DSVDIHDSIDTDENADHRHNVNSVDSLSSSDYTDTQKDFSSIIKDGGNKE

GHAENESKEYESQTEQTHEEGIMNPNKYSISEVDGIKLNEEAKHKITEKL

VDIYPSTYRTLDEPMETHGPNEKFHMFGSPYVTEEDYTEKHDYDKHEDFN

-continued

NERYSNHNKMDDFVYNAGGVVCCVLFFASITFFSMDRSNKDECDFDMCEE

VNNNDHLSNYADKEEIIEIVFDENEEKYF

Variants of SEQ ID NO:13 are also included in the scope of this invention and include embodiments whereby D at amino acid 2471 is replaced with A, K at amino acid 2560 is replaced with E, K at amino acid 3090 is replaced with N,N at amino acid 3116 replaced with T, N at amino acid 3116 is replaced with Y.

More particularly, the contiguous amino acid sequence may found in the region between about 31 amino acids N-terminal of the Prodom PD006364 homology region to about the transmembrane domain of Rh2b. The contiguous amino acid sequence may also be found in the region from about residue 2027 to 3115 of Rh2b, or more particularly from about residue 2027 to about residue 2533 of Rh2b.

In another form of the immunogenic molecule the contiguous amino acid sequence is found in the region from about residue 2098 to about residue 2597, or the region from about 2616 to 3115 of Rh2b.

In one form of the composition, the further immunogenic molecule is Rh2a, and the contiguous amino acid sequence is found in SEQ ID NO: 14, or a variant thereof:

SEQ ID NO: 14

Amino acid sequence of Rh2a (PlasmoDB AccessionNo: PF13_0198)

MKTTLFCSISFCNIIFFFLELSHEHFVGQSSNTHGASSVTDFNFSEEKNL

KSFEGKNNNNDNYASINRLYRKKPYMKRSLINLENDLFRLEPISYIQRYY

KKNINRSDIFHNKKERGSKVYSNVSSFHSFIQEGKEEVEVFSIWGSNSVL

DHIDVLRDNGTVVFSVQPYYLDIYTCKEAILFTTSFYKDLDKSSITKINE

DIEKFNEEIIKNEEQCLVGGKTDFDNLLIVLENAEKANVRKTLFDNTFND

YKNKKSSFYNCLKNKKNDYDKKIKNIKNEITKLLKNIESTGNMCKTESYV

MNNNLYLLRVNEVKSTPIDLYLNRAKELLESSSKLVNPIKMKLGDNKNMY

SIGYIHDEIKDIIKRYNFHLKHIEKGKEYIKRITQANNIADKMKKDELIK

KIFESSKHFASFKYSNEMISKLDSLFIKNEEILNNLFNNIFNIFKKKYET

YVDMKTIESKYTTVMTLSEHLLEYAMDVLKANPQKPIDPKANLDSEVVKL

QIKINEKSNELDNAISQVKTLIIIMKSFYDIIISEKASMDEMEKKELSLN

NYIEKTDYILQTYNIFKSKSNIINNNSKNISSKYITIEGLKNDIDELNSL

ISYFKDSQETLIKDDELKKNMKTDYLNNVKYIEENVTHINEIILLKDSIT

QRIADIDELNSLNLININDFINEKNISQEKVSYNLNKLYKGSFEELESEL

SHFLDTKYLFHEKKSVNELQTILNTSNNECAKLNFMKSDNNNNNNNSNII

NLLKTELSHLLSLKENIIKKLLNHIEQNIQNSSNKYTITYTDINNRMEDY

KEEIESLEVYKHTIGNIQKEYILHLYENDKNALAVHNTSMQILQYKDAIQ

NIKNKISDDIKILKKYKEMNQDLLNYYEILDKKLKDNTYIKEMHTASLVQ

ITQYIPYEDKTISELEQEFNNNNQKLDNILQDINAMNLNINILQTLNIGI

NACNTNNKNVEHLLNKKIELKNILNDQMKIIKNDDIIQDNEKENFSNVLK

KEEEKLEKELDDIKFNNLKMDIHKLLNSYDHTKQNIESNLKINLDSFEKE

KDSWVHFKSTIDSLYVEYNICNQKTHNTIKQQKNDIIELIYKRIKDINQE

IIEKVDNYYSLSDKALTKLKSIHFNIDKEKYKNPKSQENIKLLEDRVMIL

-continued

```
EKKIKEDKDALIQIKNLSHDHFVNADNEKKKQKEKEEDDEQTHYSKKRKV
MGDIYKDIKKNLDELNNKNLIDITLNEANKIESEYEKILIDDICEQITNE
AKKSDTIKEKIESYKKDIDYVDVDVSKTRNDHHLNGDKIHDSFFYEDTLN
YKAYFDKLKDLYENINKLTNESNGLKSDAHNNNTQVDKLKEINLQVFSNL
GNIIKYVEKLENTLHELKDMYEFLETIDINKILKSIHNSMKKSEEYSNET
KKIFEQSVNITNQFIEDVEILKTSINPNYESLNDDQIDDNIKSLVLKKEE
ISEKRKQVNKYITDIESNKEQSDLHLRYASRSIYVIDLFIKHEIINPSDG
KNFDIIKVKEMINKTKQVSNEAMEYANKMDEKNKDIIKIENELYNLINNN
IRSLKGVKYEKVRKQARNAIDDINNIHSNIKTILTKSKERLDEIKKQPNI
KREGDVLNNDKTKIAYITIQINNGRIESNLLNILNMKHNIDTILNKAMDY
MNDVSKSDQIVINIDSLNMNDIYNKDKDLLINILKEKQNMEAEYKKMNEM
YNYVNETEKEIIKHKKNYEIRIMEHIKKETNEKKKKFMESNNKSLTTLMD
SFRSMFYNEYINDYNINENFEKHQNILNEIYNGFNESYNIINTKMTEIIN
DNLDYNEIKEIKEVAQTEYDKLNKKVDELKNYLNNIKEQEGHRLIDYIKE
KIFNLYIKCSEQQNIIDDSYNYITVKKQYIKTIEDVKFLLDSLNTIEEKN
KSVANLEICTNKEDIKNLLKHVIKLANFSGIIVMSDTNTEITPENPLEDN
DLLNLQLYFERKHEITSTLENDSDLELDHLGSNSDESIDNLKVYNDIIEL
HTYSTQILKYLDNIQKLKGDCNDLVKDCKELRELSTALYDLKIQITSVIN
RENDISNNIDIVSNKLNEIDAIQYNFEKYKEIFDNVEEYKTLDDTKNAYI
VKKAEILKNVDINKTKEDLDIYFNDLDELEKSLTLSSNEMEIKTIVQNSY
NSFSDINKNINDIDKEMKTLIPMLDELLNEGHNIDISLYNFIIRNIQIKI
GNDIKNIREQENDTNICFEYIQNNYNFIKSDISIFNKYDDHIKVDNYISN
NIDVVNKHNSLLSEHVINATNIIENIMTSIVEINEDTEMNSLEETQDKLL
ELYENFKKEKNIINNNYKIVHFNKLKEIENSLETYNSISTNFNKINETQN
IDILKNEFNNIKTKINDKVKELVHVDSTLTLESIQTFNNLYGDLMSNIQD
VYKYEDINNVELKKVKLYIENITNLLGRINTFIKELDKYQDENNGIDKYI
EINKENNSYIIKLKEKANNLKENFSKLLQNIKRNETELYNINNNIKDDIMN
TGKSVNNIKQKFSSNLPLKEKLFQMEEMLLNINNIMNETKRISNTAAYTN
ITLQDIENNKNKENNNMNIETIDKLIDHIKIHNEKIQAEILIIDDAKRKV
KEITDNINKAFNEITENYNNENNGVIKSAKNIVDEATYLNNELDKFLLKL
NELLSHNNNDIKDLGDEKLILKEEEERKERERLEKAKQEEERKERERIEK
EKQEKERLEREKQEQLKKEEELRKKEQERQEQQQKEEALKRQEQERLQKE
EELKRQEQERLEREKQEQLQKEEELKRQEQERLQKEEALKRQEQERLQKE
EELKRQEQERLEREKQEQLQKEEELKRQEQERLQKEEALKRQEQERLQKE
EELKRQEQERLERKKIELAEREQHIKSKLESDMVKIIKDELTKEKDEIIK
NKDIKLRHSLEQKWLKHLQNILSLKIDSLLNKNDEVIKDNETQLKTNILN
SLKNQLYLNLKRELNEIIKEYEENQKKILHSNQLVNDSLEQKTNRLVDIK
PTKHGDIYTNKLSDNETEMLITSKEKKDETESTKRSGTDHTNSSESTTDD
NTNDRNFSRSKNLSVAIYTAGSVALCVLIFSSIGLLLIKTNSGDNNSNEI
NEAFEPNDDVLFKEKDEIIEITFNDNDSTI
```

Variants of SEQ ID NO:14 are also included in the scope of this invention and include embodiments whereby A at amino acid 2546 is replaced with D, E at amino acid 2613 is replaced with G, R at amino acid 2723 is replaced with K, K at amino acid 2725 replaced with Q.

More particularly, the contiguous amino acid sequence may found in the region between about 31 amino acids N-terminal of the Prodom PD006364 homology region to about the transmembrane domain of Rh2a. The contiguous amino acid sequence may also be found in the region from about residue 2133 to about residue 3065 of Rh2a.

In another form of the composition the contiguous amino acid sequence is found in the region from about residue 2098 to about residue 2597, or the region from about residue 2616 to about residue 3115 of Rh2a.

In one form of the composition, the further invasion ligand is Rh1, and the contiguous amino acid sequence is found in SEQ ID NO: 15 or a variant thereof:

```
                                        SEQ ID NO: 15
Amino acid sequence of Rh1 (PlasmoDB
Accession No: PFD0110w)
MQRWIFCNIVLHILIYLAEFSHEQESYSSNEKIRKDYSDDNNYEPTPSYE
KRKKEYGKDESYIKNYRGNNFSYDLSKNSSIFLHMGNGSNSKTLKRCNKK
KNIKTNFLRPIEEEKTVLNNYVYKGVNFLDTIKRNDSSYKFDVYKDTSFL
KNREYKELITMQYDYAYLEATKEVLYLIPKDKDYHKFYKNELEKILFNLK
DSLKLLREGYIQSKLEMIRIHSDIDILNEFHQGNIINDNYFNNEIKKKKE
DMEKYIREYNLYIYKYENQLKIKIQKLTNEVSINLNKSTCEKNCYNYILK
LEKYKNIIKDKINKWKDLPEIYIDDKSFSYTFLKDVINNKIDIYKTISSF
ISTQKQLYYFEYIYIMNKNTLNLLSYNIQKTDINSSSKYTYTKSHFLKDN
HILLSKYYTAKFIDILNKTYYYNLYKNKILLFNKYIIKLRNDLKEYAFKS
IQFIQDKIKKHKDELSIENILQEVNNIYIKYDTSINEISKYNNLIINTDL
QIVQQKLLEIKQKKNDITHKVQLINHIYKNIHDEILNKKNNEITKIIINN
IKDHKKDLQDLLLFIQQIKQYNILTDHKITQCNNYYKEIIKMKEDINHIH
IYIQPILNNLHTLKQVQNNKIKYEEHIKQILQKIYDKKESLKKIILLKDE
AQLDITLLDDLIQKQTKKQTQTQTQKQTLIQNNETIQLISGQEDKHES
NPFNHIQTYIQQKDTQNKNIQNLLKSLYNGNINTFIDTISKYILKQKDIE
LTQHVYTDEKINDYLEEIKNEQNKIDKTIDDIKIQETLKQITHIVNNIKT
IKKDLLKEFIQHLIKYMNERYQNMQQGYNNLTNYINQYEEENNNMKQYIT
TIRNIQKIYYDNIYAKEKEIRSGQYYKDFITSRKNIYNIRENISKNVDMI
KNEEKKKIQNCVDKYNSIKQYVKMLKNGDTQDENNNNNNDIYDKLIVPLD
SIKQNIDKYNTEHNFITFTNKINTHNKKNQEMMEEFIYAYKRLKILKILN
ISLKACEKNNKSINTLNDKTQELKKIVTHEIDLLQKDILTSQISNKNVLL
LNDLLKEIEQYIIDVHKLKKKSNDLFTYYEQSKNYFYFKNKKDNFDIQKT
INKMNEWLAIKNYINEINKNYQTLYEKKINVLLHNSKSYVQYFYDHIINL
ILQKKNYLENTLKTKIQDNEHSLYALQQNEEYQKVKNEKDQNEIKKIKQL
IEKNKNDILTYENNIEQIEQKNIELKTNAQNKDDQIVNTLNEVKKKIIYT
YEKVDNQISNVLKNYEEGKVEYDKNVVQNVNDADDTNDIDEINDIDEIND
IDEINDIDEINDIDEIKDIDHIKHFDDTKHFDDIYHADDTRDEYHIALSN
YIKTELRNINLQEIKNNIIKIFKEFKSAHKEIKKESEQINKEFTKMDVVI
NQLRDIDRQMLDLYKELDEKYSEFNKTKIEEINNIRENINNVEIWYEKNI
```

-continued

IEYFLRHMNDQKDKAAKYMENIDTYKNNIEIISKQINPENYVETLNKSNM

YSYVEKANDLFYKQINNIIINSNQLKNEAFTIDELQNIQKNRKNLLTKKQ

QIIQYTNEIENIFNEIKNINNILVLTNYKSILQDISQNINHVSIYTEQLH

NLYIKLEEEKEQMKTLYHKSNVLHNQINFNEDAFINNLLINIEKIKNDIT

HIKEKTNIYMIDVNKSKNNAQLYFHNTLRGNEKIEYLKNLKNSTNQQITL

QELKQVQENVEKVKDIYNQTIKYEEEIKKNYHIITDYENKINDILHNSFI

KQINMESSNNKKQTKQIIDIINDKTFEEHIKTSKTKINMLKEQSQMKHID

KTLLNEQALKLFVDINSTNNNLDNMLSEINSIQNNIHTYIQEANKSFDKF

KIICDQNVNDLLNKLSLGDLNYMNHLKNLQNEIRNMNLEKNFMLDKSKKI

DEEEKKLDILKVNISNINNSLDKLKKYYEEALFQKVKEKAEIQKENIEKI

KQEINTLSDVFKKPFFFIQLNTDSSQHEKDINNNVETYKNNIDEIYNVFI

QSYNLIQKYSSEIFSSTLNYIQTKEIKEKSIKEQNQLNQNEKEASVLLKN

IKINETIKLFKQIKNERQNDVHNIKEDYNLLQQYLNYMKNEMEQLKKYKN

DVHMDKNYVENNNGEKEKLLKETISSYYDKINNINNKLYIYKNKEDTYFN

NMIKVSEILNIIIKKKQQNEQRIVINAEYDSSLINKDEEIKKEINNQIIE

LNKHNENISNIFKDIQNIKKQSQDIITNMNDMYKSTILLVDIIQKKEEAL

NKQKNILRNIDNILNKKENIIDKVIKCNCDDYKDILIQNETEYQKLQNIN

HTYEEKKKSIDILKIKNIKQKNIQEYKNKLEQMNTIINQSIEQHVFINAD

ILQNEKIKLEEIIKNLDILDEQIMTYHNSIDELYKLGIQCDNHLITTISV

VVNKNTTKIMIHIKKQKEDIQKINNYIQTNYNIINEEALQFHRLYGHNLI

SEDDKNNLVHIIKEQKNIYTQKEIDISKIIKHVKKGLYSLNEHDMNHDTH

MNIINEHINNNILQPYTQLINMIKDIDNVFIKIQNNKFEQIQKYIEIIKS

LEQLNKNINTDNLNKLKDTQNKLINIETEMKHKQKQLINKMNDIEKDNIT

DQYMHDVQQNIFEPITLKMNEYNTLLNDNHNNNINNEHQFNHLNSLHTKI

FSHNYNKEQQQEYITNIMQRIDVFINDLDTYQYEYYFYEWNQEYKQIDKN

KINQHINNIKNNLIHVKKQFEHTLENIKNNENIFDNIQLKKKDIDDIIIN

INNTKETYLKELNKKKNVTKKKKVDEKSEINNHHTLQHDNQNVEQKNKIK

DHNLITKPNNNSSEESHQNEQMKEQNKNILEKQTRNIKPHHVHNHNHNHN

QNQKDSTKLQEQDISTHKLHNTIHEQQSKDNHQGNREKKQKNGNHERMYF

ASGIVVSILFLFSFGFVINSKNNKQEYDKEQEKQQQNDFVCDNNKMDDKS

TQKYGRNQEEVMEIFFDNDYI

The present invention includes variants of SEQ ID NO:15. It is known to the skilled person that there are a large number of single nucleotide polymorphisms in Rh1 and these and any other variants are included within the scope of the invention.

More particularly, the contiguous amino acid sequence may found in the region between about amino acid residue 1 to transmembrane domain of Rh1. The contiguous amino acid sequence may also be found in the region from about residue 1 to about residue 2897 of Rh1.

In one form of the composition, the further invasion ligand is Rh4, and the contiguous amino acid sequence is found in SEQ ID NO: 16

SEQ ID NO: 16

Amino acid sequence of Rh4 (PlasmoDB
Accession No: PFD1150c), as disclosed below.

MNKNILWITFFYFLFFLLDMYQGNDAIPSKEKKNDPEADSKNSQNQHDIN

KTHHTNNNYDLNIKDKDEKKRKNDNLINNYDYSLLKLSYNKNQDIYKNIQ

NGQKLKTDIILNSFVQINSSNILMDEIENYVKKYTESNRIMYLQFKYIYL

QSLNITVSFVPPNSPFRSYYDKNLNKDINETCHSIQTLLNNLISSKIIFK

MLETTKEQILLLWNNKKISQQNYNQENQEKSKMIDSENEKLEKYTNKFEH

NIKPHIEDIEKKVNEYINNSDCHLTCSKYKTIINNYIDEIITTNTNIYEN

KYNLPQERIIKNYNHNGINNDDNFIEYNILNADPDLRSHFITLLVSRKQL

IYIEYIYFINKHIVNKIQENFKLNQNKYIHFINSNNAVNAAKEYEYIIKY

YTTFKYLQTLNKSLYDSIYKHKINNYSHNIEDLINQLQHKINNLMIISFD

KNKSSDLMLQCTNIKKYTDDICLSIKPKALEVEYLRNINKHINKNEFLNK

FMQNETFKKNIDDKIKEMNNIYDNIYIILKQKFLNKLNEIIQNHKNKQET

KLNTTTIQELLQLLKDIKEIQTKQIDTKINTFNMYYNDIQQIKIKINQNE

KEIKKVLPQLYIPKNEQEYIQIYKNELKDRIKETQTKINLFKQILELKEK

EHYITNKHTYLNFTHKTIQQILQQQYKNNTQEKNTLAQFLYNADIKKYID

ELIPITQQIQTKMYTTNNIEHIKQILINYIQECKPIQNISEHTIYTLYQE

IKTNLENIEQKIMQNIQQTTNRLKINIKKIFDQINQKYDDLTKNINQMND

EKIGLRQMENRLKGKYEEIKKANLQDRDIKYIVQNNDANNNNNNIIIING

NNQTGDYNHILFDYTHLWDNAQFTRTKENINNLKDNIQININNIKSIIRN

LQNELNNYNTLKSNSIHIYDKIHTLEELKILTQEINDKNVIRKIYDIETI

YQNDLHNIEEIIKNITSIYYKINILNILIICIKQTYNNNKSIESLKLKIN

NLTNSTQEYINQIKAIPTNLLPEHIKQKSVSELNIYMKQIYDKLNEHVIN

NLYTKSKDSLQFYINEKNYNNNHDDHNDDHNDVYNDIKENEIYKNNKLYE

CIQIKKDVDELYNIYDQLFKNISQNYNNHSLSFVHSINNHMLSIFQDTKY

GKHKNQQILSDIENIIKQNEHTESYKNLDTSNIQLIKEQIKYFLQIFHIL

QENITTFENQYKDLIIKMNHKINNNLKDITHIVINDNNTLQEQNRIYNEL

QNKIKQIKNVSDVFTHNINYSQQILNYSQAQNSFFNIFMKFQNINNDINS

KRYNVQKKITEIINSYDIINYNKNNIKDIYQQFKNIQQQLNTTETQLNHI

KQNINHFKYFYESHQTISIVKNMQNEKLKIQEFNKKIQHFKEETQIMINK

LIQPSHIHLHKMKLPITQQQLNTILHRNEQTKNATRSYNMNEEENEMGYG

ITNKRKNSETNDMINTTIGDKTNVLKNDDQEKGKRGTSRNNNIHTNENNI

NNEHTNENNINNEHTNEKNINNEHANEKNIYNEHTNENNINYEHPNNYQQ

KNDEKISLQHKTINTSQRTIDDSNMDRNNRYNTSSQQKNNLHTNNNSNSR

YNNNHDKQNEHKYNQGKSSGKDNAYYRIFYAGGITAVLLLCSSTAFFFIK

NSNEPHHIFNIFQKEFSEADNAHSEEKEEYLPVYFDEVEDEVEDEVEDED

ENENEVENENEDFNDI

The present invention includes variant forms of SEQ ID NO:16. Variants that are included within the scope of the invention include those whereby Y at amino acid 12 is replaced with A, L at amino acid 143 is replaced with I, N at amino acid 435 is replaced with K, Q at amino acid 438 is replaced with K, T at amino acid 506 replaced with K, N at amino acid 771 is replaced with S, N at amino acid 844 is replaced with I, K at amino acid 1482 is replaced with R, or N at amino acid 1498 is replaced with I.

More particularly, the contiguous amino acid sequence is found in the region from about the MTH1187/YkoF-like superfamily domain to about the transmembrane domain of Rh4.

In another form of the composition, the contiguous amino acid sequence is found in the region from about residue 1160 to about residue 1370 of Rh4.

In one form of the composition the further invasion ligand is an erythrocyte binding antigen (EBA) protein. In that form of the composition the immunogenic comprises a contiguous amino acid sequence of an erythrocyte binding antigen (EBA) protein of the strain of Plasmodium falciparum. The EBA protein may be EBA175, EBA140, or EBA181. The contiguous amino acid sequence may comprise at least about 5, 8, 10, 20, 50 or 100 or more amino acids.

In one form of the composition, the contiguous amino acid sequence of the EBA protein is found in the region between the F2 domain and the transmembrane domain of the EBA protein. More particularly, the contiguous amino acid sequence may be found in the region from about residue 746 to about residue 1339 of the EBA protein.

Where the EBA is EBA140 the contiguous amino acid sequence is found in the region from about residue 746 to about residue 1045 of EBA140. Where the EBA is EBA175 the contiguous amino acid sequence is found in the region from about residue 761 to about residue 1271 of EBA175. Where the EBA is EBA181 the contiguous amino acid sequence is found in the region from about residue 755 to about residue 1339 of EBA181.

In one form of the composition, the further invasion ligand is EBA175, and the contiguous amino acid sequence is found in SEQ ID NO: 17:

```
The amino acid sequence of EBA175 (PlasmoDB
Accession No: MAL7P1.176) is given below
                                    (SEQ ID NO: 17)
MKCNISIYFFASFFVLYFAKARNEYDIKENEKFLDVYKEKFNELDKKKYG

NVQKTDKKIFTFIENKLDILNNSKFNKRWKSYGTPDNIDKNMSLINKHNN

EEMFNNNYQSFLSTSSLIKQNKYVPINAVRVSRILSFLDSRINNGRNTSS

NNEVLSNCREKRKGMKWDCKKKNDRSNYVCIPDRRIQLCIVNLSIIKTYT

KETMKDHFIEASKKESQLLLKKNDNKYNSKFCNDLKNSFLDYGHLAMGND

MDFGGYSTKAENKIQEVFKGAHGEISEHKIKNFRKKWWNEFREKLWEAML

SEHKNNINNCKNIPQEELQITQWIKEWHGEFLLERDNRSKLPKSKCKNNT

LYEACEKECIDPCMKYRDWIIRSKFEWHTLSKEYETQKVPKENAENYLIK

ISENKNDAKVSLLLNNCDAEYSKYCDCKHTTTLVKSVLNGNDNTIKEKRE

HIDLDDFSKFGCDKNSVDTNTKVWECKKPYKLSTKDVCVPPRRQELCLGN

IDRIYDKNLLMIKEHILAIAIYESRILKRKYKNKDDKEVCKIINKTFADI

RDIIGGTDYWNDLSNRKLVGKINTNSNYVHRNKQNDKLERDEWWKVIKKD

VWNVISWVFKDKTVCKEDDIENIPQFFRWFSEWGDDYCQDKTKMIETLKV

ECKEKPCEDDNCKRKCNSYKEWISKKKEEYNKQAKQYQEYQKGNNYKMYS

EFKSIKPEVYLKKYSEKCSNLNFEDEFKEELHSDYKNKCTMCPEVKDVPI

SIIRNNEQTSQEAVPEESTEIAHRTETRTDERKNQEPANKDLKNPQQSVG

ENGTKDLLQEDLGGSRSEDEVTQEFGVNHGIPKGEDQTLGKSDAIPNIGE

PETGISTTEESRHEEGHNKQALSTSVDEPELSDTLQLHEDTKENDKLPLE

SSTITSPTESGSSDTEETPSISEGPKGNEQKKRDDDSLSKISVSPENSRP

ETDAKDTSNLLKLKGDVDISMPKAVIGSSPNDNINVTEQGDNISGVNSKP

LSDDVRPDKNHEEVKEHTSNSDNVQQSGGIVNMNVEKELKDTLENPSSSL

DEGKAHEELSEPNLSSDQDMSNTPGPLDNTSEETTERISNNEYKVNEREG

ERTLTKEYEDIVLKSHMNRESDDGELYDENSDLSTVNDESEDAEAKMKGN

DTSEMSHNSSQHIESDQQKNDMKTVGDLGTTHVQNEISVPVTGEIDEKLR

ESKESKIHKAEEERLSHTDIHKINPEDRNSNTLHLKDIRNEENERHLTNQ

NININSQERDLQKHGFPHTMNNLHGDGVSERSQINHSHHGNRQDRGGNSGNV

LNMRSNNNNFNNIPSRYNLYDKKLDLDLYENRNDSTTKELIKKLAEINKC

ENEISVKYCDHMIHEEIPLKTCTKEKTRNLCCAVSDYCMSYFTYDSEEYY

NCTKREFDDPSYTCFRKEAFSSMPYYAGAGVLFIILVILGASQAKYQRLE

KINKNKIEKNVN
```

The present invention includes variant forms of SEQ ID NO: 17. Variants that are included in the scope of the invention include N at amino acid 157 replaced with S, E at amino acid 274 replaced with K, K at amino acid 279 replaced with E, K at amino acid 286 replaced with E, D at amino acid 336 replaced with Y, K at amino acid 388 replaced with N, P at amino acid 390 replaced with S, E at amino acid 403 replaced with K, K at amino acid 448 replaced with E, K at amino acid 478 replaced with N K at amino acid 481 replaced with I, N at amino acid 577 replaced with K, Q at amino acid 584 replaced with K, R at amino acid 664 replaced with S, S at amino acid 768 replaced with N, E at amino acid 923 replaced with K, K at amino acid 932 replaced with E, E at amino acid 1058 replaced with V, or G at amino acid 1100 replaced with D.

In one form of the composition, the further invasion ligand is EBA181, and the contiguous amino acid sequence is found in SEQ ID NO: 18:

```
The amino acid sequence of EBA181 (PlasmoDB
Accession No: MAL7P1.176) is given below
                                    (SEQ ID NO: 18)
MKGKMNMCLFFFYSILYVVLCTYVLGISEEYLKERPQGLNVETNNNNNNN

NNNNSNSNDAMSFVNEVIRFIENEKDDKEDKKVKIISRPVENTLHRYPVS

SFLNIKKYGRKGEYLNRNSFVQRSYIRGCKGKRSTHTWICENKGNNNICI

PDRRVQLCITALQDLKNSGSETTDRKLLRDKVFDSAMYETDLLWNKYGFR

GFDDFCDDVKNSYLDYKDVIFGTDLDKNNISKLVEESLKRFFKKDSSVLN

PTAWWRRYGTRLWKTMIQPYAHLGCRKPDENEPQINRWILEWGKYNCRLM

KEKEKLLTGECSVNRKKSDCSTGCNNECYTYRSLINRQRYEVSILGKKYI

KVVRYTIFRRKIVQPDNALDFLKLNCSECKDIDFKPFFEFEYGKYEEKCM

CQSYIDLKIQFKNNDICSFNAQTDTVSSDKRFCLEKKEFKPWKCDKNSFE

TVHHKGVCVSPRRQGFCLGNLNYLLNDDIYNVHNSQLLIEIIMASKQEGK

LLWKKHGTILDNQNACKYINDSYVDYKDIVIGNDLWNDNNSIKVQNNLNL

IFERNFGYKVGRNKLFKTIKELKNVWWILNRNKVWESMRCGIDEVDQRRK

TCERIDELENMPQFFRWFSQWAHFFCKEKEYWELKLNDKCTGNNGKSLCQ

DKTCQNVCTNMNYWTYTRKLAYEIQSVKYDKDRKLFSLAKDKNVTTFLKE
```

-continued

```
NAKNCSNIDFTKIFDQLDKLFKERCSCMDTQVLEVKNKEMLSIDSNSEDA

TDISEKNGEEELYVNHNSVSVASGNKEIEKSKDEKQPEKEAKQTNGTLTV

RTDKDSDRNKGKDTATDTKNSPENLKVQEHGTNGETIKEEPPKLPESSET

LQSQEQLEAEAQKQKQEEEPKKKQEEEPKKKQEEEQKREQEQKQEQEEEE

QKQEEEQQIQDQSQSGLDQSSKVGVASEQNEISSGQEQNVKSSSPEVVPQ

ETTSENGSSQDTKISSTEPNENSVVDRATDSMNLDPEKVHNENMSDPNTN

TEPDASLKDDKKEVDDAKKELQSTVSRIESNEQDVQSTPPEDTPTVEGKV

GDKAEMLTSPHATDNSESESGLNPTDDIKTTDGVVKEQEILGGGESATET

SKSNLEKPKDVEPSHEISEPVLSGTTGKEESELLKSKSIETKGETDPRSN

DQEDATDDVVENSRDDNNSLSNSVDNQSNVLNREDPIASETEVVSEPEDS

SRIITTEVPSTTVKPPDEKRSEEVGEKEAKEIKVEPVVPRAIGEPMENSV

SVQSPPNVEDVEKETLISENNGLHNDTHRGNISEKDLIDIHLLRNEAGST

ILDDSRRNGEMTEGSESDVGELQEHNFSTQQKDEKDFDQIASDREKEEIQ

KLLNIGHEEDEDVLKMDRTEDSMSDGVNSHLYYNNLSSEEKMEQYNNRDA

SKDREEILNRSNTNTCSNEHSLKYCQYMERNKDLLETCSEDKRLHLCCEI

SDYCLKFFNPKSIEYFDCTQKEFDDPTYNCFRKQRFTSMHYIAGGGIIAL

LLFILGSASYRKNLDDEKGFYDSNLNDSAFEYNNNKYNKLPYMFDQQINV

VNSDLYSEGIYDDTTTF
```

The present invention includes variant forms of SEQ ID NO: 18. Variants that are included in the scope of the invention include V at amino acid 64 replaced with L, Q at amino acid 364 replaced with H, V at amino acid 363 replaced with D, R at amino acid 358 replaced with K, N at amino acid 414 replaced with I, K at amino acid 443 replaced with Q, P at amino acid 878 replaced with Q, E at amino acid 884 replaced with Q, E at amino acid 1885 replaced with K, Q at amino acid 890 replaced with E, P at amino acid 1197 replaced with L, K at amino acid 1219 replaced with N, D at amino acid 1433 replaced with Y or N, or K at amino acid 1518 replaced with E.

In one form of the composition, the further invasion ligand is EBA141, and the contiguous amino acid sequence is found in SEQ ID NO: 19:

```
The amino acid sequence of EBA141 (PlasmoDB
Accession No: MAL7P1.176) is given below
                                        (SEQ ID NO: 19)
MKGYFNIYFLIPLIFLYNVIRINESIIGRTLYNRQDESSDISRVNSPELN

NNHKTNIYDSDYEDVNNKLINSFVENKSVKKKRSLSFINNKTKSYDIIPP

SYSYRNDKFNSLSENEDNSGNTNSNNFANTSEISIGKDNKQYTFIQKRTH

LFACGIKRKSIKWICRENSEKITVCVPDRKIQLCIANFLNSRLETMEKFK

EIFLISVNTEAKLLYNKNEGKDPSIFCNELRNSFSDFRNSFIGDDMDFGG

NTDRVKGYINKKFSDYYKEKNVEKLNNIKKEWWEKNKANLWNHMIVNHKG

NISKECAIIPAEEPQINLWIKEWNENFLMEKKRLFLNIKDKCVENKKYEA

CFGGCRLPCSSYTSFMKKSKTQMEVLTNLYKKKNSGVDKNNFLNDLFKKN

NKNDLDDFFKNEKEYDDLCDCRYTATIIKSFLNGPAKNDVDIASQINVND

LRGFGCNYKSNNEKSWNCTGTFTNKFPGTCEPPRRQTLCLGRTYLLHRGH

EEDYKEHLLGASIYEAQLLKYKYKEKDENALCSIIQNSYADLADIIKGSD
```

-continued

```
IIKDYYGKKMEENLNKVNKDKKRNEESLKIFREKWWDENKENVWKVMSAV

LKNKETCKDYDKFQKIPQFLRWFKEWGDDFCEKRKEKIYSFESFKVECKK

KDCDENTCKNKCSEYKKWIDLKKSEYEKQVDKYTKDKNKKMYDNIDEVKN

KEANVYLKEKSKECKDVNFDDKIFNESPNEYEDMCKKCDEIKYLNEIKYP

KTKHDIYDIDTFSDTFGDGTPISINANINEQQSGKDTSNTGNSETSDSPV

SHEPESDAAINVEKLSGDESSSETRGILDINDPSVTNNVNEVHDASNTQG

SVSNTSDITNGHSESSLNRTTNAQDIKIGRSGNEQSDNQENSSHSSDNSG

SLTIGQVPSEDNTQNTYDSQNPHRDTPNALASLPSDDKINEIEGFDSSRD

SENGRGDTTSNTHDVRRTNIVSERRVNSHDFIRNGMANNNAHHQYITQIE

NNGIIRGQEESAGNSVNYKDNPKRSNFSSENDHKKNIQEYNSRDTKRVRE

EIIKLSKQNKCNNEYSMEYCTYSDERNSSPGPCSREERKKLCCQISDYCL

KYFNFYSIEYYNCIKSEIKSPEYKCFKSEGQSSIPYFAAGGILVVIVLLL

SSASRMGKSNEEYDIGESNIEATFEENNYLNKLSRIFNQEVQETNISDYS

EYNYNEKNMY
```

The present invention includes variants of SEQ ID NO: 19. Variants that are included in the scope of the invention include V at amino acid 19 replaced with I, L at amino acid 112 replaced with F, I at amino acid 185 replaced with V, N at amino acid 239 replaced with S, K at amino acid 261 replaced with T.

In one form of the immunogenic molecule, the contiguous amino acid sequence of the EBA or Rh protein comprises about 5 or more amino acids. In another form, the contiguous amino acid sequence molecule comprises about 8, 10, 20, 50, or 100 amino acids. The skilled person is capable of routine experimentation designed to identify the shortest efficacious sequence, or the length of sequence that provides the greatest or most effective invasion-inhibitory response in the subject.

In some forms of the invention, the compositions contain more than one invasion ligand of the EBA family, and/or more than one invasion ligand of the Rh family. The composition may contain any combination of two or more invasion ligands derived from Rh1, Rh2a, Rh2b, Rh4. The composition may contain any combination of two or more invasion ligands derived from EBA175, EBA140 and EBA181.

It is proposed that certain compositions of the present invention may target multiple invasion ligands in order to improve efficacy, and to possibly ameliorate parasite immune evasion strategies. Data provided herein establishes that the invasion pathway mediated by the invasion ligands described herein are important for erythrocyte invasion. Applicant's findings indicate members of the EBA and Rh invasion ligand families are key targets of inhibitory antibodies. Therefore, compositions comprising multiple ligands involved in invasion via the same and/or different pathways facilitate the inhibition of invasion by the host immune response.

While EBA proteins and Rh2a, Rh2b and Rh4 are not essential for invasion, these molecules play a role in invasion of enzyme treated red cells. In particular, neuraminidase removes sialic acid residues from the erythrocyte surface and blocks invasion pathways dependent on sialic acid present on both glycophorin A and other receptors, trypsin treatment cleaves proteins such as glycophorin A and C, but does not affect glycophorin B, and chymotrypsin cleaves a non-overlapping set of proteins including glycophorin B and band 3 on the erythrocyte surface. Using this approach, invasion phenotypes can be broadly classified into two main groups: i) sialic acid (SA)-dependent invasion, demonstrated by poor invasion of neuraminidase-treated erythrocytes (neuraminidase cleaves SA on the erythrocyte surface), and ii) SA-independent invasion, demonstrated by efficient invasion of neuraminidase-treated erythrocytes, involves Rh2b and Rh4. SA-dependent (neuraminidase-sensitive) invasion of enzyme treated cells involves the three known EBAs (EBA175, EBA181, EBA140), Rh1. EBA175 and EBA140 bind to glycophorin A and C, respectively. EBA181 binds to SA on the erythrocyte surface and to band 4.1 protein.

The use of compositions further containing combinations of Rh and EBA proteins relates to the Applicant's further discovery that the *Plasmodium falciparum* parasite is capable of evading the host immune response by switching from the use of one invasion protein to another. For example, if the parasite initially utilised a Rh (e.g. Rh2b, Rh2a, Rh4)-mediated invasion pathway the host will generate antibodies capable of blocking the method of entry. The parasite is capable of then using an alternative pathway (such as an EBA-mediated pathway) in order to evade the host immune response.

In a further aspect the present invention provides a composition of the invention for use as a medicament. Accordingly, in a further aspect the present invention provides a method of treating or preventing a condition caused by or associated with infection by *Plasmodium falciparum* comprising administering to a subject in need thereof an effective amount of an immunogenic molecule described herein or a composition as described herein. The medicament is a malarial vaccine in one form of the composition.

Vaccines according to the present invention may either be prophylactic (i.e. to prevent or partially prevent infection) or therapeutic (i.e. to treat or partially treat infection), but will typically be prophylactic.

The compositions of the invention may elicit both a cell mediated immune response as well as a humoral immune response in order to effectively address a *Plasmodium* intracellular infection. This immune response will preferably induce long lasting antibodies and a cell mediated immunity that can quickly respond upon exposure to *Plasmodium*.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class I molecules.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-gamma, and TNF-beta. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response.

An enhanced TH1 immune response may include one or more of an increase in CTLs, an increase in one or more of the cytokines associated with a TH1 immune response (such as IL-2, IFN-gamma, and TNF-beta), an increase in activated macrophages, an increase in NK activity, or an increase in the production of IgG2a. Preferably, the enhanced TH1 immune response will include an increase in IgG2a production.

A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are preferred TH1 adjuvants for use in the invention.

An enhanced TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH2 immune response may be elicited using a TH2 adjuvant. A TH2 adjuvant will generally elicit increased levels of IgG1 production relative to immunization of the antigen without adjuvant. TH2 adjuvants suitable for use in the invention include, for example, mineral containing compositions, oil-emulsions, and ADP-ribosylating toxins and detoxified derivatives thereof. Mineral containing compositions, such as aluminium salts are preferred TH2 adjuvants for use in the invention.

Preferably, the invention includes a composition comprising a combination of a TH1 adjuvant and a TH2 adjuvant. Preferably, such a composition elicits an enhanced TH1 and an enhanced TH2 response, i.e., an increase in the production of both IgG1 and IgG2a production relative to immunization without an adjuvant. Still more preferably, the composition comprising a combination of a TH1 and a TH2 adjuvant elicits an increased TH1 and/or an increased TH2 immune response relative to immunization with a single adjuvant (i.e., relative to immunization with a TH1 adjuvant alone or immunization with a TH2 adjuvant alone).

The immune response may be one or both of a TH1 immune response and a TH2 response. Preferably, immune response provides for one or both of an enhanced TH1 response and an enhanced TH2 response. The TH1/TH2 response in mice may be measured by comparing IgG2a and IgG1 titres, while the TH1/TH2 response in man may be measured by comparing the levels of cytokines specific for the two types of response (e.g. the IFN-γ/IL-4 ratio).

In one form of the method of treatment or prevention the subject is a human. The human may be an infant, a child, an adolescent, or an adult. Use of the vaccine may be especially important in women in child-bearing years. Pregnant women, particularly in the second and third trimesters of pregnancy are more likely to develop severe malaria than other adults, often complicated by pulmonary oedema and hypoglycaemia. Maternal mortality is approximately 50%, which is higher than in non-pregnant adults. Fetal death and premature labor are common.

One way of monitoring vaccine efficacy for therapeutic treatment involves monitoring *Plasmodium falciparum* infection after administration of the compositions of the invention. One way of checking efficacy of prophylactic treatment involves monitoring immune responses systemically (such as monitoring the level of IgG1 and IgG2a production) against the *Plasmodium* antigens in the compositions of the invention after administration of the composition. Serum *Plasmodium* specific antibody responses may be determined post-immunisation and post-challenge.

The uses and methods are for the prevention and/or treatment of a disease caused by *Plasmodium* (e.g. malaria) and/or its clinical manifestations (e.g. prostration, impaired consciousness, respiratory distress (acidotic breathing), multiple convulsions, circulatory collapse, pulmonary oedema (radiological), abnormal bleeding, jaundice, haemoglobinuria, etc.).

The compositions of the present invention can be evaluated in in vitro and in vivo animal models prior to host, e.g., human, administration. For example, in vitro neutralization an/or invasion inhibition is suitable for testing vaccine compositions (such as immunogenic/immunoprotective compositions) directed toward *Plasmodium.*

Reaction to the vaccine may be evaluated in vitro and in vivo following host e.g. human, administration. For example, response to vaccine compositions may examined by Enzyme-Linked ImmunoSorbent Assay (ELISA). For example, ELISA may be conducted as follows: Plates (e.g. flat-bottomed microtiter plates (Maxisorp from Nunc NS or High Binding from Costar, Cat. No. 3590) may be coated with 50 μL of peptide solution or crude parasite antigen at 10 μg/mL in coating buffer. Keep the plate at 4° C. overnight. With many proteins or peptides, PBS can be used as a coating solution. Block with 100 μL of 0.5% BSA in coating buffer for 3 to 4 h at 37° C. Wash 4 times with 0.9% NaCl plus 0.05% Tween. Add 50 μL of serum samples diluted 1:1000; leave them for 1 h at 37° C. Wash 4 times with 0.9% NaCl plus 0.05% Tween. Add 50 μL of ALP-conjugated or biotinylated anti-Ig of appropriate specificity at the recommended concentration in Tween-buffer; leave for 1 h at 37° C. Wash the sample 4 times with 0.9% NaCl plus 0.05% Tween. If biotinylated antibody has been used, add 50 μL of streptavidin—ALP diluted 1:2000 in Tween-buffer; leave the sample for 1 h at 37° C. Wash the sample 4 times with 0.9% NaCl plus 0.05% Tween. Develop the sample with 50 μL of NPP (1 tablet/5 mL of substrate buffer) and read at $OD_{405}$.

Infection may be established using typical signs and symptoms of malaria. The signs and symptoms of malaria, such as fever, chills, headache and anorexia. Preferably, more specific methods of diagnosis are preferred e.g. using a scoring matrix of clinical symptoms, light microscopy which allows quantification of malaria parasites (e.g. thick or thin film blood smears from patients stained with acridine orange or Giemsa, rapid diagnostic tests (e.g. immunochromatographic tests that detect parasite-specific antigens e.g. HRP2, parasite lactate dehydrogenase (pLDH), aldolase etc) in a finger-prick blood sample, and polymerase-chain reaction.

Vaccine efficacy may be measured e.g. by examining the number and frequency of cases of malaria (e.g. asexual *Plasmodium falciparum* at any level plus a temperature greater than or equal to 37.5° C. and headache, myalgia, arthralgia, malaise, nausea, dizziness, or abdominal pain), time to first infection with *Plasmodium falciparum*, parasitemia, geometric mean parasite density in first clinical episode, adverse events, anemia (measured by for example packed cell volume less than 25% or less than 15%), absence of parasites at the end of immunization, proportion of individuals with seroconversion to the antigens of the present invention at e.g. day 75 post immunization, proportion with "efficacious seroconversion" to the antigens of the present invention (4-fold elevation in antibody titre) at day 75, number of symptomatic *Plasmodium falciparum* cases after 1, 2, or 3 doses, number of days until *Plasmodium falciparum* positive blood slide, density of *Plasmodium falciparum*, prevalence of *Plasmodium falciparum, Plasmodium vivax*, and *Plasmodium malariae*, levels of anti-Rh or anti-EBA antibody by ELISA, geometric mean parasite density in first clinical episode, lymphocyte proliferation to Rh or EBA, T-cell responses to antigen frequency of fever, malaise, nausea, Malaria requiring hospital admission, cerebral malaria (e.g. Blantyre coma score <2) etc.

The vaccine may be administered using a variety of vaccination regimes familiar to the skilled person. In one form of the invention, the vaccine composition may be administered post antimalarial treatment. Preferred antimalarials for use include the chloroquine phosphate, proguanil, primaquine, doxycycline, mefloquine, clindamycin, halofantrine, quinine sulphate, quinine dihydrochloride, gluconate, primaquine phosphate and sulfadoxine. For example, blood stage parasitaemia may be cleared with Fansidar (25 mg sulfadoxine/0.75 mg pyrimethamine per kg body weight) before each vaccination. In another form of the invention antimalarial (e.g. Fansidar) treatment is given 1 to 2 weeks before the doses (e.g. first and third doses). In another form of the invention antimalarial (e.g. Fansidar) treatment is given before the first dose.

In another form of the invention, 3 doses of vaccine composition (e.g. 0.5 mg adsorbed onto 0.312 g alum in 0.125 mL) is administered in 3 doses, 2 mg per dose to >5 year olds, 1 mg to under 5 year olds, at weeks 0, 4, and 25. In another form of the invention, 3 doses of vaccine composition (e.g. 1 mg per dose) are given subcutaneously at weeks 0, 4, and 26. In another form of the invention, 3 doses of vaccine composition is administered on days 0, 30, and 180 at different doses (e.g. 1 mg; 0.5 mg). In another form of the invention, 3 doses of vaccine composition is administered at 3 to 4 month intervals either intramuscularly or subcutaneously. In another form of the invention 3 doses of vaccine composition is administered subcutaneously on days 0, 30, and about day 180. In another form of the invention, the vaccine composition is administered in 2 doses at 4-week intervals (e.g. 0.55 mL per dose containing 4 μg or 15 μg or 13.3 μg of each antigen). In another form of the invention, 3 doses of the vaccine composition is administered (e.g. 25 μg in 250 μL AS02A adjuvant) intramuscularly in deltoid (in alternating arms) at 0, 1, and 2 months. In another form of the invention 4 doses of the vaccine composition is given (e.g. 50 μg per 0.5 mL dose) on days 0, 28, and 150; and dose 4 given in the following year. In another form of the invention, where the vaccine is a DNA vaccine, the vaccine composition is administered in two doses (e.g. 2 mg on days 0 and 21 (2 intramuscular injections each time, 1 into each deltoid muscle). In another form of the invention, where the vaccine composition comprises an immunogenic molecule covalently linked to another molecule (e.g. *Pseudomonas aeruginosa* toxin A) the composition is administered in 3 doses (e.g. at 1, 8, and 24 weeks).

The present invention may be used to generate invasion-inhibitory antibodies useful as in vitro diagnostic reagents, or as therapeutics for passive immunization. The term "antibody" includes intact immunoglobulin molecules, as well as fragments thereof which are capable of binding an antigen. These include hybrid (chimeric) antibody molecules; F(ab')2 and F(ab) fragments and Fv molecules; non-covalent heterodimers; single-chain Fv molecules (sFv); dimeric and trimeric antibody fragment constructs; minibodies; humanized antibody molecules; and any functional fragments obtained from such molecules, as well as antibodies obtained through non-conventional processes such as phage display. Preferably, the antibodies are monoclonal antibodies. Methods of obtaining monoclonal antibodies are well known in the art.

Various immunoassays (e.g., Western blots, ELISAs, radioimmunoassays, immunohistochemical assays, immunoprecipitations, invasion-inhibition assays, or other immunochemical assays known in the art) can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen. A preparation of antibodies which specifically bind to a particular antigen typically provides a detection signal at least 5-, 10-, or 20-fold higher than a detection signal provided with other proteins when used in an immunochemical assay. Preferably, the antibodies do not detect other proteins in immunochemical assays and can inimunoprecipitate the particular antigen from solution.

The surface-exposed antigens of the invention can be used to immunize a mammal, such as a mouse, rat, rabbit, guinea pig, monkey, or human, to produce polyclonal antibodies. If desired, an antigen can be conjugated to a carrier protein, such as bovine serum albumin, thyroglobulin, and keyhole limpet hemocyanin. Depending on the host species, various adjuvants can be used to increase the immunological response. Such adjuvants include those described above, as well as those not used in humans, for example, Freund's adjuvant.

Monoclonal antibodies which specifically bind to an antigen can be prepared using any technique which provides for the production of antibody molecules by continuous cell lines in culture. These techniques include, but are not limited to, the hybridoma technique, the human B-cell hybridoma technique, and the EBV-hybridoma technique.

In addition, techniques developed for the production of "chimeric antibodies," the splicing of mouse antibody genes to human antibody genes to obtain a molecule with appropriate antigen specificity and biological activity, can be used. Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions.

Alternatively, humanized antibodies can be produced using recombinant methods, as described below. Antibodies which specifically bind to a particular antigen can contain antigen binding sites which are either partially or fully humanized.

Alternatively, techniques described for the production of single chain antibodies can be adapted using methods known in the art to produce single chain antibodies which specifically bind to a particular antigen. Antibodies with related specificity, but of distinct idiotypic composition, can be generated by chain shuffling from random combinatorial immunoglobin libraries.

Single-chain antibodies also can be constructed using a DNA amplification method, such as PCR, using hybridoma cDNA as a template. Single-chain antibodies can be mono- or bispecific, and can be bivalent or tetravalent.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology.

Antibodies which specifically bind to a particular antigen also can be produced by inducing in vivo production in the lymphocyte population or by screening immunoglobulin libraries or panels of highly specific binding reagents.

Chimeric antibodies can be constructed. Binding proteins which are derived from immunoglobulins and which are multivalent and multispecific, such as "diabodies" can also be prepared.

Antibodies can be purified by methods well known in the art. For example, antibodies can be affinity purified by passage over a column to which the relevant antigen is bound. The bound antibodies can then be eluted from the column using a buffer with a high salt concentration.

In another aspect the present invention provides use of a composition described herein in the manufacture of a medicament for the treatment or prevention of a condition caused by or associated with infection by *Plasmodium falciparum*.

The invention also provides nucleic acid encoding a polypeptide immunogenic molecule of the invention.

Also provided by the present invention are nucleic acid molecules encoding the invasion ligands of the present invention. The term "nucleic acid" includes DNA and RNA, and also their analogues, such as those containing modified backbones (e.g. phosphorothioates, etc.), and also peptide nucleic acids (PNA), etc. The invention includes nucleic acid comprising sequences complementary to those described above (e.g. for antisense or probing purposes). Nucleic acid molecules as described herein may be used, for example, in the context of expression vectors in the manufacture of the immunogenic molecules described herein.

The nucleotide sequence of the invasion ligand described by SEQ ID NO: 1 is given below (SEQ ID NO: 20)

ATGATAAGAATAAAAAAAAAATTAATTTTGACCATTATATATATTCATCT

GTTTATATTAAATAGATTAAGTTTTGAAAATGCAATAAAAAAAACGAAGA

ATCAAGAAAATAATCTGACGTTACTACCAATAAAGAGCACTGAAGAAGAA

AAAGATGATATAAAAAATGGAAAGGATATAAAAAAAGAAATTGATAATGA

TAAAGAGAATATAAAAACAAATAATGCTAAAGATCATTCAACATATATAA

AATCATATTTGAATACAAATGTAAATGATGGTTTAAAATATTTGTTTATT

CCTTCTCATAATTCTTTTATAAAAAAATATTCTGTATTTA

```
ATTATAAACATTTATCTTATAATTCTATATATCATAAGTCCTCTACATAT
GGAAAGTGTATAGCTGTAGATGCTTTTATTAAGAAAATAAATGAAACATA
TGACAAAGTGAAAGTAAATGTAATGATATAAAGAATGATTTAATTGCAA
CTATAAAAAAATTAGAGCATCCTTATGATATAAATAATAAGAATGATGAT
TCCTATAGATATGATATATCTGAAGAAATCGATGATAAATCTGAAGAGAC
AGATGATGAAACCGAAGAGGTAGAAGATAGTATACAAGATACAGATAGTA
ATCATACTCCTTCAAATAAAAAAAAAAATGATCTTATGAATAGAACGTTT
AAAAAGATGATGGATGAATATAATACAAAAAAAAAAAAATTAATTAAATG
TATAAAAAACCATGAGAATGATTTTAATAAAATATGTATGGATATGAAAA
ATTATGGTACAAACCTTTTTGAACAACTTTCATGTTACAATAATAATTTC
TGTAATACAAACGGAATAAGATATCATTATGATGAATATATTCATAAATT
AATATTATCTGTTAAATCAAAAAACTTAAATAAAGACCTATCAGATATGA
CAAATATTTTACAACAAAGTGAATTATTATTAACCAATTTAAATAAAAAA
ATGGGTTCCTATATATATTGATACAATAAAATTTATACATAAAGAAAT
GAAACATATTTTTAACAGAATTGAATATCATACAAAAATAATAAACGATA
AAACTAAAATAATTCAAGACAAAATTAAATTAAATATATGGAGAACATTT
CAAAAAGATGAATTATTAAAAGAATTTTAGACATGTCAAATGAATATTC
TTTATTTATTACTAGTGATCATTTAAGACAAATGTTATATAATACATTCT
ATTCAAAAGAAAAACATTTAAATAATATATTTCATCATTTAATTTATGTA
CTACAAATGAAGTTCAATGATGTCCCAATTAAAATGGAATATTTTCAAAC
ATATAAAAAAATAAACCACTTACACAATGA
```

Where the invention requires the use of further inv

```
AATTAGATGATATCAAATTTAATAATTTGAAAATGGACATTCATAAATTG
TTGAATTCGTATGACCATACAAAGCAAATATAGAAAGCAATCTTAAAAT
AAATTTAGATTCTTTCGAAAAGGAAAAAGATAGTTGGGTTCATTTTAAA
GTACTATAGATAGTTTATATGTGGAATATAACATATGTAATCAAAAGACT
CATAATACTATCAAACAACAAAAAAATGATATCATAGAACTTATTTATAA
ACGTATAAAAGATATAAATCAAGAAATAATCGAAAAGGTAGATAATTATT
ATTCCCTGTCAGATAAAGCCTTAACTAAACTTAAATCTATTCATTTTAAT
ATTGATAAGGAAAAATATAAAAATCCCAAAAGTCAAGAAAATATTAAATT
ATTAGAAGATAGAGTTATGATACTTGAGAAAAGATTAAGGAAGATAAAG
ATGCTTTAATACAAATTAAGAATTTATCACATGATCATTTTGTAAATGCT
GATAATGAGAAAAAAAGCAGAAGGAGAAGGAGGAGGACGACGAACAAAC
ACACTATAGTAAAAAAAGAAAAGTAATGGGAGATATATATAAGGATATTA
AAAAAAACCTAGATGAGTTAAATAATAAAAATTTGATAGATATTACTTTA
AATGAAGCAAATAAAATAGAATCAGATATGAAAAAATATTAATTGATGA
TATTTGTGAACAAATTACAAATGAAGCAAAAAAAGTGATACTATTAAGG
AAAAAAATCGAATCATATAAAAAAGATATTGATTATGTAGATGTGGACGTT
TCCAAAACGAGGAACGATCATCATTTGAATGGAGATAAAATACATGATTC
TTTTTTTTATGAAGATACATTAAATTATAAAGCATATTTTGATAAATTAA
AAGATTTATATGAAAATATAAACAAGTTAACAAATGAATCAAATGGATTA
AAAAGTGATGCTCATAATAACAACACACAAGTTGATAAACTAAAAGAAAT
TAATTTACAAGTATTCAGCAATTTAGGAAATATAATTAAATATGTTGAAA
AACTTGAGAATACATTACATGAACTTAAAGATATGTACGAATTTCTAGAA
ACGATCGATATTAATAAAATATTAAAAAGTATTCATAATAGCATGAAGAA
ATCAGAAGAATATAGTAATGAAACGAAAAAAATATTTGAACAATCAGTAA
ATATAACTAATCAATTTATAGAAGATGTTGAAATATTGAAAACGTCTATT
AACCCAAACTATGAAAGCTTAAATGATGATCAAATTGATGATAATATAAA
ATCACTTGTTCTAAAGAAAGAGGAAATATCCGAAAAAAGAAAACAAGTGA
ATAAATACATAACAGATATTGAATCTAATAAAGAACAATCAGATTTACAT
TTACGATATGCATCTAGAAGTATATATGTTATTGATCTTTTTATAAAACA
TGAAATAATAAATCCTAGCGATGGAAAAAATTTTGATATTATAAAGGTTA
AAGAAATGATAAATAAAACCAAACAAGTTTCAAATGAAGCTATGGAATAT
GCTAATAAAATGGATGAAAAAAATAAGGACATTATAAAAATAGAAAATGA
ACTTTATAATTTAATTAATAATAACATCCGTTCATTAAAAGGGGTAAAAT
ATGAAAAGTTAGGAAACAAGCAAGAAATGCAATTGATGATATAAATAAT
ATACATTCTAATATTAAAACGATTTTAACCAAATCTAAAGAACGATTAGA
TGAGATTAAGAAACAACCTAACATTAAAAGAGAAGGTGATGTTTTAAATA
ATGATAAAACCAAAATAGCTTATATTACAATACAAATAAATAACGGAAGA
ATAGAATCTAATTTATTAAAATATATTAAAATATGAAACATAACATAGATAC
TATCTTGAATAAAGCTATGGATTATATGAATGATGTATCAAAATCTGACC
AGATTGTTATTAATATAGATTCTTTGAATATGAACGATATATATAATAAG
GATAAAGATCTTTTAATAAATATTTTAAAAGAAAAACAGAATATGGAGGC
AGAATATAAAAAAATGAATGAAATGTATAATTACGTTAATGAAACAGAAA
AAGAAATAATAAAACATAAAAAAAATTATGAAATAAGAATTATGGAACAT
ATAAAAAAAGAAACAAATGAAAAAAAAAAAAAAATTTATGGAATCTAATAA
CAAATCATTAACTACTTTAATGGATTCATTCAGATCTATGTTTTATAATG
AATATATAAATGATTATAATATAAATGAAATTTTGAAAAACATCAAAAT
ATATTGAATGAAATATATAATGGATTTAATGAATCATATAATATTATTAA
TACAAAAATGACTGAAATTATAAATGATAATTTAGATTATAATGAAATAA
AAGAAATTAAAGAAGTAGCACAAACAGAATATGATAAACTTAATAAAAAA
GTTGATGAATTAAAAAATTATTTGAATAATATTAAAGAACAAGAAGGACA
TCGATTAATTGATTATATAAAAGAAAAATATTTAACTTATATATAAAAT
GTTCAGAACAACAAAATATAATAGATGATTCTTATAATTATATTACAGTT
AAAAAACAGTATATTAAAACTATTGAAGATGTGAAATTTTTATTAGATTC
ATTGAACACAATAGAAGAAAAAAATAAATCAGTAGCAAATCTAGAAATTT
GTACTAATAAAGAAGATATAAAAAATTTACTTAAACATGTTATAAAGTTG
GCAAATTTTTCAGGTATTATTGTAATGTCTGATACAAATACGGAAATAAC
TCCAGAAAATCCTTTAGAAGATAATGATTTATTAAATTTACAATTATATT
TTGAAAGAAAACATGAAATAACATCAACATTGGAAAATGATTCTGATTTA
GAGTTAGATCATTTAGGTAGTAATTCGGATGAATCTATAGATAATTTAAA
GGTTTATAATGATATTATAGAATTACACACATATTCAACACAAATTCTTA
AATATTTAGATAATATTCAAAAACTTAAAGGAGATTGCAATGATTTAGTA
AAGGATTGTAAAGAATTACGTGAATTGTCTACGGCATTATATGATTTAAA
AATACAAATTACTAGTGTAATTAATAGAGAAAATGATATTTCAAATAATA
TTGATATTGTATCTAATAAATTAAATGAAATAGATGCTATACAATATAAT
TTTGAAAAATATAAAGAAATTTTTGATAATGTAGAAGAATATAAAACATT
AGATGATACAAAAAATGCATATATTGTAAAAAAGGCTGAAATTTTAAAAA
ATGTAGATATAAATAAAACAAAAGAAGATTTAGATATATATTTTAATGAC
TTAGACGAATTAGAAAAATCTCTTACATTATCATCTAATGAAATGGAAAT
TAAAACAATAGTACAGAACTCATATAATTCCTTTTCTGATATTAATAAGA
ACATTAATGATATTGATAAAGAAATGAAAACACTGATCCCTATGCTTGAT
GAATTATTAAATGAAGGACATAATATTGATATATCATTATATAATTTTAT
AATTAGAAATATTCAGATTAAAATAGGTAATGATATAAAAAAATATAAGAG
AACAGGAAAATGATACTAATATATGTTTTGAGTATATTCAAAATAATTAT
AATTTTATAAAGAGTGATATAAGTATCTTCAATAAATATGATGATCATAT
AAAAGTAGATAATTATATATCTAATAATATTGATGTTGTCAATAAACATA
ATAGTTTATTAAGTGAACATGTTATAAATGCTACAAATATTATAGAGAAT
ATTATGACAAGTATTGTCGAAATAAATGAAGATACAGAAATGAATTCTTT
AGAAGAGACACAAGACAAATTATTAGAACTATATGAAAATTTTAAGAAAG
AAAAAAATATTATAAATAATAATTATAAAATAGTACATTTTAATAAATTA
AAAGAAATAGAAAATAGTTTAGAGACATATAATTCAATATCAACAAACTT
TAATAAAATAAATGAAACACAAAATATAGATATTTTAAAAAAATGAATTTA
```

ATAATATCAAAACAAAAATTAATGATAAAGTAAAAGAATTAGTTCATGTT
GATAGTACATTAACACTTGAATCAATTCAAACGTTTAATAATTTATATGG
TGACTTGATGTCTAATATACAAGATGTATATAAATATGAAGATATTAATA
ATGTTGAATTGAAAAAGGTGAAATTATATATAGAAATATTACAAATTTA
TTAGGAAGAATAAACACATTCATAAAGGAGTTAGACAAATATCAGGATGA
AAATAATGGTATAGATAAGTATATAGAAATCAATAAGGAAAATAATAGTT
ATATAATAAAATTGAAAGAAAAAGCCAATAATCTAAAGGAAAATTTCTCA
AAATTATTACAAATATAAAAAGAAATGAAACTGAATTATATAATATAAA
TAACATAAAGGATGATATTATGAATACGGGGAAATCTGTAAATAATATAA
AACAAAAATTTTCTAGTAATTTGCCACTAAAAGAAAAATTATTTCAAATG
GAAGAGATGTTACTTAATATAAATAATATTATGAATGAAACGAAAAGAAT
ATCAAACACGGATGCATATACTAATATAACTCTCCAGGATATTGAAAATA
ATAAAAATAAAGAAAATAATAATATGAATATTGAAACAATTGATAAATTA
ATAGATCATATAAAAATACATAATGAAAAAATACAAGCAGAAATATTAAT
AATTGATGATGCCAAAAGAAAAGTAAAGGAAATAACAGATAATATTAACA
AGGCTTTTAATGAAATTACAGAAAATTATAATAATGAAAATAATGGGGTA
ATTAAATCTGCAAAAAATATTGTCGATAAAGCTACTTATTTAAATAATGA
ATTAGATAAATTTTTATTGAAATTGAATGAATTATTAAGTCATAATAATA
ATGATATAAAGGATCTTGGTGATGAAAAATTAATATTAAAGAAGAAGAA
GAAAGAAAAGAAGAGAAAGATTGGAAAAAGCGAAACAAGAAGAAGAAAG
AAAAGAGAGAGAAAGAATAGAAAAAGAAAAACAAGAGAAAGAAAGACTGG
AAAGAGAGAAACAAGAACAACTAAAAAAGAAGCATTAAAAAACAAGAG
CAAGAAAGACAAGAACAACAACAAAAAGAAGAAGCATTAAAAAGACAAGA
ACAAGAACGACTACAAAAAGAAGAAGAATTAAAAAGACAAGAGCAAGAA
GGCTGGAAAGAGAGAAACAAGAACAACTACAAAAAGAAGAAGAATTAAGA
AAAAAGAGCAGGAAAAACAACAACAAAGAAATATCCAAGAATTAGAAGA
GCAAAAAAAGCCTGAAATAATAAATGAAGCATTGGTAAAGGGGATAAAA
TACTAGAAGGAAGTGATCAGAGAAATATGGAATTAAGCAAACCTAACGTT
AGTATGGATAATACTAATAATAGTCCAATTAGTAACAGTGAAATTACAGA
AAGCGATGATATTGATAACAGTGAAAATATACATACTAGTCATATGAGTG
ACATCGAAAGTACACAAACTAGTCATAGAAGTAACACCCATGGGCAACAA
ATCAGTGATATTGTTGAAGATCAAATTACACATCCTAGTAATATTGGAGG
AGAAAAAATTACTCATAATGATGAAATTTCAATCACTGGTGAAAGAAATA
ACATTAGCGATGTTAATGATTATAGTGAAAGTAGCAACATATTTGAAAAT
GGTGACAGTACTATAAATACCAGTACAAGAAACACGTCTAGTACACATGA
TGAATCCCATATAAGTCCTATCAGCAATGCGTATGATCATGTTGTTTCAG
ATAATAAAAAAGTATGGATGAAAACATAAAAGATAAATTAAAGATAGAT
GAAAGTATAACTACAGATGAACAAATAAGATTAGATGATAATTCTAATAT
TGTTAGAATTGATAGTACTGACCAACGTGATGCTAGTAGTCATGGTAGTA
GTAATAGGGATGATGATGAAATAAGTCATGTTGGTAGCGACATTCATATG

GATAGTGTTGATATTCATGATAGTATTGACACTGATGAAAATGCTGATCA
CAGACATAATGTTAACTCTGTTGATAGTCTTAGTTCTAGTGATTACACTG
ATACACAGAAAGACTTTAGTAGTATTATTAAAGATGGGGGAAATAAAGAA
GGACATGCTGAGAATGAATCTAAAGAATATGAATCCCAAACAGAACAAAC
ACATGAAGAAGGAATTATGAATCCAAATAAATATTCAATTAGTGAAGTTG
ATGGTATTAAATTAAATGAAGAAGCTAAACATAAAATTACAGAAAAACTG
GTAGATATCTATCCTTCTACATATAGAACACTTGATGAACCTATGGAAAC
ACATGGTCCAAATGAAAAATTTCATATGTTTGGTAGTCCATATGTAACAG
AAGAAGATTACACGGAAAAACATGATTATGATAAGCATGAAGATTTCAAT
AATGAAAGGTATTCAAACCATAACAAAATGGATGATTTCGTATATAATGC
TGGAGGAGTTGTTTGTTGTGTATTATTTTTTGCAAGTATTACTTTCTTTT
CTATGGACAGATCAAATAAGGATGAATGCGATTTTGATATGTGTGAAGAA
GTAAATAATAATGATCACTTATCGAATTATGCTGATAAAGAAGAAATTAT
TGAAATTGTGTTTGATGAAAATGAAGAAAAATATTTTTAA

The nucleotide sequence of Rh4 is given below (SEQ ID NO: 22)
ATGAATAAGAATATATTGTGGATAACTTTTTTTTATTTTTATTTTTTCT
CTTGGATATGTACCAAGGAAATGACGCAATTCCCTCAAAAGAAAAAAAA
ACGATCCAGAAGCAGATTCTAAGAACTCACAGAATCAACATGATATAAAT
AAAACACACCATACGAACAATAATTATGATCTGAATATTAAGGATAAAGA
TGAGAAAAAAGAAAAAATGATAATTTAATCAATAATTATGATTACTCTC
TTTTAAAGTTATCTTATAATAAGAATCAAGATATATATAAGAATATACAA
AATGGCCAAAAGCTTAAAACAGACATAATATTAAACTCATTTGTTCAAAT
TAATTCATCAAACATATTAATGGATGAAATAGAAAATTATGTGAAAAAAT
ATACGGAATCGAATCGTATTATGTACTTACAATTTAAATATATATATCTA
CAATCCTTAAATATAACAGTATCTTTTGTACCTCCGAATTCACCATTTCG
AAGTTATTATGACAAAAATTTAAATAAAGATATAAATGAAACTTGTCATT
CCATACAAACACTTCTAAACAATCTAATATCTTCCAAAATTATATTTAAA
ATGTTAGAAACTACAAAAGAACAAATATTACTTTTATGGAATAACAAAAA
AATTAGTCAACAAAATTATAATCAAGAAATCAAGAAAAAGTAAAATGA
TCGATTCGGAAAATGAAAAACTAGAAAAGTACACAAACAAGTTTGAACAT
AATATCAAACCTCATATAGAAGATATAGAGAAAAAGTAAATGAATATAT
TAATAATTCCGATTGTCATTTAACATGTTCAAAATATAAAACAATTATCA
ATAATTATATAGATGAAATAATAACAACTAATACAAACATATACGAAAC
AAATATAATCTACCACAAGAACGAATTATCAAAAACTATAATCATAATGG
TATTAATAATGATGATAATTTTATAGAATATAATATTCTTAATGCAGATC
CTGATTTAAGATCTCATTTTATAACACTTCTTGTTTCAAGAAAACAATTA
ATCTATATTGAATATATTTATTTTATTAACAAACATATTGTAAATAAAAT
TCAAGAAAACTTTAAATTAAATCAAAATAAATATATACATTTTATTAATT
CAAATAATGCTGTTAATGCTGCTAAAGAATATGAATATATCATAAAATAT
TATACTACATTCAAATATCTACAGACATTAAATAAATCATTATACGACTC -continued

```
TATATATAAACATAAAATAAATAATTATTCTCATAACATTGAAGATCTTA
TAAACCAACTACAACATAAAATTAATAACCTAATGATTATCTCATTCGAT
AAAAATAAATCATCAGATTTAATGTTACAATGTACAAATATAAAAAATA
TACCGATGATATATGTTTATCCATTAAACCTAAAGCATTAGAAGTCGAAT
ATTTAAGAAATATAAATAAACACATCAACAAAAATGAATTCCTAAATAAA
TTCATGCAAAACGAAACATTTAAAAAAAATATAGATGATAAAATCAAAGA
AATGAATAATATATACGATAATATATATATCATATTAAAACAAAAATTCT
TAAACAAATTAAACGAAATCATACAAAATCATAAAAATAAACAAGAAACA
AAATTAAATACCACAACCATTCAAGAATTGTTACAACTTCTAAAGGATAT
TAAAGAAATACAAACAAACAAATCGATACAAAAATTAATACTTTTAATA
TGTATTATAACGATATACAACAAATAAAAATAAAGATTAATCAAAATGAA
AAAGAAATAAAAAAGGTACTCCCTCAATTATATATCCCAAAAAATGAACA
AGAATATATACAAATATATAAAAATGAATTAAAGGATAGAATAAAAGAAA
CACAAACAAAAATTAATTTATTTAAGCAAATTTTAGAATTAAAAGAAAAA
GAACATTATATTACAAACAAACATACATACCTAAATTTTACACACAAAC
TATTCAACAAATATTACAACAACAATATAAAAACAACACACAAGAAAAA
ATACACTAGCACAATTTTTATACAATGCAGATATCAAAAAATATATTGAT
GAATTAATACCTATCACACAACAAATACAAACCAAATGTATACAACAAA
TAATATAGAACATATTAAACAAATACTCATAAATTATATACAAGAATGTA
AACCTATACAAAATATATCAGAACATACTATTTATACACTATATCAAGAA
ATCAAAACAAATCTGGAAAACATCGAACAGAAAATTATGCAAATATACA
ACAAACTACAAATCGGTTAAAAATAAATATTAAAAAAATATTTGATCAAA
TAAATCAAAAATATGACGACTTAACAAAAAATATAAACCAAATGAATGAT
GAAAAAATTGGGTTACGACAAATGGAAAATAGGTTGAAAGGGAAATATGA
AGAAATAAAAAGGCAAATCTTCAAGATAGGGACATAAAATATATAGTCC
AAAATAATGATGCTAATAATAATAATAATAATATTATTATTATTAATGGT
AATAATCAAACCGGTGATTATAATCACATCTTGTTCGATTATACTCACCT
TTGGGATAATGCACAATTTACTAGAACAAAAGAAAATATAAACAACCTAA
AAGATAAATACAAATCAACATAAATAATATCAAAAGTATAATAAGAAAT
TTACAAAACGAACTAAACAATTATAATACTCTTAAAAGCAATTCCATCCA
TATTTATGATAAAATACACACATTAGAAGAATTAAAAATATTAACTCAAG
AAATTAATGATAAAAATGTTATCAGAAAAATATATGATATTGAAACCATA
TATCAAAATGATTTACATAACATAGAAGAAATTATTAAAAATATTACAAG
CATTTATTACAAAATAAATATCTTAAATATATTAATTATTTGCATCAAAC
AAACATATAATAATAATAAATCCATTGAAAGCTTAAAACTTAAAATTAAT
AACTTAACAAATTCAACACAAGAATATATTAATCAAATAAAAGCTATCCC
AACTAATTTATTACCAGAACATATAAAACAAAAAGTGTAAGCGAACTAA
ATATTTATATGAAACAAATATGATAAATTAAATGAACATGTTATTAAT
AATTTATATACAAAATCAAAGGATTCATTACAATTTTATATTAACGAAAA
AAATTATAATAATAATCATGATGATCATAATGATGACCATAATGATGTAT
ATAATGATATCAAAGAAAATGAAATATATAAAAATAATAAATTATACGAA
```

-continued

```
TGCATACAAATCAAAAAGGATGTAGACGAATTATATAATATTTATGATCA
ACTCTTTAAAAATATATCCCAAAATTATAATAACCACTCCCTTAGTTTTG
TACATTCAATAAATAATCATATGCTATCTATTTTTCAAGATACTAAATAT
GGAAAACACAAAAATCAACAAATCCTATCCGATATAGAAAATATTATAAA
ACAAAATGAACACACAGAATCATATAAAAATTTAGCACAAGTAATATAC
AACTAATAAAGAACAAATTAAATATTTCTTACAAATATTTCATATACTT
CAAGAAAATATAACCACTTTCGAAAATCAATATAAAGATTTAATTATCAA
AATGAACCATAAAATTAATAATAATCTAAAAGATATTACACATATTGTCA
TAAACGATAACAATACATTACAAGAACAAAATCGTATTTATAACGAACTT
CAAAACAAAATTAAACAAATAAAAAATGTCAGTGATGTATTCACACATAA
TATTAATTACAGTCAACAAATATTAAATTATTCTCAAGCACAAAATAGTT
TTTTTAATATATTTATGAAATTTCAAAACATTAATAATGATATTAATAGC
AAACGATATAATGTACAAAAAAAAATTACAGAGATAATCAATTCATATGA
TATAATAAATTATAACAAAAATAATATCAAAGATATTTATCAACAATTCA
AAAATATACAACAACAATTAAATACAACAGAAACGCAATTGAATCATATA
AAACAAAATATTAATCATTTCAAATATTTTTATGAATCTCATCAAACCAT
ATCTATAGTAAAGAATATGCAAAATGAAAAACTAAAAATTCAAGAATTCA
ACAAAAAAATACACACTTCAAGGAAGAAACACAAATTATGATAAACAAG
TTAATACAACCTAGCCACATACATTTACATAAAATGAAATTGCCTATAAC
TCAACAGCAACTTAATACAATTCTTCATAGAAATGAACAAACAAAAAATG
CTACAAGAAGTTACAATATGAATGAGGAGGAAAATGAAATGGGATATGGC
ATAACTAATAAAAGGAAAAATAGTGAGACAAATGACATGATAAATACCAC
CATAGGAGACAAGACAAATGTCTTAAAAAATGATGATCAAGAAAAAGGTA
AAAGGGGAACTTCCAGAAATAATAATATTCATACAAATGAAAATAATATA
AATAATGAACATACAAATGAAAATAATATAAATAATGAACATACAAATGA
AAAGAATATAAATAATGAACATGCAAATGAAAAGAATATATATAATGAAC
ATACAAATGAAAATAATATAAATTATGAACATCCAAATAATTATCAACAA
AAAAATGATGAAAAATATCACTACAACATAAAACAATTAATACATCACA
ACGTACCATAGATGATTCGAATATGGATCGAAATAATAGATATAACACAT
CATCACAACAAAAAATAATTTGCATACAAATAATAATAGTAATAGTAGA
TACAACAATAACCATGATAAACAAATGAACATAAATATAATCAAGGAAA
ATCTTCAGGGAAAGATAACGCATATTATAGAATTTTTATGCTGGAGGAA
TTACAGCTGTCTTACTTTTATGTTCAAGTACTGCATTCTTTTTTATAAAA
AACTCTAATGAACCACATCATATTTTTAATATTTTTCAAAAGGAATTTAG
TGAAGCAGATAATGCACATTCAGAAGAAAAGAAGAATATCTACCTGTCT
ATTTTGATGAAGTTGAAGATGAAGTTGAAGATGAAGTTGAAGATGAAGAT
GAAAATGAAAATGAAGTTGAAAATGAAAATGAAGATTTTAATGACATATG
A
```

The nucleotide sequence of EBA175 is given below (SEQ ID NO: 23)
ATGAAATGTAATATTAGTATATATTTTTTGCTTCCTTCTTTGTGTTATA

TTTTGCAAAAGCTAGGAATGAATATGATATAAAAGAGAATGAAAAATTTT

TAGACGTGTATAAAGAAAAATTTAATGAATTAGATAAAAAGAAATATGGA

AATGTTCAAAAAACTGATAAGAAAATATTTACTTTTATAGAAATAAATT

AGATATTTTAAATAATTCAAAATTTAATAAAAGATGGAAGAGTTATGGAA

CTCCAGATAATATAGATAAAAATATGTCTTTAATAAATAAACATAATAAT

GAAGAAATGTTTAACAACAATTATCAATCATTTTTATCGACAAGTTCATT

AATAAAGCAAATAAATATGTTCCTATTAACGCTGTACGTGTGTCTAGGA

TATTAAGTTTCCTGGATTCTAGAATTAATAATGGAAGAAATACTTCATCT

AATAACGAAGTTTTAAGTAATTGTAGGGAAAAAAGGAAAGGAATGAAATG

GGATTGTAAAAGAAAAATGATAGAAGCAACTATGTATGTATTCCTGATC

GTAGAATCCAATTATGCATTGTTAATCTTAGCATTATTAAAACATATACA

AAAGAGACCATGAAGGATCATTTCATTGAAGCCTCTAAAAAGAATCTCA

ACTTTTGCTTAAAAAAAATGATAACAAATATAATTCTAAATTTTGTAATG

ATTTGAAGAATAGTTTTTTAGATTATGGACATCTTGCTATGGGAAATGAT

ATGGATTTTGGAGGTTATTCAACTAAGGCAGAAAACAAAATTCAAGAAGT

TTTTAAAGGGGCTCATGGGAAATAAGTGAACATAAAATTAAAAATTTTA

GAAAAAAATGGTGGAATGAATTTAGAGAGAAACTTTGGGAAGCTATGTTA

TCTGAGCATAAAATAATATAAATAATTGTAAAAATATTCCCCAAGAAGA

ATTACAAATTACTCAATGGATAAAAGAATGGCATGGAGAATTTTTGCTTG

AAAGAGATAATAGATCAAAATTGCCAAAAAGTAAATGTAAAAATAATACA

TTATATGAAGCATGTGAGAAGGAATGTATTGATCCATGTATGAAATATAG

AGATTGGATTATTAGAAGTAAATTTGAATGGCATACGTTATCGAAAGAAT

ATGAAACTCAAAAAGTTCCAAAGGAAATGCGGAAAATTATTTAATCAAA

ATTTCAGAAAACAAGAATGATGCTAAAGTAAGTTTATTATTGAATAATTG

TGATGCTGAATATTCAAATATTGTGATTGTAAACATACTACTACTCTCG

TTAAAAGCGTTTTAAATGGTAACGACAATACAATTAAGGAAAAGCGTGAA

CATATTGATTTAGATGATTTTCTAAATTTGGATGTGATAAAAATTCCGT

TGATACAAACACAAAGGTGTGGGAATGTAAAAAACCTTATAAATTATCCA

CTAAAGATGTATGTGTACCTCCGAGGAGGCAAGAATTATGTCTTGGAAAC

ATTGATAGAATATACGATAAAAACCTATTAATGATAAAAGAGCATATTCT

TGCTATTGCAATATATGAATCAAGAATATTGAAACGAAAATATAAGAATA

AAGATGATAAAGAAGTTTGTAAATCATAAATAAAACTTTCGCTGATATA

AGAGATATTATAGGAGGTACTGATTATTGGAATGATTTGAGCAATAGAAA

ATTAGTAGGAAAAATTAACACAAATTCAAATTATGTTCACAGGAATAAAC

AAAATGATAAGCTTTTCGTGATGAGTGGTGGAAAGTTATTAAAAAAGAT

GTATGGAATGTGATATCATGGGTATTCAAGGATAAAACTGTTTGTAAAGA

AGATGATATTGAAAATATACCACAATTCTTCAGATGGTTTAGTGAATGGG

GTGATGATTATTGCCAGGATAAAACAAAAATGATAGAGACTCTGAAGGTT

GAATGCAAAGAAAAACCTTGTGAAGATGACAATTGTAAACGTAAATGTAA

TTCATATAAAGAATGGATATCAAAAAAAAAAGAAGAGTATAATAAACAAG

CCAAACAATACCAAGAATATCAAAAAGGAAATAATTACAAAATGTATTCT

GAATTTAAATCTATAAAACCAGAAGTTTATTTAAAGAAATACTCGGAAAA

ATGTTCTAACCTAAATTTCGAAGATGAATTTAAGGAAGAATTACATTCAG

ATTATAAAATAAATGTACGATGTGTCCAGAAGTAAAGGATGTACCAATT

TCTATAATAAGAAATAATGAACAAACTTCGCAAGAAGCAGTTCCTGAGGA

AAGCACTGAAATAGCACACAGAACGGAAACTCGTACGGATGAACGAAAAA

ATCAGGAACCAGCAAATAAGGATTTAAAGAATCCACAACAAAGTGTAGGA

GAGAACGGAACTAAAGATTTATTACAAGAAGATTTAGGAGGATCACGAAG

TGAAGACGAAGTGACACAAGAATTTGGAGTAAATCATGGAATACCTAAGG

GTGAGGATCAAACGTTAGGAAAATCTGACGCCATTCCAAACATAGGCGAA

CCCGAAACGGGAATTTCCACTACAGAAGAAAGTAGACATGAAGAAGGCCA

CAATAAACAAGCATTGTCTACTTCAGTCGATGAGCCTGAATTATCTGATA

CACTTCAATTGCATGAAGATACTAAAGAAAATGATAAACTACCCCTAGAA

TCATCTACAATCACATCTCCTACGGAAAGTGGAAGTTCTGATACAGAGGA

AACTCCATCTATCTCTGAAGGACCAAAAGGAAATGAACAAAAAAAACGTG

ATGACGATAGTTTGAGTAAAATAAGTGTATCACCAGAAAATTCAAGACCT

GAAACTGATGCTAAAGATACTTCTAACTTGTTAAAATTAAAAGGAGATGT

TGATATTAGTATGCCTAAAGCAGTTATTGGGAGCAGTCCTAATGATAATA

TAAATGTTACTGAACAAGGGGATAATATTTCCGGGGTGAATTCTAAACCT

TTATCTGATGATGTACGTCCAGATAAAAATCATGAAGAGGTGAAAGAACA

TACTAGTAATTCTGATAATGTTCAACAGTCTGGAGGAATTGTTAATATGA

ATGTTGAGAAGAACTAAAAGATACTTTAGAAAATCCTTCTAGTAGCTTG

GATGAAGGAAAAGCACATGAAGAATTATCAGAACCAAATCTAAGCAGTGA

CCAAGATATGTCTAATACACCTGGACCTTTGGATAACACCAGTGAAGAAA

CTACAGAAAGAATTAGTAATAATGAATATAAAGTTAACGAGAGGGAAGGT

GAGAGAACGCTTACTAAGGAATATGAAGATATTGTTTTGAAAAGTCATAT

GAATAGAGAATCAGACGATGGTGAATTATATGACGAAAATTCAGACTTAT

CTACTGTAAATGATGAATCAGAAGACGCTGAAGCAAAAATGAAAGGAAAT

GATACATCTGAAATGTCGCATAATAGTAGTCAACATATTGAGAGTGATCA

ACAGAAAAACGATATGAAAACTGTTGGTGATTTGGGAACCACACATGTAC

AAAACGAAATTAGTGTTCCTGTTACAGGAGAAATTGATGAAAAATTAAGG

GAAAGTAAAGAATCAAAAATTCATAAGGCTGAAGAGGAAAGATTAAGTCA

TACAGATATACATAAAATTAATCCTGAAGATAGAAATAGTAATACATTAC

ATTTAAAGATATAAGAAATGAGGAAAACGAAAGACACTTAACTAATCAA

AACATTAATATTAGTCAAGAAAGGGATTTGCAAAAACATGGATTCCATAC

CATGAATAATCTACATGGAGATGGAGTTTCCGAAAGAAGTCAAATTAATC

ATAGTCATCATGGAAACAGACAAGATCGGGGGGGAAATTCTGGGAATGTT

TTAAATATGAGATCTAATAATAATAATTTTAATAATATTCCAAGTAGATA

-continued

```
TAATTTATATGATAAAAAATTAGATTTAGATCTTTATGAAAACAGAAATG

ATAGTACAACAAAAGAATTAATAAAGAAATTAGCAGAAATAAATAAATGT

GAGAACGAAATTTCTGTAAAATATTGTGACCATATGATTCATGAAGAAAT

CCCATTAAAAACATGCACTAAAGAAAAAACAAGAAATCTGTGTTGTGCAG

TATCAGATTACTGTATGAGCTATTTTACATATGATTCAGAGGAATATTAT

AATTGTACGAAAAGGGAATTTGATGATCCATCTTATACATGTTTCAGAAA

GGAGGCTTTTTCAAGTATGCCATATTATGCAGGAGCAGGTGTGTTATTTA

TTATATTGGTTATTTTAGGTGCTTCACAAGCCAAATATCAAAGGTTAGAA

AAAATAAATAAAAATAAAATTGAGAAGAATGTAAATTAA
```

The nucleotide sequence of EBA181 is given below (SEQ ID NO: 24)

```
ATGAAAGGGAAAATGAATATGTGTTTGTTTTTTTCTATTCTATATTATA

TGTTGTATTATGTACCTATGTATTAGGTATAAGTGAAGAGTATTTGAAGG

AAAGGCCCCAAGGTTTAAATGTTGAGACTAATAATAATAATAATAATAAT

AATAATAATAATAGTAATAGTAACGATGCGATGTCTTTTGTAAATGAAGT

AATAAGGTTTATAGAAAACGAGAAGGATGATAAAGAAGATAAAAAGTGA

AGATAATATCTAGACCTGTTGAGAATACATTACATAGATATCCAGTTAGT

TCTTTTCTGAATATCAAAAAGTATGGTAGGAAAGGGGAATATTTGAATAG

AAATAGTTTTGTTCAAAGATCATATATAAGGGGTTGTAAAGGAAAAAGAA

GCACACATACATGGATATGTGAAAATAAAGGGAATAATAATATATGTATT

CCTGATAGACGTGTACAATTATGTATAACAGCTCTTCAAGATTTAAAAAA

TTCAGGATCTGAAACGACTGATAGAAAATTATTAAGAGATAAAGTATTTG

ATTCAGCTATGTATGAAACTGATTTGTTATGGAATAAATATGGTTTTCGT

GGATTTGATGATTTTTGTGACGATGTAAAAAATAGTTATTTAGATTATAA

AGATGTTATATTTGGAACCGATTTAGATAAAAATAATATATCAAAGTTAG

TAGAGGAATCATTAAAACGTTTTTTTAAAAAAGATAGTAGTGTACTTAAT

CCTACTGCTTGGTGGAAAGGTATGGAACAAGACTATGGAAAACTATGAT

ACAGCCATATGCTCATTTAGGATGTAGAAAACCTGATGAGAATGAACCTC

AGATAAATAGATGGATTCTGGAATGGGGGAAATATAATTGTAGATTAATG

AAGGAGAAAGAAAAATTGTTAACAGGAGAATGTTCTGTTAATAGAAAAAA

ATCTGACTGCTCAACCGGATGTAATAATGAGTGTTATACCTATAGGAGTC

TTATTAATAGACAAAGATATGAGGTCTCTATATTAGGAAAAAAATATATT

AAAGTAGTACGATATACTATATTTAGGAGAAAAATAGTTCAACCTGATAA

TGCTTTGGATTTTTAAAATTAAATTGTTCTGAGTGTAAGGATATTGATT

TTAAACCCTTTTTTGAATTTGAATATGGTAAATATGAAGAAAAATGTATG

TGTCAATCATATATTGATTTAAAAATCCAATTTAAAAATAATGATATTTG

TTCATTTAATGCTCAAACAGATACTGTTTCTAGCGATAAAAGATTTTGTC

TTGAAAAGAAAGAATTTAAACCATGGAAATGTGATAAAAATTCTTTTGAA

ACAGTTCATCATAAAGGTGTATGTGTGTCACCGAGAAGACAAGGTTTTTG

TTTAGGAAATTTGAACTATCTACTGAATGATGATATTTATAATGTACATA

ATTCACAACTACTTATCGAAATTATAATGGCTTCTAAACAAGAAGGAAAG
```

-continued

```
TTATTATGGAAAAAACATGGAACAATACTTGATAACCAGAATGCATGCAA

ATATATAAATGATAGTTATGTTGATTATAAAGATATAGTTATTGGAAATG

ATTTATGGAATGATAACAACTCTATAAAAGTTCAAAATAATTTAAATTTA

ATTTTTGAAAGAAATTTTGGTTATAAAGTTGGAAGAAATAAACTCTTTAA

AACAATTAAAGAATTAAAAAATGTATGGTGGATATTAAATAGAAATAAAG

TATGGGAATCAATGAGATGTGGAATTGACGAAGTAGATCAACGTAGAAAA

ACTTGTGAAAGAATAGATGAACTAGAAAACATGCCACAATTCTTTAGATG

GTTTTCACAATGGGCACATTTCTTTTGTAAGGAAAAAGAATATTGGGAAT

TAAAATTAAATGATAAATGTACAGGTAATAATGGAAAATCCTTATGTCAG

GATAAACATGTCAAAATGTGTGTACTAATATGAATTATTGGACATATAC

TAGAAAATTAGCTTATGAAATACAATCCGTAAAATATGATAAAGATAGAA

AATTATTTAGTCTTGCTAAAGACAAAAATGTAACTACATTTTTAAAGGAA

AATGCAAAAAATTGTTCTAATATAGATTTTACAAAAATATTCGATCAGCT

TGACAAACTCTTTAAGGAAAGATGTTCATGTATGGATACACAAGTTTTAG

AAGTAAAAAACAAAGAAATGTTATCTATAGACTCAAATAGTGAAGATGCG

ACAGATATAAGTGAGAAAAATGGAGAGGAAGAATTATATGTAAATCACAA

TTCTGTGAGTGTCGCAAGTGGTAATAAAGAAATCGAAAAGAGTAAGGATG

AAAAGCAACCTGAAAAGAAGCAAAACAAACTAATGGAACTTTAACCGTA

CGAACTGACAAAGATTCAGATAGAAACAAAGGAAAAGATACAGCTACTGA

TACAAAAAATTCACCTGAAAATTTAAAAGTACAGGAACATGGAACAAATG

GAGAACAATAAAAGAAGAACCACCAAAATTACCTGAATCATCTGAAACA

TTACAATCACAAGAACAATTAGAAGCAGAAGCACAAAAACAAAAACAAGA

AGAAGAACCAAAAAAAAAACAAGAAGAAGAACCAAAAAAAAAACAAGAAG

AAGAACAAAAACGAGAACAAGAACAAAAACAAGAACAAGAAGAAGAAGAA

CAAAAACAAGAAGAAGAACAACAAATACAAGATCAATCACAAAGTGGATT

AGATCAATCCTCAAAAGTAGGAGTAGCGAGTGAACAAAATGAAATTTCTT

CAGGACAAGAACAAAACGTAAAAAGCTCTTCACCTGAAGTAGTTCCACAA

GAAACAACTAGTGAAAATGGGTCATCACAAGACACAAAAATATCAAGTAC

TGAACCAAATGAGAATTCTGTTGTAGATAGAGCAACAGATAGTATGAATT

TAGATCCTGAAAAGGTTCATAATGAAAATATGAGTGATCCAAATACAAAT

ACTGAACCAGATGCATCTTTAAAAGATGATAAGAAGGAAGTTGATGATGC

CAAAAAAGAACTTCAATCTACTGTATCAAGAATTGAATCTAATGAACAGG

ACGTTCAAAGTACACCACCCGAAGATACTCCTACTGTTGAAGGAAAAGTA

GGAGATAAAGCAGAAATGTTAACTTCTCCGCATGCGACAGATAATTCTGA

GTCGGAATCAGGTTTAAATCCAACTGATGACATTAAAACAACTGATGGTG

TTGTTAAAGAACAAGAAATATTAGGGGGAGGTGAAAGTGCAACTGAAACA

TCAAAAGTAATTTAGAAAAACCTAAGGATGTTGAACCTTCTCATGAAAT

ATCTGAACCTGTTCTTTCTGGTACAACTGGTAAAGAAGAATCAGAGTTAT

TAAAAAGTAAATCGATAGAGACGAAGGGGGAAACAGATCCTCGAAGTAAT

GACCAAGAAGATGCTACTGACGATGTTGTAGAAAATAGTAGAGATGATAA

TAATAGTCTCTCTAATAGCGTAGATAATCAAAGTAATGTTTTAAATAGAG
```

-continued

```
AAGATCCTATTGCTTCTGAAACTGAAGTTGTAAGTGAACCTGAGGATTCA
AGTAGGATAATCACTACAGAAGTTCCAAGTACTACTGTAAAACCCCCTGA
TGAAAAACGATCTGAAGAAGTAGGAGAAAAAGAAGCTAAAGAAATTAAAG
TAGAACCTGTTGTACCAAGAGCCATTGGAGAACCAATGGAAAATTCTGTG
AGCGTACAGTCCCCTCCTAATGTAGAAGATGTTGAAAAAGAAACATTGAT
ATCTGAGAATAATGGATTACATAATGATACACACAGAGGAAATATCAGTG
AAAAGGATTTAATCGATATTCATTTGTTAAGAAATGAAGCGGGTAGTACA
ATATTAGATGATTCTAGAAGAAATGGAGAAATGACAGAAGGTAGCGAAAG
TGATGTTGGAGAATTACAAGAACATAATTTTAGCACACAACAAAAGATG
AAAAAGATTTTGACCAAATTGCGAGCGATAGAGAAAAAGAAGAAATTCAA
AAATTACTTAATATAGGACATGAAGAGGATGAAGATGTATTAAAAATGGA
TAGAACAGAGGATAGTATGAGTGATGGAGTTAATAGTCATTTGTATTATA
ATAATCTATCAAGTGAAGAAAAAATGGAACAATATAATAATAGAGATGCT
TCTAAAGATAGAGAAGAAATATTGAATAGGTCAAACACAAATACATGTTC
TAATGAACATTCATTAAAATATTGTCAATATATGGAAAGAAATAAGGATT
TATTAGAAACATGTTCTGAAGACAAAAGGTTACATTTATGTTGTGAAATA
TCAGATTATTGTTTAAAATTTTTCAATCCTAAATCGATAGAATACTTTGA
TTGTACACAAAAAGAATTTGATGACCCTACATATAATTGTTTTAGAAAAC
AAAGATTTACAAGTATGCATTATATTGCCGGGGGTGGTATAATAGCCCTT
TTATTGTTTATTTTAGGTTCAGCCAGCTATAGGAAGAATTTGGATGATGA
AAAAGGATTCTACGATTCTAATTTAAATGATTCTGCTTTTGAATATAATA
ATAATAAATATAATAAATTACCTTATATGTTTGATCAACAAATAAATGTA
GTAAATTCTGATTTATATTCGGAGGGTATTTATGATGACACAACGACATT
TTAA
```

The nucleotide sequence of EBA140 is given below (SEQ ID NO: 25)
```
ATGAAAGGATATTTTAATATATATTTTTTAATTCCTTTAATTTTTTTATA
TAATGTAATAAGAATAAATGAATCAATTATAGGTAGAACACTTTATAATA
GACAAGATGAATCATCAGATATTTCAAGGGTAAATTCACCCGAATTAAAT
AATAATCATAAAACTAATATATATGATTCAGATTACGAAGATGTAAATAA
TAAATTAATAAACAGTTTTGTAGAAAATAAAAGTGTGAAAAAAAAAAGGT
CTTTAAGTTTTATAAATAATAAAACAAAATCATATGATATAATTCCACCT
TCATATTCATATAGGAATGATAAATTTAATTCACTTTCCGAAAATGAAGA
TAATTCTGGAAATACAAATAGTAATAATTTCGCAAATACTTCTGAAATAT
CTATTGGAAAGGATAATAAACAATATACGTTTATACAGAAACGTACTCAT
TTGTTTGCTTGTGGAATAAAAAGAAAATCAATAAAATGGATATGTCGAGA
AAACAGTGAGAAAATTACTGTATGTGTTCCTGATAGAAAAATACAACTAT
GTATTGCAAATTTTTTAAACTCACGTTTAGAAACAATGGAAAAGTTTAAA
GAAATATTTTTAATTTCTGTTAATACAGAAGCAAAATTATTATATAACAA
AAATGAAGGAAAAGATCCCTCAATATTTTGTAATGAATTAAGAAATAGTT
TTTCAGATTTTAGAAATTCATTTATAGGTGATGATATGGATTTTGGTGGT
AATACAGATAGAGTCAAAGGATATATTAATAAGAAGTTCTCCGATTATTA
TAAGGAAAAAAATGTTGAAAAATTAAATAATATCAAAAAAGAATGGTGGG
AAAAAAATAAAGCAAATTTGTGGAATCACATGATAGTAAATCATAAAGGA
AACATAAGTAAAGAATGTGCCATAATTCCCGCGGAAGAACCTCAAATTAA
TCTATGGATAAAAGAATGGAATGAAAACTTCTTGATGGAAAAGAAGAGAT
TGTTTTTAAATATAAAAGATAAGTGTGTTGAAAACAAAAAATATGAAGCA
TGTTTTGGTGGATGTAGGCTTCCATGTTCTTCATATACATCATTTATGAA
AAAAGTAAAACACAAATGGAGGTTTTGACGAACTTGTATAAAAAGAAAA
ATTCAGGAGTGGATAAAAATAATTTTCTGAATGATCTTTTTAAAAAAAT
AATAAAAATGATTTAGATGATTTTTTCAAAAATGAAAAGGAATATGATGA
TTTATGTGATTGCAGATATACTGCTACTATTATTAAAAGTTTTCTAAATG
GTCCTGCTAAAAATGATGTAGATATTGCATCACAAATTAATGTTAATGAT
CTTCGAGGGTTTGGATGTAATTATAAAAGTAATAATGAAAAAAGTTGGAA
TTGTACTGGAACATTTACGAACAAATTTCCTGGTACATGTGAACCCCCCA
GAAGACAAACTTTATGTCTTGGACGTACATATCTTTTACATCGTGGTCAT
GAGGAAGATTATAAGGAACATTTACTTGGAGCTTCAATATATGAGGCGCA
ATTATTAAAATATAAATATAAGGAAAAGGATGAAAATGCATTGTGTAGTA
TAATACAAAATAGTTATGCAGATTTGGCAGATATTATCAAGGGATCGGAT
ATAATAAAAGATTATTATGGTAAAAAAATGGAAGAAATTTAAATAAAGT
AAACAAAGATAAAAAACGTAATGAAGAATCTTTGAAGATTTTTCGTGAAA
AATGGTGGGATGAAAACAAGGAGAATGTATGGAAAGTAATGTCAGCAGTA
CTTAAAAATAAGGAAACGTGTAAAGATTATGATAAGTTTCAAAAGATTCC
TCAATTTTTAAGATGGTTTAAGGAATGGGAGACGATTTTTGTGAGAAAA
GAAAAGAGAAAATATATTCATTTGAGTCATTTAAGGTAGAATGTAAGAAA
AAAGATTGTGATGAAAATACATGTAAAAATAAATGTAGTGAATATAAAA
ATGGATAGATTTGAAAAAAAGTGAATATGAGAAACAAGTTGATAAATACA
CAAAAGATAAAAATAAAAGATGTATGATAATATTGATGAAGTAAAAAAT
AAAGAAGCCAATGTTTACTTAAAAGAAAAATCCAAAGAATGTAAAGATGT
AAATTTCGATGATAAAATTTTTAATGAGAGTCCAAATGAATATGAAGATA
TGTGTAAAAAATGTGATGAAATAAAATATTTAAATGAAATTAAATATCCT
AAAACAAAACACGATATATATGATATAGATACATTTTCAGATACTTTTGG
TGATGGAACGCCAATAAGTATTAATGCAAATATAAATGAACAACAAAGTG
GGAAGGATACCTCAAATACTGGAAATAGTGAAACATCAGATTCACCGGTT
AGTCATGAACCAGAAAGTGATGCTGCAATTAATGTAGAAAAGTTAAGTGG
TGATGAAAGTTCAAGTGAAACAAGAGGAATATTAGATATTAATGATCCAA
GTGTTACGAACAATGTCAATGAAGTTCATGATGCTTCAAATACACAAGGT
AGTGTTTCAAATACTTCTGATATAACGAATGGACATTCGGAAAGTTCCCT
GAATAGAACAACGAATGCACAAGATATTAAAATAGGCCGTTCAGGAAATG
AACAAAGTGATAATCAAGAAAATAGTTCACATTCTAGTGATAATTCAGGT
TCTTTGACAATCGGACAAGTTCCTTCAGAGGATAATACCCAAAATACATA
```

```
TGATTCACAAAACCCTCATAGAGATACACCTAATGCATTAGCATCTTTAC

CATCAGATGATAAAATTAATGAAATAGAGGGTTTCGATTCTAGTAGAGAT

AGTGAAAATGGTAGGGGTGATACAACATCAAATACTCATGATGTACGTCG

TACGAATATAGTAAGTGAGAGACGTGTGAATAGCCATGATTTTATTAGAA

ACGGAATGGCGAATAACAATGCACATCATCAATATATAACGCAAATTGAG

AATAATGGAATCATAAGAGGACAAGAGGAAAGTGCGGGAATAGTGTTAA

TTATAAAGATAATCCAAAGAGGAGTAATTTTTCCTCCGAAAATGATCATA

AGAAAAATATACAGGAATATAATTCTAGAGATACTAAAAGAGTAAGGGAG

GAAATAATTAAATTATCGAAGCAAAATAAATGCAACAATGAATATTCCAT

GGAATATTGTACCTATTCTGACGAAAGGAATAGTTCACCGGGTCCTTGTT

CTAGAGAAGAAAGAAAGAAATTATGTTGTCAGATTTCAGATTATTGTTTA

AAATATTTTAACTTTTATTCAATTGAATATTATAATTGTATAAAATCTGA

AATTAAAAGTCCAGAATATAAATGTTTTAAAAGCGAGGGTCAATCAAGCA

TTCCTTATTTTGCTGCTGGAGGTATTTTAGTTGTAATAGTCTTACTTTTG

AGTTCAGCATCTAGAATGGGGAAAAGTAATGAAGAATATGATATAGGAGA

ATCTAATATAGAAGCAACTTTTGAAGAAAATAATTATTTAAATAAACTAT

CGCGCATATTTAATCAAGAAGTACAAGAGACAAACATTTCAGATTATTCC

GAGTACAATTATAATGAAAAGAATATGTATTAA

The nucleotide sequence of Rh2a is given
below
                                          (SEQ ID NO: 26)
ATGAAGACCACACTATTTTGTAGCATATCTTTTTGTAATATTATATTTTT

CTTCTTAGAATTAAGTCATGAGCATTTTGTTGGACAATCAAGTAATACCC

ATGGAGCATCTTCAGTTACTGATTTTAATTTTAGTGAGGAGAAAAATTTA

AAAAGTTTTGAAGGGAAGAATAATAATAATGATAATTATGCTTCAATTAA

TCGTTTATATAGGAAGAAACCATATATGAAGAGATCGCTTATAAATTTAG

AAAATGATCTTTTTAGATTAGAACCTATATCTTATATTCAAAGATATTAT

AAGAAGAATATAAACAGATCTGATATTTTTCATAATAAAAAAGAAAGAGG

TTCCAAAGTATATTCAAATGTGTCTTCATTCCATTCTTTTATTCAAGAGG

GTAAAGAAGAAGTTGAGGTTTTTTCTATATGGGGTAGTAATAGCGTTTTA

GATCATATAGATGTTCTTAGGGATAATGGAACTGTCGTTTTTTCTGTTCA

ACCATATTACCTTGATATATATACGTGTAAAGAAGCCATATTATTTACTA

CATCATTTTACAAGGATCTTGATAAAAGTTCAATTACAAAAATTAATGAA

GATATTGAAAAATTTAACGAAGAAATAATCAAGAATGAAGAACAATGTTT

AGTTGGTGGGAAAACAGATTTTGATAATTTACTTATAGTTTTAGAAAATG

CGGAAAAAGCAAATGTTAGAAAAACATTATTTGATAATACATTTAATGAT

TATAAAAATAAGAAATCTAGTTTTTACAATTGTTTGAAAAATAAAAAAAA

TGATTATGATAAGAAAATAAAGAATATAAAGAATGAGATTACAAAATTGT

TAAAAAATATTGAAAGTACAGGAAATATGTGTAAAACGGAATCATATGTT

ATGAATAATAATTTATATCTATTAAGAGTGAATGAAGTTAAAAGTACACC

TATTGATTTATACTTAAATCGAGCAAAAGAGCTATTAGAATCAAGTAGCA

AATTAGTTAATCCTATAAAAATGAAATTAGGTGATAATAAGAACATGTAC
```

```
TCTATTGGATATATACATGACGAAATTAAAGATATTATAAAAGATATAA

TTTTCATTTGAAACATATAGAAAAAGGAAAAGAATATATAAAAGGATAA

CACAAGCAAATAATATTGCAGACAAAATGAAGAAAGATGAACTTATAAAA

AAAATTTTGAATCCTCAAAACATTTTGCTAGTTTTAAATATAGCAATGA

AATGATAAGCAAATTAGATTCGTTATTTATAAAAAATGAAGAAATACTTA

ATAATTTATTCAATAATATATTTAATATATTCAAGAAAAATATGAAACA

TATGTAGATATGAAAACAATTGAATCTAAATATACAACAGTAATGACTCT

ATCAGAACATTTATTAGAATATGCAATGGATGTTTTAAAAGCTAACCCTC

AAAAACCTATTGATCCAAAAGCAAATCTGGATTCAGAAGTAGTAAAATTA

CAAATAAAAATAAATGAGAAATCAAATGAATTAGATAATGCTATAAGTCA

AGTAAAAACACTAATAATAATAATGAAATCATTTTATGATATTATTATAT

CTGAAAAAGCCTCTATGGATGAAATGGAAAAAAAGGAATTATCCTTAAAT

AATTATATTGAAAAAACAGATTATATATTACAAACGTATAATATTTTTAA

GTCTAAAAGTAATATTATAAATAATAATAGTAAAAATATTAGTTCTAAAT

ATATAACTATAGAAGGGTTAAAAAATGATATTGATGAATTAAATAGTCTT

ATATCATATTTTAAGGATTCACAAGAAACATTAATAAAAGATGATGAATT

AAAAAAAACATGAAAACGGATTATCTTAATAACGTGAAATATATAGAAG

AAAATGTTACTCATATAAATGAAATTATATTATTAAAAGATTCTATAACT

CAACGAATAGCAGATATTGATGAATTAAATAGTTTAAATTTAATAAAATAT

AAATGATTTTATAAATGAAAAGAATATATCACAAGAGAAAGTATCATATA

ATCTTAATAAATTATATAAAGGAAGTTTTGAAGAATTAGAATCTGAACTA

TCTCATTTTTTAGACACAAAATATTTGTTTCATGAAAAAAAAGTGTAAA

TGAACTTCAAACAATTTTAAATACATCAAATAATGAATGTGCTAAATTAA

ATTTTATGAAATCTGATAATAATAATAATAATAATAGTAATATAATT

AACTTGTTAAAAACTGAATTAAGTCATCTATTAAGTCTTAAAGAAAATAT

AATAAAAAAACTTTTAAATCATATAGAACAAAATATTCAAAACTCATCAA

ATAAGTATACTATTACATATACTGATATTAATAATAGAATGGAAGATTAT

AAAGAAGAAATCGAAAGTTTAGAAGTATATAAACATACCATTGGAAATAT

ACAAAAAGAATATATATTACATTTATATGAGAATGATAAAAATGCTTTAG

CTGTACATAATACATCAATGCAAATATTACAATATAAAGATGCTATACAA

AATATAAAAATAAAATTTCTGATGATATAAAAATTTTAAAGAAATATAA

AGAAATGAATCAAGATTTATTAAATTATTATGAAATTCTAGATAAAAAAT

TAAAAGATAATACATATATCAAAGAAATGCATACTGCTTCTTTAGTTCAA

ATAACTCAATATATTCCTTATGAAGATAAAACAATAAGTGAACTTGAGCA

AGAATTTAATAATAATAATCAAAAACTTGATAATATATTACAAGATATCA

ATGCAATGAATTTAAATATAAATATTCTCCAAACCTTAAATATTGGTATA

AATGCATGTAATACAAATAATAAAAATGTAGAACACTTACTTAACAAGAA

AATTGAATTAAAAAATATATTAAATGATCAAATGAAAATTATAAAAAATG

ATGATATAATTCAAGATAATGAAAAAGAAAACTTTTCAAATGTTTTAAAA

AAAGAAGAGGAAAAATTAGAAAAAGAATTAGATGATATCAAATTTAATAA

TTTGAAAATGGACATTCATAAATTGTTGAATTCGTATGACCATACAAAGC
```

```
AAAATATAGAAAGCAATCTTAAAATAAATTTAGATTCTTTCGAAAAGGAA
AAAGATAGTTGGGTTCATTTTAAAAGTACTATAGATAGTTTATATGTGGA
ATATAACATATGTAATCAAAAGACTCATAATACTATCAAACAACAAAAAA
ATGATATCATAGAACTTATTTATAAACGTATAAAAGATATAAATCAAGAA
ATAATCGAAAAGGTAGATAATTATTATTCCCTGTCAGATAAAGCCTTAAC
TAAACTTAAATCTATTCATTTTAATATTGATAAGGAAAAATATAAAAATC
CCAAAAGTCAAGAAAATATTAAATTATTAGAAGATAGAGTTATGATACTT
GAGAAAAAGATTAAGGAAGATAAAGATGCTTTAATACAAATTAAGAATTT
ATCACATGATCATTTTGTAAATGCTGATAATGAGAAAAAAAGCAGAAGG
AGAAGGAGGAGGACGACGAACAAACACACTATAGTAAAAAAGAAAAGTA
ATGGGAGATATATATAAGGATATTAAAAAAAACCTAGATGAGTTAAATAA
TAAAAATTTGATAGATATTACTTTAAATGAAGCAAATAAAATAGAATCAG
AATATGAAAAATATTAATTGATGATATTTGTGAACAAATTACAAATGAA
GCAAAAAAAGTGATACTATTAAGGAAAAAATCGAATCATATAAAAAGA
TATTGATTATGTAGATGTGGACGTTTCCAAAACGAGGAACGATCATCATT
TGAATGGAGATAAAATACATGATTCTTTTTTTATGAAGATACATTAAAT
TATAAAGCATATTTTGATAAATTAAAAGATTTATATGAAAATATAAACAA
GTTAACAAATGAATCAAATGGATTAAAAAGTGATGCTCATAATAACAACA
CACAAGTTGATAAACTAAAAGAAATTAATTTACAAGTATTCAGCAATTTA
GGAAATATAATTAAATATGTTGAAAAACTTGAGAATACATTACATGAACT
TAAAGATATGTACGAATTTCTAGAAACGATCGATATTAATAAAATATTAA
AAAGTATTCATAATAGCATGAAGAAATCAGAAGAATATAGTAATGAAACG
AAAAAAATATTTGAACAATCAGTAAATATAACTAATCAATTTATAGAAGA
TGTTGAAATATTGAAAACGTCTATTAACCCAAACTATGAAAGCTTAAATG
ATGATCAAATTGATGATAATATAAAATCACTTGTTCTAAAGAAAGAGGAA
ATATCCGAAAAAAGAAAACAAGTGAATAAATACATAACAGATATTGAATC
TAATAAAGAACAATCAGATTTACATTTACGATATGCATCTAGAAGTATAT
ATGTTATTGATCTTTTTATAAAACATGAAATAATAAATCCTAGCGATGGA
AAAAATTTTGATATTATAAAGGTTAAAGAAATGATAAATAAAACCAAACA
AGTTTCAAATGAAGCTATGGAATATGCTAATAAAATGGATGAAAAAATA
AGGACATTATAAAAATAGAAATGAACTTTATAATTTAATTAATAATAAC
ATCCGTTCATTAAAAGGGGTAAAATATGAAAAAGTTAGGAAACAAGCAAG
AAATGCAATTGATGATATAAATAATATACATTCTAATATTAAAACGATTT
TAACCAAATCTAAAGAACGATTAGATGAGATTAAGAAACAACCTAACATT
AAAAGAGAAGGTGATGTTTAAATAATGATAAAACCAAAATAGCTTATAT
TACAATACAAATAAATAACGGAAGAATAGAATCTAATTTATTAAATATAT
TAAATATGAAACATAACATAGATACTATCTTGAATAAAGCTATGGATTAT
ATGAATGATGTATCAAAATCTGACCAGATTGTTATTAATATAGATTCTTT
GAATATGAACGATATATATAATAAGGATAAAGATCTTTTAATAAAATATTT
TAAAAGAAAAACAGAATATGGAGGCAGAATATAAAAAAATGAATGAAATG
TATAATTACGTTAATGAAACAGAAAAAGAAATAATAAAACATAAAAAAAA
TTATGAAATAAGAATTATGGAACATATAAAAAAAGAAACAAATGAAAAAA
AAAAAAAATTTATGGAATCTAATAACAAATCATTAACTACTTTAATGGAT
TCATTCAGATCTATGTTTTATAATGAATATATAAATGATTATAATATAAA
TGAAAATTTTGAAAAACATCAAAATATATTGAATGAAATATATAATGGAT
TTAATGAATCATATAATATTATTAATACAAAAATGACTGAAATTATAAAT
GATAATTTAGATTATAATGAAATAAAAGAAATTAAAGAAGTAGCACAAAC
AGAATATGATAAACTTAATAAAAAAGTTGATGAATTAAAAAATTATTTGA
ATAATATTAAAGAACAAGAAGGACATCGATTAATTGATTATATAAAAGAA
AAAAATATTTAACTTATATATAAAATGTTCAGAACAACAAAATATAATAGA
TGATTCTTATAATTATATTACAGTTAAAAAACAGTATATTAAAACTATTG
AAGATGTGAAATTTTTATTAGATTCATTGAACACAATAGAAGAAAAAAAT
AAATCAGTAGCAAATCTAGAAATTTGTACTAATAAAGAAGATATAAAAAA
TTTACTTAAACATGTTATAAAGTTGGCAAATTTTTCAGGTATTATTGTAA
TGTCTGATACAAATACGGAAATAACTCCAGAAAATCCTTTAGAAGATAAT
GATTTATTAAATTTACAATTATATTTTGAAAGAAAACATGAAATAACATC
AACATTGGAAAATGATTCTGATTTAGAGTTAGATCATTTAGGTAGTAATT
CGGATGAATCTATAGATAATTTAAAGGTTTATAATGATATTATAGAATTA
CACACATATTCAACACAAATTCTTAAATATTTAGATAATATTCAAAAACT
TAAAGGAGATTGCAATGATTTAGTAAAGGATTGTAAAGAATTACGTGAAT
TGTCTACGGCATTATATGATTTAAAAATACAAATTACTAGTGTAATTAAT
AGAGAAAATGATATTTCAAATAATATTGATATTGTATCTAATAAATTAAA
TGAAATAGATGCTATACAATATAATTTTGAAAAATATAAAGAAATTTTTG
ATAATGTAGAAGAATATAAAACATTAGATGATACAAAAAATGCATATATT
GTAAAAAGGCTGAAATTTTAAAAAATGTAGATATAAATAAAACAAAAGA
AGATTTAGATATATATTTTAATGACTTAGACGAATTAGAAAAATCTCTTA
CATTATCATCTAATGAAATGGAAATTAAAACAATAGTACAGAACTCATAT
AATTCCTTTTCTGATATTAATAAGAACATTAATGATATTGATAAAGAAAT
GAAAACACTGATCCCTATGCTTGATGAATTATTAAATGAAGGACATAATA
TTGATATATCATTATATAATTTTATAATTAGAAATATTCAGATTAAAATA
GGTAATGATATAAAAAATATAAGAGAACAGGAAAATGATACTAATATATG
TTTTGAGTATATTCAAAATAATTATAATTTTATAAAGAGTGATATAAGTA
TCTTCAATAAATATGATGATCATATAAAAGTAGATAATTATATATCTAAT
AATATTGATGTTGTCAATAAACATAATAGTTTATTAAGTGAACATGTTAT
AAATGCTACAAATATTATAGAGAATATTATGACAAGTATTGTCGAAATAA
ATGAAGATACAGAAATGAATTCTTTAGAAGAGACACAAGACAAATTATTA
GAACTATATGAAAATTTTAAGAAAGAAAAAAATATTATAAATAATAATTA
TAAAATAGTACATTTTAATAAATTAAAAGAAATAGAAAATAGTTTAGAGA
CATATAATTCAATATCAACAAACTTTAATAAAATAAATGAAACACAAAAT
ATAGATATTTTAAAAAATGAATTTAATAATATCAAAACAAAAATTAATGA
TAAAGTAAAAGAATTAGTTCATGTTGATAGTACATTAACACTTGAATCAA
```

-continued

TTCAAACGTTTAATAATTTATATGGTGACTTGATGTCTAATATACAAGAT

GTATATAAATATGAAGATATTAATAATGTTGAATTGAAAAAGGTGAAATT

ATATATAGAAAATATTACAAATTTATTAGGAAGAATAAACACATTCATAA

AGGAGTTAGACAAATATCAGGATGAAAATAATGGTATAGATAAGTATATA

GAAATCAATAAGGAAAATAATAGTTATATAATAAAATTGAAAGAAAAAGC

CAATAATCTAAAGGAAAATTTCTCAAAATTATTACAAATATAAAAAGAA

ATGAAACTGAATTATATAATATAAATAACATAAAGGATGATATTATGAAT

ACGGGGAAATCTGTAAATAATATAAAACAAAAATTTTCTAGTAATTTGCC

ACTAAAAGAAAAATTATTTCAAATGGAAGAGATGTTACTTAATATAAATA

ATATTATGAATGAAACGAAAAGAATATCAAACACGGCTGCATATACTAAT

ATAACTCTCCAGGATATTGAAAATAATAAAAATAAAGAAAATAATAATAT

GAATATTGAAACAATTGATAAATTAATAGATCATATAAAAATACATAATG

AAAAAATACAAGCAGAAATATTAATAATTGATGATGCCAAAAGAAAAGTA

AAGGAAATAACAGATAATATTAACAAGGCTTTTAATGAAATTACAGAAAA

TTATAATAATGAAAATAATGGGGTAATTAAATCTGCAAAAAATATTGTCG

ATGAAGCTACTTATTTAAATAATGAATTAGATAAATTTTTATTGAAATTG

AATGAATTATTAAGTCATAATAATAATGATATAAAGGATCTTGGTGATGA

AAAATTAATATTAAAGAAGAAGAAGAAAGAAAAGAAAGAGAAAGATTGG

AAAAAGCGAAACAAGAAGAAGAAAGAAAAGAGAGAGAAAGAATAGAAAAA

GAAAAACAAGAGAAAGAAAGACTGGAAAGAGAGAAACAAGAACAACTAAA

AAAAGAAGAAGAATTAAGAAAAAAAGAGCAGGAAAGACAAGAACAACAAC

AAAAAGAAGAAGCATTAAAAAGACAAGAACAAGAACGACTACAAAAAGAA

GAAGAATTAAAAAGACAAGAGCAAGAAAGGCTGGAAAGAGAGAAACAAGA

ACAACTACAAAAAGAAGAAGAATTAAAAAGACAAGAACAAGAACGACTAC

AAAAAGAAGAAGCATTAAAAAGACAAGAACAAGAACGACTACAAAAAGAA

GAAGAATTAAAAAGACAAGAGCAAGAAAGGCTGGAAAGAGAGAAACAAGA

ACAACTACAAAAAGAAGAAGAATTAAAAAGACAAGAACAAGAACGACTAC

AAAAAGAAGAAGCATTAAAAAGACAAGAACAAGAACGACTACAAAAAGAA

GAAGAATTAAAAAGACAAGAGCAAGAAAGACTGGAAAGAAAGAAAATCGA

GTTAGCAGAAAGAGAACAACACATAAAAAGTAAACTAGAATCTGATATGG

TGAAAATAATAAAGGATGAACTAACAAAAGAAAAAGATGAAATAATAAAA

AACAAAGATATAAAACTTAGACATAGTTTGGAACAGAAATGGTTAAAACA

TTTACAAAATATATTATCGTTAAAAATAGATAGTCTATTAAATAAAAATG

ATGAGGTCATAAAAGATAATGAGACACAATTGAAAACAAATATATTGAAC

TCATTAAAAAATCAATTATATCTTAATTTGAAACGTGAACTTAATGAAAT

TATAAAGGAATACGAAGAAACCAGAAAAAAATATTGCATTCAAATCAAC

TTGTTAACGATAGTTTAGAGCAAAAAACTAATAGACTCGTCGATATTAAA

CCTACAAAGCATGGTGATATATATACTAATAAACTTTCTGATAATGAAAC

TGAAATGCTGATAACATCTAAAGAAAAAAAGATGAAACAGAATCAACTA

AAAGATCAGGAACAGATCATACTAATAGTTCGGAAAGTACTACTGATGAT

-continued

AATACCAATGATAGAAATTTTTCTCGATCAAAGAATTTGAGTGTTGCTAT

ATACACAGCAGGAAGTGTAGCTTTATGTGTGTTAATATTTTCTAGTATAG

GATTATTACTTATAAAGACTAATAGTGGAGATAACAATTCTAATGAAATT

AATGAAGCTTTTGAACCGAATGATGATGTTCTCTTTAAGGAGAAGGATGA

AATCATTGAAATCACTTTTAATGATAATGATAGTACAATTTAA

The nucleotide sequence of Rh1 is given below (SEQ ID NO: 27)

ATGCAAGGTGGATTTTCTGCAACATTGTTTTGCATATATTAATTTACTT

AGCAGAATTTAGCCATGAACAGGAAAGTTATTCTTCCAATGAAAAATAA

GAAAGGACTATTCAGATGATAATAATTATGAACCTACCCCTTCATATGAA

AAAAGAAAAAAAGAATATGGAAAAGATGAAAGTTATATAAAAAATTACAG

AGGTAATAATTTTTCCTATGATTTGTCTAAAAATTCTAGTATATTTCTTC

ACATGGGTAACGGTAGTAACTCGAAAACACTAAAAAGATGTAACAAGAAA

AAAAATATAAAGACCAATTTTTTAAGACCTATCGAGGAAGAGAAAACGGT

ATTAAATAATTATGTATATAAAGGTGAAATTTTTTAGATACAATAAAAA

GAAATGATTCCTCTTATAAATTTGATGTTTATAAAGATACTTCCTTTTTA

AAAAAATAGAGAATATAAAGAATTAATTACTATGCAGTATGATTATGCTTA

TTTAGAAGCAACAAAAGAGGTTCTTTATTTAATTCCGAAGGATAAAGATT

ATCACAAATTTTATAAAAATGAACTTGAGAAAATTCTTTTCAATTTAAAA

GATTCACTTAAATTATTAAGAGAAGGATATATACAAAGCAAACTGGAAAT

GATTAGAATCCATTCGGATATAGATATATTAAATGAGTTTCATCAAGGAA

ATATTATAAACGATAATTATTTTAATAATGAAATAAAAAAAAAAAAAGGAA

GACATGGAAAAATATATAAGAGAATATAATTTATACATATATAAATATGA

AAATCAGCTTAAAATAAAAATACAGAAATTAACAAATGAAGTTTCTATAA

ATTTAAATAAATCTACATGTGAAAAGAATTGTTATAATTATATTTTAAAA

TTAGAAAAATATAAAAATATAATAAAAGATAAGATAAATAAATGGAAAGA

TTTACCAGAAATATATATTGATGATAAAAGTTTCTCATATACATTTTTAA

AAGATGTAATAAATAATAAGATAGATATATATAAACAATAAGTTCTTTT

ATATCTACTCAGAAACAATTATATTATTTTGAATATATATATATAATGAA

TAAAAATACATTAAACCTACTTTCATATAATATACAAAAAACAGATATAA

ATTCTAGTAGTAAATACACATATACAAAATCTCATTTTTTAAAAGATAAT

CATATATTGTTATCTAAATATTATACTGCCAAATTTATTGATATCCTAAA

TAAAACATATTATTAATTTATATAAAAATAAAATTCTTTTATTCAATA

AATATATTATAAAGCTTAGAAACGATTTAAAAGAATATGCATTTAAATCT

ATACAATTTATTCAAGATAAAATCAAAAAACATAAAGATGAATTATCCAT

AGAAAATATATTACAAGAAGTTAATAATATATATAAAATATGATACTT

CGATAAATGAAATATCTAAATATAACAATTTAATTATTAATACTGATTTA

CAAATAGTACAACAAAAACTTTTAGAAATCAAACAAAAAAAAAATGATAT

TACACACAAAGTACAACTTATAAATCATATATATAAAAATATACATGATG

AAATATTAAACAAAAAAAATAATGAAATAACAAAGATTATTATAAATAAT

ATAAAAGATCATAAAAAAGATTTACAAGATCTCTTACTATTTATACAACA

-continued

AATCAAACAATATAATATATTAACAGATCATAAAATTACACAATGTAATA

ATTATTATAAGGAAATCATAAAAATGAAAGAAGATATAAATCATATTCAT

ATATATATACAACCAATTCTAAATAATTTACACACATTAAAACAAGTACA

AAATAATAAAATCAAATATGAAGAGCACATCAAACAAATATTACAAAAAA

TTTATGATAAAAAGGAATCTTTAAAAAAAATTATTCTCTTAAAAGATGAA

GCACAATTAGACATTACCCTCCTCGATGACTTAATACAAAAGCAAACAAA

AAAACAAACACAAACACAAACACAAACACAAAAACAAACACTAATACAAA

ATAATGAGACGATTCAACTTATTTCTGGACAAGAAGATAAACATGAATCC

AATCCATTTAATCATATACAAACCTATATTCAACAAAAGATACACAAAA

TAAAAACATCCAAAATCTTCTTAAATCCTTGTATAATGGAAATATTAACA

CATTCATAGACACAATTTCTAAATATATATTAAAACAAAAAGATATAGAA

TTAACACAACACGTTTATACAGACGAAAAAATTAATGATTATCTTGAAGA

AATAAAAAATGAACAAAACAAAATAGATAAGACCATCGACGATATAAAAA

TACAAGAAACATTAAAACAAATAACTCATATTGTTAACAATATAAAAACC

ATCAAAAAGGATTTGCTCAAAGAATTTATTCAACATTTAATAAAATATAT

GAACGAAAGATATCAGAATATGCAACAGGGTTATAATAATTTAACAAATT

ATATTAATCAATATGAAGAAGAAAATAATAATATGAAACAATATATTACT

ACCATACGAAATATCCAAAAAATATATTATGATAATATATATGCTAAGGA

AAAGGAAATTCGCTCGGGACAATATTATAAGGATTTTATCACATCAAGGA

AAAATATTTATAATATAAGGGAAAATATATCCAAAAATGTAGATATGATA

AAAAATGAAGAAAGAAGAAAATACAGAATTGTGTAGATAAATATAATTC

TATAAAACAATATGTAAAAATGCTTAAAAATGGAGACACACAAGATGAAA

ATAATAATAATAATAATGATATATACGACAAGTTAATTGTCCCCCTTGAT

TCAATAAAACAAAATATCGATAAATACAACACAGAACATAATTTTATAAC

ATTTACAAATAAAATAAATACACATAATAAGAAGAACCAAGAAATGATGG

AAGAATTCATATATGCATATAAAAGGTTAAAAATTTTAAAAATATTAAAT

ATATCCTTAAAAGCTTGTGAAAAAAATAATAAATCTATCAATACATTAAA

TGACAAAACACAAGAATTAAAAAAAATTGTAACACACGAAATAGATCTTC

TACAAAAAGATATTTTAACAAGTCAAATATCAAATAAAAATGTTTTATTA

TTAAACGATTTATTAAAAGAAATTGAACAATATATTATAGATGTACACAA

ATTAAAAAAAAAATCAAACGATCTATTTACATATTATGAACAATCCAAAA

ATTATTTCTATTTTAAAAACAAAAAAGATAATTTTGATATACAAAAAACA

ATCAATAAAATGAATGAATGGCTAGCTATCAAAAATTATATAAATGAAAT

TAATAAAAATTATCAAACATTATATGAAAAAAAAATAAATGTACTCCTAC

ATAATTCAAAAAGTTATGTACAATACTTTTATGATCATATAATAAATCTA

ATTCTTCAAAAAAAAATTATTTGGAAAATACTTTAAAGACAAAAATACA

AGATAACGAACATTCACTATATGCTTTACAACAAAATGAAGAATACCAAA

AGGTAAAGAACGAAAAGGATCAAAACGAAATTAAGAAAATTAAACAATTA

ATCGAAAAAATAAAAATGATATACTTACATATGAAAACAACATTGAACA

AATTGAACAAAAAAATATTGAGTTAAAAACAAATGCTCAAAATAAGGATG

ATCAAATAGTAAATACCTTAAATGAGGTTAAGAAAAAAATAATATATACA

-continued

TATGAAAAGGTAGATAATCAAATATCGAACGTTTTAAAAAATTATGAAGA

AGGAAAAGTAGAATATGATAAAAATGTTGTACAAAATGTTAACGATGCGG

ATGATACAAACGATATTGATGAAATAAACGATATTGATGAAATAAACGAT

ATTGATGAAATAAACGATATTGATGAAATAAACGATATTGATGAAATAAA

AGACATTGACCATATAAAACATTTTGACGATACAAAACATTTTGACGATA

TATACCATGCTGATGATACACGTGATGAATACCATATAGCCCTTTCAAAT

TATATAAAGACAGAACTAAGAAATATAAACCTGCAAGAAATAAAAAACAA

TATAATAAAATATTTAAAGAATTCAAATCTGCACACAAAGAAATTAAAA

AAGAATCAGAACAAATTAATAAAGAATTTACCAAAATGGATGTCGTCATA

AATCAATTAAGAGATATAGACAGACAAATGCTTGATCTTTATAAAGAATT

AGATGAAAAATATTCTGAATTTAATAAAACAAAAATTGAAGAAATAAATA

ATATAAGGGAAAATATTAATAATGTGGAAATATGGTATGAAAAAAATATA

ATTGAATATTTCTTACGTCATATGAATGATCAAAAAGATAAAGCTGCAAA

ATATATGGAAAACATTGATACATATAAAAATAATATTGAATTATTAGTA

AACAAATAAATCCAGAAAATTATGTTGAAACATTAAACAAATCAAATATG

TATTCTTATGTAGAAAAGGCTAATGATCTATTTTATAAACAAATAAATAA

TATAATCATAAATTCAAATCAACTAAAAAACGAAGCTTTTACAATAGATG

AATTACAAAATATTCAAAAAAACAGAAAAAATCTTCTTACAAAGAAACAA

CAAATTATTCAGTATACAAATGAAATAGAAAATATATTTAATGAAATTAA

AAATATTAATAACATATTAGTCTTAACAAATTATAAATCTATCCTTCAAG

ATATATCACAAAATATAAATCATGTTAGTATATATACGGAACAATTACAT

AATTTATATATAAAATTAGAAGAAGAAAAAGAACAAATGAAAACACTCTA

TCATAAATCAAATGTGTTACATAACCAAATTAATTTTAATGAAGATGCTT

TTATTAATAATTTATTAATTAATATAGAAAAAATTAAAAATGATATTACA

CATATAAAGGAAAAAACAAATATATATATGATAGATGTAAACAAATCTAA

AAATAATGCTCAACTATATTTTCATAATACACTAAGAGGTAATGAAAAAA

TAGAATATTTAAAAAATCTTAAGAATTCAACAAACCAACAAATAACTTTA

CAAGAATTAAAACAAGTACAAGAAAATGTTGAGAAGGTAAAAGATATATA

CAATCAAACTATAAAATATGAAGAAGAAATTAAAAAAAATTATCATATTA

TAACAGATTATGAGAATAAAATAAATGATATTTTACATAATTCATTTATT

AAACAAATAAATATGGAATCTAGCAATAATAAAAAACAAACAAAACAAAT

TATAGACATAATAAACGATAAAACATTTGAAGAACATATAAAAACATCCA

AAACCAAAATAAACATGCTAAAAGAACAATCACAAATGAAACATATAGAC

AAAACTTTATTAAATGAACAAGCACTCAAATTATTTGTAGATATTAATTC

TACTAATAATAATTTAGATAATATGTTATCTGAAATAAATTCTATACAAA

ATAATACATACATATATCCAAGAAGCAAACAAATCATTTGACAAATTT

AAAATTATATGTGATCAAAATGTAAACGATTTATTAAACAAATTAAGTTT

AGGAGATCTAAATTATATGAATCATTTAAAAAAATCTGCAAAACGAAATAA

GAAACATGAATCTAGAAAAAAATTTCATGTTAGATAAAAGTAAAAAAATA

GATGAGGAAGAAAAAAAATTAGATATATTAAAAGTTAACATATCAAATAT

```
AAATAATTCTTTAGATAAATTAAAAAAATATTACGAAGAAGCGCTCTTTC
AAAAGGTTAAAGAAAAAGCAGAAATTCAAAAGGAAAATATAGAAAAAATA
AAACAAGAAATAAATACACTGAGCGATGTTTTAAGAAACCATTTTTTTT
TATACAACTTAATACAGATTCATCACAACATGAAAAAGATATAAACAATA
ATGTAGAAACATATAAAAATAATATAGATGAAATATATAATGTTTTATA
CAATCATATAATTTAATACAAAAATATTCTTCAGAAATTTTTTCATCCAC
CTTGAATTATATACAAACAAAAGAAATAAAAGAAAAATCCATAAAGGAAC
AAAACCAATTAAATCAAAATGAAAAGGAAGCATCTGTTTTATTAAAAAAT
ATAAAAATAAATGAAACCATAAAATTATTTAAACAAATAAAAAATGAAAG
ACAAAACGATGTACACAATATAAAAGAGGACTATAACTTGTTACAACAAT
ATTTAAATTATATGAAAATGAAATGGAACAATTAAAAAAATATAAAAAT
GATGTTCATATGGATAAAAATTATGTTGAAAATAATAATGGTGAAAAGA
AAAATTACTTAAAGAAACCATTTCTTCATATTATGATAAAATAAATAATA
TAAATAATAAGCTATATATATATAAAAACAAAGAAGACACTTATTTTAAT
AATATGATCAAAGTATCAGAAATTTTAAACATAATTATAAAAAAAAAACA
ACAAAATGAACAAAGAATTGTTATAAATGCAGAATATGACTCTTCATTAA
TTAATAAGGATGAAGAAATTAAAAAAGAAATTAATAATCAAATAATTGAA
TTAAATAAACATAATGAAAATATTTCCAATATTTTTAAGGATATACAAAA
TATAAAAAAACAAAGTCAAGATATTATCACAAATATGAACGACATGTATA
AAAGTACAATCCTTTTAGTAGACATCATACAGAAAAAAGAAGAAGCTCTA
AATAAACAAAAAAATATTTTAAGAAATATAGACAATATATTAAATAAAAA
AGAAAATATTATAGATAAAGTTATAAAATGTAATTGTGATGATTATAAAG
ATATCTTAATACAAAACGAAACGGAATATCAAAAATTACAAAATATAAAT
CATACATATGAAGAAAAAAAAAATCAATAGATATATTAAAAATTAAAAA
TATAAAACAAAAAAATATTCAAGAATATAAAAACAAATTAGAACAAATGA
ATACAATAATTAATCAAAGTATAGAACAACATGTATTCATAAACGCTGAT
ATTTTACAAAATGAAAAATAAAATTAGAAGAAATCATAAAAAATCTAGA
TATACTAGATGAACAAATTATGACATATCATAATTCAATAGATGAATTAT
ATAAACTAGGAATACAATGTGACAATCATCTAATTACAACTATTAGTGTT
GTTGTTAATAAAAATACAACAAAAATTATGATACATATAAAAAACAAAA
AGAGGATATACAAAAAATTAATAACTATATTCAAACAAATTATAATATAA
TAAATGAAGAAGCTCTACAATTTCACAGGCTCTATGGACACAATCTTATA
AGTGAAGATGACAAAAATAATTTGGTACATATTATAAAAGAACAAAAGAA
TATATATACACAAAAGGAAATAGATATTTCTAAAATAATTAAACATGTTA
AAAAAGGATTATATTCATTGAATGAACATGATATGAATCATGATACACAT
ATGAATATAATAAATGAACATATAAATAATAATATTTTACAACCATACAC
ACAATTAATAAACATGATAAAAGATATTGATAATGTTTTTATAAAAATAC
AAAATAATAAATTCGAACAAATACAAAAATATATAGAAATTATTAAATCT
TTAGAACAATTAAATAAAAATATAAACACAGATAATTTAAATAAATTAAA
AGATACACAAAACAAATTAATAAATATAGAAACAGAAATGAAACATAAAC
AAAAACAATTAATAAACAAAATGAATGATATAGAAAAGGATAATATTACA
GATCAATATATGCATGATGTTCAGCAAAATATATTTGAACCTATAACATT
AAAAATGAATGAATATAATACATTATTAAATGATAATCATAATAATAATA
TAAATAATGAACATCAATTTAATCATTTAAATAGTCTTCATACAAAAATA
TTTAGTCATAATTATAATAAAGAACAACAACAAGAATATATAACCAACAT
CATGCAAAGAATTGATGTATTCATAAATGATTTAGATACTTACCAATATG
AATATTATTTTTATGAATGGAATCAAGAATATAAACAAATAGACAAAAAT
AAAATAAATCAACATATAAACAATATTAAAAATAATCTAATTCATGTTAA
GAAACAATTTGAACACACCTTAGAAAATATAAAAAATAATGAAAATATTT
TCGACAACATACAATTGAAAAAAAAGATATTGACGATATTATTATAAAC
ATTAATAATACAAAAGAAACATATCTAAAAGAATTGAACAAAAAAAAAAA
TGTTACAAAAAAAAAAAAAGTTGATGAAAATCAGAAATAAATAATCATC
ACACATTACAACATGATAATCAAAATGTTGAACAAAAAAATAAAATTAAA
GATCATAATTTAATAACCAAGCCAAATAACAATTCATCAGAAGAATCTCA
TCAAAATGAACAAATGAAAGAACAAAACAAAAATATACTTGAAAAACAAA
CAAGAAATATCAAACCACATCATGTTCATAATCATAATCATAATCATAAT
CAAAATCAAAAAGATTCAACAAAATTACAGGAACAAGATATATCTACACA
CAAATTACATAATACTATACATGAGCAACAAAGTAAAGATAATCATCAAG
GTAATAGAGAAAAAAAACAAAAAAATGGAAACCATGAAAGAATGTATTTT
GCCAGTGGAATAGTTGTATCCATTTTATTTTTATTTAGTTTTGGATTTGT
TATAAATAGTAAAAATAATAAACAAGAATATGATAAAGAGCAAGAAAAAC
AACAACAAAATGATTTTGTATGTGATAATAACAAAATGGATGATAAAAGC
ACACAAAAATATGGTAGAAATCAAGAAGAGGTAATGGAGATATTTTTTGA
TAATGATTATATTTAA
```

As a matter of routine, the skilled person will be able to identify the regions of the above nucleic acid molecules that encode the specific regions described for the Rh and EBA proteins described elsewhere herein. The present invention includes those specific nucleotide subsequences, and any alterations that are available by virtue of the degeneracy of the genetic code. Furthermore, the invention provides nucleic acid which can hybridise to these nucleic acid molecules, preferably under "high stringency" conditions (e.g. 65° C. in a 0.1×SSC, 0.5% SDS solution). Nucleic acid according to the invention can be prepared in many ways (e.g. by chemical synthesis, from genomic or cDNA libraries, from the organism itself, etc.) and can take various forms (e.g. single stranded, double stranded, vectors, probes, etc.). They are preferably prepared in substantially pure form (i.e. substantially free from other Plasmodial or host cell nucleic acids).

A further aspect of the present invention provides a method of screening for the presence of a *Plasmodium falciparum* invasion-inhibitory antibody directed against reticulocyte-binding homologue protein 5 (the invasion ligand) of a strain of *Plasmodium falciparum* in a subject, comprising obtaining a biological sample from the subject and identifying the presence or absence of an antibody capable of binding to an immunogenic molecule as described herein.

The invention also provides a process for producing an immunogenic molecule of the invention, comprising the step of culturing a host cell transformed with a nucleic acid as described herein under conditions which induce polypeptide expression. The isolated nucleic acid molecule is suitable for expressing a polypeptide immunogenic molecule of the invention. By 'suitable for expressing' is meant that the nucleic acid molecule is a polynucleotide that may be translated to form the polypeptide, for example RNA, or that the polynucleotide (which is preferably DNA) encoding the polypeptide of the invention is inserted into an expression vector, such as a plasmid, in proper orientation and correct reading frame for expression. The polynucleotide may be linked to the appropriate transcriptional and translational regulatory control nucleotide sequences recognised by any desired host; such controls may be incorporated in the expression vector.

The nucleic acid molecule (or polynucleotide) may be expressed in a suitable host to produce a polypeptide of the invention. Thus, the polynucleotide encoding the polypeptide of the invention may be used in accordance with known techniques, appropriately modified in view of the teachings contained herein, to construct an expression vector, which is then used to transform an appropriate host cell for the expression and production of a polypeptide of the invention The nucleic acid molecule encoding the polypeptide of the invention may be joined to a wide variety of other polynucleotide sequences for introduction into an appropriate host. The companion polynucleotide will depend upon the nature of the host, the manner of the introduction of the polynucleotide into the host, and whether episomal maintenance or integration is desired.

Generally, the nucleic acid molecule is inserted into an expression vector, for example a plasmid, in proper orientation and correct reading frame for expression. If necessary, the nucleic acid molecule may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a polynucleotide sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant nucleic acid molecule of the invention are then cultured for a sufficient time and under appropriate conditions known to those skilled in the art in view of the teachings disclosed herein to permit the expression of the polypeptide, which can then be recovered. Many expression systems are known, including bacteria (for example *E. coli* and *Bacillus subtilis*), yeasts (for example *Saccharomyces cerevisiae*), filamentous fungi (for example *Aspergillus*), plant cells, animal cells and insect cells. The peptides of the present invention may also be produced in Apicomplexa, for example, *Plasmodium falciparum*.

The vectors typically include a prokaryotic replicon, such as the ColEI ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith. Promoter sequences compatible with exemplary bacterial hosts are typically provided in plasmid vectors containing convenient restriction sites for insertion of a polynucleotide of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (Yips) and incorporate the yeast selectable markers HIS3, TRPI, LEU2 and URA3. Plasmids pRS413-416 are Yeast Centromere plasmids (YCps).

Useful vectors for transformation and/or expression in *Plasmodium falciparum* include pHC1, pHC2, pHC3, pHD22Y, pHC4, pHC5, pTgDTS.CAM5/3.KP, pHHT-TK and pHH1, and derivatives thereof. Other suitable vectors include those deposited at the Malaria Research and Reference Reagent Resource Center.

The present invention also relates to a host cell transformed with a polynucleotide vector construct of the present invention. The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., USA, and RRI available from the American Type Culture Collection (ATCC) of Rockville, Md., USA (No ATCC 31343). Preferred eukaryotic host cells include yeast, insect and mammalian cells, vertebrate cells such as those from a mouse, rat, monkey or human fibroblastic and kidney cell lines, and Apicomplexan cells. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-I cells available from the ATCC as CRL 1650 and 293 cells which are human embryonic kidney cells. Preferred insect cells are Sf9 cells which can be transfected with baculovirus expression vectors. Apicomplexan cells may include *Plasmodium falciparum* cell lines, such as a wild-type strain of P falciparum, or any of the following strains: 3D7, W2MEF, GHANA1, V1_S, RO-33, PREICH, HB3, SANTALUCIA, 7G8, SENEGAL3404, FCC-2, K1, RO-33, D6, DD2, or D10. Further suitable include those deposited at the Malaria Research and Reference Reagent Resource Center.

Transformation of appropriate cell hosts with a nucleic acid molecule of the present invention is accomplished by well known methods that typically depend on the type of vector used. With regard to transformation of prokaryotic host cells, see for example Sambrook & Russell (supra). Transformation of yeast cells is described in numerous reviews, for example see Gietz & Woods (2001) Biotechniques 30:816-228. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming and/or transfecting cells and is well known in the art for transforming yeast cell, bacterial cells, insect cells and vertebrate cells. For example, many bacterial species may be transformed by the methods described in Luchansky et al. (1988) Mol. Microbiol. 2:637-646. Methods for transformation of yeast by electroporation are disclosed in Becker & Guarente (1990) Methods Enzymol. 194:182.

Successfully transformed cells, i.e. cells that contain a nucleic acid molecule of the present invention, can be identified by well known techniques. For example, cells resulting from the introduction of an expression construct of the present invention can be grown to produce the polypeptide of the invention. Cells can be harvested and lysed and their DNA content examined for the presence of the DNA. Alternatively, the presence of the protein in the supernatant can be detected using antibodies.

In addition to assaying directly for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, a further aspect of the invention provides a vector comprising a nucleic acid molecule according as described above. The vector may be an expression vector. The vector is suitable for replication in a eukaryotic cell, such as a mammalian cell. Preferred vectors may be selected from the group consisting of pBudCE4.1 pTWIN, pShuttle, pUC18, pUC19, pBacPAK, pBR322, pBR329, pTrc99A, pKK223-3, pSVL, pMSG, pRS403 to 406, pRS413 to 416 and pPicZalpha.

A further aspect of the invention provides a host cell comprising a nucleic acid molecule as described above or a vector described above. The host cell may be a prokaryotic or a eukaryotic cell, for example a mammalian cell or a *Plasmodium falciparum* cell. The host cell may selected from the group consisting of *E. coli* strain DH5, RR1, ER2566, CHO cells (e.g. CCL61), NIH Swiss mouse embryo cells (NIH/3T3), COS-I cells (e.g. CRL 1650 and 293), Sf9 cells and yeast cell lines YPH499 to 501, or *Pichia Pastoris* such as KM71H.

In addition to the transformed host cells themselves, the present invention also contemplates a culture of those cells, preferably a monoclonal (clonally homogeneous) culture, or a culture derived from a monoclonal culture, in a nutrient medium.

The present invention will now be more fully described by reference to the following non-limiting Examples.

EXAMPLE 1

Materials and Methods

Sequence Analysis of Invasion Ligand.

Preparation of genomic DNA from 3D7, BT3, D10, HB3, MCAMP and PF120 was performed using standard techniques. The invasion ligand gene (minus the first exon encoding the signal peptide) was amplified from genomic DNA using the primers: _GeneF: 5'-CAGGATTAAGTTTTGAAAATGC-3' (SEQ ID NO: 28) and _GeneR: 5'-CCATGTTTTGTCATTTCATTG-3' (SEQ ID NO: 29) and sequenced using two additional primers _MidF 5'- GATGAT-GAAACCGAAGAG-3' (SEQ ID NO: 30) and _MidR 5'-CTGTATCTTGTATACTATC-3' (SEQ ID NO: 31). sequencing was performed using BigDye® Terminator Cycle sequencing (PerkinElmer). Single variant polymorphisms were verified by re-sequencing to avoid incorporation of polymerisation errors.

Parasite Cell Culture.

*P. falciparum* asexual parasites were maintained in human erythrocytes (blood group O+) at a hematocrit of 4% with 10% Albumax™ II (Gibco). 3D7 was originally obtained from David Walliker at Edinburgh University. Cultures were synchronized using standard techniques.

Invasion Inhibition Assays.

Methods for measuring invasion-inhibitory antibodies in serum samples have been described and evaluated in detail elsewhere [Persson, et al. J. Clin. Microbiol. (2006) 44:1665-1673]. *Plasmodium falciparum* lines are cultured in vitro as described [Beeson et al (1999) J. Infect. Dis. 180:464-472]. Synchronized (by 5% D-sorbitol) parasites are cultured with human O+ erythrocytes in RPMI-HEPES medium with hypoxanthine 50 µg/ml, NaHCO3 25 mM, gentamicin 20 µg/ml, 5% v/v heat-inactivated pooled human Australian sera, and 0.25% Albumax II (Gibco, Invitrogen, Mount Waverley, Australia) in 1% O2, 4% CO2, and 95% N2 at 37° C. Invasion inhibition assays are started at late pigmented trophozoite to schizont stage. Inhibitory activity is measured over two cycles of parasite replication. Starting parasitemia is 0.2-0.3%, hematocrit 1%, and cells are resuspended in RPMI-HEPES supplemented as described above. Assays are performed in 96-well U-bottom culture plates (25 µl of cell suspension+2.5 µl of test sample/well). All samples are tested in duplicate. After 48 hours, 5 µl of fresh culture medium is added. Parasitemia is determined by flow cytometry (FACS-Calibur, Becton Dickinson, Franklin Lakes, N.J.) after 80-90 hours using ethidium bromide (10 µg/ml, Bio-Rad, Hercules, Calif., USA) to label parasitised erythrocytes. Incubation time is influenced by the stage and synchronicity of parasite cultures at commencement of the assay, and by the length of the lifecycle of the parasite line used. Inhibitory effects of treated samples are confirmed by testing immunoglobulin purified from the same samples. All serum samples tested for inhibitory antibodies are first treated to remove non-specific inhibitors that may be present and to equilibrate pH [Persson, et al. J. Clin. Microbiol. (2006) 44:1665-1673]. Serum samples (100 µl) are dialyzed against phosphate-buffered saline (PBS; pH 7.3) in 50 kDa MWCO microdialysis tubes (2051, Chemicon, Temecula, Calif., USA) and subsequently re-concentrated to the original starting volume using centrifugal concentration tubes (100 kDa MWCO; Pall Corp., Ann Arbor, Mich., USA). Analysis of flow cytometry data is performed using FlowJo software (Tree Star Inc., Ashland, Oreg., USA). Samples from non-exposed donors are included as negative controls in all assays, and e.g. anti-MSP1 and/or anti-AMA1 antibodies are used as a positive control. Samples are tested for inhibition of the different lines in parallel in the same experiments. A difference between the lines of ≥25% in invasion is designated as the cut-off for differential inhibition by samples. A selection of sera was is tested for antibodies to the surface of uninfected erythrocytes (maintained in culture) by flow cytometry [Beeson et al (1999) J. Infect. Dis. 180: 464-472]; to determine reactivity against normal erythrocytes. *P. falciparum* merozoite invasion may be captured following treatment with 0.1 µM cytochalasin D to arrest invasion.

Growth Inhibition Assays

Inhibition assays were performed as described previously (Thompson et al, (2001), Mol. Microbiol. 41: 47-58. and Baum et al., (2005), PLoS Pathog. 1: e37) in triplicate at 4% haematocrit with 0.5% parasitemia. IgG purified rabbit anti-invasion ligand-2 or normal pre-immunisation serum (NRS) was added to 2 mg/ml in PBS. Assays were repeated at least three times to calculate mean and standard error of invasion inhibition relative to the NRS control (100%).

Enzyme Treatment of Erythrocytes.

Erythrocytes were first washed with RPMI-HEPES/25 mM NaHCO3, pH7.4, and subsequently incubated with neurminidase (0.067 units/ml; Calbiochem, 45 min) or chymotrypsin (1 mg/ml; Worthington Biochemical, 15 min) at 37° C. Control treatment was RPMI-HEPES only. After incubation, chymotrypsin-treated cells were washed once with RPMI-HEPES containing 20% human serum and twice with normal culture medium (containing 5% serum) to inhibit enzyme activity. The neurminidase-treated cells were washed with parasite culture medium three times. Treated erythrocytes were then used in invasion inhibition assays as described. All results presented are comparisons to control-treated cells.

Antisera, SDS/PAGE and Immunoblot Analysis of the Invasion Ligand.

Rabbit and mouse antisera were raised against the invasion ligand. A recombinant protein covering a central region of the invasion ligand (residues N191 to H359) using the following primers: 2F 5'-GATCggatccAATTCTATATATCAT-AAGTCCTC-3' (SEQ ID NO: 32) and 2R 5'-GATCctcgagT-TAATGATATCTTATTCCGTTTG-3' (SEQ ID NO: 33). PCR products were treated with BamHI/XhoI (small case letters underscored in primers), purified, and cloned into pGEX 4T-1 (Pharmacia Biotech). This was transformed into E. coli (strain BL21(DE3)) with positive colonies screened for protein expression. The expressed, soluble, fusion protein was affinity-purified on glutathione agarose, then used to immunize rabbits and mice. The anti—the invasion ligand antibodies were affinity-purified on the immunizing fusion protein coupled to Sepharose4B and used for indirect immunofluorescence microscopy (IFA) and immunoblots.

For immunoblots, saponin lysed parasite pellets from highly synchronous 3D7 parasites (samples taken at 8 hour intervals through the lifecycle), 3D7, D10 or transfectant parasite schizont pellets or culture supernatants (post schizont rupture) for any of the other lines were separated in sample buffer on 4-12% SDS-NuPAGE gels (Invitrogen) under reducing conditions and transferred to nitrocellulose membranes (Schleicher & Schuell). Invasion ligand rabbit polyclonal and mouse monoclonal antisera (clone 6H2) were diluted in 0.1% Tween20-PBS with 1% wt/vol skim milk [1:200 and 1:500 respectively]. Appropriate secondary antibodies were used and immunoblots were developed by enhanced chemiluminescence (ECL, Amersham Biosciences).

Invasion Ligand Vector Construction and Transfection.

C' terminal tagging of the invasion ligand with a Strep-tag II and triple Haemagluttinin (3*HA) tag was undertaken using a vector derived from pARL. Invasion ligand sequences were amplified using the primers 5'-GATCagatctCAT-GAGAATGATTTTAATAAAATATGTATGG-3' (SEQ ID NO: 34) and 5' GATCctgcagTTGTGTAAGTGGTT-TATTTTTTTTATATGTTTG-3' (SEQ ID NO: 35). was treated with BglII/PstII (small case letters underscored in primers), purified, and cloned into pARL-StrepII-3*HA (Pharmacia Biotech) generating p1.5-SHA.

Parasites were transfected as described previously with 100 μg purified plasmid DNA (QIAGEN). Positive selection for transfectants was achieved using 10 nM WR99210, followed by cycles on and off drug to select for integrants. After three cycles off drug parasites were screened with the invasion ligand antibodies and a commercial HA monoclonal (Roche Applied Science, clone 3F10) to test for successful integration of the tag.

Microscopy and Immunofluorescence for Localization of the Invasion Ligand.

Light microscopy was performed with synchronized parasites at various lifecycle stages. For indirect immunofluorescence, parasites were fixed for 5 minutes with 100% methanol at −20° C., blocked for 30 minutes in 3% Bovine Serum Albumin (BSA) in PBS then incubated for 1 hour with the relevant antisera (rabbit anti-invasion ligand [1:200]; rabbit anti-AMA1 [1:100]; rabbit anti-Rh2a/2b [1:100]; rabbit anti-PfRON4 [1:200]). Following 2×5 minute washes in 3% BSA-PBS, slides were incubated for 1 hour with appropriate Alexa Fluor 488/594 secondary antibodies (Molecular Probes) and mounted in Vectashield® (Vector Laboratories) with 10 ug/ml DAPI (Boehringer). Parasites for electron microscopy immunolabeling were fixed and prepared as described previously (Baum et al., 2008 Cell Host Microbe 3: 188-198). Samples were post-stained with 2% aqueous uranyl-acetate then 5% triple lead before observing at 120 kV on a Philips CM120 BioTWIN Transmission Electron Microscope.

Erythrocyte Binding Assays.

High percentage (3-5%) parasitemia cultures were grown until late stages (−36 hours post invasion) and transferred to medium depleted of Albumax™ II (Gibco). Post-schizont rupture, culture supernatant was centrifuged twice at 3000 rpm and store at 4° C. for use. 250 μl of culture supernatant was mixed with 50 μl of packed erythrocytes for 1 hr at room temperature. The erythrocytes were separated from supernatant by centrifugation through silicone oil dibutyl phthalate at 12000×g. Bound proteins were eluted by incubation with 10 μl 1.5 M NaCl for 15 minutes followed by centrifugation at 12000×g. Bound and unbound fractions were separated in sample buffer on 4-12% SDS-NuPAGE gels (Invitrogen) under reducing conditions and probed with relevant antibodies. To assess binding affinity an additional phosphate buffer solution (PBS) wash step was included before salt elution. Enzyme pre-treatments of erythrocytes were as described supra.

Heparin (sodium salt, porcine intestinal mucosa) or chondroitin sulfate C(CSC, from shark cartilage) were tested for their ability to inhibit the invasion ligand binding by pre-incubating concentrated culture supernatant at a dilution gradient of 0, 7, 71, 179 and 357 μg/ml (numbers relate to standard units of clinical grade heparin, in which 140U=1 mg) of either sugar. PBS was added to a final volume of 400 ul and the binding assay was repeated as described supra.

Heparin Column-binding Assay.

Heparin-agarose beads were washed once with 1% casein in PBS, once in PBS, and then blocked with 1% casein in PBS overnight at 4° C. Culture supernatants from ruptured 3D7 schizonts were concentrated 5-fold (Amicon Ultra Centrifugal Filter, 10 000MWCO (Millipore)) and incubated with beads containing 0.1% casein and 200 p g/mL of test inhibitor, or PBS as control, overnight at 4° C.; 50 μL of packed beads and 250 μL of culture supernatant were used for each test sample. Inhibitors used were heparin and CSC. Unbound proteins in the supernatant were collected through Micro Bio-Spin Chromatography Columns (Bio-Rad). After incubation, beads were washed 5 times with PBS containing 0.1% casein and 1% Triton-X100. Bound proteins were eluted from beads with 50 μL of warmed reducing sample buffer. Bound and unbound proteins were separated by SDS-PAGE under reducing conditions and blotted onto membranes for probing with antibody detection.

Expression and Refolding of Full-length the Invasion Ligand.

To generate a recombinant full-length the invasion ligand (the invasion ligand), a codon-optimised gene encoding the mature full-length invasion ligand (TOP Gene Technologies, Inc., Canada) was cloned into NdeI and BamH1 sites of pET14b vector (Novagen). The plasmid carrying the invasion ligand gene was then transformed into BL21 RIL cells for protein expression. The protein with hexa-His tag at the N-terminus was expressed in *E. coli* as an inclusion body, with soluble invasion ligand obtained by solubilizing with 6 M guanidine-HCl in 20 mM Tris, pH 8.0 containing 0.5 M NaCl and 10 mM Tcep. After centrifugation, the invasion ligand was purified from the clear supernatant by passing over Ni-resin (Qiagen) in the presence of guanidine-HCl. The purified invasion ligand was then refolded into PBS containing 10% glycerol, 1 mM reduced glutathione and 0.1 mM oxidized glutathione by dilution. After incubation at room temperature for three hours, the sample was centrifuged at 14,500 rpm at 4° C. for 5 minutes. The supernatant containing refolded invasion ligand was collected for experiments with the concentration of refolded protein ranging from 10 to 50 µg/mL.

Antibodies to Recombinant Proteins by ELISA.

96-well plates (Maxisorp, Nunc, Roskilde, Denmark) are coated with recombinant GST fusion proteins at 0.5 µg/ml in PBS overnight at 4° C. Plates are washed and blocked with 10% skim milk powder (Diploma, Rowville, Australia) in PBS Tween 0.05% for 2 hours. After washing, serum samples (100 µl/well in duplicate), at 1/500 dilution in PBS Tween 0.05% plus 5% skim milk, are incubated for two hours. Plates are washed and incubated for one hour with HRP-conjugated anti-human IgG at 1/5000 (Chemicon, Melbourne, Australia) in PBS Tween 0.05% plus 5% milk. After washing, colour is developed by adding OPhenylenediamine (Sigma, Castle Hill, Australia; stopped with concentrated sulphuric acid) or azino-bis(3-ethylbenthiazoline-6-sulfonic acid) liquid substrate system (Sigma-Aldrich, Sydney; stopped with 1% SDS) and absorbance read by spectrophotometry. All washes are performed with PBS containing 0.05% Tween 20, and all incubations are at room temperature. For each serum, the absorbance from wells containing GST only is deducted from the absorbance from EBA or Rh GST fusion proteins. Positive and negative controls are included on all plates to enable standardisation. Recombinant proteins used are the invasion ligand (e.g. amino acids 1 to 526) EBA140 (e.g. amino acids 746-1045), EBA175 W2mef and 3D7 alleles (e.g. amino acids 761-1271), EBA181 (e.g. amino acids 755-1339), Rh4 (e.g. amino acids 1160-1370), and Rh2 (e.g. amino acids 2027-2533). Schizonts are separated on a 60% Percoll gradient, washed three times in serum-free RPMI 1640, pelleted by centrifugation and resuspended. The cells are lysed through freeze-thawing and the supernatant is preserved. Antibody reactivity of a sample is considered positive if the O.D. was >mean+3SD of the nonexposed controls.

Study Population and Serum Samples.

Serum samples (50 adults and 100 children aged 14 years) are randomly selected from a community-based cross-sectional survey of children and adults resident in the Kilifi District, Kenya, in 1998, a year that was preceded with a relatively high incidence of malaria in the region. The area is endemic for *Plasmodium falciparum*. Samples are also obtained from non-exposed adult residents in Melbourne, Australia (n=20) and Oxford, UK (n=20). Ethical approval is obtained from the Ethics Committee of the Kenya Medical Research Institute, Nairobi, Kenya and from the Walter and Eliza Hall Institute Ethics Committee, Melbourne, Australia. All samples are obtained after written informed consent. All serum samples are tested for antibodies by ELISA. A subset of these samples is randomly selected for use in invasion inhibition assays. The same samples are used in all comparative inhibition assays.

Papua New Guinea Clinical Study.

206 children aged 5-14, resident in the Madang Province PNG, were enrolled and treated with artesunate to clear any existing parasitemia (Michon P., et al., AJTMH 2007). Children were screened every 2 weeks for the presence of blood-stage parasitemia or any signs or symptoms of clinical illness. Malaria episodes were also identified at participant-initiated visit to the local health clinic. Malaria episodes were defined as presence of fever or symptoms of fever together with a parasitemia of *P. falciparum* of greater than 5000 parasites/ul. Antibodies are measured to recombinant Rh and EBA proteins (as described above). Children are categorized into high, medium, or low responder groups to each antigen on the basis of terciles of rankings, and risk of malaria episodes from time zero to 6 months is calculated for each antibody group and plotted.

Statistical Analysis.

Statistical analyses are performed with SPSS and STATA software. The chi squared test or Fischer's exact test is used for comparisons of proportions. For comparisons of continuous variables, Mann-Whitney U test or Kruskal-Wallis tests are used for non-parametric data, and t-tests or ANOVA were used for normally-distributed data, as appropriate. Associations between antibodies to recombinant antigens by ELISA and invasion-inhibitory antibodies are examined by two approaches. Tests are for correlations between ELISA OD values and total invasion inhibition by samples, or the extent of differential inhibition of two comparison parasite lines, and the mean or median inhibition by samples grouped as high or low responders according to reactivity by ELISA is compared. For all analyses $p<0.05$ is classified as statistically significant.

EXAMPLE 2

Examination of Immune Selection of Invasion Ligand

Applicant identifies a *Plasmodium falciparum* immunogen invasion ligand which differs from other *falciparum* immunogens in that it is considerably smaller, with a predicted molecular weight of 62.5 kDa and importantly, lacks a C-terminal transmembrane domain.

To investigate whether the invasion ligand is a target for host-mediated positive selection, Applicant sequenced the entire gene in seven different laboratory strains. The sequences showed the presence of six non-synonymous (but no silent) polymorphisms, predominantly in the N-terminal half of the gene. The imbalance in substitutions that alter amino acid residues is indicates selection favouring diversity in the protein, indicating the invasion ligand elicits an immune response. Intriguingly, one of these polymorphisms is a non-conservative Cys to Tyr residue change (at position 203), which may have significant structural and functional implications. While no orthologues of the invasion ligand are identifiable in syntenic regions of mouse malaria genomes, Applicant identified an orthologue of the invasion ligand in the closely related chimpanzee parasite, *P. reichenowi*, suggesting that this locus evolved after the divergence of rodent and primate malaria parasites. The invasion ligand protein has six cysteine residues in the 3D7 and W2mef parasite lines, but only five (the first at position 203 being absent) in the other lines sequenced. While *P. reichenowi* invasion ligand (which has five cysteine residues) lacks Cys 329, it does however have an additional cysteine further towards the N-terminus, suggesting that not all of the cysteines are paired as disulphide bonds in the protein, with some (such as Cys 203 and 329) possibly unpaired or buried within the protein structure.

EXAMPLE 3

Invasion Ligand is Expressed in all *P. falciparum* Strains Tested and is Important for Parasite Survival In order to determine the temporal expression pattern and subcellular localisation of the invasion ligand Applicant raised polyclonal and monoclonal antibodies against a central fragment that incorporated six cysteine residues from 3D7 (FIG. 1C). Immunoblots using both the polyclonal and monoclonal antibodies identified a protein band of ~63 kDa, the predicted molecular weight of the invasion ligand, expressed predominantly in mature schizont stages (40-48 h) (FIG. 1C). Also observed was a smaller product of 45 kDa that likely corresponds to a processed fragment of full length invasion ligand (FIG. 1C).

Rh proteins show differential levels of expression and, for Rh2a/b, considerable amounts of size diversity across strains that have been analysed. While the invasion ligand gene from different *P. falciparum* strains does reveal a small number of polymorphisms no predicted differences in molecular weight are seen. To experimentally determine if the protein showed any marked differences in the level of expression or unexpected size diversity, Applicant performed immunoblots with culture supernatants from a diverse panel of parasite lines. The 45 kDa processed product was detected in all parasite strains tested and shows no expression level variation (FIG. 1D) consistent with it having an important function across all strains.

To address the function of the invasion ligand Applicant attempted to disrupt the gene in 3D7, W2mef, HB3 and D10 using the vector pCC1, a vector that has been used successfully to knock out several *P. falciparum* genes. Despite numerous attempts to derive lines lacking expression of the invasion ligand, the gene proved refractory to disruption. The gene can be targeted with similar plasmid constructs as long as the gene is reconstituted, as demonstrated by Applicant's ability to C-terminally tag the invasion ligand with a triple HA in both 3D7 and D10 (as discussed below). This suggests that the invasion ligand is important for parasite survival.

EXAMPLE 4

The Invasion Ligand Co-localizes with Apical Proteins and the Tight Junction During Invasion An apical subcellular localisation in the merozoite would be expected if the invasion ligand were involved in merozoite invasion. Immunofluorescence microscopy with anti-invasion ligand antibodies showed that the protein gives a speckled pattern in schizont stages and localizes at the apical end of the merozoites, probably in the rhoptries (FIG. 2A). In order to further characterise the invasion ligand, a Strep II and Haemagglutinin (HA) tag was inserted at the 3' end of the invasion ligand gene by homologous recombination in frame with the last amino acid of the protein to derive parasite lines 3D7-invasion ligandHA and D10-invasion ligandHA (FIG. 2B). Immunoblots with culture supernatant from the transgenic lines 3D7-invasion ligandHA and D10-invasion ligandHA showed the invasion ligand protein, larger by approximately 5 kDa, when probed with anti-HA and the invasion ligand antibodies; consistent with successful tagging (FIG. 2C). Immunoprecipitation using anti-invasion ligand antibodies confirmed the tagging and specificity of the antibodies and, with the detection of the processed product, suggests that processing of the invasion ligand occurs at the N-terminus of the protein.

Figures 3A, 3B, 3C:
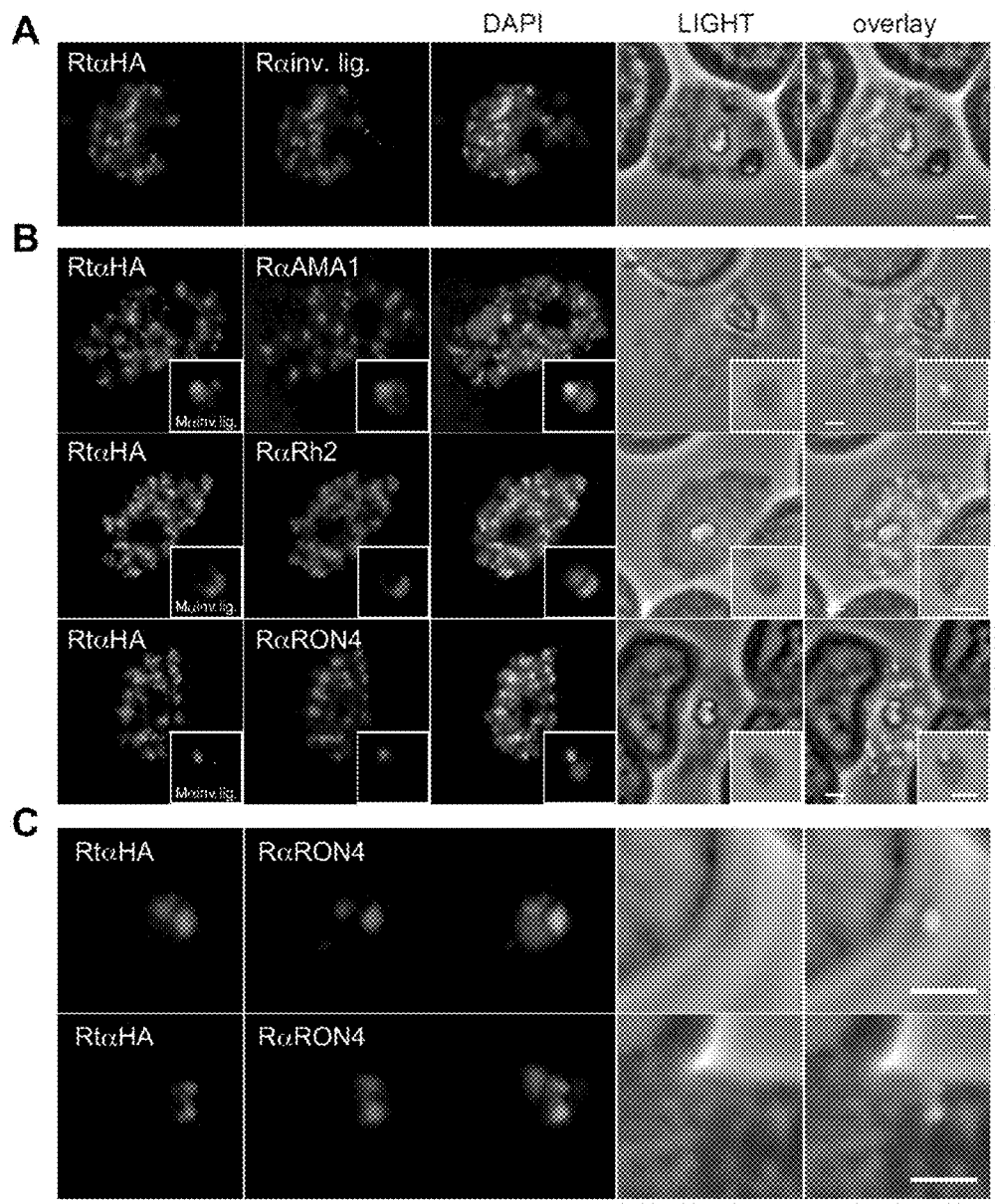
(FIG. 3A) Immunofluorescence and phase contrast micrographs of late segmented schizonts with anti-HA antibodies to detect the chimeric invasion ligand along with co-localisation using antibodies to invasion ligand. The panels from left to right are rat anti-HA, rabbit anti-invasion ligand, overlay of both with DAPI nuclear stain, phase contrast image and overlay of all images.
(FIG. 3B) Immunofluorescence and phase contrast images of late schizonts or free merozoites (insets) to co-localise invasion ligand with AMA1 (top panel), Rh2a/b (middle panel) and RON4 (bottom panel). Each panel from left top right corresponds to anti-HA antibodies (to detect invasion ligand), rabbit anti-AMA1 or anti-Rh2a/b or anti-RON4, overlay of each with DAPI nuclear stain, phase contrast and overlay of all images. Insets show individual merozoites.
(FIG. 3C) Co-localization of rat anti-HA with rabbit antisera against RON4 (a tight junction marker during invasion) in invading merozoites arrested using cytochalasin D. DAPI nuclear stain. Scale bars=1 μM.

To further localise the invasion ligand in schizont stages and during merozoite invasion, Applicant performed immunofluorescence on fixed parasites including probes to other proteins known to play a role in invasion (FIG. 3). Localisation of the anti-HA antibodies was identical to that observed for invasion ligand-specific antibodies, providing evidence that the tagged protein could be used to follow the protein during invasion (FIG. 3A and FIG. 7). The invasion ligand showed essentially no co-localisation with AMA1, suggesting it is not present within micronemes, the known subcellular localisation of AMA1 (FIG. 3B). In contrast, the orthologue Rh2a/b showed a very similar pattern of localisation with respect to the invasion ligand (FIG. 3B). Rh2a/b localises to the neck of the rhoptries by both immunofluorescence and immuno-electron microscopy suggesting that the invasion ligand is also localised to these structures. RON4, is a recently described protein that has also been shown to be present in the neck of the rhoptries prior to invasion. It shows a very similar localisation pattern compared to the invasion ligand, adding further support to the invasion ligand's presence in the rhoptry neck. Immuno-electron microscopy of late schizonts confirmed localisation to the rhoptries, predominantly in the main body of these large secretory organelles using both anti-HA and anti-invasion ligand antibodies (FIG. 7). Some staining was also observed at the periphery of the rhoptry body though, unlike PfRh2a/b and RON4, none was seen definitively in the rhoptry neck, suggesting the invasion ligand may localise differently to other invasion ligand proteins.

Immunofluorescence microscopy of merozoites that have been arrested during invasion, shows that the invasion ligand co-localises with RON4 and AMA1 at the moving tight junction that forms between the invading merozoite and the host erythrocyte (FIG. 3C and FIG. 8). AMA1 and RON4 are known to form a complex and associate at the tight junction in malaria parasites and *Toxoplasma gondii*. Taken together, these results imply that the invasion ligand plays an important role in entry of the parasite into the host erythrocyte.

EXAMPLE 5

The Invasion Ligand Binds to a Novel Receptor on the Red Cell Surface

As discussed supra, Rh1 and Rh4 both bind to the surface of the erythrocyte and their properties suggest a specific interaction with a host receptor. In red blood cell binding assays with concentrated culture supernatant both the 68 and 45 kDa protein products of the invasion ligand were found to bind to the host cell, with the smaller processed form binding at significantly increased levels suggesting a higher affinity interaction (FIG. 4A). Similar binding results were observed with the invasion ligand HA tagged protein (data not shown). Invasion ligand binding to erythrocytes was insensitive to chymotrypsin, trypsin and neuraminidase in contrast to the neuraminidase and trypsin sensitivity of EBA175 binding (FIG. 4B) and in a manner unlike any previously shown erythrocyte binding parasite adhesin. These results suggest that this protein binds to erythrocytes in a sialic acid independent manner, in contrast to other ligands such as EBA175, EBA140, EBA181 and Rh1.

Searching through the sequence of the invasion ligand it is possible to identify several putative heparin binding motifs (conforming to the xBBxBx or xBBBxxBx binding motifs, where x is hydropathic and B is basic). The form of heparin associated with the human erythrocyte is heparan sulfate, expressed as a proteoglycan, consisting of a sulfated carbohydrate chain covalently attached to core proteins and epitopes on the erythrocyte surface. Because of its insensitivity to neuraminidase we reasoned that heparin-binding could explain the invasion ligand's binding insensitivity to the standard suite of enzyme treatments. In in vitro binding assays heparin was able to inhibit binding of the invasion ligand in a dose-dependent manner which was more sensitive than that observed for the sialic acid binding ligand EBA175 (FIG. 4C). To determine if this inhibition of binding was specific, chondroitin sulfate C(CSC), a glycosaminoglycan expressed extensively across tissues as a chondroitin sulfate proteogylcan, was also tested. CSC did not inhibit either the invasion ligand or EBA175 binding, even at high concentrations (FIG. 4C). The affinity of the invasion ligand for heparin was further strengthened by the ability of agarose beads, coated in heparin, to selectively deplete the invasion ligand from concentrated supernatant (FIG. 4D). In the same assay, selective depletion of the invasion ligand could be inhibited by pre-incubating with soluble heparin but not CSC (FIG. 4D), suggesting that during invasion the invasion ligand binds to the erythrocyte via a novel receptor that includes a carbohydrate (and as such highly charged) moiety related to heparin.

EXAMPLE 6

Antibodies Against the Invasion Ligand Inhibit Invasion in vitro and Recombinant Full-length Invasion Ligand is Recognized by Human Immune Sera from Malaria Endemic Populations Antibodies against the invasion ligand were tested for their ability to inhibit invasion into untreated and enzyme treated parasites. Invasion of 3D7 wild type parasites into untreated erythrocytes showed no significant inhibition with these antibodies compared with invasion in the presence of normal pre-immune rabbit serum (mean inhibition 96.6% with 95% CI±6.1, FIG. 5A). However, when the repertoire of potential surface receptors was depleted by enzymatic pre-treatment of target erythrocytes, inhibition increased significantly. Inhibition of invasion by anti-invasion ligand was marked following 0.1 µM trypsin pre-treatment of erythrocytes (mean inhibition 80.3%, with 95% CI±5.6) compared with normal serum and, though less significantly, following 1.0 µM chymotrypsin—(mean inhibition 90.2%, with 95% CI±8.1) or neuraminidase—(mean inhibition 91.0% with 95%, CI±7.3) pre-treatment.

An immunoblot using soluble recombinant invasion ligand (generated from refolding of the invasion ligand from E. coli inclusion bodies) demonstrates that the invasion ligand is recognized by pooled human sera from malaria-endemic communities but significantly not from pooled malaria-non-exposed immune sera (FIG. 5). This indicates that the invasion ligand, as discussed supra for other members of the Rh family, is recognized in natural malaria infections.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as broadly described herein.

The claims defining the invention are as follows:

1. A composition comprising a combination of:
   (a) an isolated immunogenic molecule consisting of a sequence selected from the group consisting of SEQ ID NOS: 2, 4, 5, 6, 7, 8, 9, 10, 11 and 12, or an isolated immunogenic molecule consisting of a sequence selected from the group consisting of the amino acid sequence set forth in SEQ ID NOS: 2, 4, 5, 6, 7, 8, 9, 10, 11 and 12 except for the amino acid substitution in a corresponding residue where applicable in any of SEQ ID NOS: 2, 4, 5, 6, 7, 8, 9, 10, 11 and 12 selected from: E at amino acid 25 in SEQ ID NO: 2 is replaced with K, Y at amino acid 124 in SEQ ID NO: 2 is replaced with H, H at amino acid 125 in SEQ ID NO: 2 is replaced with N, S at amino acid 174 in SEQ ID NO: 2 is replaced with Y, C at amino acid 180 in SEQ ID NO: 2 is replaced with Y, I at amino acid 181 in SEQ ID NO: 2 is replaced with K or R, N at amino acid 324 is replaced with Y or D, Y at amino acid 335 in SEQ ID NO: 2 is replaced with F, E at amino acid 339 in SEQ ID NO: 2 is replaced with D, V at amino acid 348 in SEQ ID NO: 2 is replaced with I, I at amino acid 384 in SEQ ID NO: 2 is replaced with V, I at amino acid 387 in SEQ ID NO: 2 is replaced with M, and K at amino acid 406 in SEQ ID NO: 2 is replaced with N;
   (b) an isolated immunogenic molecule consisting of amino acids 761-1271 of the erythrocyte binding antigen (EBA) protein EBA175 of SEQ ID NO: 17 or an isolated immunogenic molecule consisting of amino acids 761-1271 of the erythrocyte binding antigen (EBA) protein EBA175 of SEQ ID NO: 17 except for the amino acid substitution selected from: S at amino acid 768 in SEQ ID NO: 17 replaced with N, E at amino acid 923 of SEQ ID NO: 17 replaced with K, K at amino acid 932 in SEQ ID NO: 17 replaced with E, E at amino acid 1058 in SEQ ID NO: 17 replaced with V, and G at amino acid 1100 in SEQ ID NO: 17 replaced with D; and (c) an effective amount of a vaccine adjuvant;

wherein the composition induces an immune response to a strain of *Plasmodium falciparum* when administered to a subject.

2. The composition according to claim 1, wherein the immune response is an invasion-inhibitory immune response.

3. The composition according to claim 1 wherein the strain of *Plasmodium falciparum* is a wild type strain.

4. The composition according to claim 1 further comprising a pharmaceutically acceptable excipient.

5. A method of treating a condition caused by or associated with infection by *Plasmodium falciparum* comprising administering to a subject in need thereof an effective amount of the composition according to claim 1.

6. A composition comprising a combination of:

(a) an isolated immunogenic molecule consisting of a sequence selected from the group consisting of SEQ ID NOS: 2, 4, 5, 6, 7, 8, 9, 10, 11 and 12, or an isolated immunogenic molecule consisting of a sequence selected from the group consisting of the amino acid sequence set forth in SEQ ID NOS: 2, 4, 5, 6, 7, 8, 9, 10, 11 and 12except for the amino acid substitution in a corresponding residue where applicable in any of SEQ ID NOS: 2, 4, 5, 6, 7, 8, 9, 10, 11 and 12 selected from:

E at amino acid 25 in SEQ ID NO: 2 is replaced with K, Y at amino acid 124 in SEQ ID NO: 2 is replaced with H, H at amino acid 125 in SEQ ID NO: 2 is replaced with N, S at amino acid 174in SEQ ID NO: 2 is replaced with Y, C at amino acid 180 in SEQ ID NO: 2 is replaced with Y, I at amino acid 181 in SEQ ID NO: 2 is replaced with K or R, N at amino acid 324 is replaced with Y or D, Y at amino acid 335 in SEQ ID NO: 2 is replaced with F, E at amino acid 339 in SEQ ID NO: 2 is replaced with D, V at amino acid 348 in SEQ ID NO: 2 is replaced with I, I at amino acid 384 in SEQ ID NO: 2 is replaced with V, I at amino acid 387 in SEQ ID NO: 2 is replaced with M, and K at amino acid 406 in SEQ ID NO: 2 is replaced with N;

(b) an isolated immunogenic molecule consisting of amino acids 761-1271 of the erythrocyte binding antigen (EBA) protein EBA175 of SEQ ID NO: 17 or an isolated immunogenic molecule consisting of amino acids 761-1271 of the erythrocyte binding antigen (EBA) protein EBA175 of SEQ ID NO: 17 except for the amino acid substitution selected from: S at amino acid 768 in SEQ ID NO: 17 replaced with N, E at amino acid 923 of SEQ ID NO: 17 replaced with K, K at amino acid 932 in SEQ ID NO: 17 replaced with E, E at amino acid 1058 in SEQ ID NO: 17 replaced with V, and G at amino acid 1100 in SEQ ID NO: 17 replaced with D; and (c) an effective amount of a vaccine adjuvant;

wherein at least one immunogenic molecule is fused to Glutathione S-transferase (GST) or histidine (HIS) tag or is conjugated to a carrier protein and wherein the composition induces an immune response to *Plasmodium falciparum* when administered to a subject.

7. The composition of claim 6 wherein the immunogenic molecule of subpart (b) is fused to Glutathione S-transferase (GST) or histidine (HIS) tag or is conjugated to a carrier protein.

8. The composition of claim 6 wherein the immunogenic molecule of subpart (b) is a Fusion protein or is conjugated to a carrier protein.

\* \* \* \* \*

SEQUENCE LISTING

```
<160> NUMBER OF SEQ ID NOS: 35

<210> SEQ ID NO 1
<211> LENGTH: 526
<212> TYPE: PRT
<213> ORGANISM: Plasmodium falciparum

<400> SEQUENCE: 1

Met Ile Arg Ile Lys Lys Lys Leu Ile Leu Thr Ile Ile Tyr Ile His
1               5                   10                  15

Leu Phe Ile Leu Asn Arg Leu Ser Phe Glu Asn Ala Ile Lys Lys Thr
            20                  25                  30

Lys Asn Gln Glu Asn Asn Leu Thr Leu Leu Pro Ile Lys Ser Thr Glu
        35                  40                  45

Glu Glu Lys Asp Asp Ile Lys Asn Gly Lys Asp Ile Lys Lys Glu Ile
    50                  55                  60

Asp Asn Asp Lys Glu Asn Ile Lys Thr Asn Asn Ala Lys Asp His Ser
65                  70                  75                  80

Thr Tyr Ile Lys Ser Tyr Leu Asn Thr Asn Val Asn Asp Gly Leu Lys
                85                  90                  95

Tyr Leu Phe Ile Pro Ser His Asn Ser Phe Ile Lys Lys Tyr Ser Val
            100                 105                 110

Phe Asn Gln Ile Asn Asp Gly Met Leu Leu Asn Glu Lys Asn Asp Val
        115                 120                 125
```

Lys Asn Asn Glu Asp Tyr Lys Asn Val Asp Tyr Lys Asn Val Asn Phe
130                 135                 140

Leu Gln Tyr His Phe Lys Glu Leu Ser Asn Tyr Asn Ile Ala Asn Ser
145                 150                 155                 160

Ile Asp Ile Leu Gln Glu Lys Glu Gly His Leu Asp Phe Val Ile Ile
                165                 170                 175

Pro His Tyr Thr Phe Leu Asp Tyr Tyr Lys His Leu Ser Tyr Asn Ser
                180                 185                 190

Ile Tyr His Lys Ser Ser Thr Tyr Gly Lys Cys Ile Ala Val Asp Ala
            195                 200                 205

Phe Ile Lys Lys Ile Asn Glu Thr Tyr Asp Lys Val Lys Ser Lys Cys
210                 215                 220

Asn Asp Ile Lys Asn Asp Leu Ile Ala Thr Ile Lys Lys Leu Glu His
225                 230                 235                 240

Pro Tyr Asp Ile Asn Asn Lys Asn Asp Ser Tyr Arg Tyr Asp Ile
                245                 250                 255

Ser Glu Glu Ile Asp Asp Lys Ser Glu Glu Thr Asp Asp Glu Thr Glu
                260                 265                 270

Glu Val Glu Asp Ser Ile Gln Asp Thr Asp Ser Asn His Thr Pro Ser
            275                 280                 285

Asn Lys Lys Lys Asn Asp Leu Met Asn Arg Thr Phe Lys Lys Met Met
290                 295                 300

Asp Glu Tyr Asn Thr Lys Lys Lys Leu Ile Lys Cys Ile Lys Asn
305                 310                 315                 320

His Glu Asn Asp Phe Asn Lys Ile Cys Met Asp Met Lys Asn Tyr Gly
                325                 330                 335

Thr Asn Leu Phe Glu Gln Leu Ser Cys Tyr Asn Asn Phe Cys Asn
            340                 345                 350

Thr Asn Gly Ile Arg Tyr His Tyr Asp Glu Tyr Ile His Lys Leu Ile
            355                 360                 365

Leu Ser Val Lys Ser Lys Asn Leu Asn Lys Asp Leu Ser Asp Met Thr
370                 375                 380

Asn Ile Leu Gln Gln Ser Glu Leu Leu Leu Thr Asn Leu Asn Lys Lys
385                 390                 395                 400

Met Gly Ser Tyr Ile Tyr Ile Asp Thr Ile Lys Phe Ile His Lys Glu
                405                 410                 415

Met Lys His Ile Phe Asn Arg Ile Glu Tyr His Thr Lys Ile Ile Asn
                420                 425                 430

Asp Lys Thr Lys Ile Ile Gln Asp Lys Ile Lys Leu Asn Ile Trp Arg
            435                 440                 445

Thr Phe Gln Lys Asp Glu Leu Leu Lys Arg Ile Leu Asp Met Ser Asn
450                 455                 460

Glu Tyr Ser Leu Phe Ile Thr Ser Asp His Leu Arg Gln Met Leu Tyr
465                 470                 475                 480

Asn Thr Phe Tyr Ser Lys Glu Lys His Leu Asn Asn Ile Phe His His
                485                 490                 495

Leu Ile Tyr Val Leu Gln Met Lys Phe Asn Asp Val Pro Ile Lys Met
            500                 505                 510

Glu Tyr Phe Gln Thr Tyr Lys Lys Asn Lys Pro Leu Thr Gln
            515                 520                 525

<210> SEQ ID NO 2
<211> LENGTH: 503

```
<212> TYPE: PRT
<213> ORGANISM: Plasmodium falciparum

<400> SEQUENCE: 2

Ser Phe Glu Asn Ala Ile Lys Lys Thr Lys Asn Gln Glu Asn Asn Leu
1               5                   10                  15

Thr Leu Leu Pro Ile Lys Ser Thr Glu Glu Lys Asp Asp Ile Lys
            20                  25                  30

Asn Gly Lys Asp Ile Lys Lys Glu Ile Asp Asn Asp Lys Glu Asn Ile
            35                  40                  45

Lys Thr Asn Asn Ala Lys Asp His Ser Thr Tyr Ile Lys Ser Tyr Leu
    50                  55                  60

Asn Thr Asn Val Asn Asp Gly Leu Lys Tyr Leu Phe Ile Pro Ser His
65                  70                  75                  80

Asn Ser Phe Ile Lys Lys Tyr Ser Val Phe Asn Gln Ile Asn Asp Gly
                85                  90                  95

Met Leu Leu Asn Glu Lys Asn Asp Val Lys Asn Glu Asp Tyr Lys
            100                 105                 110

Asn Val Asp Tyr Lys Asn Val Asn Phe Leu Gln Tyr His Phe Lys Glu
            115                 120                 125

Leu Ser Asn Tyr Asn Ile Ala Asn Ser Ile Asp Ile Leu Gln Glu Lys
    130                 135                 140

Glu Gly His Leu Asp Phe Val Ile Ile Pro His Tyr Thr Phe Leu Asp
145                 150                 155                 160

Tyr Tyr Lys His Leu Ser Tyr Asn Ser Ile Tyr His Lys Ser Ser Thr
                165                 170                 175

Tyr Gly Lys Cys Ile Ala Val Asp Ala Phe Ile Lys Lys Ile Asn Glu
            180                 185                 190

Thr Tyr Asp Lys Val Lys Ser Lys Cys Asn Asp Ile Lys Asn Asp Leu
            195                 200                 205

Ile Ala Thr Ile Lys Lys Leu Glu His Pro Tyr Asp Ile Asn Asn Lys
    210                 215                 220

Asn Asp Asp Ser Tyr Arg Tyr Asp Ile Ser Glu Glu Ile Asp Asp Lys
225                 230                 235                 240

Ser Glu Glu Thr Asp Asp Glu Thr Glu Glu Val Glu Asp Ser Ile Gln
                245                 250                 255

Asp Thr Asp Ser Asn His Thr Pro Ser Asn Lys Lys Asn Asp Leu
            260                 265                 270

Met Asn Arg Thr Phe Lys Lys Met Met Asp Glu Tyr Asn Thr Lys Lys
            275                 280                 285

Lys Lys Leu Ile Lys Cys Ile Lys Asn His Glu Asn Asp Phe Asn Lys
    290                 295                 300

Ile Cys Met Asp Met Lys Asn Tyr Gly Thr Asn Leu Phe Glu Gln Leu
305                 310                 315                 320

Ser Cys Tyr Asn Asn Phe Cys Asn Thr Asn Gly Ile Arg Tyr His
                325                 330                 335

Tyr Asp Glu Tyr Ile His Lys Leu Ile Leu Ser Val Lys Ser Lys Asn
            340                 345                 350

Leu Asn Lys Asp Leu Ser Asp Met Thr Asn Ile Leu Gln Gln Ser Glu
    355                 360                 365

Leu Leu Leu Thr Asn Leu Asn Lys Lys Met Gly Ser Tyr Ile Tyr Ile
370                 375                 380

Asp Thr Ile Lys Phe Ile His Lys Glu Met Lys His Ile Phe Asn Arg
385                 390                 395                 400
```

```
Ile Glu Tyr His Thr Lys Ile Ile Asn Asp Lys Thr Lys Ile Ile Gln
            405                 410                 415

Asp Lys Ile Lys Leu Asn Ile Trp Arg Thr Phe Gln Lys Asp Glu Leu
        420                 425                 430

Leu Lys Arg Ile Leu Asp Met Ser Asn Glu Tyr Ser Leu Phe Ile Thr
    435                 440                 445

Ser Asp His Leu Arg Gln Met Leu Tyr Asn Thr Phe Tyr Ser Lys Glu
450                 455                 460

Lys His Leu Asn Asn Ile Phe His His Leu Ile Tyr Val Leu Gln Met
465                 470                 475                 480

Lys Phe Asn Asp Val Pro Ile Lys Met Glu Tyr Phe Gln Thr Tyr Lys
                485                 490                 495

Lys Asn Lys Pro Leu Thr Gln
            500
```

<210> SEQ ID NO 3
<211> LENGTH: 379
<212> TYPE: PRT
<213> ORGANISM: Plasmodium falciparum

<400> SEQUENCE: 3

```
His Phe Lys Glu Leu Ser Asn Tyr Asn Ile Ala Asn Ser Ile Asp Ile
1               5                   10                  15

Leu Gln Glu Lys Glu Gly His Leu Asp Phe Val Ile Ile Pro His Tyr
            20                  25                  30

Thr Phe Leu Asp Tyr Tyr Lys His Leu Ser Tyr Asn Ser Ile Tyr His
        35                  40                  45

Lys Ser Ser Thr Tyr Gly Lys Cys Ile Ala Val Asp Ala Phe Ile Lys
    50                  55                  60

Lys Ile Asn Glu Thr Tyr Asp Lys Val Lys Ser Lys Cys Asn Asp Ile
65                  70                  75                  80

Lys Asn Asp Leu Ile Ala Thr Ile Lys Lys Leu Glu His Pro Tyr Asp
                85                  90                  95

Ile Asn Asn Lys Asn Asp Asp Ser Tyr Arg Tyr Asp Ile Ser Glu Glu
            100                 105                 110

Ile Asp Asp Lys Ser Glu Glu Thr Asp Asp Glu Thr Glu Glu Val Glu
        115                 120                 125

Asp Ser Ile Gln Asp Thr Asp Ser Asn His Thr Pro Ser Asn Lys Lys
130                 135                 140

Lys Asn Asp Leu Met Asn Arg Thr Phe Lys Lys Met Met Asp Glu Tyr
145                 150                 155                 160

Asn Thr Lys Lys Lys Lys Leu Ile Lys Cys Ile Lys Asn His Glu Asn
                165                 170                 175

Asp Phe Asn Lys Ile Cys Met Asp Met Lys Asn Tyr Gly Thr Asn Leu
            180                 185                 190

Phe Glu Gln Leu Ser Cys Tyr Asn Asn Phe Cys Asn Thr Asn Gly
        195                 200                 205

Ile Arg Tyr His Tyr Asp Glu Tyr Ile His Lys Leu Ile Leu Ser Val
    210                 215                 220

Lys Ser Lys Asn Leu Asn Lys Asp Leu Ser Asp Met Thr Asn Ile Leu
225                 230                 235                 240

Gln Gln Ser Glu Leu Leu Leu Thr Asn Leu Asn Lys Lys Met Gly Ser
                245                 250                 255

Tyr Ile Tyr Ile Asp Thr Ile Lys Phe Ile His Lys Glu Met Lys His
```

```
                260                 265                 270
Ile Phe Asn Arg Ile Glu Tyr His Thr Lys Ile Ile Asn Asp Lys Thr
            275                 280                 285
Lys Ile Ile Gln Asp Lys Ile Lys Leu Asn Ile Trp Arg Thr Phe Gln
        290                 295                 300
Lys Asp Glu Leu Leu Lys Arg Ile Leu Asp Met Ser Asn Glu Tyr Ser
305                 310                 315                 320
Leu Phe Ile Thr Ser Asp His Leu Arg Gln Met Leu Tyr Asn Thr Phe
                325                 330                 335
Tyr Ser Lys Glu Lys His Leu Asn Asn Ile Phe His His Leu Ile Tyr
            340                 345                 350
Val Leu Gln Met Lys Phe Asn Asp Val Pro Ile Lys Met Glu Tyr Phe
        355                 360                 365
Gln Thr Tyr Lys Lys Asn Lys Pro Leu Thr Gln
    370                 375

<210> SEQ ID NO 4
<211> LENGTH: 384
<212> TYPE: PRT
<213> ORGANISM: Plasmodium falciparum

<400> SEQUENCE: 4

Asn Phe Leu Gln Tyr His Phe Lys Glu Leu Ser Asn Tyr Asn Ile Ala
1               5                   10                  15
Asn Ser Ile Asp Ile Leu Gln Glu Lys Glu Gly His Leu Asp Phe Val
            20                  25                  30
Ile Ile Pro His Tyr Thr Phe Leu Asp Tyr Tyr Lys His Leu Ser Tyr
        35                  40                  45
Asn Ser Ile Tyr His Lys Ser Ser Thr Tyr Gly Lys Cys Ile Ala Val
    50                  55                  60
Asp Ala Phe Ile Lys Lys Ile Asn Glu Thr Tyr Asp Lys Val Lys Ser
65                  70                  75                  80
Lys Cys Asn Asp Ile Lys Asn Asp Leu Ile Ala Thr Ile Lys Lys Leu
                85                  90                  95
Glu His Pro Tyr Asp Ile Asn Asn Lys Asn Asp Asp Ser Tyr Arg Tyr
            100                 105                 110
Asp Ile Ser Glu Glu Ile Asp Asp Lys Ser Glu Glu Thr Asp Asp Glu
        115                 120                 125
Thr Glu Glu Val Glu Asp Ser Ile Gln Asp Thr Asp Ser Asn His Thr
    130                 135                 140
Pro Ser Asn Lys Lys Lys Asn Asp Leu Met Asn Arg Thr Phe Lys Lys
145                 150                 155                 160
Met Met Asp Glu Tyr Asn Thr Lys Lys Lys Leu Ile Lys Cys Ile
                165                 170                 175
Lys Asn His Glu Asn Asp Phe Asn Lys Ile Cys Met Asp Met Lys Asn
            180                 185                 190
Tyr Gly Thr Asn Leu Phe Glu Gln Leu Ser Cys Tyr Asn Asn Asn Phe
        195                 200                 205
Cys Asn Thr Asn Gly Ile Arg Tyr His Tyr Asp Glu Tyr Ile His Lys
    210                 215                 220
Leu Ile Leu Ser Val Lys Ser Lys Asn Leu Asn Lys Asp Leu Ser Asp
225                 230                 235                 240
Met Thr Asn Ile Leu Gln Gln Ser Glu Leu Leu Leu Thr Asn Leu Asn
                245                 250                 255
```

```
Lys Lys Met Gly Ser Tyr Ile Tyr Ile Asp Thr Ile Lys Phe Ile His
            260                 265                 270

Lys Glu Met Lys His Ile Phe Asn Arg Ile Glu Tyr His Thr Lys Ile
        275                 280                 285

Ile Asn Asp Lys Thr Lys Ile Ile Gln Asp Lys Ile Lys Leu Asn Ile
    290                 295                 300

Trp Arg Thr Phe Gln Lys Asp Glu Leu Leu Lys Arg Ile Leu Asp Met
305                 310                 315                 320

Ser Asn Glu Tyr Ser Leu Phe Ile Thr Ser Asp His Leu Arg Gln Met
                325                 330                 335

Leu Tyr Asn Thr Phe Tyr Ser Lys Glu Lys His Leu Asn Asn Ile Phe
            340                 345                 350

His His Leu Ile Tyr Val Leu Gln Met Lys Phe Asn Asp Val Pro Ile
        355                 360                 365

Lys Met Glu Tyr Phe Gln Thr Tyr Lys Lys Asn Lys Pro Leu Thr Gln
    370                 375                 380

<210> SEQ ID NO 5
<211> LENGTH: 389
<212> TYPE: PRT
<213> ORGANISM: Plasmodium falciparum

<400> SEQUENCE: 5

Asp Tyr Lys Asn Val Asn Phe Leu Gln Tyr His Phe Lys Glu Leu Ser
1               5                   10                  15

Asn Tyr Asn Ile Ala Asn Ser Ile Asp Ile Leu Gln Glu Lys Glu Gly
            20                  25                  30

His Leu Asp Phe Val Ile Ile Pro His Tyr Thr Phe Leu Asp Tyr Tyr
        35                  40                  45

Lys His Leu Ser Tyr Asn Ser Ile Tyr His Lys Ser Ser Thr Tyr Gly
    50                  55                  60

Lys Cys Ile Ala Val Asp Ala Phe Ile Lys Lys Ile Asn Glu Thr Tyr
65                  70                  75                  80

Asp Lys Val Lys Ser Lys Cys Asn Asp Ile Lys Asn Asp Leu Ile Ala
                85                  90                  95

Thr Ile Lys Lys Leu Glu His Pro Tyr Asp Ile Asn Asn Lys Asn Asp
            100                 105                 110

Asp Ser Tyr Arg Tyr Asp Ile Ser Glu Glu Ile Asp Asp Lys Ser Glu
        115                 120                 125

Glu Thr Asp Asp Glu Thr Glu Glu Val Glu Asp Ser Ile Gln Asp Thr
    130                 135                 140

Asp Ser Asn His Thr Pro Ser Asn Lys Lys Asn Asp Leu Met Asn
145                 150                 155                 160

Arg Thr Phe Lys Lys Met Met Asp Glu Tyr Asn Thr Lys Lys Lys Lys
                165                 170                 175

Leu Ile Lys Cys Ile Lys Asn His Glu Asn Asp Phe Asn Lys Ile Cys
            180                 185                 190

Met Asp Met Lys Asn Tyr Gly Thr Asn Leu Phe Glu Gln Leu Ser Cys
        195                 200                 205

Tyr Asn Asn Asn Phe Cys Asn Thr Asn Gly Ile Arg Tyr His Tyr Asp
    210                 215                 220

Glu Tyr Ile His Lys Leu Ile Leu Ser Val Lys Ser Lys Asn Leu Asn
225                 230                 235                 240

Lys Asp Leu Ser Asp Met Thr Asn Ile Leu Gln Gln Ser Glu Leu Leu
                245                 250                 255
```

```
Leu Thr Asn Leu Asn Lys Lys Met Gly Ser Tyr Ile Tyr Ile Asp Thr
            260                 265                 270

Ile Lys Phe Ile His Lys Glu Met Lys His Ile Phe Asn Arg Ile Glu
        275                 280                 285

Tyr His Thr Lys Ile Ile Asn Asp Lys Thr Lys Ile Ile Gln Asp Lys
    290                 295                 300

Ile Lys Leu Asn Ile Trp Arg Thr Phe Gln Lys Asp Glu Leu Leu Lys
305                 310                 315                 320

Arg Ile Leu Asp Met Ser Asn Glu Tyr Ser Leu Phe Ile Thr Ser Asp
                325                 330                 335

His Leu Arg Gln Met Leu Tyr Asn Thr Phe Tyr Ser Lys Glu Lys His
            340                 345                 350

Leu Asn Asn Ile Phe His His Leu Ile Tyr Val Leu Gln Met Lys Phe
        355                 360                 365

Asn Asp Val Pro Ile Lys Met Glu Tyr Phe Gln Thr Tyr Lys Lys Asn
    370                 375                 380

Lys Pro Leu Thr Gln
385

<210> SEQ ID NO 6
<211> LENGTH: 374
<212> TYPE: PRT
<213> ORGANISM: Plasmodium falciparum

<400> SEQUENCE: 6

Ser Asn Tyr Asn Ile Ala Asn Ser Ile Asp Ile Leu Gln Glu Lys Glu
1               5                   10                  15

Gly His Leu Asp Phe Val Ile Ile Pro His Tyr Thr Phe Leu Asp Tyr
            20                  25                  30

Tyr Lys His Leu Ser Tyr Asn Ser Ile Tyr His Lys Ser Ser Thr Tyr
        35                  40                  45

Gly Lys Cys Ile Ala Val Asp Ala Phe Ile Lys Lys Ile Asn Glu Thr
    50                  55                  60

Tyr Asp Lys Val Lys Ser Lys Cys Asn Asp Ile Lys Asn Asp Leu Ile
65                  70                  75                  80

Ala Thr Ile Lys Lys Leu Glu His Pro Tyr Asp Ile Asn Asn Lys Asn
                85                  90                  95

Asp Asp Ser Tyr Arg Tyr Asp Ile Ser Glu Ile Asp Asp Lys Ser
            100                 105                 110

Glu Glu Thr Asp Asp Glu Thr Glu Val Glu Asp Ser Ile Gln Asp
        115                 120                 125

Thr Asp Ser Asn His Thr Pro Ser Asn Lys Lys Asn Asp Leu Met
    130                 135                 140

Asn Arg Thr Phe Lys Lys Met Met Asp Glu Tyr Asn Thr Lys Lys Lys
145                 150                 155                 160

Lys Leu Ile Lys Cys Ile Lys Asn His Glu Asn Asp Phe Asn Lys Ile
                165                 170                 175

Cys Met Asp Met Lys Asn Tyr Gly Thr Asn Leu Phe Glu Gln Leu Ser
            180                 185                 190

Cys Tyr Asn Asn Asn Phe Cys Asn Thr Asn Gly Ile Arg Tyr His Tyr
        195                 200                 205

Asp Glu Tyr Ile His Lys Leu Ile Leu Ser Val Lys Ser Lys Asn Leu
    210                 215                 220

Asn Lys Asp Leu Ser Asp Met Thr Asn Ile Leu Gln Gln Ser Glu Leu
```

```
                225                 230                 235                 240
Leu Leu Thr Asn Leu Asn Lys Lys Met Gly Ser Tyr Ile Tyr Ile Asp
                    245                 250                 255

Thr Ile Lys Phe Ile His Lys Glu Met Lys His Ile Phe Asn Arg Ile
                260                 265                 270

Glu Tyr His Thr Lys Ile Ile Asn Asp Lys Thr Lys Ile Ile Gln Asp
            275                 280                 285

Lys Ile Lys Leu Asn Ile Trp Arg Thr Phe Gln Lys Asp Glu Leu Leu
        290                 295                 300

Lys Arg Ile Leu Asp Met Ser Asn Glu Tyr Ser Leu Phe Ile Thr Ser
305                 310                 315                 320

Asp His Leu Arg Gln Met Leu Tyr Asn Thr Phe Tyr Ser Lys Glu Lys
                    325                 330                 335

His Leu Asn Asn Ile Phe His His Leu Ile Tyr Val Leu Gln Met Lys
                340                 345                 350

Phe Asn Asp Val Pro Ile Lys Met Glu Tyr Phe Gln Thr Tyr Lys Lys
            355                 360                 365

Asn Lys Pro Leu Thr Gln
        370

<210> SEQ ID NO 7
<211> LENGTH: 369
<212> TYPE: PRT
<213> ORGANISM: Plasmodium falciparum

<400> SEQUENCE: 7

Ala Asn Ser Ile Asp Ile Leu Gln Glu Lys Glu Gly His Leu Asp Phe
1               5                   10                  15

Val Ile Ile Pro His Tyr Thr Phe Leu Asp Tyr Tyr Lys His Leu Ser
                20                  25                  30

Tyr Asn Ser Ile Tyr His Lys Ser Ser Thr Tyr Gly Lys Cys Ile Ala
            35                  40                  45

Val Asp Ala Phe Ile Lys Lys Ile Asn Glu Thr Tyr Asp Lys Val Lys
        50                  55                  60

Ser Lys Cys Asn Asp Ile Lys Asn Asp Leu Ile Ala Thr Ile Lys Lys
65                  70                  75                  80

Leu Glu His Pro Tyr Asp Ile Asn Asn Lys Asn Asp Asp Ser Tyr Arg
                85                  90                  95

Tyr Asp Ile Ser Glu Glu Ile Asp Asp Lys Ser Glu Thr Asp Asp
            100                 105                 110

Glu Thr Glu Glu Val Glu Asp Ser Ile Gln Asp Thr Asp Ser Asn His
        115                 120                 125

Thr Pro Ser Asn Lys Lys Asn Asp Leu Met Asn Arg Thr Phe Lys
    130                 135                 140

Lys Met Met Asp Glu Tyr Asn Thr Lys Lys Lys Leu Ile Lys Cys
145                 150                 155                 160

Ile Lys Asn His Glu Asn Asp Phe Asn Lys Ile Cys Met Asp Met Lys
                165                 170                 175

Asn Tyr Gly Thr Asn Leu Phe Glu Gln Leu Ser Cys Tyr Asn Asn Asn
            180                 185                 190

Phe Cys Asn Thr Asn Gly Ile Arg Tyr His Tyr Asp Glu Tyr Ile His
        195                 200                 205

Lys Leu Ile Leu Ser Val Lys Ser Lys Asn Leu Asn Lys Asp Leu Ser
    210                 215                 220
```

```
Asp Met Thr Asn Ile Leu Gln Gln Ser Glu Leu Leu Thr Asn Leu
225                 230                 235                 240

Asn Lys Lys Met Gly Ser Tyr Ile Tyr Ile Asp Thr Ile Lys Phe Ile
                245                 250                 255

His Lys Glu Met Lys His Ile Phe Asn Arg Ile Glu Tyr His Thr Lys
            260                 265                 270

Ile Ile Asn Asp Lys Thr Lys Ile Ile Gln Asp Lys Ile Lys Leu Asn
        275                 280                 285

Ile Trp Arg Thr Phe Gln Lys Asp Glu Leu Leu Lys Arg Ile Leu Asp
    290                 295                 300

Met Ser Asn Glu Tyr Ser Leu Phe Ile Thr Ser Asp His Leu Arg Gln
305                 310                 315                 320

Met Leu Tyr Asn Thr Phe Tyr Ser Lys Glu Lys His Leu Asn Asn Ile
                325                 330                 335

Phe His His Leu Ile Tyr Val Leu Gln Met Lys Phe Asn Asp Val Pro
            340                 345                 350

Ile Lys Met Glu Tyr Phe Gln Thr Tyr Lys Lys Asn Lys Pro Leu Thr
        355                 360                 365

Gln

<210> SEQ ID NO 8
<211> LENGTH: 170
<212> TYPE: PRT
<213> ORGANISM: Plasmodium falciparum

<400> SEQUENCE: 8

Asn Ser Ile Tyr His Lys Ser Ser Thr Tyr Gly Lys Cys Ile Ala Val
1               5                   10                  15

Asp Ala Phe Ile Lys Lys Ile Asn Glu Thr Tyr Asp Lys Val Lys Ser
            20                  25                  30

Lys Cys Asn Asp Ile Lys Asn Asp Leu Ile Ala Thr Ile Lys Lys Leu
        35                  40                  45

Glu His Pro Tyr Asp Ile Asn Asn Lys Asn Asp Asp Ser Tyr Arg Tyr
    50                  55                  60

Asp Ile Ser Glu Glu Ile Asp Asp Lys Ser Glu Thr Asp Asp Glu
65                  70                  75                  80

Thr Glu Glu Val Glu Asp Ser Ile Gln Asp Thr Asp Ser Asn His Thr
                85                  90                  95

Pro Ser Asn Lys Lys Lys Asn Asp Leu Met Asn Arg Thr Phe Lys Lys
            100                 105                 110

Met Met Asp Glu Tyr Asn Thr Lys Lys Lys Leu Ile Lys Cys Ile
        115                 120                 125

Lys Asn His Glu Asn Asp Phe Asn Lys Ile Cys Met Asp Met Lys Asn
    130                 135                 140

Tyr Gly Thr Asn Leu Phe Glu Gln Leu Ser Cys Tyr Asn Asn Asn Phe
145                 150                 155                 160

Cys Asn Thr Asn Gly Ile Arg Tyr His Tyr
                165                 170

<210> SEQ ID NO 9
<211> LENGTH: 157
<212> TYPE: PRT
<213> ORGANISM: Plasmodium falciparum

<400> SEQUENCE: 9

Ile Ala Val Asp Ala Phe Ile Lys Lys Ile Asn Glu Thr Tyr Asp Lys
```

```
                1               5                  10                 15
Val Lys Ser Lys Cys Asn Asp Ile Lys Asn Asp Leu Ile Ala Thr Ile
                20                 25                 30

Lys Lys Leu Glu His Pro Tyr Asp Ile Asn Asn Lys Asn Asp Asp Ser
                35                 40                 45

Tyr Arg Tyr Asp Ile Ser Glu Glu Ile Asp Asp Lys Ser Glu Glu Thr
                50                 55                 60

Asp Asp Glu Thr Glu Glu Val Glu Asp Ser Ile Gln Asp Thr Asp Ser
65                 70                 75                 80

Asn His Thr Pro Ser Asn Lys Lys Asn Asp Leu Met Asn Arg Thr
                85                 90                 95

Phe Lys Lys Met Met Asp Glu Tyr Asn Thr Lys Lys Lys Leu Ile
                100                105                110

Lys Cys Ile Lys Asn His Glu Asn Asp Phe Asn Lys Ile Cys Met Asp
                115                120                125

Met Lys Asn Tyr Gly Thr Asn Leu Phe Glu Gln Leu Ser Cys Tyr Asn
                130                135                140

Asn Asn Phe Cys Asn Thr Asn Gly Ile Arg Tyr His Tyr
145                150                155

<210> SEQ ID NO 10
<211> LENGTH: 147
<212> TYPE: PRT
<213> ORGANISM: Plasmodium falciparum

<400> SEQUENCE: 10

Ile Ala Val Asp Ala Phe Ile Lys Lys Ile Asn Glu Thr Tyr Asp Lys
1               5                  10                 15

Val Lys Ser Lys Cys Asn Asp Ile Lys Asn Asp Leu Ile Ala Thr Ile
                20                 25                 30

Lys Lys Leu Glu His Pro Tyr Asp Ile Asn Asn Lys Asn Asp Asp Ser
                35                 40                 45

Tyr Arg Tyr Asp Ile Ser Glu Glu Ile Asp Asp Lys Ser Glu Glu Thr
                50                 55                 60

Asp Asp Glu Thr Glu Glu Val Glu Asp Ser Ile Gln Asp Thr Asp Ser
65                 70                 75                 80

Asn His Thr Pro Ser Asn Lys Lys Asn Asp Leu Met Asn Arg Thr
                85                 90                 95

Phe Lys Lys Met Met Asp Glu Tyr Asn Thr Lys Lys Lys Leu Ile
                100                105                110

Lys Cys Ile Lys Asn His Glu Asn Asp Phe Asn Lys Ile Cys Met Asp
                115                120                125

Met Lys Asn Tyr Gly Thr Asn Leu Phe Glu Gln Leu Ser Cys Tyr Asn
                130                135                140

Asn Asn Phe
145

<210> SEQ ID NO 11
<211> LENGTH: 141
<212> TYPE: PRT
<213> ORGANISM: Plasmodium falciparum

<400> SEQUENCE: 11

Ile Ala Val Asp Ala Phe Ile Lys Lys Ile Asn Glu Thr Tyr Asp Lys
1               5                  10                 15

Val Lys Ser Lys Cys Asn Asp Ile Lys Asn Asp Leu Ile Ala Thr Ile
```

```
                    20                  25                  30
Lys Lys Leu Glu His Pro Tyr Asp Ile Asn Asn Lys Asn Asp Asp Ser
                35                  40                  45

Tyr Arg Tyr Asp Ile Ser Glu Glu Ile Asp Asp Lys Ser Glu Glu Thr
    50                  55                  60

Asp Asp Glu Thr Glu Glu Val Glu Asp Ser Ile Gln Asp Thr Asp Ser
65                  70                  75                  80

Asn His Thr Pro Ser Asn Lys Lys Asn Asp Leu Met Asn Arg Thr
                85                  90                  95

Phe Lys Lys Met Met Asp Glu Tyr Asn Thr Lys Lys Lys Leu Ile
                100                 105                 110

Lys Cys Ile Lys Asn His Glu Asn Asp Phe Asn Lys Ile Cys Met Asp
                115                 120                 125

Met Lys Asn Tyr Gly Thr Asn Leu Phe Glu Gln Leu Ser
                130                 135                 140
```

<210> SEQ ID NO 12
<211> LENGTH: 125
<212> TYPE: PRT
<213> ORGANISM: Plasmodium falciparum

<400> SEQUENCE: 12

```
Ile Ala Val Asp Ala Phe Ile Lys Lys Ile Asn Glu Thr Tyr Asp Lys
1               5                   10                  15

Val Lys Ser Lys Cys Asn Asp Ile Lys Asn Asp Leu Ile Ala Thr Ile
                20                  25                  30

Lys Lys Leu Glu His Pro Tyr Asp Ile Asn Asn Lys Asn Asp Asp Ser
                35                  40                  45

Tyr Arg Tyr Asp Ile Ser Glu Glu Ile Asp Asp Lys Ser Glu Glu Thr
    50                  55                  60

Asp Asp Glu Thr Glu Glu Val Glu Asp Ser Ile Gln Asp Thr Asp Ser
65                  70                  75                  80

Asn His Thr Pro Ser Asn Lys Lys Asn Asp Leu Met Asn Arg Thr
                85                  90                  95

Phe Lys Lys Met Met Asp Glu Tyr Asn Thr Lys Lys Lys Leu Ile
                100                 105                 110

Lys Cys Ile Lys Asn His Glu Asn Asp Phe Asn Lys Ile
        115                 120                 125
```

<210> SEQ ID NO 13
<211> LENGTH: 3179
<212> TYPE: PRT
<213> ORGANISM: Plasmodium falciparum

<400> SEQUENCE: 13

```
Met Lys Arg Ser Leu Ile Asn Leu Glu Asn Asp Leu Phe Arg Leu Glu
1               5                   10                  15

Pro Ile Ser Tyr Ile Gln Arg Tyr Tyr Lys Lys Asn Ile Asn Arg Ser
                20                  25                  30

Asp Ile Phe His Asn Lys Lys Glu Arg Gly Ser Lys Val Tyr Ser Asn
                35                  40                  45

Val Ser Ser Phe His Ser Phe Ile Gln Glu Gly Lys Glu Glu Val
    50                  55                  60

Val Phe Ser Ile Trp Gly Ser Asn Ser Val Leu Asp His Ile Asp Val
65                  70                  75                  80

Leu Arg Asp Asn Gly Thr Val Val Phe Ser Val Gln Pro Tyr Tyr Leu
```

-continued

```
                    85                  90                  95
Asp Ile Tyr Thr Cys Lys Glu Ala Ile Leu Phe Thr Thr Ser Phe Tyr
                100                 105                 110
Lys Asp Leu Asp Lys Ser Ser Ile Thr Lys Ile Asn Glu Asp Ile Glu
            115                 120                 125
Lys Phe Asn Glu Glu Ile Ile Lys Asn Glu Glu Gln Cys Leu Val Gly
        130                 135                 140
Gly Lys Thr Asp Phe Asp Asn Leu Leu Ile Val Leu Glu Asn Ala Glu
145                 150                 155                 160
Lys Ala Asn Val Arg Lys Thr Leu Phe Asp Asn Thr Phe Asn Asp Tyr
                165                 170                 175
Lys Asn Lys Lys Ser Ser Phe Tyr Asn Cys Leu Lys Asn Lys Lys Asn
            180                 185                 190
Asp Tyr Asp Lys Lys Ile Lys Asn Ile Lys Asn Glu Ile Thr Lys Leu
        195                 200                 205
Leu Lys Asn Ile Glu Ser Thr Gly Asn Met Cys Lys Thr Glu Ser Tyr
    210                 215                 220
Val Met Asn Asn Asn Leu Tyr Leu Leu Arg Val Asn Glu Val Lys Ser
225                 230                 235                 240
Thr Pro Ile Asp Leu Tyr Leu Asn Arg Ala Lys Glu Leu Leu Glu Ser
                245                 250                 255
Ser Ser Lys Leu Val Asn Pro Ile Lys Met Lys Leu Gly Asp Asn Lys
            260                 265                 270
Asn Met Tyr Ser Ile Gly Tyr Ile His Asp Glu Ile Lys Asp Ile Ile
        275                 280                 285
Lys Arg Tyr Asn Phe His Leu Lys His Ile Glu Lys Gly Lys Glu Tyr
    290                 295                 300
Ile Lys Arg Ile Thr Gln Ala Asn Asn Ile Ala Asp Lys Met Lys Lys
305                 310                 315                 320
Asp Glu Leu Ile Lys Lys Ile Phe Glu Ser Ser Lys His Phe Ala Ser
                325                 330                 335
Phe Lys Tyr Ser Asn Glu Met Ile Ser Lys Leu Asp Ser Leu Phe Ile
            340                 345                 350
Lys Asn Glu Glu Ile Leu Asn Asn Leu Phe Asn Asn Ile Phe Asn Ile
        355                 360                 365
Phe Lys Lys Lys Tyr Glu Thr Tyr Val Asp Met Lys Thr Ile Glu Ser
    370                 375                 380
Lys Tyr Thr Thr Val Met Thr Leu Ser Glu His Leu Leu Glu Tyr Ala
385                 390                 395                 400
Met Asp Val Leu Lys Ala Asn Pro Gln Lys Pro Ile Asp Pro Lys Ala
                405                 410                 415
Asn Leu Asp Ser Glu Val Val Lys Leu Gln Ile Lys Ile Asn Glu Lys
            420                 425                 430
Ser Asn Glu Leu Asp Asn Ala Ile Ser Gln Val Lys Thr Leu Ile Ile
        435                 440                 445
Ile Met Lys Ser Phe Tyr Asp Ile Ile Ser Glu Lys Ala Ser Met
    450                 455                 460
Asp Glu Met Glu Lys Lys Glu Leu Ser Leu Asn Asn Tyr Ile Glu Lys
465                 470                 475                 480
Thr Asp Tyr Ile Leu Gln Thr Tyr Asn Ile Phe Lys Ser Lys Ser Asn
                485                 490                 495
Ile Ile Asn Asn Asn Ser Lys Asn Ile Ser Ser Lys Tyr Ile Thr Ile
            500                 505                 510
```

```
Glu Gly Leu Lys Asn Asp Ile Asp Glu Leu Asn Ser Leu Ile Ser Tyr
            515                 520                 525

Phe Lys Asp Ser Gln Glu Thr Leu Ile Lys Asp Asp Glu Leu Lys Lys
            530                 535                 540

Asn Met Lys Thr Asp Tyr Leu Asn Asn Val Lys Tyr Ile Glu Glu Asn
545                 550                 555                 560

Val Thr His Ile Asn Glu Ile Ile Leu Leu Lys Asp Ser Ile Thr Gln
            565                 570                 575

Arg Ile Ala Asp Ile Asp Glu Leu Asn Ser Leu Asn Leu Ile Asn Ile
            580                 585                 590

Asn Asp Phe Ile Asn Glu Lys Asn Ile Ser Gln Glu Lys Val Ser Tyr
            595                 600                 605

Asn Leu Asn Lys Leu Tyr Lys Gly Ser Phe Glu Glu Leu Glu Ser Glu
            610                 615                 620

Leu Ser His Phe Leu Asp Thr Lys Tyr Leu Phe His Glu Lys Lys Ser
625                 630                 635                 640

Val Asn Glu Leu Gln Thr Ile Leu Asn Thr Ser Asn Glu Cys Ala
            645                 650                 655

Lys Leu Asn Phe Met Lys Ser Asp Asn Asn Asn Asn Asn Asn Ser
            660                 665                 670

Asn Ile Ile Asn Leu Leu Lys Thr Glu Leu Ser His Leu Leu Ser Leu
            675                 680                 685

Lys Glu Asn Ile Ile Lys Lys Leu Leu Asn His Ile Glu Gln Asn Ile
            690                 695                 700

Gln Asn Ser Ser Asn Lys Tyr Thr Ile Thr Tyr Thr Asp Ile Asn Asn
705                 710                 715                 720

Arg Met Glu Asp Tyr Lys Glu Glu Ile Glu Ser Leu Glu Val Tyr Lys
            725                 730                 735

His Thr Ile Gly Asn Ile Gln Lys Glu Tyr Ile Leu His Leu Tyr Glu
            740                 745                 750

Asn Asp Lys Asn Ala Leu Ala Val His Asn Thr Ser Met Gln Ile Leu
            755                 760                 765

Gln Tyr Lys Asp Ala Ile Gln Asn Ile Lys Asn Lys Ile Ser Asp Asp
            770                 775                 780

Ile Lys Ile Leu Lys Lys Tyr Lys Glu Met Asn Gln Asp Leu Leu Asn
785                 790                 795                 800

Tyr Tyr Glu Ile Leu Asp Lys Lys Leu Lys Asp Asn Thr Tyr Ile Lys
            805                 810                 815

Glu Met His Thr Ala Ser Leu Val Gln Ile Thr Gln Tyr Ile Pro Tyr
            820                 825                 830

Glu Asp Lys Thr Ile Ser Glu Leu Glu Gln Glu Phe Asn Asn Asn
            835                 840                 845

Gln Lys Leu Asp Asn Ile Leu Gln Asp Ile Asn Ala Met Asn Leu Asn
            850                 855                 860

Ile Asn Ile Leu Gln Thr Leu Asn Ile Gly Ile Asn Ala Cys Asn Thr
865                 870                 875                 880

Asn Asn Lys Asn Val Glu His Leu Leu Asn Lys Lys Ile Glu Leu Lys
            885                 890                 895

Asn Ile Leu Asn Asp Gln Met Lys Ile Ile Lys Asn Asp Asp Ile Ile
            900                 905                 910

Gln Asp Asn Glu Lys Glu Asn Phe Ser Asn Val Leu Lys Lys Glu Glu
            915                 920                 925
```

```
Glu Lys Leu Glu Lys Glu Leu Asp Asp Ile Lys Phe Asn Asn Leu Lys
    930             935                 940

Met Asp Ile His Lys Leu Leu Asn Ser Tyr Asp His Thr Lys Gln Asn
945             950                 955                 960

Ile Glu Ser Asn Leu Lys Ile Asn Leu Asp Ser Phe Glu Lys Glu Lys
            965                 970                 975

Asp Ser Trp Val His Phe Lys Ser Thr Ile Asp Ser Leu Tyr Val Glu
            980                 985                 990

Tyr Asn Ile Cys Asn Gln Lys Thr His Asn Thr Ile Lys Gln Gln Lys
            995                 1000                1005

Asn Asp Ile Ile Glu Leu Ile Tyr Lys Arg Ile Lys Asp Ile Asn Gln
    1010            1015                1020

Glu Ile Ile Glu Lys Val Asp Asn Tyr Ser Leu Ser Asp Lys Ala
1025            1030                1035                1040

Leu Thr Lys Leu Lys Ser Ile His Phe Asn Ile Asp Lys Glu Lys Tyr
                1045                1050                1055

Lys Asn Pro Lys Ser Gln Glu Asn Ile Lys Leu Leu Glu Asp Arg Val
            1060                1065                1070

Met Ile Leu Glu Lys Lys Ile Lys Glu Asp Lys Asp Ala Leu Ile Gln
    1075                1080                1085

Ile Lys Asn Leu Ser His Asp His Phe Val Asn Ala Asp Asn Glu Lys
    1090                1095                1100

Lys Lys Gln Lys Glu Lys Glu Glu Asp Asp Glu Gln Thr His Tyr Ser
1105                1110                1115                1120

Lys Lys Arg Lys Val Met Gly Asp Ile Tyr Lys Asp Ile Lys Lys Asn
                1125                1130                1135

Leu Asp Glu Leu Asn Asn Lys Asn Leu Ile Asp Ile Thr Leu Asn Glu
                1140                1145                1150

Ala Asn Lys Ile Glu Ser Glu Tyr Glu Lys Ile Leu Ile Asp Asp Ile
            1155                1160                1165

Cys Glu Gln Ile Thr Asn Glu Ala Lys Lys Ser Asp Thr Ile Lys Glu
    1170                1175                1180

Lys Ile Glu Ser Tyr Lys Lys Asp Ile Asp Tyr Val Asp Val Asp Val
1185                1190                1195                1200

Ser Lys Thr Arg Asn Asp His His Leu Asn Gly Asp Lys Ile His Asp
            1205                1210                1215

Ser Phe Phe Tyr Glu Asp Thr Leu Asn Tyr Lys Ala Tyr Phe Asp Lys
            1220                1225                1230

Leu Lys Asp Leu Tyr Glu Asn Ile Asn Lys Leu Thr Asn Glu Ser Asn
    1235                1240                1245

Gly Leu Lys Ser Asp Ala His Asn Asn Thr Gln Val Asp Lys Leu
    1250                1255                1260

Lys Glu Ile Asn Leu Gln Val Phe Ser Asn Leu Gly Asn Ile Ile Lys
1265                1270                1275                1280

Tyr Val Glu Lys Leu Glu Asn Thr Leu His Glu Leu Lys Asp Met Tyr
                1285                1290                1295

Glu Phe Leu Glu Thr Ile Asp Ile Asn Lys Ile Leu Lys Ser Ile His
                1300                1305                1310

Asn Ser Met Lys Lys Ser Glu Tyr Ser Asn Glu Thr Lys Lys Ile
            1315                1320                1325

Phe Glu Gln Ser Val Asn Ile Thr Asn Gln Phe Ile Glu Asp Val Glu
    1330                1335                1340

Ile Leu Lys Thr Ser Ile Asn Pro Asn Tyr Glu Ser Leu Asn Asp Asp
```

```
                1345                1350                1355                1360
Gln Ile Asp Asp Asn Ile Lys Ser Leu Val Leu Lys Lys Glu Glu Ile
                1365                1370                1375

Ser Glu Lys Arg Lys Gln Val Asn Lys Tyr Ile Thr Asp Ile Glu Ser
            1380                1385                1390

Asn Lys Glu Gln Ser Asp Leu His Leu Arg Tyr Ala Ser Arg Ser Ile
        1395                1400                1405

Tyr Val Ile Asp Leu Phe Ile Lys His Glu Ile Asn Pro Ser Asp
    1410                1415                1420

Gly Lys Asn Phe Asp Ile Ile Lys Val Lys Glu Met Ile Asn Lys Thr
1425                1430                1435                1440

Lys Gln Val Ser Asn Glu Ala Met Glu Tyr Ala Asn Lys Met Asp Glu
                1445                1450                1455

Lys Asn Lys Asp Ile Ile Lys Ile Glu Asn Glu Leu Tyr Asn Leu Ile
            1460                1465                1470

Asn Asn Asn Ile Arg Ser Leu Lys Gly Val Lys Tyr Glu Lys Val Arg
        1475                1480                1485

Lys Gln Ala Arg Asn Ala Ile Asp Asp Ile Asn Asn Ile His Ser Asn
    1490                1495                1500

Ile Lys Thr Ile Leu Thr Lys Ser Lys Glu Arg Leu Asp Glu Ile Lys
1505                1510                1515                1520

Lys Gln Pro Asn Ile Lys Arg Glu Gly Asp Val Leu Asn Asn Asp Lys
                1525                1530                1535

Thr Lys Ile Ala Tyr Ile Thr Ile Gln Ile Asn Asn Gly Arg Ile Glu
            1540                1545                1550

Ser Asn Leu Leu Asn Ile Leu Asn Met Lys His Asn Ile Asp Thr Ile
        1555                1560                1565

Leu Asn Lys Ala Met Asp Tyr Met Asn Asp Val Ser Lys Ser Asp Gln
    1570                1575                1580

Ile Val Ile Asn Ile Asp Ser Leu Asn Met Asn Asp Ile Tyr Asn Lys
1585                1590                1595                1600

Asp Lys Asp Leu Leu Ile Asn Ile Leu Lys Glu Lys Gln Asn Met Glu
                1605                1610                1615

Ala Glu Tyr Lys Lys Met Asn Glu Met Tyr Asn Tyr Val Asn Glu Thr
            1620                1625                1630

Glu Lys Glu Ile Ile Lys His Lys Lys Asn Tyr Glu Ile Arg Ile Met
        1635                1640                1645

Glu His Ile Lys Lys Glu Thr Asn Glu Lys Lys Lys Lys Phe Met Glu
    1650                1655                1660

Ser Asn Asn Lys Ser Leu Thr Thr Leu Met Asp Ser Phe Arg Ser Met
1665                1670                1675                1680

Phe Tyr Asn Glu Tyr Ile Asn Asp Tyr Asn Ile Asn Glu Asn Phe Glu
                1685                1690                1695

Lys His Gln Asn Ile Leu Asn Glu Ile Tyr Asn Gly Phe Asn Glu Ser
            1700                1705                1710

Tyr Asn Ile Ile Asn Thr Lys Met Thr Glu Ile Ile Asn Asp Asn Leu
        1715                1720                1725

Asp Tyr Asn Glu Ile Lys Glu Ile Lys Glu Val Ala Gln Thr Glu Tyr
    1730                1735                1740

Asp Lys Leu Asn Lys Lys Val Asp Glu Leu Lys Asn Tyr Leu Asn Asn
1745                1750                1755                1760

Ile Lys Glu Gln Glu Gly His Arg Leu Ile Asp Tyr Ile Lys Glu Lys
                1765                1770                1775
```

```
Ile Phe Asn Leu Tyr Ile Lys Cys Ser Glu Gln Gln Asn Ile Ile Asp
            1780                1785                1790

Asp Ser Tyr Asn Tyr Ile Thr Val Lys Lys Gln Tyr Ile Lys Thr Ile
            1795                1800                1805

Glu Asp Val Lys Phe Leu Leu Asp Ser Leu Asn Thr Ile Glu Glu Lys
            1810                1815                1820

Asn Lys Ser Val Ala Asn Leu Glu Ile Cys Thr Asn Lys Glu Asp Ile
1825                1830                1835                1840

Lys Asn Leu Leu Lys His Val Ile Lys Leu Ala Asn Phe Ser Gly Ile
                1845                1850                1855

Ile Val Met Ser Asp Thr Asn Thr Glu Ile Thr Pro Glu Asn Pro Leu
                1860                1865                1870

Glu Asp Asn Asp Leu Leu Asn Leu Gln Leu Tyr Phe Glu Arg Lys His
                1875                1880                1885

Glu Ile Thr Ser Thr Leu Glu Asn Asp Ser Asp Leu Glu Leu Asp His
                1890                1895                1900

Leu Gly Ser Asn Ser Asp Glu Ser Ile Asp Asn Leu Lys Val Tyr Asn
1905                1910                1915                1920

Asp Ile Ile Glu Leu His Thr Tyr Ser Thr Gln Ile Leu Lys Tyr Leu
                1925                1930                1935

Asp Asn Ile Gln Lys Leu Lys Gly Asp Cys Asn Asp Leu Val Lys Asp
                1940                1945                1950

Cys Lys Glu Leu Arg Glu Leu Ser Thr Ala Leu Tyr Asp Leu Lys Ile
                1955                1960                1965

Gln Ile Thr Ser Val Ile Asn Arg Glu Asn Asp Ile Ser Asn Asn Ile
                1970                1975                1980

Asp Ile Val Ser Asn Lys Leu Asn Glu Ile Asp Ala Ile Gln Tyr Asn
1985                1990                1995                2000

Phe Glu Lys Tyr Lys Glu Ile Phe Asp Asn Val Glu Glu Tyr Lys Thr
                2005                2010                2015

Leu Asp Asp Thr Lys Asn Ala Tyr Ile Val Lys Lys Ala Glu Ile Leu
                2020                2025                2030

Lys Asn Val Asp Ile Asn Lys Thr Lys Glu Asp Leu Asp Ile Tyr Phe
                2035                2040                2045

Asn Asp Leu Asp Glu Leu Glu Lys Ser Leu Thr Leu Ser Ser Asn Glu
                2050                2055                2060

Met Glu Ile Lys Thr Ile Val Gln Asn Ser Tyr Asn Ser Phe Ser Asp
2065                2070                2075                2080

Ile Asn Lys Asn Ile Asn Asp Ile Asp Lys Glu Met Lys Thr Leu Ile
                2085                2090                2095

Pro Met Leu Asp Glu Leu Leu Asn Glu Gly His Asn Ile Asp Ile Ser
                2100                2105                2110

Leu Tyr Asn Phe Ile Ile Arg Asn Ile Gln Ile Lys Ile Gly Asn Asp
            2115                2120                2125

Ile Lys Asn Ile Arg Glu Gln Glu Asn Asp Thr Asn Ile Cys Phe Glu
            2130                2135                2140

Tyr Ile Gln Asn Asn Tyr Asn Phe Ile Lys Ser Asp Ile Ser Ile Phe
2145                2150                2155                2160

Asn Lys Tyr Asp Asp His Ile Lys Val Asp Asn Tyr Ile Ser Asn Asn
                2165                2170                2175

Ile Asp Val Val Asn Lys His Asn Ser Leu Leu Ser Glu His Val Ile
                2180                2185                2190
```

```
Asn Ala Thr Asn Ile Ile Glu Asn Ile Met Thr Ser Ile Val Glu Ile
             2195                2200                2205

Asn Glu Asp Thr Glu Met Asn Ser Leu Glu Glu Thr Gln Asp Lys Leu
        2210                2215                2220

Leu Glu Leu Tyr Glu Asn Phe Lys Lys Glu Lys Asn Ile Ile Asn Asn
2225                2230                2235                2240

Asn Tyr Lys Ile Val His Phe Asn Lys Leu Lys Glu Ile Glu Asn Ser
             2245                2250                2255

Leu Glu Thr Tyr Asn Ser Ile Ser Thr Asn Phe Asn Lys Ile Asn Glu
        2260                2265                2270

Thr Gln Asn Ile Asp Ile Leu Lys Asn Glu Phe Asn Asn Ile Lys Thr
             2275                2280                2285

Lys Ile Asn Asp Lys Val Lys Glu Leu Val His Val Asp Ser Thr Leu
        2290                2295                2300

Thr Leu Glu Ser Ile Gln Thr Phe Asn Asn Leu Tyr Gly Asp Leu Met
2305                2310                2315                2320

Ser Asn Ile Gln Asp Val Tyr Lys Tyr Glu Asp Ile Asn Asn Val Glu
             2325                2330                2335

Leu Lys Lys Val Lys Leu Tyr Ile Glu Asn Ile Thr Asn Leu Leu Gly
        2340                2345                2350

Arg Ile Asn Thr Phe Ile Lys Glu Leu Asp Lys Tyr Gln Asp Glu Asn
        2355                2360                2365

Asn Gly Ile Asp Lys Tyr Ile Glu Ile Asn Lys Glu Asn Asn Ser Tyr
        2370                2375                2380

Ile Ile Lys Leu Lys Glu Lys Ala Asn Asn Leu Lys Glu Asn Phe Ser
2385                2390                2395                2400

Lys Leu Leu Gln Asn Ile Lys Arg Asn Glu Thr Glu Leu Tyr Asn Ile
             2405                2410                2415

Asn Asn Ile Lys Asp Asp Ile Met Asn Thr Gly Lys Ser Val Asn Asn
             2420                2425                2430

Ile Lys Gln Lys Phe Ser Ser Asn Leu Pro Leu Lys Glu Lys Leu Phe
        2435                2440                2445

Gln Met Glu Glu Met Leu Leu Asn Ile Asn Asn Ile Met Asn Glu Thr
        2450                2455                2460

Lys Arg Ile Ser Asn Thr Asp Ala Tyr Thr Asn Ile Thr Leu Gln Asp
2465                2470                2475                2480

Ile Glu Asn Asn Lys Asn Lys Glu Asn Asn Met Asn Ile Glu Thr
             2485                2490                2495

Ile Asp Lys Leu Ile Asp His Ile Lys Ile His Asn Glu Lys Ile Gln
        2500                2505                2510

Ala Glu Ile Leu Ile Ile Asp Asp Ala Lys Arg Lys Val Lys Glu Ile
        2515                2520                2525

Thr Asp Asn Ile Asn Lys Ala Phe Asn Glu Ile Thr Glu Asn Tyr Asn
        2530                2535                2540

Asn Glu Asn Asn Gly Val Ile Lys Ser Ala Lys Asn Ile Val Asp Lys
2545                2550                2555                2560

Ala Thr Tyr Leu Asn Asn Glu Leu Asp Lys Phe Leu Leu Lys Leu Asn
             2565                2570                2575

Glu Leu Leu Ser His Asn Asn Asp Ile Lys Asp Leu Gly Asp Glu
        2580                2585                2590

Lys Leu Ile Leu Lys Glu Glu Glu Arg Lys Glu Arg Glu Arg Leu
        2595                2600                2605

Glu Lys Ala Lys Gln Glu Glu Glu Arg Lys Glu Arg Glu Arg Ile Glu
```

-continued

```
                2610                2615                2620
Lys Glu Lys Gln Glu Lys Glu Arg Leu Glu Arg Glu Lys Gln Glu Gln
2625                2630                2635                2640

Leu Lys Lys Glu Ala Leu Lys Lys Gln Glu Gln Glu Arg Gln Glu Gln
            2645                2650                2655

Gln Gln Lys Glu Glu Ala Leu Lys Arg Gln Glu Gln Glu Arg Leu Gln
            2660                2665                2670

Lys Glu Glu Glu Leu Lys Arg Gln Glu Gln Glu Arg Leu Glu Arg Glu
            2675                2680                2685

Lys Gln Glu Gln Leu Gln Lys Glu Glu Glu Leu Arg Lys Lys Glu Gln
            2690                2695                2700

Glu Lys Gln Gln Gln Arg Asn Ile Gln Glu Leu Glu Glu Gln Lys Lys
2705                2710                2715                2720

Pro Glu Ile Ile Asn Glu Ala Leu Val Lys Gly Asp Lys Ile Leu Glu
            2725                2730                2735

Gly Ser Asp Gln Arg Asn Met Glu Leu Ser Lys Pro Asn Val Ser Met
            2740                2745                2750

Asp Asn Thr Asn Asn Ser Pro Ile Ser Asn Ser Glu Ile Thr Glu Ser
            2755                2760                2765

Asp Asp Ile Asp Asn Ser Glu Asn Ile His Thr Ser His Met Ser Asp
            2770                2775                2780

Ile Glu Ser Thr Gln Thr Ser His Arg Ser Asn Thr His Gly Gln Gln
2785                2790                2795                2800

Ile Ser Asp Ile Val Glu Asp Gln Ile Thr His Pro Ser Asn Ile Gly
            2805                2810                2815

Gly Glu Lys Ile Thr His Asn Asp Glu Ile Ser Ile Thr Gly Glu Arg
            2820                2825                2830

Asn Asn Ile Ser Asp Val Asn Asp Tyr Ser Glu Ser Ser Asn Ile Phe
            2835                2840                2845

Glu Asn Gly Asp Ser Thr Ile Asn Thr Ser Thr Arg Asn Thr Ser Ser
            2850                2855                2860

Thr His Asp Glu Ser His Ile Ser Pro Ile Ser Asn Ala Tyr Asp His
2865                2870                2875                2880

Val Val Ser Asp Asn Lys Lys Ser Met Asp Glu Asn Ile Lys Asp Lys
            2885                2890                2895

Leu Lys Ile Asp Glu Ser Ile Thr Thr Asp Glu Gln Ile Arg Leu Asp
            2900                2905                2910

Asp Asn Ser Asn Ile Val Arg Ile Asp Ser Thr Asp Gln Arg Asp Ala
            2915                2920                2925

Ser Ser His Gly Ser Ser Asn Arg Asp Asp Asp Glu Ile Ser His Val
            2930                2935                2940

Gly Ser Asp Ile His Met Asp Ser Val Asp Ile His Asp Ser Ile Asp
2945                2950                2955                2960

Thr Asp Glu Asn Ala Asp His Arg His Asn Val Asn Ser Val Asp Ser
            2965                2970                2975

Leu Ser Ser Ser Asp Tyr Thr Asp Thr Gln Lys Asp Phe Ser Ser Ile
            2980                2985                2990

Ile Lys Asp Gly Gly Asn Lys Glu Gly His Ala Glu Asn Glu Ser Lys
            2995                3000                3005

Glu Tyr Glu Ser Gln Thr Glu Gln Thr His Glu Glu Gly Ile Met Asn
            3010                3015                3020

Pro Asn Lys Tyr Ser Ile Ser Glu Val Asp Gly Ile Lys Leu Asn Glu
3025                3030                3035                3040
```

```
Glu Ala Lys His Lys Ile Thr Glu Lys Leu Val Asp Ile Tyr Pro Ser
            3045                3050                3055

Thr Tyr Arg Thr Leu Asp Glu Pro Met Glu Thr His Gly Pro Asn Glu
            3060                3065                3070

Lys Phe His Met Phe Gly Ser Pro Tyr Val Thr Glu Glu Asp Tyr Thr
            3075                3080                3085

Glu Lys His Asp Tyr Asp Lys His Glu Asp Phe Asn Asn Glu Arg Tyr
            3090                3095                3100

Ser Asn His Asn Lys Met Asp Asp Phe Val Tyr Asn Ala Gly Gly Val
3105                3110                3115                3120

Val Cys Cys Val Leu Phe Phe Ala Ser Ile Thr Phe Phe Ser Met Asp
            3125                3130                3135

Arg Ser Asn Lys Asp Glu Cys Asp Phe Asp Met Cys Glu Glu Val Asn
            3140                3145                3150

Asn Asn Asp His Leu Ser Asn Tyr Ala Asp Lys Glu Glu Ile Ile Glu
            3155                3160                3165

Ile Val Phe Asp Glu Asn Glu Glu Lys Tyr Phe
            3170                3175

<210> SEQ ID NO 14
<211> LENGTH: 3130
<212> TYPE: PRT
<213> ORGANISM: Plasmodium falciparum

<400> SEQUENCE: 14

Met Lys Thr Thr Leu Phe Cys Ser Ile Ser Phe Cys Asn Ile Ile Phe
1               5                   10                  15

Phe Phe Leu Glu Leu Ser His Glu His Phe Val Gly Gln Ser Ser Asn
            20                  25                  30

Thr His Gly Ala Ser Ser Val Thr Asp Phe Asn Phe Ser Glu Glu Lys
        35                  40                  45

Asn Leu Lys Ser Phe Glu Gly Lys Asn Asn Asn Asp Asn Tyr Ala
    50                  55                  60

Ser Ile Asn Arg Leu Tyr Arg Lys Lys Pro Tyr Met Lys Arg Ser Leu
65                  70                  75                  80

Ile Asn Leu Glu Asn Asp Leu Phe Arg Leu Glu Pro Ile Ser Tyr Ile
                85                  90                  95

Gln Arg Tyr Tyr Lys Lys Asn Ile Asn Arg Ser Asp Ile Phe His Asn
            100                 105                 110

Lys Lys Glu Arg Gly Ser Lys Val Tyr Ser Asn Val Ser Ser Phe His
        115                 120                 125

Ser Phe Ile Gln Glu Gly Lys Glu Glu Val Glu Val Phe Ser Ile Trp
130                 135                 140

Gly Ser Asn Ser Val Leu Asp His Ile Asp Val Leu Arg Asp Asn Gly
145                 150                 155                 160

Thr Val Val Phe Ser Val Gln Pro Tyr Tyr Leu Asp Ile Tyr Thr Cys
                165                 170                 175

Lys Glu Ala Ile Leu Phe Thr Thr Ser Phe Tyr Lys Asp Leu Asp Lys
            180                 185                 190

Ser Ser Ile Thr Lys Ile Asn Glu Asp Ile Glu Lys Phe Asn Glu Glu
        195                 200                 205

Ile Ile Lys Asn Glu Glu Gln Cys Leu Val Gly Gly Lys Thr Asp Phe
    210                 215                 220

Asp Asn Leu Leu Ile Val Leu Glu Asn Ala Glu Lys Ala Asn Val Arg
```

-continued

```
               225                 230                 235                 240
Lys Thr Leu Phe Asp Asn Thr Phe Asn Asp Tyr Lys Asn Lys Lys Ser
                    245                 250                 255

Ser Phe Tyr Asn Cys Leu Lys Asn Lys Asn Asp Tyr Asp Lys Lys
                    260                 265                 270

Ile Lys Asn Ile Lys Asn Glu Ile Thr Lys Leu Leu Lys Asn Ile Glu
                    275                 280                 285

Ser Thr Gly Asn Met Cys Lys Thr Glu Ser Tyr Val Met Asn Asn Asn
                    290                 295                 300

Leu Tyr Leu Leu Arg Val Asn Glu Val Lys Ser Thr Pro Ile Asp Leu
305                 310                 315                 320

Tyr Leu Asn Arg Ala Lys Glu Leu Leu Glu Ser Ser Lys Leu Val
                    325                 330                 335

Asn Pro Ile Lys Met Lys Leu Gly Asp Asn Lys Asn Met Tyr Ser Ile
                    340                 345                 350

Gly Tyr Ile His Asp Glu Ile Lys Asp Ile Ile Lys Arg Tyr Asn Phe
                    355                 360                 365

His Leu Lys His Ile Glu Lys Gly Lys Glu Tyr Ile Lys Arg Ile Thr
370                 375                 380

Gln Ala Asn Asn Ile Ala Asp Lys Met Lys Lys Asp Glu Leu Ile Lys
385                 390                 395                 400

Lys Ile Phe Glu Ser Ser Lys His Phe Ala Ser Phe Lys Tyr Ser Asn
                    405                 410                 415

Glu Met Ile Ser Lys Leu Asp Ser Leu Phe Ile Lys Asn Glu Glu Ile
                    420                 425                 430

Leu Asn Asn Leu Phe Asn Asn Ile Phe Asn Ile Phe Lys Lys Lys Tyr
                    435                 440                 445

Glu Thr Tyr Val Asp Met Lys Thr Ile Glu Ser Lys Tyr Thr Thr Val
                    450                 455                 460

Met Thr Leu Ser Glu His Leu Leu Glu Tyr Ala Met Asp Val Leu Lys
465                 470                 475                 480

Ala Asn Pro Gln Lys Pro Ile Asp Pro Lys Ala Asn Leu Asp Ser Glu
                    485                 490                 495

Val Val Lys Leu Gln Ile Lys Ile Asn Glu Lys Ser Asn Glu Leu Asp
                    500                 505                 510

Asn Ala Ile Ser Gln Val Lys Thr Leu Ile Ile Met Lys Ser Phe
                    515                 520                 525

Tyr Asp Ile Ile Ile Ser Glu Lys Ala Ser Met Asp Glu Met Glu Lys
                    530                 535                 540

Lys Glu Leu Ser Leu Asn Asn Tyr Ile Glu Lys Thr Asp Tyr Ile Leu
545                 550                 555                 560

Gln Thr Tyr Asn Ile Phe Lys Ser Lys Ser Ile Ile Asn Asn Asn
                    565                 570                 575

Ser Lys Asn Ile Ser Ser Lys Tyr Ile Thr Ile Glu Gly Leu Lys Asn
                    580                 585                 590

Asp Ile Asp Glu Leu Asn Ser Leu Ile Ser Tyr Phe Lys Asp Ser Gln
                    595                 600                 605

Glu Thr Leu Ile Lys Asp Glu Leu Lys Lys Asn Met Lys Thr Asp
                    610                 615                 620

Tyr Leu Asn Asn Val Lys Tyr Ile Glu Glu Asn Val Thr His Ile Asn
625                 630                 635                 640

Glu Ile Ile Leu Leu Lys Asp Ser Ile Thr Gln Arg Ile Ala Asp Ile
                    645                 650                 655
```

-continued

```
Asp Glu Leu Asn Ser Leu Asn Leu Ile Asn Ile Asn Asp Phe Ile Asn
            660                 665                 670

Glu Lys Asn Ile Ser Gln Glu Lys Val Ser Tyr Asn Leu Asn Lys Leu
            675                 680                 685

Tyr Lys Gly Ser Phe Glu Glu Leu Glu Ser Gly Leu Ser His Phe Leu
            690                 695                 700

Asp Thr Lys Tyr Leu Phe His Glu Lys Ser Val Asn Glu Leu Gln
705                 710                 715                 720

Thr Ile Leu Asn Thr Ser Asn Asn Glu Cys Ala Lys Leu Asn Phe Met
                725                 730                 735

Lys Ser Asp Asn Asn Asn Asn Asn Ser Asn Ile Ile Asn Leu
            740                 745                 750

Leu Lys Thr Glu Leu Ser His Leu Leu Ser Leu Lys Glu Asn Ile Ile
            755                 760                 765

Lys Lys Leu Leu Asn His Ile Glu Gln Asn Ile Gln Asn Ser Ser Asn
            770                 775                 780

Lys Tyr Thr Ile Thr Tyr Thr Asp Ile Asn Asn Arg Met Glu Asp Tyr
785                 790                 795                 800

Lys Glu Glu Ile Glu Ser Leu Glu Val Tyr Lys His Thr Ile Gly Asn
            805                 810                 815

Ile Gln Lys Glu Tyr Ile Leu His Leu Tyr Glu Asn Asp Lys Asn Ala
            820                 825                 830

Leu Ala Val His Asn Thr Ser Met Gln Ile Leu Gln Tyr Lys Asp Ala
            835                 840                 845

Ile Gln Asn Ile Lys Asn Lys Ile Ser Asp Asp Ile Lys Ile Leu Lys
            850                 855                 860

Lys Tyr Lys Glu Met Asn Gln Asp Leu Leu Asn Tyr Tyr Glu Ile Leu
865                 870                 875                 880

Asp Lys Lys Leu Lys Asp Asn Thr Tyr Ile Lys Glu Met His Thr Ala
                885                 890                 895

Ser Leu Val Gln Ile Thr Gln Tyr Ile Pro Tyr Glu Asp Lys Thr Ile
            900                 905                 910

Ser Glu Leu Glu Gln Glu Phe Asn Asn Asn Gln Lys Leu Asp Asn
            915                 920                 925

Ile Leu Gln Asp Ile Asn Ala Met Asn Leu Asn Ile Asn Ile Leu Gln
            930                 935                 940

Thr Leu Asn Ile Gly Ile Asn Ala Cys Asn Thr Asn Asn Lys Asn Val
945                 950                 955                 960

Glu His Leu Leu Asn Lys Lys Ile Glu Leu Lys Asn Ile Leu Asn Asp
                965                 970                 975

Gln Met Lys Ile Ile Lys Asn Asp Asp Ile Ile Gln Asp Asn Glu Lys
            980                 985                 990

Glu Asn Phe Ser Asn Val Leu Lys Lys Glu Glu Lys Leu Glu Lys
            995                 1000                1005

Glu Leu Asp Asp Ile Lys Phe Asn Asn Leu Lys Met Asp Ile His Lys
            1010                1015                1020

Leu Leu Asn Ser Tyr Asp His Thr Lys Gln Asn Ile Glu Ser Asn Leu
1025                1030                1035                1040

Lys Ile Asn Leu Asp Ser Phe Glu Lys Glu Lys Asp Ser Trp Val His
                1045                1050                1055

Phe Lys Ser Thr Ile Asp Ser Leu Tyr Val Glu Tyr Asn Ile Cys Asn
            1060                1065                1070
```

-continued

Gln Lys Thr His Asn Thr Ile Lys Gln Gln Lys Asn Asp Ile Ile Glu
        1075                1080                1085

Leu Ile Tyr Lys Arg Ile Lys Asp Ile Asn Gln Glu Ile Ile Glu Lys
    1090                1095                1100

Val Asp Asn Tyr Tyr Ser Leu Ser Asp Lys Ala Leu Thr Lys Leu Lys
1105                1110                1115                1120

Ser Ile His Phe Asn Ile Asp Lys Glu Lys Tyr Lys Asn Pro Lys Ser
            1125                1130                1135

Gln Glu Asn Ile Lys Leu Leu Glu Asp Arg Val Met Ile Leu Glu Lys
            1140                1145                1150

Lys Ile Lys Glu Asp Lys Asp Ala Leu Ile Gln Ile Lys Asn Leu Ser
        1155                1160                1165

His Asp His Phe Val Asn Ala Asp Asn Glu Lys Lys Lys Gln Lys Glu
    1170                1175                1180

Lys Glu Glu Asp Asp Glu Gln Thr His Tyr Ser Lys Lys Arg Lys Val
1185                1190                1195                1200

Met Gly Asp Ile Tyr Lys Asp Ile Lys Lys Asn Leu Asp Glu Leu Asn
            1205                1210                1215

Asn Lys Asn Leu Ile Asp Ile Thr Leu Asn Glu Ala Asn Lys Ile Glu
            1220                1225                1230

Ser Glu Tyr Glu Lys Ile Leu Ile Asp Asp Ile Cys Glu Gln Ile Thr
        1235                1240                1245

Asn Glu Ala Lys Lys Ser Asp Thr Ile Lys Glu Lys Ile Glu Ser Tyr
    1250                1255                1260

Lys Lys Asp Ile Asp Tyr Val Asp Val Asp Val Ser Lys Thr Arg Asn
1265                1270                1275                1280

Asp His His Leu Asn Gly Asp Lys Ile His Asp Ser Phe Phe Tyr Glu
            1285                1290                1295

Asp Thr Leu Asn Tyr Lys Ala Tyr Phe Asp Lys Leu Lys Asp Leu Tyr
        1300                1305                1310

Glu Asn Ile Asn Lys Leu Thr Asn Glu Ser Asn Gly Leu Lys Ser Asp
        1315                1320                1325

Ala His Asn Asn Asn Thr Gln Val Asp Lys Leu Lys Glu Ile Asn Leu
    1330                1335                1340

Gln Val Phe Ser Asn Leu Gly Asn Ile Ile Lys Tyr Val Glu Lys Leu
1345                1350                1355                1360

Glu Asn Thr Leu His Glu Leu Lys Asp Met Tyr Glu Phe Leu Glu Thr
            1365                1370                1375

Ile Asp Ile Asn Lys Ile Leu Lys Ser Ile His Asn Ser Met Lys Lys
            1380                1385                1390

Ser Glu Glu Tyr Ser Asn Glu Thr Lys Lys Ile Phe Glu Gln Ser Val
        1395                1400                1405

Asn Ile Thr Asn Gln Phe Ile Glu Asp Val Glu Ile Leu Lys Thr Ser
    1410                1415                1420

Ile Asn Pro Asn Tyr Glu Ser Leu Asn Asp Gln Ile Asp Asp Asn
1425                1430                1435                1440

Ile Lys Ser Leu Val Leu Lys Lys Glu Glu Ile Ser Glu Lys Arg Lys
            1445                1450                1455

Gln Val Asn Lys Tyr Ile Thr Asp Ile Glu Ser Asn Lys Glu Gln Ser
            1460                1465                1470

Asp Leu His Leu Arg Tyr Ala Ser Arg Ser Ile Tyr Val Ile Asp Leu
        1475                1480                1485

Phe Ile Lys His Glu Ile Ile Asn Pro Ser Asp Gly Lys Asn Phe Asp

```
            1490              1495              1500

Ile Ile Lys Val Lys Glu Met Ile Asn Lys Thr Lys Gln Val Ser Asn
1505              1510              1515              1520

Glu Ala Met Glu Tyr Ala Asn Lys Met Asp Glu Lys Asn Lys Asp Ile
                  1525              1530              1535

Ile Lys Ile Glu Asn Glu Leu Tyr Asn Leu Ile Asn Asn Ile Arg
            1540              1545              1550

Ser Leu Lys Gly Val Lys Tyr Glu Lys Val Arg Lys Gln Ala Arg Asn
            1555              1560              1565

Ala Ile Asp Asp Ile Asn Asn Ile His Ser Asn Ile Lys Thr Ile Leu
            1570              1575              1580

Thr Lys Ser Lys Glu Arg Leu Asp Glu Ile Lys Lys Gln Pro Asn Ile
1585              1590              1595              1600

Lys Arg Glu Gly Asp Val Leu Asn Asp Lys Thr Lys Ile Ala Tyr
                  1605              1610              1615

Ile Thr Ile Gln Ile Asn Asn Gly Arg Ile Glu Ser Asn Leu Leu Asn
                  1620              1625              1630

Ile Leu Asn Met Lys His Asn Ile Asp Thr Ile Leu Asn Lys Ala Met
                  1635              1640              1645

Asp Tyr Met Asn Asp Val Ser Lys Ser Asp Gln Ile Val Ile Asn Ile
            1650              1655              1660

Asp Ser Leu Asn Met Asn Asp Ile Tyr Asn Lys Asp Lys Asp Leu Leu
1665              1670              1675              1680

Ile Asn Ile Leu Lys Glu Lys Gln Asn Met Glu Ala Glu Tyr Lys Lys
                  1685              1690              1695

Met Asn Glu Met Tyr Asn Tyr Val Asn Glu Thr Glu Lys Glu Ile Ile
                  1700              1705              1710

Lys His Lys Lys Asn Tyr Glu Ile Arg Ile Met Glu His Ile Lys Lys
                  1715              1720              1725

Glu Thr Asn Glu Lys Lys Lys Phe Met Gly Ser Asn Asn Lys Ser
                  1730              1735              1740

Leu Thr Thr Leu Met Asp Ser Phe Arg Ser Met Phe Tyr Asn Glu Tyr
1745              1750              1755              1760

Ile Asn Asp Tyr Asn Ile Asn Glu Asn Phe Glu Lys His Gln Asn Ile
                  1765              1770              1775

Leu Asn Glu Ile Tyr Asn Gly Phe Asn Glu Ser Tyr Asn Ile Ile Asn
                  1780              1785              1790

Thr Lys Met Thr Glu Ile Ile Asn Asp Asn Leu Asp Tyr Asn Glu Ile
                  1795              1800              1805

Lys Glu Ile Lys Glu Val Ala Gln Thr Glu Tyr Asp Lys Leu Asn Lys
            1810              1815              1820

Lys Val Asp Glu Leu Lys Asn Tyr Leu Asn Asn Ile Lys Glu Gln Glu
1825              1830              1835              1840

Gly His Arg Leu Ile Asp Tyr Ile Lys Glu Lys Ile Phe Asn Leu Tyr
                  1845              1850              1855

Ile Lys Cys Ser Glu Gln Gln Asn Ile Ile Asp Asp Ser Tyr Asn Tyr
                  1860              1865              1870

Ile Thr Val Lys Lys Gln Tyr Ile Lys Thr Ile Glu Asp Val Lys Phe
            1875              1880              1885

Leu Leu Asp Ser Leu Asn Thr Ile Glu Glu Lys Asn Lys Ser Val Ala
            1890              1895              1900

Asn Leu Glu Ile Cys Thr Asn Lys Glu Asp Ile Lys Asn Leu Leu Lys
1905              1910              1915              1920
```

His Val Ile Lys Leu Ala Asn Phe Ser Gly Ile Ile Val Met Ser Asp
            1925                1930                1935
Thr Asn Thr Glu Ile Thr Pro Glu Asn Pro Leu Glu Asp Asn Asp Leu
            1940                1945                1950
Leu Asn Leu Gln Leu Tyr Phe Glu Arg Lys His Glu Ile Thr Ser Thr
            1955                1960                1965
Leu Glu Asn Asp Ser Asp Leu Glu Leu Asp His Leu Gly Ser Asn Ser
            1970                1975                1980
Asp Glu Ser Ile Asp Asn Leu Lys Val Tyr Asn Asp Ile Ile Glu Leu
1985                1990                1995                2000
His Thr Tyr Ser Thr Gln Ile Leu Lys Tyr Leu Asp Asn Ile Gln Lys
            2005                2010                2015
Leu Lys Gly Asp Cys Asn Asp Leu Val Lys Asp Cys Lys Glu Leu Arg
            2020                2025                2030
Glu Leu Ser Thr Ala Leu Tyr Asp Leu Lys Ile Gln Ile Thr Ser Val
            2035                2040                2045
Ile Asn Arg Glu Asn Asp Ile Ser Asn Asn Ile Asp Ile Val Ser Asn
            2050                2055                2060
Lys Leu Asn Glu Ile Asp Ala Ile Gln Tyr Asn Phe Glu Lys Tyr Lys
2065                2070                2075                2080
Glu Ile Phe Asp Asn Val Glu Glu Tyr Lys Thr Leu Asp Asp Thr Lys
            2085                2090                2095
Asn Ala Tyr Ile Val Lys Lys Ala Glu Ile Leu Lys Asn Val Asp Ile
            2100                2105                2110
Asn Lys Thr Lys Glu Asp Leu Asp Ile Tyr Phe Asn Asp Leu Asp Glu
            2115                2120                2125
Leu Glu Lys Ser Leu Thr Leu Ser Ser Asn Glu Met Glu Ile Lys Thr
            2130                2135                2140
Ile Val Gln Asn Ser Tyr Asn Ser Phe Ser Asp Ile Asn Lys Asn Ile
2145                2150                2155                2160
Asn Asp Ile Asp Lys Glu Met Lys Thr Leu Ile Pro Met Leu Asp Glu
            2165                2170                2175
Leu Leu Asn Glu Gly His Asn Ile Asp Ile Ser Leu Tyr Asn Phe Ile
            2180                2185                2190
Ile Arg Asn Ile Gln Ile Lys Ile Gly Asn Asp Ile Lys Asn Ile Arg
            2195                2200                2205
Glu Gln Glu Asn Asp Thr Asn Ile Cys Phe Glu Tyr Ile Gln Asn Asn
            2210                2215                2220
Tyr Asn Phe Ile Lys Ser Asp Ile Ser Ile Phe Asn Lys Tyr Asp Asp
2225                2230                2235                2240
His Ile Lys Val Asp Asn Tyr Ile Ser Asn Asn Ile Asp Val Val Asn
            2245                2250                2255
Lys His Asn Ser Leu Leu Ser Glu His Val Ile Asn Ala Thr Asn Ile
            2260                2265                2270
Ile Glu Asn Ile Met Thr Ser Ile Val Glu Ile Asn Glu Asp Thr Glu
            2275                2280                2285
Met Asn Ser Leu Glu Glu Thr Gln Asp Lys Leu Leu Glu Leu Tyr Glu
            2290                2295                2300
Asn Phe Lys Lys Glu Lys Asn Ile Ile Asn Asn Asn Tyr Lys Ile Val
2305                2310                2315                2320
His Phe Asn Lys Leu Lys Glu Ile Glu Asn Ser Leu Glu Thr Tyr Asn
            2325                2330                2335

-continued

```
Ser Ile Ser Thr Asn Phe Asn Lys Ile Asn Glu Thr Gln Asn Ile Asp
            2340                2345                2350
Ile Leu Lys Asn Glu Phe Asn Asn Ile Lys Thr Lys Ile Asn Asp Lys
        2355                2360                2365
Val Lys Glu Leu Val His Val Asp Ser Thr Leu Thr Leu Glu Ser Ile
    2370                2375                2380
Gln Thr Phe Asn Asn Leu Tyr Gly Asp Leu Met Ser Asn Ile Gln Asp
2385                2390                2395                2400
Val Tyr Lys Tyr Glu Asp Ile Asn Asn Val Glu Leu Lys Val Lys
            2405                2410                2415
Leu Tyr Ile Glu Asn Ile Thr Asn Leu Leu Gly Arg Ile Asn Thr Phe
        2420                2425                2430
Ile Lys Glu Leu Asp Lys Tyr Gln Asp Glu Asn Asn Gly Ile Asp Lys
    2435                2440                2445
Tyr Ile Glu Ile Asn Lys Glu Asn Asn Ser Tyr Ile Ile Lys Leu Lys
        2450                2455                2460
Glu Lys Ala Asn Asn Leu Lys Glu Asn Phe Ser Lys Leu Leu Gln Asn
2465                2470                2475                2480
Ile Lys Arg Asn Glu Thr Glu Leu Tyr Asn Ile Asn Asn Ile Lys Asp
            2485                2490                2495
Asp Ile Met Asn Thr Gly Lys Ser Val Asn Asn Ile Lys Gln Lys Phe
        2500                2505                2510
Ser Ser Asn Leu Pro Leu Lys Glu Lys Leu Phe Gln Met Glu Glu Met
    2515                2520                2525
Leu Leu Asn Ile Asn Asn Ile Met Asn Glu Thr Lys Arg Ile Ser Asn
        2530                2535                2540
Thr Ala Ala Tyr Thr Asn Ile Thr Leu Gln Asp Ile Glu Asn Asn Lys
2545                2550                2555                2560
Asn Lys Glu Asn Asn Asn Met Asn Ile Glu Thr Ile Asp Lys Leu Ile
            2565                2570                2575
Asp His Ile Lys Ile His Asn Glu Lys Ile Gln Ala Glu Ile Leu Ile
        2580                2585                2590
Ile Asp Asp Ala Lys Arg Lys Val Lys Glu Ile Thr Asp Asn Ile Asn
    2595                2600                2605
Lys Ala Phe Asn Glu Ile Thr Glu Asn Tyr Asn Asn Glu Asn Asn Gly
        2610                2615                2620
Val Ile Lys Ser Ala Lys Asn Ile Val Asp Glu Ala Thr Tyr Leu Asn
2625                2630                2635                2640
Asn Glu Leu Asp Lys Phe Leu Lys Leu Asn Glu Leu Leu Ser His
            2645                2650                2655
Asn Asn Asn Asp Ile Lys Asp Leu Gly Asp Glu Lys Leu Ile Leu Lys
        2660                2665                2670
Glu Glu Glu Glu Arg Lys Glu Arg Glu Arg Leu Glu Lys Ala Lys Gln
    2675                2680                2685
Glu Glu Glu Arg Lys Glu Arg Glu Arg Ile Glu Lys Glu Lys Gln Glu
        2690                2695                2700
Lys Glu Arg Leu Glu Arg Glu Lys Gln Glu Gln Leu Lys Lys Glu Glu
2705                2710                2715                2720
Glu Leu Arg Lys Lys Glu Gln Glu Arg Gln Glu Gln Gln Lys Glu
            2725                2730                2735
Glu Ala Leu Lys Arg Gln Glu Gln Glu Arg Leu Gln Lys Glu Glu Glu
        2740                2745                2750
Leu Lys Arg Gln Glu Gln Glu Arg Leu Glu Arg Glu Lys Gln Glu Gln
```

```
                        2755                2760                2765
Leu Gln Lys Glu Glu Leu Lys Arg Gln Glu Gln Glu Arg Leu Gln
            2770                2775                2780
Lys Glu Glu Ala Leu Lys Arg Gln Gln Glu Arg Leu Gln Lys Glu
2785                2790                2795                2800
Glu Glu Leu Lys Arg Gln Glu Gln Arg Leu Glu Arg Glu Lys Gln
                2805                2810                2815
Glu Gln Leu Gln Lys Glu Glu Leu Lys Arg Gln Glu Gln Glu Arg
            2820                2825                2830
Leu Gln Lys Glu Glu Ala Leu Lys Arg Gln Glu Gln Glu Arg Leu Gln
            2835                2840                2845
Lys Glu Glu Glu Leu Lys Arg Gln Gln Glu Arg Leu Glu Arg Lys
            2850                2855                2860
Lys Ile Glu Leu Ala Glu Arg Gln His Ile Lys Ser Lys Leu Glu
2865                2870                2875                2880
Ser Asp Met Val Lys Ile Ile Lys Asp Glu Leu Thr Lys Glu Lys Asp
                2885                2890                2895
Glu Ile Ile Lys Asn Lys Asp Ile Lys Leu Arg His Ser Leu Glu Gln
            2900                2905                2910
Lys Trp Leu Lys His Leu Gln Asn Ile Leu Ser Leu Lys Ile Asp Ser
            2915                2920                2925
Leu Leu Asn Lys Asn Asp Glu Val Ile Lys Asp Asn Glu Thr Gln Leu
            2930                2935                2940
Lys Thr Asn Ile Leu Asn Ser Leu Lys Asn Gln Leu Tyr Leu Asn Leu
2945                2950                2955                2960
Lys Arg Glu Leu Asn Glu Ile Ile Lys Glu Tyr Glu Glu Asn Gln Lys
                2965                2970                2975
Lys Ile Leu His Ser Asn Gln Leu Val Asn Asp Ser Leu Glu Gln Lys
            2980                2985                2990
Thr Asn Arg Leu Val Asp Ile Lys Pro Thr Lys His Gly Asp Ile Tyr
            2995                3000                3005
Thr Asn Lys Leu Ser Asp Asn Glu Thr Glu Met Leu Ile Thr Ser Lys
3010                3015                3020
Glu Lys Lys Asp Glu Thr Glu Ser Thr Lys Arg Ser Gly Thr Asp His
3025                3030                3035                3040
Thr Asn Ser Ser Glu Ser Thr Thr Asp Asp Asn Thr Asn Asp Arg Asn
                3045                3050                3055
Phe Ser Arg Ser Lys Asn Leu Ser Val Ala Ile Tyr Thr Ala Gly Ser
            3060                3065                3070
Val Ala Leu Cys Val Leu Ile Phe Ser Ser Ile Gly Leu Leu Leu Ile
            3075                3080                3085
Lys Thr Asn Ser Gly Asp Asn Ser Asn Glu Ile Asn Glu Ala Phe
            3090                3095                3100
Glu Pro Asn Asp Asp Val Leu Phe Lys Glu Lys Asp Glu Ile Ile Glu
3105                3110                3115                3120
Ile Thr Phe Asn Asp Asn Asp Ser Thr Ile
                3125                3130

<210> SEQ ID NO 15
<211> LENGTH: 2971
<212> TYPE: PRT
<213> ORGANISM: Plasmodium falciparum

<400> SEQUENCE: 15
```

-continued

```
Met Gln Arg Trp Ile Phe Cys Asn Ile Val Leu His Ile Leu Ile Tyr
 1               5                  10                  15
Leu Ala Glu Phe Ser His Glu Gln Ser Tyr Ser Ser Asn Glu Lys
             20                  25                  30
Ile Arg Lys Asp Tyr Ser Asp Asp Asn Asn Tyr Glu Pro Thr Pro Ser
             35                  40                  45
Tyr Glu Lys Arg Lys Lys Glu Tyr Gly Lys Asp Glu Ser Tyr Ile Lys
 50              55                  60
Asn Tyr Arg Gly Asn Asn Phe Ser Tyr Asp Leu Ser Lys Asn Ser Ser
 65                  70                  75                  80
Ile Phe Leu His Met Gly Asn Gly Ser Asn Ser Lys Thr Leu Lys Arg
                 85                  90                  95
Cys Asn Lys Lys Lys Asn Ile Lys Thr Asn Phe Leu Arg Pro Ile Glu
                100                 105                 110
Glu Glu Lys Thr Val Leu Asn Asn Tyr Val Tyr Lys Gly Val Asn Phe
                115                 120                 125
Leu Asp Thr Ile Lys Arg Asn Asp Ser Ser Tyr Lys Phe Asp Val Tyr
             130                 135                 140
Lys Asp Thr Ser Phe Leu Lys Asn Arg Glu Tyr Lys Glu Leu Ile Thr
145                 150                 155                 160
Met Gln Tyr Asp Tyr Ala Tyr Leu Glu Ala Thr Lys Glu Val Leu Tyr
                 165                 170                 175
Leu Ile Pro Lys Asp Lys Asp Tyr His Lys Phe Tyr Lys Asn Glu Leu
             180                 185                 190
Glu Lys Ile Leu Phe Asn Leu Lys Asp Ser Leu Lys Leu Leu Arg Glu
             195                 200                 205
Gly Tyr Ile Gln Ser Lys Leu Glu Met Ile Arg Ile His Ser Asp Ile
 210                 215                 220
Asp Ile Leu Asn Glu Phe His Gln Gly Asn Ile Ile Asn Asp Asn Tyr
225                 230                 235                 240
Phe Asn Asn Glu Ile Lys Lys Lys Glu Asp Met Glu Lys Tyr Ile
                 245                 250                 255
Arg Glu Tyr Asn Leu Tyr Ile Tyr Lys Tyr Glu Asn Gln Leu Lys Ile
                 260                 265                 270
Lys Ile Gln Lys Leu Thr Asn Glu Val Ser Ile Asn Leu Asn Lys Ser
             275                 280                 285
Thr Cys Glu Lys Asn Cys Tyr Asn Tyr Ile Leu Lys Leu Glu Lys Tyr
             290                 295                 300
Lys Asn Ile Ile Lys Asp Lys Ile Asn Lys Trp Lys Asp Leu Pro Glu
305                 310                 315                 320
Ile Tyr Ile Asp Asp Lys Ser Phe Ser Tyr Thr Phe Leu Lys Asp Val
                 325                 330                 335
Ile Asn Asn Lys Ile Asp Ile Tyr Lys Thr Ile Ser Ser Phe Ile Ser
             340                 345                 350
Thr Gln Lys Gln Leu Tyr Tyr Phe Glu Tyr Ile Tyr Ile Met Asn Lys
             355                 360                 365
Asn Thr Leu Asn Leu Leu Ser Tyr Asn Ile Gln Lys Thr Asp Ile Asn
         370                 375                 380
Ser Ser Ser Lys Tyr Thr Tyr Thr Lys Ser His Phe Leu Lys Asp Asn
385                 390                 395                 400
His Ile Leu Leu Ser Lys Tyr Tyr Thr Ala Lys Phe Ile Asp Ile Leu
                 405                 410                 415
Asn Lys Thr Tyr Tyr Tyr Asn Leu Tyr Lys Asn Lys Ile Leu Leu Phe
```

-continued

```
            420                 425                 430
Asn Lys Tyr Ile Ile Lys Leu Arg Asn Asp Leu Lys Glu Tyr Ala Phe
            435                 440                 445

Lys Ser Ile Gln Phe Ile Gln Asp Lys Ile Lys Lys His Lys Asp Glu
            450                 455                 460

Leu Ser Ile Glu Asn Ile Leu Gln Glu Val Asn Asn Ile Tyr Ile Lys
465                 470                 475                 480

Tyr Asp Thr Ser Ile Asn Glu Ile Ser Lys Tyr Asn Asn Leu Ile Ile
                485                 490                 495

Asn Thr Asp Leu Gln Ile Val Gln Gln Lys Leu Leu Glu Ile Lys Gln
            500                 505                 510

Lys Lys Asn Asp Ile Thr His Lys Val Gln Leu Ile Asn His Ile Tyr
            515                 520                 525

Lys Asn Ile His Asp Glu Ile Leu Asn Lys Asn Asn Glu Ile Thr
            530                 535                 540

Lys Ile Ile Ile Asn Asn Ile Lys Asp His Lys Lys Asp Leu Gln Asp
545                 550                 555                 560

Leu Leu Leu Phe Ile Gln Gln Ile Lys Gln Tyr Asn Ile Leu Thr Asp
                565                 570                 575

His Lys Ile Thr Gln Cys Asn Asn Tyr Tyr Lys Glu Ile Ile Lys Met
            580                 585                 590

Lys Glu Asp Ile Asn His Ile His Ile Tyr Ile Gln Pro Ile Leu Asn
            595                 600                 605

Asn Leu His Thr Leu Lys Gln Val Gln Asn Asn Lys Ile Lys Tyr Glu
            610                 615                 620

Glu His Ile Lys Gln Ile Leu Gln Lys Ile Tyr Asp Lys Lys Glu Ser
625                 630                 635                 640

Leu Lys Lys Ile Ile Leu Leu Lys Asp Glu Ala Gln Leu Asp Ile Thr
                645                 650                 655

Leu Leu Asp Asp Leu Ile Gln Lys Gln Thr Lys Lys Gln Thr Gln Thr
            660                 665                 670

Gln Thr Gln Thr Gln Lys Gln Thr Leu Ile Gln Asn Asn Glu Thr Ile
            675                 680                 685

Gln Leu Ile Ser Gly Gln Glu Asp Lys His Glu Ser Asn Pro Phe Asn
            690                 695                 700

His Ile Gln Thr Tyr Ile Gln Gln Lys Asp Thr Gln Asn Lys Asn Ile
705                 710                 715                 720

Gln Asn Leu Leu Lys Ser Leu Tyr Asn Gly Asn Ile Asn Thr Phe Ile
                725                 730                 735

Asp Thr Ile Ser Lys Tyr Ile Leu Lys Gln Lys Asp Ile Glu Leu Thr
            740                 745                 750

Gln His Val Tyr Thr Asp Glu Lys Ile Asn Asp Tyr Leu Glu Glu Ile
            755                 760                 765

Lys Asn Glu Gln Asn Lys Ile Asp Lys Thr Ile Asp Asp Ile Lys Ile
            770                 775                 780

Gln Glu Thr Leu Lys Gln Ile Thr His Ile Val Asn Asn Ile Lys Thr
785                 790                 795                 800

Ile Lys Lys Asp Leu Leu Lys Glu Phe Ile Gln His Leu Ile Lys Tyr
                805                 810                 815

Met Asn Glu Arg Tyr Gln Asn Met Gln Gln Gly Tyr Asn Asn Leu Thr
            820                 825                 830

Asn Tyr Ile Asn Gln Tyr Glu Glu Glu Asn Asn Met Lys Gln Tyr
            835                 840                 845
```

-continued

Ile Thr Thr Ile Arg Asn Ile Gln Lys Ile Tyr Tyr Asp Asn Ile Tyr
            850                 855                 860

Ala Lys Glu Lys Glu Ile Arg Ser Gly Gln Tyr Tyr Lys Asp Phe Ile
865                 870                 875                 880

Thr Ser Arg Lys Asn Ile Tyr Asn Ile Arg Glu Asn Ile Ser Lys Asn
                885                 890                 895

Val Asp Met Ile Lys Asn Glu Glu Lys Lys Ile Gln Asn Cys Val
            900                 905                 910

Asp Lys Tyr Asn Ser Ile Lys Gln Tyr Val Lys Met Leu Lys Asn Gly
            915                 920                 925

Asp Thr Gln Asp Glu Asn Asn Asn Asn Asn Asp Ile Tyr Asp Lys
            930                 935                 940

Leu Ile Val Pro Leu Asp Ser Ile Lys Gln Asn Ile Asp Lys Tyr Asn
945                 950                 955                 960

Thr Glu His Asn Phe Ile Thr Phe Thr Asn Lys Ile Asn Thr His Asn
                965                 970                 975

Lys Lys Asn Gln Glu Met Met Glu Glu Phe Ile Tyr Ala Tyr Lys Arg
                980                 985                 990

Leu Lys Ile Leu Lys Ile Leu Asn Ile Ser Leu Lys Ala Cys Glu Lys
            995                 1000                1005

Asn Asn Lys Ser Ile Asn Thr Leu Asn Asp Lys Thr Gln Glu Leu Lys
            1010                1015                1020

Lys Ile Val Thr His Glu Ile Asp Leu Leu Gln Lys Asp Ile Leu Thr
1025                1030                1035                1040

Ser Gln Ile Ser Asn Lys Asn Val Leu Leu Leu Asn Asp Leu Leu Lys
                1045                1050                1055

Glu Ile Glu Gln Tyr Ile Ile Asp Val His Lys Leu Lys Lys Ser
                1060                1065                1070

Asn Asp Leu Phe Thr Tyr Tyr Glu Gln Ser Lys Asn Tyr Phe Tyr Phe
                1075                1080                1085

Lys Asn Lys Lys Asp Asn Phe Asp Ile Gln Lys Thr Ile Asn Lys Met
            1090                1095                1100

Asn Glu Trp Leu Ala Ile Lys Asn Tyr Ile Asn Glu Ile Asn Lys Asn
1105                1110                1115                1120

Tyr Gln Thr Leu Tyr Glu Lys Lys Ile Asn Val Leu His Asn Ser
                1125                1130                1135

Lys Ser Tyr Val Gln Tyr Phe Tyr Asp His Ile Ile Asn Leu Ile Leu
                1140                1145                1150

Gln Lys Lys Asn Tyr Leu Glu Asn Thr Leu Lys Thr Lys Ile Gln Asp
            1155                1160                1165

Asn Glu His Ser Leu Tyr Ala Leu Gln Gln Asn Glu Glu Tyr Gln Lys
            1170                1175                1180

Val Lys Asn Glu Lys Asp Gln Asn Glu Ile Lys Lys Ile Lys Gln Leu
1185                1190                1195                1200

Ile Glu Lys Asn Lys Asn Asp Ile Leu Thr Tyr Glu Asn Asn Ile Glu
            1205                1210                1215

Gln Ile Glu Gln Lys Asn Ile Glu Leu Lys Thr Asn Ala Gln Asn Lys
                1220                1225                1230

Asp Asp Gln Ile Val Asn Thr Leu Asn Glu Val Lys Lys Lys Ile Ile
            1235                1240                1245

Tyr Thr Tyr Glu Lys Val Asp Asn Gln Ile Ser Asn Val Leu Lys Asn
1250                1255                1260

-continued

```
Tyr Glu Glu Gly Lys Val Glu Tyr Asp Lys Asn Val Val Gln Asn Val
1265                1270                1275                1280

Asn Asp Ala Asp Asp Thr Asn Asp Ile Asp Glu Ile Asn Asp Ile Asp
            1285                1290                1295

Glu Ile Asn Asp Ile Asp Glu Ile Asn Asp Ile Asp Glu Ile Asn Asp
        1300                1305                1310

Ile Asp Glu Ile Lys Asp Ile Asp His Ile Lys His Phe Asp Asp Thr
    1315                1320                1325

Lys His Phe Asp Asp Ile Tyr His Ala Asp Asp Thr Arg Asp Glu Tyr
        1330                1335                1340

His Ile Ala Leu Ser Asn Tyr Ile Lys Thr Glu Leu Arg Asn Ile Asn
1345                1350                1355                1360

Leu Gln Glu Ile Lys Asn Asn Ile Ile Lys Ile Phe Lys Glu Phe Lys
            1365                1370                1375

Ser Ala His Lys Glu Ile Lys Lys Glu Ser Glu Gln Ile Asn Lys Glu
        1380                1385                1390

Phe Thr Lys Met Asp Val Val Ile Asn Gln Leu Arg Asp Ile Asp Arg
    1395                1400                1405

Gln Met Leu Asp Leu Tyr Lys Glu Leu Asp Glu Lys Tyr Ser Glu Phe
1410                1415                1420

Asn Lys Thr Lys Ile Glu Glu Ile Asn Asn Ile Arg Glu Asn Ile Asn
1425                1430                1435                1440

Asn Val Glu Ile Trp Tyr Glu Lys Asn Ile Ile Glu Tyr Phe Leu Arg
            1445                1450                1455

His Met Asn Asp Gln Lys Asp Lys Ala Ala Lys Tyr Met Glu Asn Ile
        1460                1465                1470

Asp Thr Tyr Lys Asn Asn Ile Glu Ile Ile Ser Lys Gln Ile Asn Pro
    1475                1480                1485

Glu Asn Tyr Val Glu Thr Leu Asn Lys Ser Asn Met Tyr Ser Tyr Val
1490                1495                1500

Glu Lys Ala Asn Asp Leu Phe Tyr Lys Gln Ile Asn Asn Ile Ile Ile
1505                1510                1515                1520

Asn Ser Asn Gln Leu Lys Asn Glu Ala Phe Thr Ile Asp Glu Leu Gln
            1525                1530                1535

Asn Ile Gln Lys Asn Arg Lys Asn Leu Leu Thr Lys Lys Gln Gln Ile
        1540                1545                1550

Ile Gln Tyr Thr Asn Glu Ile Glu Asn Ile Phe Asn Glu Ile Lys Asn
    1555                1560                1565

Ile Asn Asn Ile Leu Val Leu Thr Asn Tyr Lys Ser Ile Leu Gln Asp
1570                1575                1580

Ile Ser Gln Asn Ile Asn His Val Ser Ile Tyr Thr Glu Gln Leu His
1585                1590                1595                1600

Asn Leu Tyr Ile Lys Leu Glu Glu Glu Lys Glu Gln Met Lys Thr Leu
            1605                1610                1615

Tyr His Lys Ser Asn Val Leu His Asn Gln Ile Asn Phe Asn Glu Asp
        1620                1625                1630

Ala Phe Ile Asn Asn Leu Leu Ile Asn Ile Glu Lys Ile Lys Asn Asp
    1635                1640                1645

Ile Thr His Ile Lys Glu Lys Thr Asn Ile Tyr Met Ile Asp Val Asn
1650                1655                1660

Lys Ser Lys Asn Asn Ala Gln Leu Tyr Phe His Asn Thr Leu Arg Gly
1665                1670                1675                1680

Asn Glu Lys Ile Glu Tyr Leu Lys Asn Leu Lys Asn Ser Thr Asn Gln
```

```
                  1685                1690                1695

Gln Ile Thr Leu Gln Glu Leu Lys Gln Val Gln Glu Asn Val Glu Lys
            1700                1705                1710

Val Lys Asp Ile Tyr Asn Gln Thr Ile Lys Tyr Glu Glu Ile Lys
        1715                1720                1725

Lys Asn Tyr His Ile Ile Thr Asp Tyr Glu Asn Lys Ile Asn Asp Ile
        1730                1735                1740

Leu His Asn Ser Phe Ile Lys Gln Ile Asn Met Glu Ser Ser Asn Asn
1745                1750                1755                1760

Lys Lys Gln Thr Lys Gln Ile Ile Asp Ile Ile Asn Asp Lys Thr Phe
            1765                1770                1775

Glu Glu His Ile Lys Thr Ser Lys Thr Lys Ile Asn Met Leu Lys Glu
            1780                1785                1790

Gln Ser Gln Met Lys His Ile Asp Lys Thr Leu Leu Asn Glu Gln Ala
            1795                1800                1805

Leu Lys Leu Phe Val Asp Ile Asn Ser Thr Asn Asn Asn Leu Asp Asn
        1810                1815                1820

Met Leu Ser Glu Ile Asn Ser Ile Gln Asn Asn Ile His Thr Tyr Ile
1825                1830                1835                1840

Gln Glu Ala Asn Lys Ser Phe Asp Lys Phe Lys Ile Ile Cys Asp Gln
            1845                1850                1855

Asn Val Asn Asp Leu Leu Asn Lys Leu Ser Leu Gly Asp Leu Asn Tyr
        1860                1865                1870

Met Asn His Leu Lys Asn Leu Gln Asn Glu Ile Arg Asn Met Asn Leu
            1875                1880                1885

Glu Lys Asn Phe Met Leu Asp Lys Ser Lys Lys Ile Asp Glu Glu Glu
            1890                1895                1900

Lys Lys Leu Asp Ile Leu Lys Val Asn Ile Ser Asn Ile Asn Asn Ser
1905                1910                1915                1920

Leu Asp Lys Leu Lys Lys Tyr Tyr Glu Glu Ala Leu Phe Gln Lys Val
                1925                1930                1935

Lys Glu Lys Ala Glu Ile Gln Lys Glu Asn Ile Glu Lys Ile Lys Gln
            1940                1945                1950

Glu Ile Asn Thr Leu Ser Asp Val Phe Lys Lys Pro Phe Phe Phe Ile
        1955                1960                1965

Gln Leu Asn Thr Asp Ser Ser Gln His Glu Lys Asp Ile Asn Asn Asn
        1970                1975                1980

Val Glu Thr Tyr Lys Asn Asn Ile Asp Glu Ile Tyr Asn Val Phe Ile
1985                1990                1995                2000

Gln Ser Tyr Asn Leu Ile Gln Lys Tyr Ser Ser Glu Ile Phe Ser Ser
                2005                2010                2015

Thr Leu Asn Tyr Ile Gln Thr Lys Glu Ile Lys Glu Lys Ser Ile Lys
            2020                2025                2030

Glu Gln Asn Gln Leu Asn Gln Asn Glu Lys Glu Ala Ser Val Leu Leu
            2035                2040                2045

Lys Asn Ile Lys Ile Asn Glu Thr Ile Lys Leu Phe Lys Gln Ile Lys
        2050                2055                2060

Asn Glu Arg Gln Asn Asp Val His Asn Ile Lys Glu Asp Tyr Asn Leu
2065                2070                2075                2080

Leu Gln Gln Tyr Leu Asn Tyr Met Lys Asn Glu Met Glu Gln Leu Lys
                2085                2090                2095

Lys Tyr Lys Asn Asp Val His Met Asp Lys Asn Tyr Val Glu Asn Asn
            2100                2105                2110
```

```
Asn Gly Glu Lys Glu Lys Leu Leu Lys Glu Thr Ile Ser Ser Tyr Tyr
        2115                2120                2125
Asp Lys Ile Asn Asn Ile Asn Asn Lys Leu Tyr Ile Tyr Lys Asn Lys
        2130                2135                2140
Glu Asp Thr Tyr Phe Asn Asn Met Ile Lys Val Ser Glu Ile Leu Asn
2145                2150                2155                2160
Ile Ile Ile Lys Lys Lys Gln Gln Asn Glu Gln Arg Ile Val Ile Asn
                2165                2170                2175
Ala Glu Tyr Asp Ser Ser Leu Ile Asn Lys Asp Glu Ile Lys Lys
        2180                2185                2190
Glu Ile Asn Asn Gln Ile Ile Glu Leu Asn Lys His Asn Glu Asn Ile
        2195                2200                2205
Ser Asn Ile Phe Lys Asp Ile Gln Asn Ile Lys Lys Gln Ser Gln Asp
        2210                2215                2220
Ile Ile Thr Asn Met Asn Asp Met Tyr Lys Ser Thr Ile Leu Leu Val
2225                2230                2235                2240
Asp Ile Ile Gln Lys Lys Glu Glu Ala Leu Asn Lys Gln Lys Asn Ile
                2245                2250                2255
Leu Arg Asn Ile Asp Asn Ile Leu Asn Lys Lys Glu Asn Ile Ile Asp
        2260                2265                2270
Lys Val Ile Lys Cys Asn Cys Asp Asp Tyr Lys Asp Ile Leu Ile Gln
        2275                2280                2285
Asn Glu Thr Glu Tyr Gln Lys Leu Gln Asn Ile Asn His Thr Tyr Glu
        2290                2295                2300
Glu Lys Lys Lys Ser Ile Asp Ile Leu Lys Ile Lys Asn Ile Lys Gln
2305                2310                2315                2320
Lys Asn Ile Gln Glu Tyr Lys Asn Lys Leu Glu Gln Met Asn Thr Ile
                2325                2330                2335
Ile Asn Gln Ser Ile Glu Gln His Val Phe Ile Asn Ala Asp Ile Leu
        2340                2345                2350
Gln Asn Glu Lys Ile Lys Leu Glu Glu Ile Ile Lys Asn Leu Asp Ile
        2355                2360                2365
Leu Asp Glu Gln Ile Met Thr Tyr His Asn Ser Ile Asp Glu Leu Tyr
        2370                2375                2380
Lys Leu Gly Ile Gln Cys Asp Asn His Leu Ile Thr Thr Ile Ser Val
2385                2390                2395                2400
Val Val Asn Lys Asn Thr Thr Lys Ile Met Ile His Ile Lys Lys Gln
                2405                2410                2415
Lys Glu Asp Ile Gln Lys Ile Asn Asn Tyr Ile Gln Thr Asn Tyr Asn
                2420                2425                2430
Ile Ile Asn Glu Glu Ala Leu Gln Phe His Arg Leu Tyr Gly His Asn
                2435                2440                2445
Leu Ile Ser Glu Asp Asp Lys Asn Asn Leu Val His Ile Ile Lys Glu
        2450                2455                2460
Gln Lys Asn Ile Tyr Thr Gln Lys Glu Ile Asp Ile Ser Lys Ile Ile
2465                2470                2475                2480
Lys His Val Lys Lys Gly Leu Tyr Ser Leu Asn Glu His Asp Met Asn
                2485                2490                2495
His Asp Thr His Met Asn Ile Ile Asn Glu His Ile Asn Asn Asn Ile
                2500                2505                2510
Leu Gln Pro Tyr Thr Gln Leu Ile Asn Met Ile Lys Asp Ile Asp Asn
                2515                2520                2525
```

```
Val Phe Ile Lys Ile Gln Asn Asn Lys Phe Glu Gln Ile Gln Lys Tyr
            2530                2535                2540

Ile Glu Ile Ile Lys Ser Leu Glu Gln Leu Asn Lys Asn Ile Asn Thr
2545                2550                2555                2560

Asp Asn Leu Asn Lys Leu Lys Asp Thr Gln Asn Lys Leu Ile Asn Ile
                2565                2570                2575

Glu Thr Glu Met Lys His Lys Gln Lys Gln Leu Ile Asn Lys Met Asn
            2580                2585                2590

Asp Ile Glu Lys Asp Asn Ile Thr Asp Gln Tyr Met His Asp Val Gln
        2595                2600                2605

Gln Asn Ile Phe Glu Pro Ile Thr Leu Lys Met Asn Glu Tyr Asn Thr
    2610                2615                2620

Leu Leu Asn Asp Asn His Asn Asn Ile Asn Asn Glu His Gln Phe
2625                2630                2635                2640

Asn His Leu Asn Ser Leu His Thr Lys Ile Phe Ser His Asn Tyr Asn
                2645                2650                2655

Lys Glu Gln Gln Gln Glu Tyr Ile Thr Asn Ile Met Gln Arg Ile Asp
            2660                2665                2670

Val Phe Ile Asn Asp Leu Asp Thr Tyr Gln Tyr Glu Tyr Tyr Phe Tyr
        2675                2680                2685

Glu Trp Asn Gln Glu Tyr Lys Gln Ile Asp Lys Asn Lys Ile Asn Gln
    2690                2695                2700

His Ile Asn Asn Ile Lys Asn Asn Leu Ile His Val Lys Lys Gln Phe
2705                2710                2715                2720

Glu His Thr Leu Glu Asn Ile Lys Asn Asn Glu Asn Ile Phe Asp Asn
                2725                2730                2735

Ile Gln Leu Lys Lys Lys Asp Ile Asp Asp Ile Ile Asn Ile Asn
            2740                2745                2750

Asn Thr Lys Glu Thr Tyr Leu Lys Glu Leu Asn Lys Lys Lys Asn Val
        2755                2760                2765

Thr Lys Lys Lys Val Asp Glu Lys Ser Glu Ile Asn Asn His His
    2770                2775                2780

Thr Leu Gln His Asp Asn Gln Asn Val Glu Gln Lys Asn Lys Ile Lys
2785                2790                2795                2800

Asp His Asn Leu Ile Thr Lys Pro Asn Asn Asn Ser Ser Glu Glu Ser
                2805                2810                2815

His Gln Asn Glu Gln Met Lys Glu Gln Asn Lys Asn Ile Leu Glu Lys
            2820                2825                2830

Gln Thr Arg Asn Ile Lys Pro His His Val His Asn His Asn His Asn
        2835                2840                2845

His Asn Gln Asn Gln Lys Asp Ser Thr Lys Leu Gln Glu Gln Asp Ile
    2850                2855                2860

Ser Thr His Lys Leu His Asn Thr Ile His Glu Gln Gln Ser Lys Asp
2865                2870                2875                2880

Asn His Gln Gly Asn Arg Glu Lys Lys Gln Lys Asn Gly Asn His Glu
                2885                2890                2895

Arg Met Tyr Phe Ala Ser Gly Ile Val Val Ser Ile Leu Phe Leu Phe
            2900                2905                2910

Ser Phe Gly Phe Val Ile Asn Ser Lys Asn Asn Lys Gln Glu Tyr Asp
        2915                2920                2925

Lys Glu Gln Glu Lys Gln Gln Gln Asn Asp Phe Val Cys Asp Asn Asn
    2930                2935                2940

Lys Met Asp Asp Lys Ser Thr Gln Lys Tyr Gly Arg Asn Gln Glu Glu
```

Val Met Glu Ile Phe Phe Asp Asn Asp Tyr Ile
                2965                2970

<210> SEQ ID NO 16
<211> LENGTH: 1716
<212> TYPE: PRT
<213> ORGANISM: Plasmodium falciparum

<400> SEQUENCE: 16

Met Asn Lys Asn Ile Leu Trp Ile Thr Phe Phe Tyr Phe Leu Phe Phe
1               5                   10                  15

Leu Leu Asp Met Tyr Gln Gly Asn Asp Ala Ile Pro Ser Lys Glu Lys
            20                  25                  30

Lys Asn Asp Pro Glu Ala Asp Ser Lys Asn Ser Gln Asn Gln His Asp
        35                  40                  45

Ile Asn Lys Thr His His Thr Asn Asn Asn Tyr Asp Leu Asn Ile Lys
    50                  55                  60

Asp Lys Asp Glu Lys Lys Arg Lys Asn Asp Asn Leu Ile Asn Asn Tyr
65                  70                  75                  80

Asp Tyr Ser Leu Leu Lys Leu Ser Tyr Asn Lys Asn Gln Asp Ile Tyr
                85                  90                  95

Lys Asn Ile Gln Asn Gly Gln Lys Leu Lys Thr Asp Ile Ile Leu Asn
            100                 105                 110

Ser Phe Val Gln Ile Asn Ser Ser Asn Ile Leu Met Asp Glu Ile Glu
        115                 120                 125

Asn Tyr Val Lys Lys Tyr Thr Glu Ser Asn Arg Ile Met Tyr Leu Gln
    130                 135                 140

Phe Lys Tyr Ile Tyr Leu Gln Ser Leu Asn Ile Thr Val Ser Phe Val
145                 150                 155                 160

Pro Pro Asn Ser Pro Phe Arg Ser Tyr Tyr Asp Lys Asn Leu Asn Lys
                165                 170                 175

Asp Ile Asn Glu Thr Cys His Ser Ile Gln Thr Leu Leu Asn Asn Leu
            180                 185                 190

Ile Ser Ser Lys Ile Ile Phe Lys Met Leu Glu Thr Thr Lys Glu Gln
        195                 200                 205

Ile Leu Leu Leu Trp Asn Asn Lys Lys Ile Ser Gln Gln Asn Tyr Asn
    210                 215                 220

Gln Glu Asn Gln Glu Lys Ser Lys Met Ile Asp Ser Glu Asn Glu Lys
225                 230                 235                 240

Leu Glu Lys Tyr Thr Asn Lys Phe Glu His Asn Ile Lys Pro His Ile
                245                 250                 255

Glu Asp Ile Glu Lys Lys Val Asn Glu Tyr Ile Asn Asn Ser Asp Cys
            260                 265                 270

His Leu Thr Cys Ser Lys Tyr Lys Thr Ile Ile Asn Asn Tyr Ile Asp
        275                 280                 285

Glu Ile Ile Thr Thr Asn Thr Asn Ile Tyr Glu Asn Lys Tyr Asn Leu
    290                 295                 300

Pro Gln Glu Arg Ile Ile Lys Asn Tyr Asn His Asn Gly Ile Asn Asn
305                 310                 315                 320

Asp Asp Asn Phe Ile Glu Tyr Asn Ile Leu Asn Ala Asp Pro Asp Leu
                325                 330                 335

Arg Ser His Phe Ile Thr Leu Leu Val Ser Arg Lys Gln Leu Ile Tyr
            340                 345                 350

-continued

```
Ile Glu Tyr Ile Tyr Phe Ile Asn Lys His Ile Val Asn Lys Ile Gln
        355                 360                 365

Glu Asn Phe Lys Leu Asn Gln Asn Lys Tyr Ile His Phe Ile Asn Ser
    370                 375                 380

Asn Asn Ala Val Asn Ala Ala Lys Glu Tyr Glu Tyr Ile Ile Lys Tyr
385                 390                 395                 400

Tyr Thr Thr Phe Lys Tyr Leu Gln Thr Leu Asn Lys Ser Leu Tyr Asp
            405                 410                 415

Ser Ile Tyr Lys His Lys Ile Asn Asn Tyr Ser His Asn Ile Glu Asp
            420                 425                 430

Leu Ile Asn Gln Leu Gln His Lys Ile Asn Asn Leu Met Ile Ile Ser
        435                 440                 445

Phe Asp Lys Asn Lys Ser Ser Asp Leu Met Leu Gln Cys Thr Asn Ile
    450                 455                 460

Lys Lys Tyr Thr Asp Asp Ile Cys Leu Ser Ile Lys Pro Lys Ala Leu
465                 470                 475                 480

Glu Val Glu Tyr Leu Arg Asn Ile Asn Lys His Ile Asn Lys Asn Glu
            485                 490                 495

Phe Leu Asn Lys Phe Met Gln Asn Glu Thr Phe Lys Lys Asn Ile Asp
        500                 505                 510

Asp Lys Ile Lys Glu Met Asn Asn Ile Tyr Asp Asn Ile Tyr Ile Ile
    515                 520                 525

Leu Lys Gln Lys Phe Leu Asn Lys Leu Asn Glu Ile Ile Gln Asn His
        530                 535                 540

Lys Asn Lys Gln Glu Thr Lys Leu Asn Thr Thr Thr Ile Gln Glu Leu
545                 550                 555                 560

Leu Gln Leu Leu Lys Asp Ile Lys Glu Ile Gln Thr Lys Gln Ile Asp
            565                 570                 575

Thr Lys Ile Asn Thr Phe Asn Met Tyr Tyr Asn Asp Ile Gln Gln Ile
        580                 585                 590

Lys Ile Lys Ile Asn Gln Asn Glu Lys Glu Ile Lys Lys Val Leu Pro
    595                 600                 605

Gln Leu Tyr Ile Pro Lys Asn Glu Gln Glu Tyr Ile Gln Ile Tyr Lys
        610                 615                 620

Asn Glu Leu Lys Asp Arg Ile Lys Glu Thr Gln Thr Lys Ile Asn Leu
625                 630                 635                 640

Phe Lys Gln Ile Leu Glu Leu Lys Lys Glu His Tyr Ile Thr Asn
            645                 650                 655

Lys His Thr Tyr Leu Asn Phe Thr His Lys Thr Ile Gln Gln Ile Leu
        660                 665                 670

Gln Gln Gln Tyr Lys Asn Asn Thr Gln Glu Lys Asn Thr Leu Ala Gln
    675                 680                 685

Phe Leu Tyr Asn Ala Asp Ile Lys Lys Tyr Ile Asp Glu Leu Ile Pro
    690                 695                 700

Ile Thr Gln Gln Ile Gln Thr Lys Met Tyr Thr Thr Asn Asn Ile Glu
705                 710                 715                 720

His Ile Lys Gln Ile Leu Ile Asn Tyr Ile Gln Glu Cys Lys Pro Ile
            725                 730                 735

Gln Asn Ile Ser Glu His Thr Ile Tyr Thr Leu Tyr Gln Glu Ile Lys
        740                 745                 750

Thr Asn Leu Glu Asn Ile Glu Gln Lys Ile Met Gln Asn Ile Gln Gln
    755                 760                 765

Thr Thr Asn Arg Leu Lys Ile Asn Ile Lys Lys Ile Phe Asp Gln Ile
```

```
            770                 775                 780
Asn Gln Lys Tyr Asp Asp Leu Thr Lys Asn Ile Asn Gln Met Asn Asp
785                 790                 795                 800

Glu Lys Ile Gly Leu Arg Gln Met Glu Asn Arg Leu Lys Gly Lys Tyr
                805                 810                 815

Glu Glu Ile Lys Lys Ala Asn Leu Gln Asp Arg Asp Ile Lys Tyr Ile
                820                 825                 830

Val Gln Asn Asp Ala Asn Asn Asn Asn Ile Ile Ile
                835                 840                 845

Asn Gly Asn Asn Gln Thr Gly Asp Tyr Asn His Ile Leu Phe Asp Tyr
850                 855                 860

Thr His Leu Trp Asp Asn Ala Gln Phe Thr Arg Thr Lys Glu Asn Ile
865                 870                 875                 880

Asn Asn Leu Lys Asp Asn Ile Gln Ile Asn Ile Asn Asn Ile Lys Ser
                885                 890                 895

Ile Ile Arg Asn Leu Gln Asn Glu Leu Asn Asn Tyr Asn Thr Leu Lys
                900                 905                 910

Ser Asn Ser Ile His Ile Tyr Asp Lys Ile His Thr Leu Glu Glu Leu
                915                 920                 925

Lys Ile Leu Thr Gln Glu Ile Asn Asp Lys Asn Val Ile Arg Lys Ile
                930                 935                 940

Tyr Asp Ile Glu Thr Ile Tyr Gln Asn Asp Leu His Asn Ile Glu Glu
945                 950                 955                 960

Ile Ile Lys Asn Ile Thr Ser Ile Tyr Tyr Lys Ile Asn Ile Leu Asn
                965                 970                 975

Ile Leu Ile Ile Cys Ile Lys Gln Thr Tyr Asn Asn Asn Lys Ser Ile
                980                 985                 990

Glu Ser Leu Lys Leu Lys Ile Asn Asn Leu Thr Asn Ser Thr Gln Glu
                995                 1000                1005

Tyr Ile Asn Gln Ile Lys Ala Ile Pro Thr Asn Leu Leu Pro Glu His
                1010                1015                1020

Ile Lys Gln Lys Ser Val Ser Glu Leu Asn Ile Tyr Met Lys Gln Ile
1025                1030                1035                1040

Tyr Asp Lys Leu Asn Glu His Val Ile Asn Asn Leu Tyr Thr Lys Ser
                1045                1050                1055

Lys Asp Ser Leu Gln Phe Tyr Ile Asn Glu Lys Asn Tyr Asn Asn Asn
                1060                1065                1070

His Asp Asp His Asn Asp Asp His Asn Asp Val Tyr Asn Asp Ile Lys
                1075                1080                1085

Glu Asn Glu Ile Tyr Lys Asn Asn Lys Leu Tyr Glu Cys Ile Gln Ile
                1090                1095                1100

Lys Lys Asp Val Asp Glu Leu Tyr Asn Ile Tyr Asp Gln Leu Phe Lys
1105                1110                1115                1120

Asn Ile Ser Gln Asn Tyr Asn Asn His Ser Leu Ser Phe Val His Ser
                1125                1130                1135

Ile Asn Asn His Met Leu Ser Ile Phe Gln Asp Thr Lys Tyr Gly Lys
                1140                1145                1150

His Lys Asn Gln Gln Ile Leu Ser Asp Ile Glu Asn Ile Ile Lys Gln
                1155                1160                1165

Asn Glu His Thr Glu Ser Tyr Lys Asn Leu Asp Thr Ser Asn Ile Gln
                1170                1175                1180

Leu Ile Lys Glu Gln Ile Lys Tyr Phe Leu Gln Ile Phe His Ile Leu
1185                1190                1195                1200
```

```
Gln Glu Asn Ile Thr Thr Phe Glu Asn Gln Tyr Lys Asp Leu Ile Ile
                1205                1210                1215
Lys Met Asn His Lys Ile Asn Asn Leu Lys Asp Ile Thr His Ile
                1220                1225                1230
Val Ile Asn Asp Asn Asn Thr Leu Gln Glu Gln Asn Arg Ile Tyr Asn
                1235                1240                1245
Glu Leu Gln Asn Lys Ile Lys Gln Ile Lys Asn Val Ser Asp Val Phe
                1250                1255                1260
Thr His Asn Ile Asn Tyr Ser Gln Gln Ile Leu Asn Tyr Ser Gln Ala
1265                1270                1275                1280
Gln Asn Ser Phe Phe Asn Ile Phe Met Lys Phe Gln Asn Ile Asn Asn
                1285                1290                1295
Asp Ile Asn Ser Lys Arg Tyr Asn Val Gln Lys Lys Ile Thr Glu Ile
                1300                1305                1310
Ile Asn Ser Tyr Asp Ile Ile Asn Tyr Asn Lys Asn Asn Ile Lys Asp
                1315                1320                1325
Ile Tyr Gln Gln Phe Lys Asn Ile Gln Gln Gln Leu Asn Thr Thr Glu
                1330                1335                1340
Thr Gln Leu Asn His Ile Lys Gln Asn Ile Asn His Phe Lys Tyr Phe
1345                1350                1355                1360
Tyr Glu Ser His Gln Thr Ile Ser Ile Val Lys Asn Met Gln Asn Glu
                1365                1370                1375
Lys Leu Lys Ile Gln Glu Phe Asn Lys Lys Ile Gln His Phe Lys Glu
                1380                1385                1390
Glu Thr Gln Ile Met Ile Asn Lys Leu Ile Gln Pro Ser His Ile His
                1395                1400                1405
Leu His Lys Met Lys Leu Pro Ile Thr Gln Gln Leu Asn Thr Ile
                1410                1415                1420
Leu His Arg Asn Glu Gln Thr Lys Asn Ala Thr Arg Ser Tyr Asn Met
1425                1430                1435                1440
Asn Glu Glu Glu Asn Glu Met Gly Tyr Gly Ile Thr Asn Lys Arg Lys
                1445                1450                1455
Asn Ser Glu Thr Asn Asp Met Ile Asn Thr Thr Ile Gly Asp Lys Thr
                1460                1465                1470
Asn Val Leu Lys Asn Asp Asp Gln Glu Lys Gly Lys Arg Gly Thr Ser
                1475                1480                1485
Arg Asn Asn Asn Ile His Thr Asn Glu Asn Asn Ile Asn Asn Glu His
                1490                1495                1500
Thr Asn Glu Asn Asn Ile Asn Asn Glu His Thr Asn Glu Lys Asn Ile
1505                1510                1515                1520
Asn Asn Glu His Ala Asn Glu Lys Asn Ile Tyr Asn Glu His Thr Asn
                1525                1530                1535
Glu Asn Asn Ile Asn Tyr Glu His Pro Asn Asn Tyr Gln Gln Lys Asn
                1540                1545                1550
Asp Glu Lys Ile Ser Leu Gln His Lys Thr Ile Asn Thr Ser Gln Arg
                1555                1560                1565
Thr Ile Asp Asp Ser Asn Met Asp Arg Asn Asn Arg Tyr Asn Thr Ser
                1570                1575                1580
Ser Gln Gln Lys Asn Asn Leu His Thr Asn Asn Ser Asn Ser Arg
1585                1590                1595                1600
Tyr Asn Asn Asn His Asp Lys Gln Asn Glu His Lys Tyr Asn Gln Gly
                1605                1610                1615
```

-continued

Lys Ser Ser Gly Lys Asp Asn Ala Tyr Tyr Arg Ile Phe Tyr Ala Gly
              1620                1625                1630

Gly Ile Thr Ala Val Leu Leu Cys Ser Ser Thr Ala Phe Phe Phe
    1635                1640                1645

Ile Lys Asn Ser Asn Glu Pro His His Ile Phe Asn Ile Phe Gln Lys
    1650                1655                1660

Glu Phe Ser Glu Ala Asp Asn Ala His Ser Glu Glu Lys Glu Glu Tyr
1665                1670                1675                1680

Leu Pro Val Tyr Phe Asp Glu Val Glu Asp Val Glu Asp Glu Val
                1685                1690                1695

Glu Asp Glu Asp Glu Asn Glu Asn Glu Val Glu Asn Asn Glu Asp
            1700                1705                1710

Phe Asn Asp Ile
        1715

<210> SEQ ID NO 17
<211> LENGTH: 1462
<212> TYPE: PRT
<213> ORGANISM: Plasmodium falciparum

<400> SEQUENCE: 17

Met Lys Cys Asn Ile Ser Ile Tyr Phe Phe Ala Ser Phe Phe Val Leu
1               5                   10                  15

Tyr Phe Ala Lys Ala Arg Asn Glu Tyr Asp Ile Lys Glu Asn Glu Lys
                20                  25                  30

Phe Leu Asp Val Tyr Lys Glu Lys Phe Asn Glu Leu Asp Lys Lys Lys
            35                  40                  45

Tyr Gly Asn Val Gln Lys Thr Asp Lys Lys Ile Phe Thr Phe Ile Glu
    50                  55                  60

Asn Lys Leu Asp Ile Leu Asn Asn Ser Lys Phe Asn Lys Arg Trp Lys
65                  70                  75                  80

Ser Tyr Gly Thr Pro Asp Asn Ile Asp Lys Asn Met Ser Leu Ile Asn
                85                  90                  95

Lys His Asn Asn Glu Glu Met Phe Asn Asn Tyr Gln Ser Phe Leu
            100                 105                 110

Ser Thr Ser Ser Leu Ile Lys Gln Asn Lys Tyr Val Pro Ile Asn Ala
        115                 120                 125

Val Arg Val Ser Arg Ile Leu Ser Phe Leu Asp Ser Arg Ile Asn Asn
    130                 135                 140

Gly Arg Asn Thr Ser Ser Asn Asn Glu Val Leu Ser Asn Cys Arg Glu
145                 150                 155                 160

Lys Arg Lys Gly Met Lys Trp Asp Cys Lys Lys Asn Asp Arg Ser
                165                 170                 175

Asn Tyr Val Cys Ile Pro Asp Arg Arg Ile Gln Leu Cys Ile Val Asn
            180                 185                 190

Leu Ser Ile Ile Lys Thr Tyr Thr Lys Glu Thr Met Lys Asp His Phe
    195                 200                 205

Ile Glu Ala Ser Lys Lys Glu Ser Gln Leu Leu Leu Lys Lys Asn Asp
    210                 215                 220

Asn Lys Tyr Asn Ser Lys Phe Cys Asn Asp Leu Lys Asn Ser Phe Leu
225                 230                 235                 240

Asp Tyr Gly His Leu Ala Met Gly Asn Asp Met Asp Phe Gly Gly Tyr
                245                 250                 255

Ser Thr Lys Ala Glu Asn Lys Ile Gln Glu Val Phe Lys Gly Ala His
            260                 265                 270

```
Gly Glu Ile Ser Glu His Lys Ile Lys Asn Phe Arg Lys Lys Trp Trp
        275                 280                 285

Asn Glu Phe Arg Glu Lys Leu Trp Glu Ala Met Leu Ser Glu His Lys
    290                 295                 300

Asn Asn Ile Asn Asn Cys Lys Asn Ile Pro Gln Glu Glu Leu Gln Ile
305                 310                 315                 320

Thr Gln Trp Ile Lys Glu Trp His Gly Glu Phe Leu Leu Glu Arg Asp
                325                 330                 335

Asn Arg Ser Lys Leu Pro Lys Ser Lys Cys Lys Asn Asn Thr Leu Tyr
            340                 345                 350

Glu Ala Cys Glu Lys Glu Cys Ile Asp Pro Cys Met Lys Tyr Arg Asp
        355                 360                 365

Trp Ile Ile Arg Ser Lys Phe Glu Trp His Thr Leu Ser Lys Glu Tyr
    370                 375                 380

Glu Thr Gln Lys Val Pro Lys Glu Asn Ala Glu Asn Tyr Leu Ile Lys
385                 390                 395                 400

Ile Ser Glu Asn Lys Asn Asp Ala Lys Val Ser Leu Leu Leu Asn Asn
                405                 410                 415

Cys Asp Ala Glu Tyr Ser Lys Tyr Cys Asp Cys Lys His Thr Thr Thr
            420                 425                 430

Leu Val Lys Ser Val Leu Asn Gly Asn Asp Asn Thr Ile Lys Glu Lys
        435                 440                 445

Arg Glu His Ile Asp Leu Asp Asp Phe Ser Lys Phe Gly Cys Asp Lys
    450                 455                 460

Asn Ser Val Asp Thr Asn Thr Lys Val Trp Glu Cys Lys Lys Pro Tyr
465                 470                 475                 480

Lys Leu Ser Thr Lys Asp Val Cys Val Pro Pro Arg Arg Gln Glu Leu
                485                 490                 495

Cys Leu Gly Asn Ile Asp Arg Ile Tyr Asp Lys Asn Leu Leu Met Ile
            500                 505                 510

Lys Glu His Ile Leu Ala Ile Ala Ile Tyr Glu Ser Arg Ile Leu Lys
        515                 520                 525

Arg Lys Tyr Lys Asn Lys Asp Asp Lys Glu Val Cys Lys Ile Ile Asn
    530                 535                 540

Lys Thr Phe Ala Asp Ile Arg Asp Ile Ile Gly Gly Thr Asp Tyr Trp
545                 550                 555                 560

Asn Asp Leu Ser Asn Arg Lys Leu Val Gly Lys Ile Asn Thr Asn Ser
                565                 570                 575

Asn Tyr Val His Arg Asn Lys Gln Asn Asp Lys Leu Phe Arg Asp Glu
            580                 585                 590

Trp Trp Lys Val Ile Lys Lys Asp Val Trp Asn Val Ile Ser Trp Val
        595                 600                 605

Phe Lys Asp Lys Thr Val Cys Lys Glu Asp Ile Glu Asn Ile Pro
    610                 615                 620

Gln Phe Phe Arg Trp Phe Ser Glu Trp Gly Asp Tyr Cys Gln Asp
625                 630                 635                 640

Lys Thr Lys Met Ile Glu Thr Leu Lys Val Glu Cys Lys Glu Lys Pro
                645                 650                 655

Cys Glu Asp Asp Asn Cys Lys Arg Lys Cys Asn Ser Tyr Lys Glu Trp
            660                 665                 670

Ile Ser Lys Lys Lys Glu Glu Tyr Asn Lys Gln Ala Lys Gln Tyr Gln
        675                 680                 685
```

```
Glu Tyr Gln Lys Gly Asn Asn Tyr Lys Met Tyr Ser Glu Phe Lys Ser
690                 695                 700
Ile Lys Pro Glu Val Tyr Leu Lys Lys Tyr Ser Glu Lys Cys Ser Asn
705                 710                 715                 720
Leu Asn Phe Glu Asp Glu Phe Lys Glu Glu Leu His Ser Asp Tyr Lys
                    725                 730                 735
Asn Lys Cys Thr Met Cys Pro Glu Val Lys Asp Val Pro Ile Ser Ile
                740                 745                 750
Ile Arg Asn Asn Glu Gln Thr Ser Gln Glu Ala Val Pro Glu Glu Ser
                755                 760                 765
Thr Glu Ile Ala His Arg Thr Glu Thr Arg Thr Asp Glu Arg Lys Asn
770                 775                 780
Gln Glu Pro Ala Asn Lys Asp Leu Lys Asn Pro Gln Gln Ser Val Gly
785                 790                 795                 800
Glu Asn Gly Thr Lys Asp Leu Leu Gln Glu Asp Leu Gly Ser Arg
                805                 810                 815
Ser Glu Asp Glu Val Thr Gln Glu Phe Gly Val Asn His Gly Ile Pro
                820                 825                 830
Lys Gly Glu Asp Gln Thr Leu Gly Lys Ser Asp Ala Ile Pro Asn Ile
                835                 840                 845
Gly Glu Pro Glu Thr Gly Ile Ser Thr Thr Glu Glu Ser Arg His Glu
850                 855                 860
Glu Gly His Asn Lys Gln Ala Leu Ser Thr Ser Val Asp Glu Pro Glu
865                 870                 875                 880
Leu Ser Asp Thr Leu Gln Leu His Glu Asp Thr Lys Glu Asn Asp Lys
                885                 890                 895
Leu Pro Leu Glu Ser Ser Thr Ile Thr Ser Pro Thr Glu Ser Gly Ser
                900                 905                 910
Ser Asp Thr Glu Glu Thr Pro Ser Ile Ser Glu Gly Pro Lys Gly Asn
                915                 920                 925
Glu Gln Lys Lys Arg Asp Asp Ser Leu Ser Lys Ile Ser Val Ser
                930                 935                 940
Pro Glu Asn Ser Arg Pro Glu Thr Asp Ala Lys Asp Thr Ser Asn Leu
945                 950                 955                 960
Leu Lys Leu Lys Gly Asp Val Asp Ile Ser Met Pro Lys Ala Val Ile
                965                 970                 975
Gly Ser Ser Pro Asn Asp Asn Ile Asn Val Thr Glu Gln Gly Asp Asn
                980                 985                 990
Ile Ser Gly Val Asn Ser Lys Pro Leu Ser Asp Val Arg Pro Asp
                995                 1000                1005
Lys Asn His Glu Glu Val Lys Glu His Thr Ser Asn Ser Asp Asn Val
        1010                1015                1020
Gln Gln Ser Gly Gly Ile Val Asn Met Asn Val Glu Lys Glu Leu Lys
        1025                1030                1035                1040
Asp Thr Leu Glu Asn Pro Ser Ser Leu Asp Glu Gly Lys Ala His
                1045                1050                1055
Glu Glu Leu Ser Glu Pro Asn Leu Ser Ser Asp Gln Asp Met Ser Asn
                1060                1065                1070
Thr Pro Gly Pro Leu Asp Asn Thr Ser Glu Glu Thr Thr Glu Arg Ile
                1075                1080                1085
Ser Asn Asn Glu Tyr Lys Val Asn Glu Arg Glu Gly Glu Arg Thr Leu
        1090                1095                1100
Thr Lys Glu Tyr Glu Asp Ile Val Leu Lys Ser His Met Asn Arg Glu
```

```
                1105                1110                1115                1120
Ser Asp Asp Gly Glu Leu Tyr Asp Glu Asn Ser Asp Leu Ser Thr Val
                    1125                1130                1135

Asn Asp Glu Ser Glu Asp Ala Glu Ala Lys Met Lys Gly Asn Asp Thr
                1140                1145                1150

Ser Glu Met Ser His Asn Ser Ser Gln His Ile Glu Ser Asp Gln Gln
                1155                1160                1165

Lys Asn Asp Met Lys Thr Val Gly Asp Leu Gly Thr Thr His Val Gln
            1170                1175                1180

Asn Glu Ile Ser Val Pro Val Thr Gly Glu Ile Asp Glu Lys Leu Arg
1185                1190                1195                1200

Glu Ser Lys Glu Ser Lys Ile His Lys Ala Glu Glu Glu Arg Leu Ser
                1205                1210                1215

His Thr Asp Ile His Lys Ile Asn Pro Glu Asp Arg Asn Ser Asn Thr
                1220                1225                1230

Leu His Leu Lys Asp Ile Arg Asn Glu Glu Asn Glu Arg His Leu Thr
                1235                1240                1245

Asn Gln Asn Ile Asn Ile Ser Gln Glu Arg Asp Leu Gln Lys His Gly
            1250                1255                1260

Phe His Thr Met Asn Asn Leu His Gly Asp Gly Val Ser Glu Arg Ser
1265                1270                1275                1280

Gln Ile Asn His Ser His His Gly Asn Arg Gln Asp Arg Gly Gly Asn
                1285                1290                1295

Ser Gly Asn Val Leu Asn Met Arg Ser Asn Asn Asn Asn Phe Asn Asn
                1300                1305                1310

Ile Pro Ser Arg Tyr Asn Leu Tyr Asp Lys Lys Leu Asp Leu Asp Leu
                1315                1320                1325

Tyr Glu Asn Arg Asn Asp Ser Thr Thr Lys Glu Leu Ile Lys Lys Leu
            1330                1335                1340

Ala Glu Ile Asn Lys Cys Glu Asn Glu Ile Ser Val Lys Tyr Cys Asp
1345                1350                1355                1360

His Met Ile His Glu Glu Ile Pro Leu Lys Thr Cys Thr Lys Glu Lys
                1365                1370                1375

Thr Arg Asn Leu Cys Cys Ala Val Ser Asp Tyr Cys Met Ser Tyr Phe
                1380                1385                1390

Thr Tyr Asp Ser Glu Glu Tyr Tyr Asn Cys Thr Lys Arg Glu Phe Asp
            1395                1400                1405

Asp Pro Ser Tyr Thr Cys Phe Arg Lys Glu Ala Phe Ser Ser Met Pro
            1410                1415                1420

Tyr Tyr Ala Gly Ala Gly Val Leu Phe Ile Ile Leu Val Ile Leu Gly
1425                1430                1435                1440

Ala Ser Gln Ala Lys Tyr Gln Arg Leu Glu Lys Ile Asn Lys Asn Lys
                1445                1450                1455

Ile Glu Lys Asn Val Asn
            1460

<210> SEQ ID NO 18
<211> LENGTH: 1567
<212> TYPE: PRT
<213> ORGANISM: Plasmodium falciparum

<400> SEQUENCE: 18

Met Lys Gly Lys Met Asn Met Cys Leu Phe Phe Phe Tyr Ser Ile Leu
1               5                   10                  15
```

```
Tyr Val Val Leu Cys Thr Tyr Val Leu Gly Ile Ser Glu Glu Tyr Leu
             20                  25                  30

Lys Glu Arg Pro Gln Gly Leu Asn Val Glu Thr Asn Asn Asn Asn Asn
         35                  40                  45

Asn Asn Asn Asn Asn Asn Ser Asn Ser Asn Asp Ala Met Ser Phe Val
 50                  55                  60

Asn Glu Val Ile Arg Phe Ile Glu Asn Glu Lys Asp Asp Lys Glu Asp
 65                  70                  75                  80

Lys Lys Val Lys Ile Ile Ser Arg Pro Val Glu Asn Thr Leu His Arg
                 85                  90                  95

Tyr Pro Val Ser Ser Phe Leu Asn Ile Lys Lys Tyr Gly Arg Lys Gly
                100                 105                 110

Glu Tyr Leu Asn Arg Asn Ser Phe Val Gln Arg Ser Tyr Ile Arg Gly
        115                 120                 125

Cys Lys Gly Lys Arg Ser Thr His Thr Trp Ile Cys Glu Asn Lys Gly
        130                 135                 140

Asn Asn Asn Ile Cys Ile Pro Asp Arg Arg Val Gln Leu Cys Ile Thr
145                 150                 155                 160

Ala Leu Gln Asp Leu Lys Asn Ser Gly Ser Glu Thr Thr Asp Arg Lys
                165                 170                 175

Leu Leu Arg Asp Lys Val Phe Asp Ser Ala Met Tyr Glu Thr Asp Leu
                180                 185                 190

Leu Trp Asn Lys Tyr Gly Phe Arg Gly Phe Asp Asp Phe Cys Asp Asp
                195                 200                 205

Val Lys Asn Ser Tyr Leu Asp Tyr Lys Asp Val Ile Phe Gly Thr Asp
210                 215                 220

Leu Asp Lys Asn Asn Ile Ser Lys Leu Val Glu Glu Ser Leu Lys Arg
225                 230                 235                 240

Phe Phe Lys Lys Asp Ser Ser Val Leu Asn Pro Thr Ala Trp Trp Arg
                245                 250                 255

Arg Tyr Gly Thr Arg Leu Trp Lys Thr Met Ile Gln Pro Tyr Ala His
                260                 265                 270

Leu Gly Cys Arg Lys Pro Asp Glu Asn Glu Pro Gln Ile Asn Arg Trp
            275                 280                 285

Ile Leu Glu Trp Gly Lys Tyr Asn Cys Arg Leu Met Lys Glu Lys Glu
290                 295                 300

Lys Leu Leu Thr Gly Glu Cys Ser Val Asn Arg Lys Lys Ser Asp Cys
305                 310                 315                 320

Ser Thr Gly Cys Asn Asn Glu Cys Tyr Thr Tyr Arg Ser Leu Ile Asn
                325                 330                 335

Arg Gln Arg Tyr Glu Val Ser Ile Leu Gly Lys Lys Tyr Ile Lys Val
            340                 345                 350

Val Arg Tyr Thr Ile Phe Arg Arg Lys Ile Val Gln Pro Asp Asn Ala
        355                 360                 365

Leu Asp Phe Leu Lys Leu Asn Cys Ser Glu Cys Lys Asp Ile Asp Phe
        370                 375                 380

Lys Pro Phe Phe Glu Phe Glu Tyr Gly Lys Tyr Glu Glu Lys Cys Met
385                 390                 395                 400

Cys Gln Ser Tyr Ile Asp Leu Lys Ile Gln Phe Lys Asn Asn Asp Ile
                405                 410                 415

Cys Ser Phe Asn Ala Gln Thr Asp Thr Val Ser Ser Asp Lys Arg Phe
            420                 425                 430

Cys Leu Glu Lys Lys Glu Phe Lys Pro Trp Lys Cys Asp Lys Asn Ser
```

```
                435                 440                 445
Phe Glu Thr Val His His Lys Gly Val Cys Val Ser Pro Arg Arg Gln
450                 455                 460

Gly Phe Cys Leu Gly Asn Leu Asn Tyr Leu Leu Asn Asp Asp Ile Tyr
465                 470                 475                 480

Asn Val His Asn Ser Gln Leu Leu Ile Glu Ile Met Ala Ser Lys
                485                 490                 495

Gln Glu Gly Lys Leu Leu Trp Lys Lys His Gly Thr Ile Leu Asp Asn
                500                 505                 510

Gln Asn Ala Cys Lys Tyr Ile Asn Asp Ser Tyr Val Asp Tyr Lys Asp
                515                 520                 525

Ile Val Ile Gly Asn Asp Leu Trp Asn Asp Asn Ser Ile Lys Val
530                 535                 540

Gln Asn Asn Leu Asn Leu Ile Phe Glu Arg Asn Phe Gly Tyr Lys Val
545                 550                 555                 560

Gly Arg Asn Lys Leu Phe Lys Thr Ile Lys Glu Leu Lys Asn Val Trp
                565                 570                 575

Trp Ile Leu Asn Arg Asn Lys Val Trp Glu Ser Met Arg Cys Gly Ile
                580                 585                 590

Asp Glu Val Asp Gln Arg Arg Lys Thr Cys Glu Arg Ile Asp Glu Leu
            595                 600                 605

Glu Asn Met Pro Gln Phe Phe Arg Trp Phe Ser Gln Trp Ala His Phe
610                 615                 620

Phe Cys Lys Glu Lys Glu Tyr Trp Glu Leu Lys Leu Asn Asp Lys Cys
625                 630                 635                 640

Thr Gly Asn Asn Gly Lys Ser Leu Cys Gln Asp Lys Thr Cys Gln Asn
                645                 650                 655

Val Cys Thr Asn Met Asn Tyr Trp Thr Tyr Thr Arg Lys Leu Ala Tyr
                660                 665                 670

Glu Ile Gln Ser Val Lys Tyr Asp Lys Asp Arg Lys Leu Phe Ser Leu
            675                 680                 685

Ala Lys Asp Lys Asn Val Thr Thr Phe Leu Lys Glu Asn Ala Lys Asn
690                 695                 700

Cys Ser Asn Ile Asp Phe Thr Lys Ile Phe Asp Gln Leu Asp Lys Leu
705                 710                 715                 720

Phe Lys Glu Arg Cys Ser Cys Met Asp Thr Gln Val Leu Glu Val Lys
                725                 730                 735

Asn Lys Glu Met Leu Ser Ile Asp Ser Asn Ser Glu Asp Ala Thr Asp
                740                 745                 750

Ile Ser Glu Lys Asn Gly Glu Glu Glu Leu Tyr Val Asn His Asn Ser
            755                 760                 765

Val Ser Val Ala Ser Gly Asn Lys Glu Ile Glu Lys Ser Lys Asp Glu
770                 775                 780

Lys Gln Pro Glu Lys Glu Ala Lys Gln Thr Asn Gly Thr Leu Thr Val
785                 790                 795                 800

Arg Thr Asp Lys Asp Ser Asp Arg Asn Lys Gly Lys Asp Thr Ala Thr
                805                 810                 815

Asp Thr Lys Asn Ser Pro Glu Asn Leu Lys Val Gln Glu His Gly Thr
                820                 825                 830

Asn Gly Glu Thr Ile Lys Glu Pro Pro Lys Leu Pro Glu Ser Ser
            835                 840                 845

Glu Thr Leu Gln Ser Gln Glu Gln Leu Glu Ala Glu Ala Gln Lys Gln
850                 855                 860
```

```
Lys Gln Glu Glu Glu Pro Lys Lys Gln Glu Glu Pro Lys Lys
865                 870                 875                 880

Lys Gln Glu Glu Glu Gln Lys Arg Glu Gln Glu Gln Lys Gln Glu Gln
                885                 890                 895

Glu Glu Glu Glu Gln Lys Gln Glu Glu Gln Gln Ile Gln Asp Gln
                900                 905                 910

Ser Gln Ser Gly Leu Asp Gln Ser Ser Lys Val Gly Val Ala Ser Glu
                915                 920                 925

Gln Asn Glu Ile Ser Ser Gly Gln Glu Gln Asn Val Lys Ser Ser Ser
        930                 935                 940

Pro Glu Val Val Pro Gln Glu Thr Thr Ser Glu Asn Gly Ser Ser Gln
945                 950                 955                 960

Asp Thr Lys Ile Ser Ser Thr Glu Pro Asn Glu Asn Ser Val Val Asp
                965                 970                 975

Arg Ala Thr Asp Ser Met Asn Leu Asp Pro Glu Lys Val His Asn Glu
                980                 985                 990

Asn Met Ser Asp Pro Asn Thr Asn Thr Glu Pro Asp Ala Ser Leu Lys
                995                 1000                1005

Asp Asp Lys Lys Glu Val Asp Asp Ala Lys Lys Glu Leu Gln Ser Thr
        1010                1015                1020

Val Ser Arg Ile Glu Ser Asn Glu Gln Asp Val Gln Ser Thr Pro Pro
1025                1030                1035                1040

Glu Asp Thr Pro Thr Val Glu Gly Lys Val Gly Asp Lys Ala Glu Met
                1045                1050                1055

Leu Thr Ser Pro His Ala Thr Asp Asn Ser Glu Ser Glu Ser Gly Leu
                1060                1065                1070

Asn Pro Thr Asp Asp Ile Lys Thr Thr Asp Gly Val Val Lys Glu Gln
                1075                1080                1085

Glu Ile Leu Gly Gly Gly Glu Ser Ala Thr Gly Thr Ser Lys Ser Asn
        1090                1095                1100

Leu Glu Lys Pro Lys Asp Val Glu Pro Ser His Glu Ile Ser Glu Pro
1105                1110                1115                1120

Val Leu Ser Gly Thr Thr Gly Lys Glu Glu Ser Glu Leu Leu Lys Ser
                1125                1130                1135

Lys Ser Ile Glu Thr Lys Gly Glu Thr Asp Pro Arg Ser Asn Asp Gln
                1140                1145                1150

Glu Asp Ala Thr Asp Asp Val Val Glu Asn Ser Arg Asp Asp Asn Asn
                1155                1160                1165

Ser Leu Ser Asn Ser Val Asp Asn Gln Ser Asn Val Leu Asn Arg Glu
        1170                1175                1180

Asp Pro Ile Ala Ser Glu Thr Glu Val Val Ser Glu Pro Glu Asp Ser
1185                1190                1195                1200

Ser Arg Ile Ile Thr Thr Glu Val Pro Ser Thr Thr Val Lys Pro Pro
                1205                1210                1215

Asp Glu Lys Arg Ser Glu Glu Val Gly Glu Lys Glu Ala Lys Glu Ile
                1220                1225                1230

Lys Val Glu Pro Val Val Pro Arg Ala Ile Gly Glu Pro Met Glu Asn
                1235                1240                1245

Ser Val Ser Val Gln Ser Pro Pro Asn Val Glu Asp Val Glu Lys Glu
        1250                1255                1260

Thr Leu Ile Ser Glu Asn Asn Gly Leu His Asn Asp Thr His Arg Gly
1265                1270                1275                1280
```

-continued

```
Asn Ile Ser Glu Lys Asp Leu Ile Asp Ile His Leu Leu Arg Asn Glu
            1285                1290                1295

Ala Gly Ser Thr Ile Leu Asp Asp Ser Arg Arg Asn Gly Glu Met Thr
        1300                1305                1310

Glu Gly Ser Glu Ser Asp Val Gly Glu Leu Gln Glu His Asn Phe Ser
        1315                1320                1325

Thr Gln Gln Lys Asp Glu Lys Asp Phe Asp Gln Ile Ala Ser Asp Arg
        1330                1335                1340

Glu Lys Glu Glu Ile Gln Lys Leu Leu Asn Ile Gly His Glu Glu Asp
1345                1350                1355                1360

Glu Asp Val Leu Lys Met Asp Arg Thr Glu Asp Ser Met Ser Asp Gly
            1365                1370                1375

Val Asn Ser His Leu Tyr Tyr Asn Asn Leu Ser Ser Glu Glu Lys Met
        1380                1385                1390

Glu Gln Tyr Asn Asn Arg Asp Ala Ser Lys Asp Arg Glu Glu Ile Leu
        1395                1400                1405

Asn Arg Ser Asn Thr Asn Thr Cys Ser Asn Glu His Ser Leu Lys Tyr
        1410                1415                1420

Cys Gln Tyr Met Glu Arg Asn Lys Asp Leu Leu Glu Thr Cys Ser Glu
1425                1430                1435                1440

Asp Lys Arg Leu His Leu Cys Cys Glu Ile Ser Asp Tyr Cys Leu Lys
            1445                1450                1455

Phe Phe Asn Pro Lys Ser Ile Glu Tyr Phe Asp Cys Thr Gln Lys Glu
        1460                1465                1470

Phe Asp Asp Pro Thr Tyr Asn Cys Phe Arg Lys Gln Arg Phe Thr Ser
        1475                1480                1485

Met His Tyr Ile Ala Gly Gly Ile Ile Ala Leu Leu Leu Phe Ile
        1490                1495                1500

Leu Gly Ser Ala Ser Tyr Arg Lys Asn Leu Asp Asp Glu Lys Gly Phe
1505                1510                1515                1520

Tyr Asp Ser Asn Leu Asn Asp Ser Ala Phe Glu Tyr Asn Asn Asn Lys
            1525                1530                1535

Tyr Asn Lys Leu Pro Tyr Met Phe Asp Gln Gln Ile Asn Val Val Asn
        1540                1545                1550

Ser Asp Leu Tyr Ser Glu Gly Ile Tyr Asp Asp Thr Thr Thr Phe
        1555                1560                1565

<210> SEQ ID NO 19
<211> LENGTH: 1210
<212> TYPE: PRT
<213> ORGANISM: Plasmodium falciparum

<400> SEQUENCE: 19

Met Lys Gly Tyr Phe Asn Ile Tyr Phe Leu Ile Pro Leu Ile Phe Leu
1               5                   10                  15

Tyr Asn Val Ile Arg Ile Asn Glu Ser Ile Ile Gly Arg Thr Leu Tyr
            20                  25                  30

Asn Arg Gln Asp Glu Ser Ser Asp Ile Ser Arg Val Asn Ser Pro Glu
        35                  40                  45

Leu Asn Asn Asn His Lys Thr Asn Ile Tyr Asp Ser Asp Tyr Glu Asp
    50                  55                  60

Val Asn Asn Lys Leu Ile Asn Ser Phe Val Glu Asn Lys Ser Val Lys
65                  70                  75                  80

Lys Lys Arg Ser Leu Ser Phe Ile Asn Asn Lys Thr Lys Ser Tyr Asp
            85                  90                  95
```

-continued

```
Ile Ile Pro Pro Ser Tyr Ser Tyr Arg Asn Asp Lys Phe Asn Ser Leu
            100                 105                 110

Ser Glu Asn Glu Asp Asn Ser Gly Asn Thr Asn Ser Asn Asn Phe Ala
        115                 120                 125

Asn Thr Ser Glu Ile Ser Ile Gly Lys Asp Asn Lys Gln Tyr Thr Phe
    130                 135                 140

Ile Gln Lys Arg Thr His Leu Phe Ala Cys Gly Ile Lys Arg Lys Ser
145                 150                 155                 160

Ile Lys Trp Ile Cys Arg Glu Asn Ser Glu Lys Ile Thr Val Cys Val
                165                 170                 175

Pro Asp Arg Lys Ile Gln Leu Cys Ile Ala Asn Phe Leu Asn Ser Arg
            180                 185                 190

Leu Glu Thr Met Glu Lys Phe Lys Glu Ile Phe Leu Ile Ser Val Asn
        195                 200                 205

Thr Glu Ala Lys Leu Leu Tyr Asn Lys Asn Glu Gly Lys Asp Pro Ser
    210                 215                 220

Ile Phe Cys Asn Glu Leu Arg Asn Ser Phe Ser Asp Phe Arg Asn Ser
225                 230                 235                 240

Phe Ile Gly Asp Asp Met Asp Phe Gly Gly Asn Thr Asp Arg Val Lys
                245                 250                 255

Gly Tyr Ile Asn Lys Lys Phe Ser Asp Tyr Tyr Lys Glu Lys Asn Val
            260                 265                 270

Glu Lys Leu Asn Asn Ile Lys Lys Glu Trp Trp Glu Lys Asn Lys Ala
        275                 280                 285

Asn Leu Trp Asn His Met Ile Val Asn His Lys Gly Asn Ile Ser Lys
    290                 295                 300

Glu Cys Ala Ile Ile Pro Ala Glu Pro Gln Ile Asn Leu Trp Ile
305                 310                 315                 320

Lys Glu Trp Asn Glu Asn Phe Leu Met Glu Lys Lys Arg Leu Phe Leu
                325                 330                 335

Asn Ile Lys Asp Lys Cys Val Glu Asn Lys Lys Tyr Glu Ala Cys Phe
            340                 345                 350

Gly Gly Cys Arg Leu Pro Cys Ser Ser Tyr Thr Ser Phe Met Lys Lys
        355                 360                 365

Ser Lys Thr Gln Met Glu Val Leu Thr Asn Leu Tyr Lys Lys Lys Asn
    370                 375                 380

Ser Gly Val Asp Lys Asn Asn Phe Leu Asn Asp Leu Phe Lys Lys Asn
385                 390                 395                 400

Asn Lys Asn Asp Leu Asp Asp Phe Phe Lys Asn Glu Lys Glu Tyr Asp
                405                 410                 415

Asp Leu Cys Asp Cys Arg Tyr Thr Ala Thr Ile Ile Lys Ser Phe Leu
            420                 425                 430

Asn Gly Pro Ala Lys Asn Asp Val Asp Ile Ala Ser Gln Ile Asn Val
        435                 440                 445

Asn Asp Leu Arg Gly Phe Gly Cys Asn Tyr Lys Ser Asn Asn Glu Lys
    450                 455                 460

Ser Trp Asn Cys Thr Gly Thr Phe Thr Asn Lys Phe Pro Gly Thr Cys
465                 470                 475                 480

Glu Pro Pro Arg Arg Gln Thr Leu Cys Leu Gly Arg Thr Tyr Leu Leu
                485                 490                 495

His Arg Gly His Glu Glu Asp Tyr Lys Glu His Leu Leu Gly Ala Ser
            500                 505                 510
```

-continued

```
Ile Tyr Glu Ala Gln Leu Leu Lys Tyr Lys Lys Asp Glu
        515                 520                 525

Asn Ala Leu Cys Ser Ile Ile Gln Asn Ser Tyr Ala Asp Leu Ala Asp
530                 535                 540

Ile Ile Lys Gly Ser Asp Ile Ile Lys Asp Tyr Tyr Gly Lys Lys Met
545                 550                 555                 560

Glu Glu Asn Leu Asn Lys Val Asn Lys Asp Lys Lys Arg Asn Glu Glu
                565                 570                 575

Ser Leu Lys Ile Phe Arg Glu Lys Trp Trp Asp Glu Asn Lys Glu Asn
                580                 585                 590

Val Trp Lys Val Met Ser Ala Val Leu Lys Asn Lys Glu Thr Cys Lys
        595                 600                 605

Asp Tyr Asp Lys Phe Gln Lys Ile Pro Gln Phe Leu Arg Trp Phe Lys
        610                 615                 620

Glu Trp Gly Asp Asp Phe Cys Glu Lys Arg Lys Glu Lys Ile Tyr Ser
625                 630                 635                 640

Phe Glu Ser Phe Lys Val Glu Cys Lys Lys Lys Asp Cys Asp Glu Asn
                645                 650                 655

Thr Cys Lys Asn Lys Cys Ser Glu Tyr Lys Lys Trp Ile Asp Leu Lys
                660                 665                 670

Lys Ser Glu Tyr Glu Lys Gln Val Asp Lys Tyr Thr Lys Asp Lys Asn
        675                 680                 685

Lys Lys Met Tyr Asp Asn Ile Asp Glu Val Lys Asn Lys Glu Ala Asn
        690                 695                 700

Val Tyr Leu Lys Glu Lys Ser Lys Glu Cys Lys Asp Val Asn Phe Asp
705                 710                 715                 720

Asp Lys Ile Phe Asn Glu Ser Pro Asn Glu Tyr Glu Asp Met Cys Lys
                725                 730                 735

Lys Cys Asp Glu Ile Lys Tyr Leu Asn Glu Ile Lys Tyr Pro Lys Thr
                740                 745                 750

Lys His Asp Ile Tyr Asp Ile Asp Thr Phe Ser Asp Thr Phe Gly Asp
        755                 760                 765

Gly Thr Pro Ile Ser Ile Asn Ala Asn Ile Asn Glu Gln Gln Ser Gly
770                 775                 780

Lys Asp Thr Ser Asn Thr Gly Asn Ser Glu Thr Ser Asp Ser Pro Val
785                 790                 795                 800

Ser His Glu Pro Glu Ser Asp Ala Ala Ile Asn Val Glu Lys Leu Ser
                805                 810                 815

Gly Asp Glu Ser Ser Glu Thr Arg Gly Ile Leu Asp Ile Asn Asp
        820                 825                 830

Pro Ser Val Thr Asn Asn Val Asn Glu Val His Asp Ala Ser Asn Thr
                835                 840                 845

Gln Gly Ser Val Ser Asn Thr Ser Asp Ile Thr Asn His Ser Glu
850                 855                 860

Ser Ser Leu Asn Arg Thr Thr Asn Ala Gln Asp Ile Lys Ile Gly Arg
865                 870                 875                 880

Ser Gly Asn Glu Gln Ser Asp Asn Gln Glu Asn Ser Ser His Ser Ser
                885                 890                 895

Asp Asn Ser Gly Ser Leu Thr Ile Gly Gln Val Pro Ser Glu Asp Asn
        900                 905                 910

Thr Gln Asn Thr Tyr Asp Ser Gln Asn Pro His Arg Asp Thr Pro Asn
        915                 920                 925

Ala Leu Ala Ser Leu Pro Ser Asp Asp Lys Ile Asn Glu Ile Glu Gly
```

```
                    930             935             940
Phe Asp Ser Ser Arg Asp Ser Glu Asn Gly Arg Gly Asp Thr Thr Ser
945                 950             955                 960

Asn Thr His Asp Val Arg Arg Thr Asn Ile Val Ser Glu Arg Arg Val
                965             970                 975

Asn Ser His Asp Phe Ile Arg Asn Gly Met Ala Asn Asn Ala His
            980             985             990

His Gln Tyr Ile Thr Gln Ile Glu Asn Asn Gly Ile Ile Arg Gly Gln
        995             1000            1005

Glu Glu Ser Ala Gly Asn Ser Val Asn Tyr Lys Asp Asn Pro Lys Arg
    1010            1015            1020

Ser Asn Phe Ser Ser Glu Asn Asp His Lys Lys Asn Ile Gln Glu Tyr
1025            1030            1035            1040

Asn Ser Arg Asp Thr Lys Arg Val Arg Glu Glu Ile Ile Lys Leu Ser
            1045            1050            1055

Lys Gln Asn Lys Cys Asn Asn Glu Tyr Ser Met Glu Tyr Cys Thr Tyr
            1060            1065            1070

Ser Asp Glu Arg Asn Ser Ser Pro Gly Pro Cys Ser Arg Glu Glu Arg
            1075            1080            1085

Lys Lys Leu Cys Cys Gln Ile Ser Asp Tyr Cys Leu Lys Tyr Phe Asn
            1090            1095            1100

Phe Tyr Ser Ile Glu Tyr Tyr Asn Cys Ile Lys Ser Glu Ile Lys Ser
1105            1110            1115            1120

Pro Glu Tyr Lys Cys Phe Lys Ser Glu Gly Gln Ser Ser Ile Pro Tyr
                1125            1130            1135

Phe Ala Ala Gly Gly Ile Leu Val Val Ile Val Leu Leu Leu Ser Ser
            1140            1145            1150

Ala Ser Arg Met Gly Lys Ser Asn Glu Glu Tyr Asp Ile Gly Glu Ser
            1155            1160            1165

Asn Ile Glu Ala Thr Phe Glu Glu Asn Asn Tyr Leu Asn Lys Leu Ser
    1170            1175            1180

Arg Ile Phe Asn Gln Glu Val Gln Glu Thr Asn Ile Ser Asp Tyr Ser
1185            1190            1195            1200

Glu Tyr Asn Tyr Asn Glu Lys Asn Met Tyr
            1205            1210

<210> SEQ ID NO 20
<211> LENGTH: 1581
<212> TYPE: DNA
<213> ORGANISM: Plasmodium falciparum

<400> SEQUENCE: 20
atgataagaa taaaaaaaaa attaattttg accattatat atattcatct gtttatatta    60
aatagattaa gttttgaaaa tgcaataaaa aaaacgaaga atcaagaaaa taatctgacg   120
ttactaccaa taaagagcac tgaagaagaa aaagatgata taaaaaatgg aaaggatata   180
aaaaaagaaa ttgataatga taaagagaat ataaaaacaa ataatgctaa agatcattca   240
acatatataa aatcatattt gaatacaaat gtaaatgatg gtttaaaata tttgtttatt   300
ccttctcata attcttttat aaaaaaatat tctgtattta atcaaataaa tgatggcatg   360
ttattaaatg aaaaaaatga tgtgaaaaat aatgaagact ataaaaatgt ggattataaa   420
aatgttaatt ttttacaata tcattttaaa gagttatcaa attataacat tgcaaattct   480
attgatattt tacaagaaaa agaaggacat ttggattttg ttataatacc tcattatact   540
```

| | |
|---|---|
| tttttagatt attataaaca tttatcttat aattctatat atcataagtc ctctacatat | 600 |
| ggaaagtgta tagctgtaga tgcttttatt aagaaaataa atgaaacata tgacaaagtg | 660 |
| aaaagtaaat gtaatgatat aaagaatgat ttaattgcaa ctataaaaaa attagagcat | 720 |
| ccttatgata taaataataa gaatgatgat tcctatagat atgatatatc tgaagaaatc | 780 |
| gatgataaat ctgaagagac agatgatgaa accgaagagg tagaagatag tatacaagat | 840 |
| acagatagta atcatactcc ttcaaataaa aaaaaaaatg atcttatgaa tagaacgttt | 900 |
| aaaagatga tggatgaata taatacaaaa aaaaaaaat taattaaatg tataaaaaac | 960 |
| catgagaatg attttaataa aatatgtatg gatatgaaaa attatggtac aaaccttttt | 1020 |
| gaacaacttt catgttacaa taataatttc tgtaatacaa acggaataag atatcattat | 1080 |
| gatgaatata ttcataaatt aatattatct gttaaatcaa aaaacttaaa taaagaccta | 1140 |
| tcagatatga caaatatttt acaacaaagt gaattattat taaccaattt aaataaaaaa | 1200 |
| atgggttcct atatatatat tgatacaata aaatttatac ataagaaat gaaacatatt | 1260 |
| tttaacagaa ttgaatatca tacaaaaata ataaacgata aaactaaaat aattcaagac | 1320 |
| aaaattaaat taaatatatg gagaacattt caaaaagatg aattattaaa aagaatttta | 1380 |
| gacatgtcaa atgaatattc tttatttatt actagtgatc atttaagaca aatgttatat | 1440 |
| aatacattct attcaaaaga aaaacattta aataatatat ttcatcattt aatttatgta | 1500 |
| ctacaaatga agttcaatga tgtcccaatt aaaatggaat attttcaaac atataaaaaa | 1560 |
| aataaaccac ttacacaatg a | 1581 |

<210> SEQ ID NO 21
<211> LENGTH: 9540
<212> TYPE: DNA
<213> ORGANISM: Plasmodium falciparum

<400> SEQUENCE: 21

| | |
|---|---|
| atgaagagat cgcttataaa tttagaaaat gatctttta gattgaaacc tatatcttat | 60 |
| attcaaagat attataagaa gaatataaac agatctgata ttttcataa taaaaaagaa | 120 |
| agaggttcca agtatattc aaatgtgtct tcattccatt ctttattca agagggtaaa | 180 |
| gaagaagttg aggttttttc tatatggggt agtaatagcg ttttagatca tatagatgtt | 240 |
| cttagggata atggaactgt cgttttttct gttcaaccat attaccttga tatatatacg | 300 |
| tgtaaagaag ccatattatt tactacatca ttttacaagg atcttgataa aagttcaatt | 360 |
| acaaaaatta atgaagatat tgaaaaattt aacgaagaaa taatcaagaa tgaagaacaa | 420 |
| tgtttagttg gtgggaaaac agattttgat aatttactta gtttttaga aaatgcggaa | 480 |
| aaagcaaatg ttagaaaaac attatttgat aatacattta atgattataa aataagaaa | 540 |
| tctagttttt acaattgttt gaaaataaa aaaatgatt atgataagaa ataaagaat | 600 |
| ataagaatg agattacaaa attgttaaaa aatattgaaa gtacaggaaa tatgtgtaaa | 660 |
| acggaatcat atgttatgaa taataattta tatctattaa gagtgaatga agttaaaagt | 720 |
| acacctattg attatactt aaatcgagca aaagagctat tagaatcaag tagcaaatta | 780 |
| gttaatccta taaaaatgaa attaggtgat aataagaaca tgtactctat tggatatata | 840 |
| catgacgaaa ttaaagatat tataaaaaga tataattttc atttgaaaca tatagaaaaa | 900 |
| ggaaaagaat atataaaaag gataacacaa gcaataataa ttgcagacaa aatgaagaaa | 960 |
| gatgaactta taaaaaaaat ttttgaatcc tcaaacatt ttgctagttt taaatatagc | 1020 |
| aatgaaatga taagcaaatt agattcgtta tttataaaaa atgaagaaat acttaataat | 1080 |

```
ttattcaata atatatttaa tatattcaag aaaaaatatg aaacatatgt agatatgaaa    1140
acaattgaat ctaaatatac aacagtaatg actctatcag aacatttatt agaatatgca    1200
atggatgttt taaaagctaa ccctcaaaaa cctattgatc caaaagcaaa tctggattca    1260
gaagtagtaa aattacaaat aaaaataaat gagaaatcaa atgaattaga taatgctata    1320
agtcaagtaa aaacactaat aataataatg aaatcatttt atgatattat tatatctgaa    1380
aaagcctcta tggatgaaat ggaaaaaaag gaattatcct taaataatta tattgaaaaa    1440
acagattata tattacaaac gtataatatt tttaagtcta aaagtaatat tataaataat    1500
aatagtaaaa atattagttc taaatatata actatagaag ggttaaaaaa tgatattgat    1560
gaattaaata gtcttatatc atattttaag gattcacaag aaacattaat aaaagatgat    1620
gaattaaaaa aaaacatgaa aacggattat cttaataacg tgaaatatat agaagaaaat    1680
gttactcata taaatgaaat tatattatta aaagattcta taactcaacg aatagcagat    1740
attgatgaat taaatagttt aaatttaata aatataaatg atttttataaa tgaaaagaat    1800 atatcacaag agaaagtatc atataatctt aataaattat ataaaggaag ttttgaagaa    1860
ttagaatctg aactatctca ttttttagac acaaaatatt tgtttcatga aaaaaaaagt    1920
gtaaatgaac ttcaaacaat tttaaataca tcaaataatg aatgtgctaa attaaatttt    1980
atgaaatctg ataataataa taataataat aatagtaata taattaactt gttaaaaact    2040
gaattaagtc atctattaag tcttaaagaa aatataataa aaaaactttt aaatcatata    2100
gaacaaaata ttcaaaactc atcaaataag tatactatta catatactga tattaataat    2160
agaatggaag attataaaga agaaatcgaa agtttagaag tatataaaca taccattgga    2220
aatatacaaa aagaatatat attacatttta tatgagaatg ataaaaatgc tttagctgta    2280
cataatacat caatgcaaat attacaatat aaagatgcta tacaaaatat aaaaaataaa    2340
atttctgatg atataaaaat tttaagaaaa tataagaaaa tgaatcaaga tttattaaat    2400
tattatgaaa ttctagataa aaaattaaaa gataatacat atatcaaaga aatgcatact    2460
gcttctttag ttcaaataac tcaatatatt ccttatgaag ataaaacaat aagtgaactt    2520
gagcaagaat ttaataataa taatcaaaaa cttgataata tattcaaaga tatcaatgca    2580
atgaatttaa atataaatat tctccaaacc ttaaatattg gtataaatgc atgtaataca    2640
aataataaaa atgtagaaca cttacttaac aagaaaattg aattaaaaaa tatattaaat    2700
gatcaaatga aaattataaa aaatgatgat ataattcaag ataatgaaaa agaaaacttt    2760
tcaaatgttt taaaaaaaga agaggaaaaa ttagaaaaag aattagatga tatcaaatttt   2820 aataatttga aaatggacat tcataaattg ttgaattcgt atgaccatac aaagcaaaat    2880
atagaaagca atcttaaaat aaatttagat tctttcgaaa aggaaaaaga tagttgggtt    2940
cattttaaaa gtactataga tagtttatat gtggaatata acatatgtaa tcaaaagact    3000
cataatacta tcaaacaaca aaaaaatgat atcatagaac ttatttataa acgtataaaa    3060
gatataaatc aagaaataat cgaaaaggta gataattatt attccctgtc agataaagcc    3120
ttaactaaac ttaaatctat tcattttaat attgataagg aaaatataaa aaatcccaaa    3180
agtcaagaaa atattaaatt attagaagat agagttatga tacttgagaa aaagattaag    3240
gaagataaag atgctttaat acaaattaag aatttatcac atgatcattt tgtaaatgct    3300
gataatgaga aaaaaaagca gaaggagaag gaggaggacg acgaacaaac acactatagt    3360
aaaaaaagaa aagtaatggg agatatatat aaggatatta aaaaaaacct agatgagtta    3420
```

```
aataataaaa atttgataga tattacttta aatgaagcaa ataaaataga atcagaatat    3480
gaaaaaatat taattgatga tatttgtgaa caaattacaa atgaagcaaa aaaaagtgat    3540
actattaagg aaaaaatcga atcatataaa aaagatattg attatgtaga tgtggacgtt    3600
tccaaaacga ggaacgatca tcatttgaat ggagataaaa tacatgattc ttttttttat    3660
gaagatacat taaattataa agcatatttt gataaattaa aagatttata tgaaaatata    3720
aacaagttaa caaatgaatc aaatggatta aaaagtgatg ctcataataa caacacacaa    3780
gttgataaac taaagaaat taatttacaa gtattcagca atttaggaaa tataattaaa    3840
tatgttgaaa aacttgagaa tacattacat gaacttaaag atatgtacga atttctagaa    3900
acgatcgata ttaataaaat attaaaaagt attcataata gcatgaagaa atcagaagaa    3960
tatagtaatg aaacgaaaaa aatatttgaa caatcagtaa atataactaa tcaatttata    4020
gaagatgttg aaatattgaa aacgtctatt aacccaaact atgaaagctt aaatgatgat    4080
caaattgatg ataatataaa atcacttgtt ctaaagaaag aggaaatatc cgaaaaaaga    4140
aaacaagtga ataaatacat aacagatatt gaatctaata aagaacaatc agatttacat    4200
ttacgatatg catctagaag tatatatgtt attgatcttt ttataaaaca tgaaataata    4260
aatcctagcg atggaaaaaa ttttgatatt ataaggttta agaaatgat aaataaaacc    4320 aaacaagttt caaatgaagc tatggaatat gctaataaaa tggatgaaaa aaataaggac    4380
attataaaaa tagaaaatga actttataat ttaattaata ataacatccg ttcattaaaa    4440
ggggtaaaat atgaaaaagt taggaaacaa gcaagaaatg caattgatga tataaataat    4500
atacattcta atattaaaac gattttaacc aaatctaaag aacgattaga tgagattaag    4560
aaacaaccta acattaaaag agaaggtgat gttttaaata atgataaaac caaaatagct    4620 tatattcaa tacaaataaa taacggaaga atagaatcta atttattaaa tatattaaat    4680
atgaaacata acatagatac tatcttgaat aaagctatgg attatatgaa tgatgtatca    4740
aaatctgacc agattgttat taatatagat tctttgaata tgaacgatat atataataag    4800
gataaagatc ttttaataaa tattttaaaa gaaaaacaga atatggaggc agaatataaa    4860
aaaatgaatg aaatgtataa ttacgttaat gaaacagaaa aagaaataat aaaacataaa    4920
aaaaattatg aaataagaat tatggaacat ataaaaaaag aaacaaatga aaaaaaaaaa    4980
aaatttatgg aatctaataa caaatcatta actactttaa tggattcatt cagatctatg    5040
ttttataatg aatatataaa tgattataat ataaatgaaa attttgaaaa acatcaaaat    5100
atattgaatg aaatatataa tggatttaat gaatcatata atattattaa tacaaaaatg    5160
actgaaatta taaatgataa tttagattat aatgaaataa aagaaattaa agaagtagca    5220
caaacagaat atgataaact taataaaaaa gttgatgaat taaaaaatta tttgaataat    5280
attaaagaac aagaaggaca tcgattaatt gattatataa aagaaaaat atttaactta    5340 tatataaaat gttcagaaca acaaaatata atagatgatt cttataatta tattacagtt    5400
aaaaaacagt atattaaaac tattgaagat gtgaaatttt tattagattc attgaacaca    5460
atagaagaaa aaaataaatc agtagcaaat ctagaaattt gtactaataa agaagatata    5520
aaaaatttac ttaaacatgt tataaagttg gcaaatttt caggtattat tgtaatgtct    5580
gatacaaata cggaaataac tccagaaaat cctttagaag ataatgattt attaaattta    5640
caattatatt ttgaaagaaa acatgaaata acatcaacat tggaaaatga ttctgattta    5700
gagttagatc atttaggtag taattcggat gaatctatag ataatttaaa ggtttataat    5760
gatattatag aattacacac atattcaaca caaattctta aatatttaga taatattcaa    5820
```

```
aaacttaaag gagattgcaa tgatttagta aaggattgta aagaattacg tgaattgtct    5880
acggcattat atgatttaaa aatacaaatt actagtgtaa ttaatagaga aaatgatatt    5940
tcaaataata ttgatattgt atctaataaa ttaaatgaaa tagatgctat acaatataat    6000
tttgaaaaat ataagaaat  ttttgataat gtagaagaat ataaaacatt agatgataca    6060
aaaaatgcat atattgtaaa aaaggctgaa atttttaaaaa atgtagatat aaataaaaca   6120
aaagaagatt tagatatata ttttaatgac ttagacgaat tagaaaaatc tcttacatta    6180
tcatctaatg aaatggaaat taaaacaata gtacagaact catataattc cttttctgat    6240
attaataaga acattaatga tattgataaa gaaatgaaaa cactgatccc tatgcttgat    6300
gaattattaa atgaaggaca taatattgat atatcattat ataattttat aattagaaat    6360
attcagatta aaataggtaa tgatataaaa aatataagag aacaggaaaa tgatactaat    6420
atatgttttg agtatattca aaataattat aatttataa  agagtgatat aagtatcttc    6480
aataaatatg atgatcatat aaaagtagat aattatatat ctaataatat tgatgttgtc    6540
aataaacata atagtttatt aagtgaacat gttataaatg ctacaaatat tatagagaat    6600
attatgacaa gtattgtcga aataaatgaa gatacagaaa tgaattcttt agaagagaca    6660
caagacaaat tattagaact atatgaaaat tttaagaaag aaaaaaatat tataaataat    6720
aattataaaa tagtacattt taataaatta aaagaaatag aaaatagttt agagacatat    6780
aattcaatat caacaaactt taataaaata aatgaaacac aaaatataga tattttaaaa    6840
aatgaattta ataatatcaa aacaaaaatt aatgataaag taaagaatt  agttcatgtt    6900 gatagtacat taacacttga atcaattcaa acgtttaata atttatatgg tgacttgatg    6960
tctaatatac aagatgtata taaatatgaa gatattaata atgttgaatt gaaaaaggtg    7020
aaattatata tagaaaatat tacaaattta ttaggaagaa taaacacatt cataaaggag    7080
ttagacaaat atcaggatga aaataatggt atagataagt atatagaaat caataaggaa    7140
aataatagtt atataataaa attgaaagaa aaagccaata atctaaagga aaatttctca    7200
aaattattac aaaatataaa aagaaatgaa actgaattat ataatataaa taacataaag    7260
gatgatatta tgaatacggg gaaatctgta aataatataa aacaaaaatt ttctagtaat    7320
ttgccactaa aagaaaaatt atttcaaatg gaagagatgt tacttaatat aaataatatt    7380
atgaatgaaa cgaaaagaat atcaaacacg gatgcatata ctaatataac tctccaggat    7440
attgaaaata ataaaaataa agaaaataat aatatgaata ttgaaacaat tgataaatta    7500
atagatcata taaaaataca taatgaaaaa atacaagcag aaatattaat aattgatgat    7560
gccaaaagaa aagtaaagga aataacagat aatattaaca aggcttttaa tgaaattaca    7620
gaaaattata ataatgaaaa taatgggta  attaaatctg caaaaaatat tgtcgataaa    7680
gctacttatt taaataatga attagataaa ttttttattga aattgaatga attattaagt    7740
cataataata atgatataaa ggatcttggt gatgaaaaat taatattaaa agaagaagaa    7800
gaaagaaaag aaagagaaag attggaaaaa gcgaaacaag aagaagaaag aaaagagaga    7860
gaaagaatag aaaaagaaaa acaagagaaa gaaagactgg aaagagagaa acaagaacaa    7920
ctaaaaaaag aagcattaaa aaaacaagag caagaaagac aagaacaaca acaaaaagaa    7980
gaagcattaa aaagacaaga acaagaacga ctacaaaaag aagaagaatt aaaaagacaa    8040
gagcaagaaa ggctggaaag agagaaacaa gaacaactac aaaaagaaga agaattaaga    8100 aaaaagagc  aggaaaaaca acaacaaaga aatatccaag aattagaaga gcaaaaaaag    8160
```

| | |
|---|---|
| cctgaaataa taaatgaagc attggtaaag ggggataaaa tactagaagg aagtgatcag | 8220 |
| agaaatatgg aattaagcaa acctaacgtt agtatggata atactaataa tagtccaatt | 8280 |
| agtaacagtg aaattacaga aagcgatgat attgataaca gtgaaaatat acatactagt | 8340 |
| catatgagtg acatcgaaag tacacaaact agtcatagaa gtaacaccca tgggcaacaa | 8400 |
| atcagtgata ttgttgaaga tcaaattaca catcctagta atattggagg agaaaaaatt | 8460 |
| actcataatg atgaaatttc aatcactggt gaaagaaata acattagcga tgttaatgat | 8520 |
| tatagtgaaa gtagcaacat atttgaaaat ggtgacagta ctataaatac cagtacaaga | 8580 |
| aacacgtcta gtacacatga tgaatcccat ataagtccta tcagcaatgc gtatgatcat | 8640 |
| gttgtttcag ataataaaaa aagtatggat gaaaacataa aagataaatt aaagatagat | 8700 |
| gaaagtataa ctacagatga acaaataaga ttagatgata attctaatat tgttagaatt | 8760 |
| gatagtactg accaacgtga tgctagtagt catggtagta gtaataggga tgatgatgaa | 8820 |
| ataagtcatg ttggtagcga cattcatatg gatagtgttg atattcatga tagtattgac | 8880 |
| actgatgaaa atgctgatca cagacataat gttaactctg ttgatagtct tagttctagt | 8940 |
| gattacactg atacacagaa agactttagt agtattatta agatgggggg aaataaagaa | 9000 |
| ggacatgctg agaatgaatc taagaatat gaatcccaaa cagaacaaac acatgaagaa | 9060 |
| ggaattatga atccaaataa atattcaatt agtgaagttg atggtattaa attaaatgaa | 9120 |
| gaagctaaac ataaaattac agaaaaactg gtagatatct atccttctac atatagaaca | 9180 |
| cttgatgaac ctatggaaac acatggtcca aatgaaaaat tcatatgtt tggtagtcca | 9240 |
| tatgtaacag aagaagatta cacggaaaaa catgattatg ataagcatga agatttcaat | 9300 |
| aatgaaaggt attcaaacca taacaaaatg gatgatttcg tatataatgc tggaggagtt | 9360 |
| gtttgttgtg tattatttt tgcaagtatt actttctttt ctatggacag atcaaataag | 9420 |
| gatgaatgcg attttgatat gtgtgaagaa gtaaataata atgatcactt atcgaattat | 9480 |
| gctgataaag aagaaattat tgaaattgtg tttgatgaaa atgaagaaaa atattttaa | 9540 |

<210> SEQ ID NO 22
<211> LENGTH: 5151
<212> TYPE: DNA
<213> ORGANISM: Plasmodium falciparum

<400> SEQUENCE: 22

| | |
|---|---|
| atgaataaga atatattgtg gataactttt ttttattttt tatttttct cttggatatg | 60 |
| taccaaggaa atgacgcaat tccctcaaaa gaaaaaaaaa acgatccaga agcagattct | 120 |
| aagaactcac agaatcaaca tgatataaat aaaacacacc atacgaacaa taattatgat | 180 |
| ctgaatatta aggataaaga tgagaaaaaa agaaaaaatg ataatttaat caataattat | 240 |
| gattactctc tttttaaagtt atcttataat aagaatcaag atatatataa gaatatacaa | 300 |
| aatggccaaa agcttaaaac agacataata ttaaactcat tgttcaaat taattcatca | 360 |
| aacatattaa tggatgaaat agaaaattat gtgaaaaat atacgaaatc gaatcgtatt | 420 |
| atgtacttac aatttaaata tatatatcta caatccttaa atataacagt atcttttgta | 480 |
| cctccgaatt caccatttcg aagttattat gacaaaaatt taaataaaga tataaatgaa | 540 |
| acttgtcatt ccatacaaac acttctaaac aatctaatat cttccaaaat tatatttaaa | 600 |
| atgttagaaa ctacaaaaga acaaatatta cttttatgga ataacaaaaa aattagtcaa | 660 |
| caaaattata atcaagaaaa tcaagaaaaa agtaaaatga tcgattcgga aaatgaaaaa | 720 |
| ctagaaaagt acacaaacaa gtttgaacat aatatcaaac ctcatataga agatatagag | 780 |

```
aaaaaagtaa atgaatatat taataattcc gattgtcatt taacatgttc aaaatataaa    840
acaattatca ataattatat agatgaaata ataacaacta atacaaacat atacgaaaac    900
aaatataatc taccacaaga acgaattatc aaaaactata atcataatgg tattaataat    960
gatgataatt ttatagaata taatattctt aatgcagatc ctgatttaag atctcatttt   1020
ataacacttc ttgtttcaag aaaacaatta atctatattg aatatattta ttttattaac   1080
aaacatattg taaataaaat tcaagaaaac tttaaattaa atcaaaataa atatatacat   1140
tttattaatt caaataatgc tgttaatgct gctaaagaat atgaatatat cataaaatat   1200
tatactacat tcaaatatct acagacatta aataaatcat tatacgactc tatatataaa   1260
cataaaataa ataattattc tcataacatt gaagatctta taaaccaact acaacataaa   1320
attaataacc taatgattat ctcattcgat aaaaataaat catcagattt aatgttacaa   1380
tgtacaaata taaaaaaata taccgatgat atatgtttat ccattaaacc taaagcatta   1440
gaagtcgaat atttaagaaa tataaataaa cacatcaaca aaaatgaatt cctaaataaa   1500
ttcatgcaaa acgaaacatt taaaaaaaat atagatgata aaatcaaaga atgaataat    1560
atatacgata atatatatat catattaaaa caaaaattct taaacaaatt aaacgaaatc   1620
atacaaaatc ataaaaataa acaagaaaca aaattaaata ccacaaccat tcaagaattg   1680
ttacaacttc taaaggatat taaagaaata caaacaaaac aaatcgatac aaaaattaat   1740
acttttaata tgtattataa cgatatacaa caaataaaaa taaagattaa tcaaaatgaa   1800
aaagaaataa aaaaggtact ccctcaatta tatatcccaa aaaatgaaca agaatatata   1860
caaatatata aaaatgaatt aaaggataga ataaaagaaa cacaaacaaa aattaattta   1920
tttaagcaaa ttttagaatt aaaagaaaaa gaacattata ttacaaacaa acatacatac   1980
ctaaatttta cacacaaaac tattcaacaa atattacaac aacaatataa aaacaacaca   2040
caagaaaaaa atacactagc acaatttta tacaatgcag atatcaaaaa atatattgat    2100
gaattaatac ctatcacaca acaaatacaa accaaaatgt atacaacaaa taatatagaa   2160
catattaaac aaatactcat aaattatata caagaatgta aacctataca aaatatatca   2220
gaacatacta tttatacact atatcaagaa atcaaaacaa atctggaaaa catcgaacag   2280
aaaattatgc aaaatataca acaaactaca atcggttaa aaataaatat taaaaaaata    2340
tttgatcaaa taaatcaaaa atatgacgac ttaacaaaaa atataaaacca aatgaatgat   2400
gaaaaaattg ggttacgaca aatggaaaat aggttgaaag ggaaatatga agaaatcaaa   2460
aaggcaaatc ttcaagatag ggacataaaa tatatagtcc aaaataatga tgctaataat   2520
aataataata atattattat tattaatggt aataatcaaa ccggtgatta taatcacatc   2580
ttgttcgatt atactcacct ttgggataat gcacaattta ctagaacaaa agaaatata    2640
aacaacctaa aagataatat acaaatcaac ataaataata tcaaaagtat aataagaaat   2700
ttacaaaacg aactaaacaa ttataatact cttaaaagca attccatcca tatttatgat   2760
aaaatacaca cattagaaga attaaaaata ttaactcaag aaattaatga taaaaatgtt   2820
atcagaaaaa tatatgatat tgaaaccata tatcaaaatg atttacataa catagaagaa   2880
attattaaaa atattacaag catttattac aaaataaata tcttaaatat attaattatt   2940
tgcatcaaac aaacatataa taataataaa tccattgaaa gcttaaaact taaaattaat   3000
aacttaacaa attcaacaca agaatatatt aatcaaataa aagctatccc aactaattta   3060
ttaccagaac atataaaaca aaaagtgtta agcgaactaa atatttatat gaaacaaata   3120
```

| | |
|---|---|
| tatgataaat taaatgaaca tgttattaat aatttatata caaaatcaaa ggattcatta | 3180 |
| caattttata ttaacgaaaa aaattataat aataatcatg atgatcataa tgatgaccat | 3240 |
| aatgatgtat ataatgatat caagaaaat gaaatatata aaaataataa attatacgaa | 3300 |
| tgcatacaaa tcaaaaagga tgtagacgaa ttatataata tttatgatca actcttaaa | 3360 |
| aatatatccc aaaattataa taaccactcc cttagttttg tacattcaat aaataatcat | 3420 |
| atgctatcta tttttcaaga tactaaatat ggaaaacaca aaaatcaaca aatcctatcc | 3480 |
| gatatagaaa atattataaa acaaaatgaa cacacagaat catataaaa tttagacaca | 3540 |
| agtaatatac aactaataaa agaacaaatt aaatatttct tacaaatatt tcatatactt | 3600 |
| caagaaaata taaccacttt cgaaaatcaa tataaagatt taattatcaa aatgaaccat | 3660 |
| aaaattaata ataatctaaa agatattaca catattgtca taaacgataa caatacatta | 3720 |
| caagaacaaa atcgtattta taacgaactt caaaacaaaa ttaaacaaat aaaaaatgtc | 3780 |
| agtgatgtat tcacacataa tattaattac agtcaacaaa tattaaatta ttctcaagca | 3840 |
| caaaatagtt ttttaatat atttatgaaa tttcaaaaca ttaataatga tattaatagc | 3900 |
| aaacgatata atgtacaaaa aaaaattaca gagataatca attcatatga tataataaat | 3960 |
| tataacaaaa ataatatcaa agatatttat caacaattca aaaatataca acaacaatta | 4020 |
| aatacaacag aaacgcaatt gaatcatata aaacaaaata ttaatcattt caaatatttt | 4080 |
| tatgaatctc atcaaaccat atctatagta aagaatatgc aaaatgaaaa actaaaaatt | 4140 |
| caagaattca acaaaaaaat acaacacttc aaggaagaaa cacaaattat gataaacaag | 4200 |
| ttaatacaac ctagccacat acatttacat aaaatgaaat tgcctataac tcaacagcaa | 4260 |
| cttaatacaa ttcttcatag aaatgaacaa acaaaaaatg ctacaagaag ttacaatatg | 4320 |
| aatgaggagg aaaatgaaat gggatatggc ataactaata aaaggaaaaa tagtgagaca | 4380 |
| aatgacatga taaataccac cataggagac aagacaaatg tcttaaaaaa tgatgatcaa | 4440 |
| gaaaaaggta aaaggggaac ttccagaaat aataatattc atacaaatga aaataatata | 4500 |
| aataatgaac atacaaatga aaataatata aataatgaac atacaaatga aagaatata | 4560 |
| aataatgaac atgcaaatga aagaatata tataatgaac atacaaatga aaataatata | 4620 |
| aattatgaac atccaaataa ttatcaacaa aaaaatgatg aaaaaatatc actacaacat | 4680 |
| aaaacaatta atacatcaca acgtaccata gatgattcga atatggatcg aaataataga | 4740 |
| tataacacat catcacaaca aaaaaataat ttgcatacaa ataataatag taatagtaga | 4800 |
| tacaacaata accatgataa acaaaatgaa cataaatata tcaaggaaa atcttcaggg | 4860 |
| aaagataacg catattatag aatttttttat gctggaggaa ttacagctgt cttactttta | 4920 |
| tgttcaagta ctgcattctt ttttataaaa aactctaatg aaccacatca tatttttaat | 4980 |
| attttcaaa aggaatttag tgaagcagat aatgcacatt cagaagaaaa agaagaatat | 5040 |
| ctacctgtct attttgatga agttgaagat gaagttgaag atgaagttga agatgaagat | 5100 |
| gaaaatgaaa atgaagttga aaatgaaaat gaagatttta atgacatatg a | 5151 |

<210> SEQ ID NO 23
<211> LENGTH: 4389
<212> TYPE: DNA
<213> ORGANISM: Plasmodium falciparum

<400> SEQUENCE: 23

| | |
|---|---|
| atgaaatgta atattagtat atattttttt gcttccttct ttgtgttata ttttgcaaaa | 60 |
| gctaggaatg aatatgatat aaaagagaat gaaaaatttt tagacgtgta taagaaaaa | 120 |

```
tttaatgaat tagataaaaa gaaatatgga aatgttcaaa aaactgataa gaaaatattt      180
acttttatag aaaataaatt agatatttta aataattcaa aatttaataa aagatggaag      240
agttatggaa ctccagataa tatagataaa aatatgtctt taataaataa acataataat      300
gaagaaatgt ttaacaacaa ttatcaatca tttttatcga caagttcatt aataaagcaa      360
aataaatatg ttcctattaa cgctgtacgt gtgtctagga tattaagttt cctggattct      420
agaattaata atggaagaaa tacttcatct aataacgaag ttttaagtaa ttgtagggaa      480 aaaggaaag gaatgaaatg ggattgtaaa aagaaaaatg atagaagcaa ctatgtatgt       540
attcctgatc gtagaatcca attatgcatt gttaatctta gcattattaa aacatataca      600
aaagagacca tgaaggatca tttcattgaa gcctctaaaa aagaatctca acttttgctt      660
aaaaaaaatg ataacaaata taattctaaa ttttgtaatg atttgaagaa tagtttttta      720
gattatggac atcttgctat gggaaatgat atggattttg gaggttattc aactaaggca      780
gaaaacaaaa ttcaagaagt ttttaaaggg gctcatgggg aataagtga acataaaatt       840 aaaaatttta gaaaaaaatg gtggaatgaa tttagagaga actttggga agctatgtta       900 tctgagcata aaataatat aaataattgt aaaaatattc cccaagaaga attacaaatt       960
actcaatgga taaagaatg gcatggagaa tttttgcttg aaagagataa tagatcaaaa      1020
ttgccaaaaa gtaaatgtaa aaataataca ttatatgaag catgtgagaa ggaatgtatt      1080
gatccatgta tgaaatatag agattggatt attagaagta aatttgaatg gcatacgtta      1140
tcgaaagaat atgaaactca aaaagttcca aggaaaatg cggaaaatta tttaatcaaa       1200
atttcagaaa acaagaatga tgctaaagta agtttattat tgaataattg tgatgctgaa      1260
tattcaaaat attgtgattg taaacatact actactctcg ttaaaagcgt tttaaatggt      1320
aacgacaata caattaagga aaagcgtgaa catattgatt tagatgattt ttctaaattt      1380
ggatgtgata aaaattccgt tgatacaaac acaaaggtgt gggaatgtaa aaaaccttat      1440
aaattatcca ctaaagatgt atgtgtacct ccgaggaggc aagaattatg tcttggaaac      1500
attgatagaa tatacgataa aaacctatta atgataaaag agcatattct tgctattgca      1560
atatatgaat caagaatatt gaaacgaaaa tataagaata aagatgataa agaagtttgt      1620
aaaatcataa ataaaacttt cgctgatata agagatatta taggaggtac tgattattgg      1680
aatgatttga gcaatagaaa attagtagga aaaattaaca caaattcaaa ttatgttcac      1740
aggaataaac aaaatgataa gcttttttcgt gatgagtggt ggaaagttat taaaaaagat      1800
gtatggaatg tgatatcatg ggtattcaag gataaaactg tttgtaaaga agatgatatt      1860
gaaaatatac cacaattctt cagatggttt agtgaatggg gtgatgatta ttgccaggat      1920
aaaacaaaaa tgatagagac tctgaaggtt gaatgcaaag aaaaaccttg tgaagatgac      1980
aattgtaaac gtaaatgtaa ttcatataaa gaatggatat caaaaaaaaa agaagagtat      2040
aataaacaag ccaaacaata ccaagaatat caaaaaggaa ataattacaa aatgtattct      2100
gaatttaaat ctataaaacc agaagtttat ttaaagaaat actcggaaaa atgttctaac      2160
ctaaatttcg aagatgaatt taaggaagaa ttacattcag attataaaaa taaatgtacg      2220
atgtgtccag aagtaaagga tgtaccaatt tctataataa gaataatga acaaacttcg       2280 caagaagcag ttcctgagga aagcactgaa atagcacaca gaacggaaac tcgtacggat      2340
gaacgaaaaa atcaggaacc agcaaataag gatttaaaga atccacaaca aagtgtagga      2400
gagaacggaa ctaaagattt attacaagaa gatttaggag gatcacgaag tgaagacgaa      2460
```

-continued

```
gtgacacaag aatttggagt aaatcatgga atacctaagg gtgaggatca aacgttagga      2520
aaatctgacg ccattccaaa cataggcgaa cccgaaacgg gaatttccac tacagaagaa      2580
agtagacatg aagaaggcca caataaacaa gcattgtcta cttcagtcga tgagcctgaa      2640
ttatctgata cacttcaatt gcatgaagat actaaagaaa atgataaact accccctagaa     2700 tcatctacaa tcacatctcc tacggaaagt ggaagttctg atacagagga aactccatct     2760
atctctgaag gaccaaaagg aaatgaacaa aaaaacgtg atgacgatag tttgagtaaa       2820
ataagtgtat caccagaaaa ttcaagacct gaaactgatg ctaaagatac ttctaacttg      2880
ttaaaattaa aaggagatgt tgatattagt atgcctaaag cagttattgg gagcagtcct      2940
aatgataata taaatgttac tgaacaaggg gataatattt ccggggtgaa ttctaaacct     3000
ttatctgatg atgtacgtcc agataaaaat catgaagagg tgaaagaaca tactagtaat     3060
tctgataatg ttcaacagtc tggaggaatt gttaatatga atgttgagaa agaactaaaa     3120
gatactttag aaaatccttc tagtagcttg gatgaaggaa aagcacatga agaattatca     3180
gaaccaaatc taagcagtga ccaagatatg tctaatacac ctggaccttt ggataacacc     3240
agtgaagaaa ctacagaaag aattagtaat aatgaatata aagttaacga gagggaaggt    3300
gagagaacgc ttactaagga atatgaagat attgttttga aaagtcatat gaatagaaa      3360 tcagacgatg gtgaattata tgacgaaaat tcagacttat ctactgtaaa tgatgaatca     3420
gaagacgctg aagcaaaaat gaaggaaat gatacatctg aaatgtcgca taatagtagt     3480
caacatattg agagtgatca acagaaaaac gatatgaaaa ctgttggtga tttgggaacc    3540
acacatgtac aaaacgaaat tagtgttcct gttacaggag aaattgatga aaattaagg     3600 gaaagtaaag aatcaaaaat tcataaggct gaagaggaaa gattaagtca tacagatata    3660
cataaaatta atcctgaaga tagaaatagt aatacattac atttaaaaga tataagaaat    3720
gaggaaaacg aaagacactt aactaatcaa acattaata ttagtcaaga aagggatttg      3780
caaaaacatg gattccatac catgaataat ctacatggag atggagtttc cgaaagaagt    3840
caaattaatc atagtcatca tggaaacaga caagatcggg ggggaaattc tgggaatgtt    3900
ttaaatatga gatctaataa taataatttt aataatattc caagtagata taatttatat   3960
gataaaaaat tagatttaga tctttatgaa aacagaaatg atagtacaac aaaagaatta    4020
ataaagaaat tagcagaaat aaataaatgt gagaacgaaa tttctgtaaa atattgtgac    4080
catatgattc atgaagaaat cccattaaaa acatgcacta agaaaaaac aagaaatctg     4140 tgttgtgcag tatcagatta ctgtatgagc tatttacat atgattcaga ggaatattat    4200
aattgtacga aagggaatt tgatgatcca tcttatacat gtttcagaaa ggaggctttt    4260
tcaagtatgc catattatgc aggagcaggt gtgttattta ttatattggt tatttttaggt    4320 gcttcacaag ccaaatatca aaggttagaa aaaataaata aaaataaat tgagaagaat    4380 gtaaattaa                                                             4389
```

<210> SEQ ID NO 24
<211> LENGTH: 4704
<212> TYPE: DNA
<213> ORGANISM: Plasmodium falciparum

<400> SEQUENCE: 24

```
atgaaaggga aaatgaatat gtgtttgttt ttttctatt ctatattata tgttgtatta        60
tgtacctatg tattaggtat aagtgaagag tatttgaagg aaaggcccca aggttttaaat   120 gttgagacta ataataataa taataataat aataataata atagtaatag taacgatgcg     180
```

```
atgtcttttg taaatgaagt aataaggttt atagaaaacg agaaggatga taaagaagat      240
aaaaaagtga agataatatc tagacctgtt gagaatacat acatagata tccagttagt      300 tcttttctga atatcaaaaa gtatggtagg aaagggaat atttgaatag aaatagtttt      360
gttcaaagat catatataag ggggttgtaaa ggaaaaagaa gcacacatac atggatatgt      420
gaaaataaag ggaataataa tatatgtatt cctgatagac gtgtacaatt atgtataaca      480
gctcttcaag atttaaaaaa ttcaggatct gaaacgactg atagaaaatt attaagagat      540
aaagtatttg attcagctat gtatgaaact gatttgttat ggaataaata tggttttcgt      600
ggatttgatg attttttgtga cgatgtaaaa aatagttatt tagattataa agatgttata      660
tttggaaccg atttagataa aaataatata tcaaagttag tagaggaatc attaaaacgt      720
ttttttaaaa aagatagtag tgtacttaat cctactgctt ggtggagaag gtatggaaca      780
agactatgga aaactatgat acagccatat gctcatttag gatgtagaaa acctgatgag      840
aatgaacctc agataaatag atggattctg gaatggggga aatataattg tagattaatg      900
aaggagaaag aaaaattgtt aacaggagaa tgttctgtta atagaaaaaa atctgactgc      960
tcaaccggat gtaataatga gtgttatacc tataggagtc ttattaatag acaaagatat     1020
gaggtctcta tattaggaaa aaaatatatt aaagtagtac gatatactat atttaggaga     1080
aaaatagttc aacctgataa tgctttggat tttttaaaat taaattgttc tgagtgtaag     1140
gatattgatt ttaaaccctt ttttgaattt gaatatggta aatatgaaga aaaatgtatg     1200
tgtcaatcat atattgattt aaaaatccaa tttaaaaata atgatatttg ttcatttaat     1260
gctcaaacag atactgtttc tagcgataaa agattttgtc ttgaaaagaa agaatttaaa     1320
ccatggaaat gtgataaaaa ttcttttgaa acagttcatc ataaaggtgt atgtgtgtca     1380
ccgagaagac aaggttttg tttaggaaat ttgaactatc tactgaatga tgatatttat     1440
aatgtacata attcacaact acttatcgaa attataatgg cttctaaaca agaaggaaag     1500
ttattatgga aaaaacatgg aacaatactt gataaccaga atgcatgcaa atatataaat     1560
gatagttatg ttgattataa agatatagtt attggaaatg atttatgaa tgataacaac     1620 tctataaaag ttcaaaataa tttaaattta atttttgaaa gaaattttgg ttataaagtt     1680
ggaagaaata aactctttaa aacaattaaa gaattaaaaa atgtatggtg gatattaaat     1740
agaaataaag tatgggaatc aatgagatgt ggaattgacg aagtagatca acgtagaaaa     1800
acttgtgaaa gaatagatga actagaaaac atgccacaat tctttagatg gttttcacaa     1860
tgggcacatt tcttttgtaa ggaaaaagaa tattgggaat taaaattaaa tgataaatgt     1920
acaggtaata atggaaaatc cttatgtcag gataaaacat gtcaaaatgt gtgtactaat     1980
atgaattatt ggacatatac tagaaaatta gcttatgaaa tacaatccgt aaaatatgat     2040
aaagatagaa aattatttag tcttgctaaa gacaaaaatg taactacatt tttaaaggaa     2100
aatgcaaaaa attgttctaa tatagatttt acaaaaatat tcgatcagct tgacaaactc     2160
tttaaggaaa gatgttcatg tatggataca caagttttag aagtaaaaaa caaagaaatg     2220
ttatctatag actcaaatag tgaagatgcg acagatataa gtgagaaaaa tggagaggaa     2280
gaattatatg taaatcacaa ttctgtgagt gtcgcaagtg gtaataaaga aatcgaaaag     2340
agtaaggatg aaaagcaacc tgaaaaagaa gcaaacaaa ctaatggaac tttaaccgta     2400
cgaactgaca aagattcaga tagaaacaaa ggaaaagata cagctactga tacaaaaaat     2460
tcacctgaaa atttaaaagt acaggaacat ggaacaaatg gagaaacaat aaaagaagaa     2520
```

```
ccaccaaaat tacctgaatc atctgaaaca ttacaatcac aagaacaatt agaagcagaa    2580
gcacaaaaac aaaaacaaga agaagaacca aaaaaaaaac aagaagaaga accaaaaaaa    2640
aaacaagaag aagaacaaaa acgagaacaa gaacaaaaac aagaacaaga agaagaagaa    2700 caaaacaag aagaagaaca acaaatacaa gatcaatcac aaagtggatt agatcaatcc    2760
tcaaaagtag gagtagcgag tgaacaaaat gaaatttctt caggacaaga acaaaacgta    2820
aaaagctctt cacctgaagt agttccacaa gaaacaacta gtgaaaatgg gtcatcacaa    2880
gacacaaaaa tatcaagtac tgaaccaaat gagaattctg ttgtagatag agcaacagat    2940
agtatgaatt tagatcctga aaaggttcat aatgaaaata tgagtgatcc aaatacaaat    3000
actgaaccag atgcatcttt aaaagatgat aagaaggaag ttgatgatgc caaaaaagaa    3060
cttcaatcta ctgtatcaag aattgaatct aatgaacagg acgttcaaag tacaccaccc    3120
gaagatactc ctactgttga aggaaaagta ggagataaag cagaaatgtt aacttctccg    3180
catgcgacag ataattctga gtcggaatca ggtttaaatc caactgatga cattaaaaca    3240
actgatggtg ttgttaaaga acaagaaata ttaggggag gtgaaagtgc aactgaaaca    3300
tcaaaaagta atttagaaaa acctaaggat gttgaacctt ctcatgaaat atctgaacct    3360
gttctttctg gtacaactgg taagaagaa tcagagttat aaaaagtaa atcgatagag    3420 acgaaggggg aaacagatcc tcgaagtaat gaccaagaag atgctactga cgatgttgta    3480
gaaaatagta gagatgataa taatagtctc tctaatagcg tagataatca aagtaatgtt    3540
ttaaatagag aagatcctat tgcttctgaa actgaagttg taagtgaacc tgaggattca    3600
agtaggataa tcactacaga agttccaagt actactgtaa accccctga tgaaaacga    3660 tctgaagaag taggagaaaa agaagctaaa gaaattaaag tagaacctgt tgtaccaaga    3720
gccattggag aaccaatgga aaattctgtg agcgtacagt cccctcctaa tgtagaagat    3780
gttgaaaaag aaacattgat atctgagaat aatggattac ataatgatac acacagagga    3840
aatatcagtg aaaaggattt aatcgatatt catttgttaa gaaatgaagc gggtagtaca    3900
atattagatg attctagaag aaatggagaa atgacagaag gtagcgaaag tgatgttgga    3960
gaattacaag aacataattt tagcacacaa caaaaagatg aaaaagattt tgaccaaatt    4020
gcgagcgata gagaaaaaga agaaattcaa aaattactta atataggaca tgaagaggat    4080
gaagatgtat taaaaatgga tagaacgagg atagtatga gtgatggagt taatagtcat    4140
ttgtattata ataatctatc aagtgaagaa aaaatggaac aatataataa tagagatgct    4200
tctaaagata gagaagaaat attgaatagg tcaaacacaa atacatgttc taatgaacat    4260
tcattaaaat attgtcaata tatggaaaga aataaggatt tattagaaac atgttctgaa    4320
gacaaaaggt tacatttatg ttgtgaaata tcagattatt gtttaaaatt tttcaatcct    4380
aaatcgatag aatactttga ttgtacacaa aaagaatttg atgaccctac atataattgt    4440
tttagaaaac aaagatttac aagtatgcat tatattgccg ggggtggtat aatagccctt    4500
ttattgttta ttttaggttc agccagctat aggaagaatt tggatgatga aaaaggattc    4560
tacgattcta atttaaatga ttctgctttt gaatataata ataataaata taataaatta    4620
ccttatatgt ttgatcaaca aataaatgta gtaaattctg atttatattc ggagggtatt    4680
tatgatgaca caacgacatt ttaa                                           4704
```

<210> SEQ ID NO 25
<211> LENGTH: 3633
<212> TYPE: DNA
<213> ORGANISM: Plasmodium falciparum

<400> SEQUENCE: 25

```
atgaaaggat attttaatat atatttttta attcctttaa ttttttttata taatgtaata      60
agaataaatg aatcaattat aggtagaaca ctttataata gacaagatga atcatcagat     120
atttcaaggg taaattcacc cgaattaaat aataatcata aaactaatat atatgattca     180
gattacgaag atgtaaataa taaattaata aacagttttg tagaaaataa aagtgtgaaa     240
aaaaaaaggt ctttaagttt tataaataat aaaacaaaat catatgatat aattccacct     300
tcatattcat ataggaatga taaatttaat tcactttccg aaaatgaaga taattctgga     360
aatacaaata gtaataattt cgcaaatact tctgaaatat ctattggaaa ggataataaa     420
caatatacgt ttatacagaa acgtactcat ttgtttgctt gtggaataaa aagaaaatca     480
ataaaatgga tatgtcgaga aaacagtgag aaaattactg tatgtgttcc tgatagaaaa     540
atacaactat gtattgcaaa tttttaaac tcacgtttag aaacaatgga aaagtttaaa     600
gaaatatttt taatttctgt taatacagaa gcaaaattat tatataacaa aaatgaagga     660
aaagatccct caatattttg taatgaatta agaaatagtt tttcagatt tagaaattca       720
tttataggtg atgatatgga ttttggtggt aatacagata gagtcaaagg atatattaat     780
aagaagttct ccgattatta taaggaaaaa aatgttgaaa aattaaataa tatcaaaaaa     840
gaatggtggg aaaaaaataa agcaaatttg tggaatcaca tgatagtaaa tcataaagga     900
aacataagta agaatgtgc cataattccc gcggaagaac ctcaaattaa tctatggata       960
aaagaatgga atgaaaactt cttgatggaa aagaagagat tgttttttaaa tataaaagat   1020
aagtgtgttg aaaacaaaaa atatgaagca tgttttggtg gatgtaggct tccatgttct    1080
tcatatacat catttatgaa aaaagtaaa acacaaatgg aggttttgac gaacttgtat      1140
aaaagaaaa attcaggagt ggataaaaat aattttctga atgatctttt taaaaaaaat      1200
aataaaaatg atttagatga ttttttcaaa aatgaaaagg aatatgatga tttatgtgat    1260
tgcagatata ctgctactat tattaaaagt tttctaaatg gtcctgctaa aaatgatgta    1320
gatattgcat cacaaattaa tgttaatgat cttcgagggt ttggatgtaa ttataaaagt    1380
aataatgaaa aagttggaa ttgtactgga acatttacga acaaatttcc tggtacatgt      1440
gaaccccca gaagacaaac tttatgtctt ggacgtacat atcttttaca tcgtggtcat      1500
gaggaagatt ataggaaca tttacttgga gcttcaatat gaggcgca attattaaaa        1560
tataaatata aggaaaagga tgaaatgca ttgtgtagta taatacaaaa tagttatgca      1620
gatttggcag atattatcaa gggatcggat ataataaaag attattatgg taaaaaaatg    1680
gaagaaaatt taaataaagt aaacaaagat aaaaaacgta atgaagaatc tttgaagatt    1740
tttcgtgaaa atggtggga tgaaacaag gagaatgtat ggaaagtaat gtcagcagta      1800
cttaaaaata aggaaacgtg taaagattat gataagtttc aaaagattcc tcaattttta    1860
agatggttta aggaatgggg agacgatttt tgtgagaaaa gaaagagaa atatattca        1920
tttgagtcat ttaaggtaga atgtaagaaa aaagattgtg atgaaaatac atgtaaaaat    1980
aaatgtagtg aatataaaaa atggatagat ttgaaaaaaa gtgaatatga gaaacaagtt    2040
gataaataca caaagataa aaataaaaag atgtatgata atattgatga agtaaaaaat    2100
aaagaagcca atgtttactt aaaagaaaaa tccaaagaat gtaaagatgt aaatttcgat    2160
gataaaattt ttaatgagag tccaaatgaa tatgaagata tgtgtaaaaa atgtgatgaa    2220
ataaaatatt taaatgaaat taaatatcct aaaacaaaac acgatatata tgatatagat    2280
```

```
acattttcag atacttttgg tgatggaacg ccaataagta ttaatgcaaa tataaatgaa    2340
caacaaagtg ggaaggatac ctcaaatact ggaaatagtg aaacatcaga ttcaccggtt    2400
agtcatgaac cagaaagtga tgctgcaatt aatgtagaaa agttaagtgg tgatgaaagt    2460
tcaagtgaaa caagaggaat attagatatt aatgatccaa gtgttacgaa caatgtcaat    2520
gaagttcatg atgcttcaaa tacacaaggt agtgtttcaa atacttctga tataacgaat    2580
ggacattcgg aaagttccct gaatagaaca acgaatgcac aagatattaa ataggccgt    2640 tcaggaaatg aacaaagtga taatcaagaa atagttcac attctagtga taattcaggt    2700
tctttgacaa tcggacaagt tccttcagag ataatacccc aaaatacata tgattcacaa    2760
aaccctcata gagatacacc taatgcatta gcatctttac catcagatga taaaattaat    2820
gaaatagagg gtttcgattc tagtagagat agtgaaaatg gtaggggtga tacaacatca    2880
aatactcatg atgtacgtcg tacgaatata gtaagtgaga gacgtgtgaa tagccatgat    2940
tttattagaa acggaatggc gaataacaat gcacatcatc aatatataac gcaaattgag    3000
aataatggaa tcataagagg acaagaggaa agtgcgggga atagtgttaa ttataaagat    3060
aatccaaaga ggagtaatttt ttcctccgaa aatgatcata agaaaaatat acaggaatat    3120
aattctagag atactaaaag agtaagggag gaaataatta aattatcgaa gcaaaataaa    3180
tgcaacaatg aatattccat ggaatattgt acctattctg acgaaaggaa tagttcaccg    3240
ggtccttgtt ctagagaaga aagaaagaaa ttatgttgtc agatttcaga ttattgttta    3300
aaatatttta acttttattc aattgaatat tataattgta taaaatctga aattaaaagt    3360
ccagaatata aatgttttaa aagcgagggt caatcaagca ttccttattt tgctgctgga    3420 ggtatttag ttgtaatagt cttacttttg agttcagcat ctagaatggg gaaaagtaat    3480
gaagaatatg atataggaga atctaatata gaagcaactt tgaagaaaaa taattattta    3540 aataaaactat cgcgcatatt taatcaagaa gtacaagaga caaacatttc agattattcc    3600
gagtacaatt ataatgaaaa gaatatgtat taa                                 3633
```

<210> SEQ ID NO 26
<211> LENGTH: 9393
<212> TYPE: DNA
<213> ORGANISM: Plasmodium falciparum

<400> SEQUENCE: 26

```
atgaagacca cactattttg tagcatatct ttttgtaata ttatattttt cttcttagaa      60
ttaagtcatg agcattttgt tggacaatca gtaatacccc atggagcatc ttcagttact    120
gattttaatt ttagtgagga gaaaaattta aaaagttttg aagggaagaa taataataat    180
gataattatg cttcaattaa tcgtttatat aggaagaaac catatatgaa gagatcgctt    240
ataaatttag aaaatgatct ttttagatta gaacctatat cttatattca aagatattat    300
aagaagaata taaacagatc tgatattttt cataataaaa aagaaagagg ttccaaagta    360
tattcaaatg tgtcttcatt ccattctttt attcaagagg gtaaagaaga agttgaggtt    420
ttttctatat ggggtagtaa tagcgtttta gatcatatag atgttcttag ggataatgga    480
actgtcgttt tttctgttca accatattac cttgatatat atacgtgtaa agaagccata    540
ttatttacta catcatttta caaggatctt gataaaagtt caattacaaa attaatgaa    600 gatattgaaa atttaacgaa agaaataatc aagaatgaag aacaatgttt agttggtggg    660
aaaacagatt ttgataattt acttatagtt ttagaaaatg cggaaaaagc aaatgttaga    720 aaacattat ttgataatac atttaatgat tataaaaata agaaatctag ttttttacaat    780
```

```
tgtttgaaaa ataaaaaaaa tgattatgat aagaaaataa agaatataaa gaatgagatt    840
acaaaattgt taaaaatat tgaaagtaca ggaaatatgt gtaaacgga atcatatgtt      900 atgaataata atttatatct attaagagtg aatgaagtta aaagtacacc tattgattta    960
tacttaaatc gagcaaaaga gctattagaa tcaagtagca aattagttaa tcctataaaa    1020
atgaaattag gtgataataa gaacatgtac tctattggat atatacatga cgaaattaaa    1080
gatattataa aaagatataa ttttcatttg aaacatatag aaaaaggaaa agaatatata    1140
aaaaggataa cacaagcaaa taatattgca gacaaaatga agaaagatga acttataaaa    1200 aaaattttg aatcctcaaa acattttgct agttttaaat atagcaatga aatgataagc    1260
aaattagatt cgttatttat aaaaaatgaa gaaatactta ataatttatt caataatata    1320
tttaatatat tcaagaaaaa atatgaaaca tatgtagata tgaaaacaat tgaatctaaa    1380
tatacaacag taatgactct atcagaacat ttattagaat atgcaatgga tgttttaaaa    1440
gctaaccctc aaaaacctat tgatccaaaa gcaaatctgg attcagaagt agtaaaatta    1500
caaataaaaa taaatgagaa atcaaatgaa ttagataatg ctataagtca agtaaaaaca    1560
ctaataataa taatgaaatc attttatgat attattatat ctgaaaaagc ctctatggat    1620
gaaatggaaa aaaaggaatt atccttaaat aattatattg aaaaaacaga ttatatatta    1680
caaacgtata atattttaa gtctaaaagt aatattataa ataataatag taaaaatatt    1740
agttctaaat atataactat agaagggtta aaaaatgata ttgatgaatt aaatagtctt    1800
atatcatatt ttaaggattc acaagaaaca ttaataaaag atgatgaatt aaaaaaaaac    1860
atgaaaacgg attatcttaa taacgtgaaa tatatagaag aaaatgttac tcatataaat    1920
gaaattatat tattaaaaga ttctataact caacgaatag cagatattga tgaattaaat    1980
agtttaaatt taataaatat aaatgatttt ataaatgaaa agaatatatc acaagagaaa    2040
gtatcatata atcttaataa attatataaa ggaagttttg aagaattaga atctgaacta    2100
tctcattttt tagacacaaa atatttgttt catgaaaaaa aaagtgtaaa tgaacttcaa    2160 acaatttaa atacatcaaa taatgaatgt gctaaattaa attttatgaa atctgataat    2220
aataataata ataataatag taatataatt aacttgttaa aaactgaatt aagtcatcta    2280
ttaagtctta aagaaaatat aataaaaaaa cttttaaatc atatagaaca aaatattcaa    2340
aactcatcaa ataagtatac tattacatat actgatatta ataatagaat ggaagattat    2400
aaagaagaaa tcgaaagttt agaagtatat aaacatacca ttggaaatat acaaaaagaa    2460
tatatattac atttatatga gaatgataaa aatgctttag ctgtacataa tacatcaatg    2520
caaatattac aatataaaga tgctatacaa aatataaaaa ataaaatttc tgatgatata    2580
aaaattttaa agaaatataa agaaatgaat caagatttat taaattatta tgaaattcta    2640
gataaaaaat taaagataaa tacatatatc aaagaaatgc atactgcttc tttagttcaa    2700
ataactcaat atattcctta tgaagataaa acaataagtg aacttgagca agaatttaat    2760
aataataatc aaaaacttga taatatatta caagatatca atgcaatgaa tttaaatata    2820
aatattctcc aaaaccttaaa tattggtata aatgcatgta atacaaataa taaaaatgta    2880
gaacacttac ttaacaagaa aattgaatta aaaaaatatat taaatgatca aatgaaaatt    2940
ataaaaaatg atgatataat tcaagataat gaaaagaaa actttcaaa tgttttaaaa    3000 aaagaagagg aaaaattaga aaagaatta atgatgatatca aatttaataa tttgaaaatg    3060
gacattcata aattgttgaa ttcgtatgac catacaaagc aaaatataga aagcaatctt    3120
```

```
aaaataaatt tagattctttc gaaaaggaa aaagatagtt gggttcattt taaaagtact    3180
atagatagtt tatatgtgga atataacata tgtaatcaaa agactcataa tactatcaaa    3240
caacaaaaaa atgatatcat agaacttatt tataaacgta taaagatat  aaatcaagaa    3300
ataatcgaaa aggtagataa ttattattcc ctgtcagata aagccttaac taaacttaaa    3360
tctattcatt ttaatattga taaggaaaaa tataaaaatc ccaaaagtca agaaaatatt    3420
aaattattag aagatagagt tatgatactt gagaaaaaga ttaaggaaga taaagatgct    3480
ttaatacaaa ttaagaattt atcacatgat cattttgtaa atgctgataa tgagaaaaaa    3540
aagcagaagg agaaggagga ggacgacgaa caaacacact atagtaaaaa aagaaaagta    3600
atgggagata tatataagga tattaaaaaa aacctagatg agttaaataa taaaaatttg    3660
atagatatta ctttaaatga agcaaataaa atagaatcag aatatgaaaa aatattaatt    3720
gatgatattt gtgaacaaat tacaaatgaa gcaaaaaaaa gtgatactat taaggaaaaa    3780
atcgaatcat ataaaaaaga tattgattat gtagatgtgg acgtttccaa aacgaggaac    3840
gatcatcatt tgaatggaga taaaatacat gattctttt  tttatgaaga tacattaaat    3900
tataaagcat atttttgataa attaaaagat ttatatgaaa atataaacaa gttaacaaat    3960
gaatcaaatg gattaaaaag tgatgctcat aataacaaca cacaagttga taaactaaaa    4020
gaaattaatt tacaagtatt cagcaatttta ggaaatataa ttaaatatgt tgaaaaactt    4080
gagaatacat tacatgaact taaagatatg tacgaatttc tagaaacgat cgatattaat    4140
aaaatattaa aaagtattca taatagcatg aagaaatcag aagaatatag taatgaaacg    4200
aaaaaaatat ttgaacaatc agtaaatata actaatcaat ttatagaaga tgttgaaata    4260
ttgaaaacgt ctattaaccc aaactatgaa agcttaaatg atgatcaaat tgatgataat    4320
ataaaatcac ttgttctaaa gaaagaggaa atatccgaaa aaagaaaaca agtgaataaa    4380
tacataacag atattgaatc taataaagaa caatcagatt tacatttacg atatgcatct    4440
agaagtatat atgttattga tcttttttata aaacatgaaa taataaatcc tagcgatgga    4500
aaaaattttg atattataaa ggttaaagaa atgataaata aaaccaaaca agtttcaaat    4560
gaagctatgg aatatgctaa taaaatggat gaaaaaaata aggacattat aaaaatagaa    4620
aatgaacttt ataatttaat taataataac atccgttcat taaaggggt  aaaatatgaa    4680
aaagttagga aacaagcaag aaatgcaatt gatgatataa ataatataca ttctaatatt    4740
aaaacgattt taaccaaatc taaagaacga ttagatgaga ttaagaaaca acctaacatt    4800
aaaagagaag gtgatgtttt aaataatgat aaaaccaaaa tagcttatat tacaatacaa    4860
ataaataacg gaagaataga atctaatttta ttaaatatat taaatatgaa acataacata    4920
gatactatct tgaataaagc tatggattat atgaatgatg tatcaaaatc tgaccagatt    4980
gttattaata tagattcttt gaatatgaac gatatatata ataaggataa agatcttta   5040
ataaatattt taaagaaaaa acagaatatg gaggcagaat ataaaaaat gaatgaaatg    5100
tataattacg ttaatgaaac agaaaaagaa ataataaaac ataaaaaaaa ttatgaaata    5160
agaattatgg aacatataaa aaagaaaca  aatgaaaaaa aaaaaaaatt tatggaatct    5220
aataacaaat cattaactac tttaatggat tcattcagat ctatgttttta taatgaatat    5280
ataaatgatt ataatataaa tgaaatttt  gaaaacatc  aaaatatatt gaatgaaata    5340
tataatggat ttaatgaatc atataatatt attaatacaa aaatgactga attataaat    5400
gataatttag attataatga aataaaagaa attaagaag  tagcacaaac agaatatgat    5460
aaacttaata aaaagttga  tgaattaaaa aattatttga ataatattaa agaacaagaa    5520
```

```
ggacatcgat taattgatta tataaaagaa aaatatttta acttatatat aaaatgttca   5580
gaacaacaaa atataataga tgattcttat aattatatta cagttaaaaa acagtatatt   5640
aaaactattg aagatgtgaa attttatta gattcattga acacaataga agaaaaaaat    5700
aaatcagtag caaatctaga aatttgtact aataaagaag atataaaaaa tttacttaaa   5760
catgttataa agttggcaaa ttttcaggt attattgtaa tgtctgatac aaatacggaa    5820
ataactccag aaaatccttt agaagataat gatttattaa atttacaatt atattttgaa   5880
agaaaacatg aaataacatc aacattggaa aatgattctg atttagagtt agatcattta   5940
ggtagtaatt cggatgaatc tatagataat ttaaaggttt ataatgatat tatagaatta   6000
cacacatatt caacacaaat tcttaaatat ttagataata ttcaaaaact taaaggagat   6060
tgcaatgatt tagtaaagga ttgtaaagaa ttacgtgaat tgtctacggc attatatgat   6120
ttaaaaatac aaattactag tgtaattaat agagaaaatg atatttcaaa taatattgat   6180
attgtatcta ataaattaaa tgaaatagat gctatacaat ataattttga aaaatataaa   6240 gaaattttg ataatgtaga agaatataaa acattagatg atacaaaaaa tgcatatatt    6300
gtaaaaaagg ctgaaatttt aaaaaatgta gatataaata aaacaaaaga gatttagat    6360 atatatttta atgacttaga cgaattagaa aaatctctta cattatcatc taatgaaatg   6420
gaaattaaaa caatagtaca gaactcatat aattcctttt ctgatattaa taagaacatt   6480
aatgatattg ataaagaaat gaaacactg atccctatgc ttgatgaatt attaaatgaa    6540
ggacataata ttgatatatc attatataat tttataatta gaaatattca gattaaaata   6600
ggtaatgata taaaaatat aagagaacag gaaaatgata ctaatatatg ttttgagtat    6660
attcaaaata attataattt tataaagagt gatataagta tcttcaataa atatgatgat   6720
catataaaag tagataatta tatatctaat aatattgatg ttgtcaataa acataatagt   6780
ttattaagtg aacatgttat aaatgctaca aatatatag agaatattat gacaagtatt    6840
gtcgaaataa atgaagatac agaaatgaat tctttagaag agacacaaga caaattatta   6900
gaactatatg aaaattttaa gaagaaaaa aatattataa ataataatta taaaatagta    6960
cattttaata aattaaaaga aatagaaaat agtttagaga catataattc aatatcaaca   7020
aactttaata aaataaatga aacacaaaat atagatattt taaaaaatga atttaataat   7080
atcaaaacaa aaattaatga taaagtaaaa gaattagttc atgttgatag tacattaaca   7140
cttgaatcaa ttcaaacgtt taataattta tatggtgact tgatgtctaa tatacaagat   7200
gtatataaat atgaagatat taataatgtt gaattgaaaa aggtgaaatt atatatagaa   7260
aatattacaa atttattagg aagaataaac acattcataa aggagttaga caaatatcag   7320
gatgaaaata atggtataga taagtatata gaaatcaata aggaaaataa tagttatata   7380
ataaaattga agaaaaagc caataatcta aaggaaaatt tctcaaaatt attacaaaat   7440 ataaaagaa atgaaactga attatataat ataaataaca taaggatga tattatgaat     7500 acggggaaat ctgtaaataa tataaaacaa aaattttcta gtaatttgcc actaaaagaa   7560
aaattatttc aaatggaaga gatgttactt aatataaata atattatgaa tgaaacgaaa   7620
agaatatcaa acacggctgc atatactaat ataactctcc aggatattga aaataataaa   7680
aataaagaaa ataataatat gaatattgaa acaattgata aattaataga tcatataaaa   7740
atacataatg aaaaaataca agcagaaata ttaataattg atgatgccaa aagaaaagta   7800
aaggaaataa cagataatat taacaaggct tttaatgaaa ttacagaaaa ttataataat   7860
```

| | |
|---|---|
| gaaaataatg gggtaattaa atctgcaaaa aatattgtcg atgaagctac ttatttaaat | 7920 |
| aatgaattag ataaattttt attgaaattg aatgaattat taagtcataa taataatgat | 7980 |
| ataaaggatc ttggtgatga aaaattaata ttaaagaag aagaagaaag aaaagaaaga | 8040 |
| gaaagattgg aaaagcgaa acaagaagaa gaaagaaaag agagaaaag aatagaaaaa | 8100 |
| gaaaacaag agaaagaaag actggaaaga gagaaacaag aacaactaaa aaaagaagaa | 8160 |
| gaattaagaa aaaagagca ggaaagacaa gaacaacaac aaaaagaaga agcattaaaa | 8220 |
| agacaagaac aagaacgact acaaaaagaa gaagaattaa aaagacaaga gcaagaaagg | 8280 |
| ctggaaagag agaaacaaga acaactacaa aaagaagaag aattaaaaag acaagaacaa | 8340 |
| gaacgactac aaaaagaaga agcattaaaa agacaagaac aagaacgact acaaaaagaa | 8400 |
| gaagaattaa aaagacaaga gcaagaaagg ctggaaagag agaaacaaga acaactacaa | 8460 |
| aaagaagaag aattaaaaag acaagaacaa gaacgactac aaaaagaaga agcattaaaa | 8520 |
| agacaagaac aagaacgact acaaaaagaa gaagaattaa aaagacaaga gcaagaaaga | 8580 |
| ctggaaagaa agaaaatcga gttagcagaa agagaacaac acataaaaag taaactagaa | 8640 |
| tctgatatgg tgaaaataat aaaggatgaa ctaacaaaag aaaaagatga ataataaaa | 8700 |
| aacaaagata taaaacttag acatagtttg aacagaaat ggttaaaaca tttacaaaat | 8760 |
| atattatcgt taaaaataga tagtctatta aataaaaatg atgaggtcat aaaagataat | 8820 |
| gagacacaat tgaaaacaaa tatattgaac tcattaaaaa atcaattata tcttaatttg | 8880 |
| aaacgtgaac ttaatgaaat tataaaggaa tacgaagaaa accagaaaaa aatattgcat | 8940 |
| tcaaatcaac ttgttaacga tagtttagag caaaaaacta atagactcgt cgatattaaa | 9000 |
| cctacaaagc atggtgatat atatactaat aaactttctg ataatgaaac tgaaatgctg | 9060 |
| ataacatcta agaaaaaaa agatgaaaca gaatcaacta aaagatcagg aacagatcat | 9120 |
| actaatagtt cggaaagtac tactgatgat aataccaatg atagaaattt ttctcgatca | 9180 |
| aagaatttga gtgttgctat atacacagca ggaagtgtag ctttatgtgt gttaatattt | 9240 |
| tctagtatag gattattact tataaagact aatagtggag ataacaattc taatgaaatt | 9300 |
| aatgaagctt tgaaccgaa tgatgatgtt ctctttaagg agaaggatga aatcattgaa | 9360 |
| atcactttta atgataatga tagtacaatt taa | 9393 |

<210> SEQ ID NO 27
<211> LENGTH: 8916
<212> TYPE: DNA
<213> ORGANISM: Plasmodium falciparum

<400> SEQUENCE: 27

| | |
|---|---|
| atgcaaaggt ggattttctg caacattgtt ttgcatatat taatttactt agcagaattt | 60 |
| agccatgaac aggaaagtta ttcttccaat gaaaaaataa gaaaggacta ttcagatgat | 120 |
| aataattatg aacctacccc ttcatatgaa aaagaaaaa agaatatgg aaaagatgaa | 180 |
| agttatataa aaaattacag aggtaataat ttttcctatg atttgtctaa aaattctagt | 240 |
| atatttcttc acatgggtaa cggtagtaac tcgaaaacac taaaagatg taacaagaaa | 300 |
| aaaaatataa agaccaattt tttaagacct atcgaggaag agaaaacggt attaaataat | 360 |
| tatgtatata aggtgtaaa ttttttagat acaataaaaa gaatgattc ctcttataaa | 420 |
| tttgatgttt ataagagatac ttccttttta aaaatagag aatataaga attaattact | 480 |
| atgcagtatg attatgctta tttagaagca acaaagagg ttctttattt aattccgaag | 540 |
| gataaagatt atcacaaatt ttataaaaat gaacttgaga aaattctttt caatttaaaa | 600 |

```
gattcactta aattattaag agaaggatat atacaaagca aactggaaat gattagaatc      660
cattcggata tagatatatt aaatgagttt catcaaggaa atattataaa cgataattat      720
tttaataatg aaataaaaaa aaaaaaggaa gacatggaaa atatataag agaatataat      780 ttatacatat ataaatatga aaatcagctt aaaataaaaa tacagaaatt aacaaatgaa      840
gtttctataa atttaaataa atctacatgt gaaaagaatt gttataatta tattttaaaa      900
ttagaaaaat ataaaaatat aataaaagat aagataaata aatggaaaga tttaccagaa      960
atatatattg atgataaaag tttctcatat acatttttaa aagatgtaat aaataataag     1020
atagatatat ataaaacaat aagttctttt atatctactc agaaacaatt atattatttt     1080
gaatatatat ataatgaa taaaaataca ttaaacctac tttcatataa tatacaaaaa       1140
acagatataa attctagtag taaatacaca tatacaaaat ctcatttttt aaagataat     1200 catatattgt tatctaaata ttatactgcc aaatttattg atatcctaaa taaaacatat     1260
tattataatt tatataaaaa taaaattctt ttattcaata aatatattat aaagcttaga    1320
aacgatttaa aagaatatgc atttaaatct atacaattta ttcaagataa aatcaaaaaa    1380
cataaagatg aattatccat agaaaatata ttacaagaag ttaataatat atatataaaa    1440
tatgatactt cgataaatga aatatctaaa tataacaatt taattattaa tactgattta    1500
caaatagtac aacaaaaact tttagaaatc aaacaaaaaa aaaatgatat tacacacaaa    1560
gtacaactta taaatcatat atataaaaat atacatgatg aaatattaaa caaaaaaaat    1620
aatgaaataa caaagattat tataaataat ataaagatc ataaaaaaga tttacaagat    1680
ctcttactat ttatacaaca aatcaaacaa tataatatat taacagatca taaaattaca    1740
caatgtaata attattataa ggaaatcata aaaatgaaag aagatataaa tcatattcat    1800
atatatatac aaccaattct aaataattta cacacattaa aacaagtaca aaataataaa    1860
atcaaatatg aagagcacat caaacaaata ttacaaaaaa tttatgataa aaaggaatct    1920
ttaaaaaaaa ttattctctt aaaagatgaa gcacaattag acattaccct cctcgatgac    1980
ttaatacaaa agcaaacaaa aaaacaaaca caaacacaaa cacaaacaca aaacaaaca     2040 ctaatacaaa ataatgagac gattcaactt atttctggac aagaagataa acatgaatcc    2100 aatccatttta atcatataca aacctatatt caacaaaaag atacacaaaa taaaaacatc    2160
caaaatcttc ttaaatcctt gtataatgga aatattaaca cattcataga cacaatttct    2220
aaatatatat taaaacaaaa agatatagaa ttaacacaac acgtttatac agacgaaaaa    2280
attaatgatt atcttgaaga aataaaaaat gaacaaaaca aaatagataa gaccatcgac    2340
gatataaaaa tacaagaaac attaaaacaa ataactcata ttgttaacaa tataaaaacc    2400
atcaaaaagg atttgctcaa agaatttatt caacatttaa taaaatatat gaacgaaaga    2460
tatcagaata tgcaacaggg ttataataat ttaacaaatt atattaatca atatgaagaa    2520
gaaaataata atatgaaaca atatattact accatacgaa atatccaaaa aatatatatt    2580
gataatatat atgctaagga aaaggaaatt cgctcgggac aatattataa ggattttatc    2640
acatcaagga aaaatattta taatataagg gaaaatatat ccaaaaatgt agatatgata    2700
aaaaatgaag aaaagaagaa aatacagaat tgtgtagata aatataattc tataaaacaa    2760
tatgtaaaaa tgcttaaaaa tggagacaca caagatgaaa ataataataa taataatgat    2820
atatacgaca agttaattgt ccccccttgat tcaataaaac aaaatatcga taaatacaac    2880
acagaacata attttataac atttacaaat aaaataaata cacataataa gaagaaccaa    2940
```

```
gaaatgatgg aagaattcat atatgcatat aaaaggttaa aaattttaaa aatattaaat    3000
atatccttaa aagcttgtga aaaaaataat aaatctatca atacattaaa tgacaaaaca    3060
caagaattaa aaaaaattgt aacacacgaa atagatcttc tacaaaaaga tattttaaca    3120
agtcaaatat caaataaaaa tgttttatta ttaaacgatt tattaaaaga aattgaacaa    3180
tatattatag atgtacacaa attaaaaaaa aaatcaaacg atctatttac atattatgaa    3240
caatccaaaa attatttcta ttttaaaaac aaaaagata attttgatat acaaaaaaca    3300
atcaataaaa tgaatgaatg gctagctatc aaaaattata taaatgaaat taataaaaat    3360
tatcaaacat tatatgaaaa aaaaataaat gtactcctac ataattcaaa aagttatgta    3420
caatactttt atgatcatat aataaatcta attcttcaaa aaaaaaatta tttggaaaat    3480
acttttaaga caaaaataca agataacgaa cattcactat atgctttaca acaaaatgaa    3540
gaataccaaa aggtaaagaa cgaaaggat caaaacgaaa ttaagaaaat taaacaatta    3600
atcgaaaaaa ataaaaatga tatacttaca tatgaaaaca acattgaaca aattgaacaa    3660
aaaaatattg agttaaaaac aaatgctcaa aataaggatg atcaaatagt aaatacctta    3720
aatgaggtta agaaaaaaat aatatataca tatgaaaagg tagataatca aatatcgaac    3780
gttttaaaaa attatgaaga aggaaaagta gaatatgata aaaatgttgt acaaaatgtt    3840
aacgatgcgg atgatacaaa cgatattgat gaaataaacg atattgatga aataaacgat    3900
attgatgaaa taacgatat tgatgaaata acgatattg atgaaataaa agacattgac    3960
catataaaac attttgacga tacaaaacat tttgacgata tataccatgc tgatgataca    4020
cgtgatgaat accatatagc cctttcaaat tatataaaga cagaactaag aaatataaac    4080
ctgcaagaaa taaaaaacaa tataataaaa atatttaaag aattcaaatc tgcacacaaa    4140
gaaattaaaa aagaatcaga acaaattaat aaagaattta ccaaaatgga tgtcgtcata    4200
aatcaattaa gagatataga cagacaaatg cttgatcttt ataaagaatt agatgaaaaa    4260
tattctgaat ttaataaaac aaaaattgaa gaaataaata atataaggga aaatattaat    4320
aatgtggaaa tatggtatga aaaaaatata attgaatatt tcttacgtca tatgaatgat    4380
caaaaagata aagctgcaaa atatatgaaa aacattgata catataaaaa taatattgaa    4440
attattagta aacaaataaa tccagaaaat tatgttgaaa cattaaacaa atcaaatatg    4500
tattcttatg tagaaaaggc taatgatcta ttttataaac aaataaataa tataatcata    4560
aattcaaatc aactaaaaaa cgaagctttt acaatagatg aattacaaaa tattcaaaaa    4620
aacagaaaaa atcttcttac aaagaaacaa caaattattc agtatacaaa tgaaatagaa    4680
aatatattta atgaaattaa aaatattaat aacatattag tcttaacaaa ttataaatct    4740
atccttcaag atatatcaca aaatataaat catgttagta tatatacgga acaattcat    4800 aatttatata taaaattaga agaagaaaaa gaacaaatga aaacactcta tcataaatca    4860
aatgtgttac ataaccaaat taattttaat gaagatgctt ttattaataa tttattaatt    4920
aatatagaaa aaattaaaaa tgatattaca catataaagg aaaaaacaaa tatatatatg    4980
atagatgtaa acaaatctaa aaataatgct caactatatt ttcataatac actaagaggt    5040
aatgaaaaaa tagaatattt aaaaaatctt aagaattcaa caaaccaaca aataacttta    5100
caagaattaa aacaagtaca agaaaatgtt gagaaggtaa aagatatata caatcaaact    5160
ataaaatatg aagaagaaat taaaaaaaat tatcatatta taacagatta tgagaataaa    5220
ataaatgata ttttacataa ttcatttatt aaacaaataa atatggaatc tagcaataat    5280
aaaaaacaaa caaacaaat tatagacata ataaacgata aacatttga agaacatata    5340
```

```
aaaacatcca aaaccaaaat aaacatgcta aaagaacaat cacaaatgaa acatatagac    5400
aaaactttat taaatgaaca agcactcaaa ttatttgtag atattaattc tactaataat    5460
aatttagata atatgttatc tgaaataaat tctatacaaa ataatataca tacatatatc    5520
caagaagcaa acaaatcatt tgacaaattt aaaattatat gtgatcaaaa tgtaaacgat    5580
ttattaaaca aattaagttt aggagatcta aattatatga atcatttaaa aaatctgcaa    5640
aacgaaataa gaaacatgaa tctagaaaaa aatttcatgt tagataaaag taaaaaaata    5700
gatgaggaag aaaaaaaatt agatatatta aaagttaaca tatcaaatat aaataattct    5760
ttagataaat taaaaaaata ttacgaagaa gcgctctttc aaaaggttaa agaaaaagca    5820
gaaattcaaa aggaaaatat agaaaaaata aaacaagaaa taaatacact gagcgatgtt    5880
tttaagaaac catttttttt tatacaactt aatacagatt catcacaaca tgaaaaagat    5940
ataaacaata atgtagaaac atataaaaat aatatagatg aaatatataa tgttttttata   6000 caatcatata atttaataca aaaatattct tcagaaattt tttcatccac cttgaattat    6060
atacaaacaa aagaaataaa agaaaaatcc ataaggaaac aaaaccaatt aaatcaaaat    6120
gaaaaggaag catctgtttt attaaaaaat ataaaaataa atgaaaccat aaaattattt    6180
aaacaaataa aaaatgaaag acaaaacgat gtacacaata taaaagagga ctataacttg    6240
ttacaacaat atttaaatta tatgaaaaat gaaatggaac aattaaaaaa atataaaaat    6300
gatgttcata tggataaaaa ttatgttgaa aataataatg gtgaaaaaga aaaattactt    6360
aaagaaacca tttcttcata ttatgataaa ataaataata taaataataa gctatatata    6420
tataaaaaca aagaagacac ttatttaat aatatgatca aagtatcaga aatttttaaac    6480 ataattataa aaaaaaaaca acaaaatgaa caaagaattg ttataaatgc agaatatgac    6540
tcttcattaa ttaataagga tgaagaaatt aaaaaagaaa ttaataatca aataattgaa    6600
ttaaataaac ataatgaaaa tatttccaat atttttaagg atatacaaaa tataaaaaaa    6660
caaagtcaag atattatcac aaatatgaac gacatgtata aagtacaat cctttttagta    6720 gacatcatac agaaaaaaga agaagctcta aataaacaaa aaaatatttt aagaaatata    6780
gacaatatat taaataaaaa agaaaatatt atagataaag ttataaaatg taattgtgat    6840
gattataaag atatcttaat acaaaacgaa acggaatatc aaaaattaca aaatataaat    6900
catacatatg aagaaaaaaa aaaatcaata gatatattaa aaattaaaaa tataaaacaa    6960
aaaaatattc aagaatataa aaacaaatta gaacaaatga atacaataat taatcaaagt    7020
atagaacaac atgtattcat aaacgctgat attttacaaa atgaaaaaat aaaattagaa    7080
gaaatcataa aaaatctaga tatactagat gaacaaatta tgacatatca taattcaata    7140
gatgaattat ataaactagg aatacaatgt gacaatcatc taattacaac tattagtgtt    7200
gttgttaata aaaatacaac aaaaattatg atacatataa aaaacaaaa agaggatata    7260 caaaaaatta ataactatat tcaaacaaat tataatataa taaatgaaga agctctacaa    7320
tttcacaggc tctatggaca caatcttata agtgaagatg acaaaaataa tttggtacat    7380
attataaaag aacaaagaa tatatataca caaaaggaaa tagatatttc taaaataatt    7440
aaacatgtta aaaaaggatt atattcattg aatgaacatg atatgaatca tgatacacat    7500
atgaatataa taaatgaaca tataaataat aatatttac aaccatacac acaattaata    7560
aacatgataa aagatattga taatgttttt ataaaaatac aaaataataa attcgaacaa    7620
atacaaaaat atatagaaat tattaaatct ttagaacaat taaataaaaa tataaacaca    7680
```

```
gataatttaa ataaattaaa agatacacaa aacaaattaa taaatataga aacagaaatg    7740
aaacataaac aaaaacaatt aataaacaaa atgaatgata tagaaaagga taatattaca    7800
gatcaatata tgcatgatgt tcagcaaaat atatttgaac ctataacatt aaaaatgaat    7860
gaatataata cattattaaa tgataatcat aataataata taaataatga acatcaattt    7920
aatcatttaa atagtcttca tacaaaaata tttagtcata attataataa agaacaacaa    7980
caagaatata taaccaacat catgcaaaga attgatgtat tcataaatga tttagatact    8040
taccaatatg aatattattt ttatgaatgg aatcaagaat ataaacaaat agacaaaaat    8100
aaaataaatc aacatataaa caatattaaa aataatctaa ttcatgttaa gaaacaattt    8160
gaacacacct tagaaaatat aaaaaataat gaaatatttt tcgacaacat acaattgaaa    8220
aaaaaagata ttgacgatat tattataaac attaataata caaagaaaac atatctaaaa    8280
gaattgaaca aaaaaaaaaa tgttacaaaa aaaaaaaaag ttgatgaaaa atcagaaata    8340
aataatcatc acacattaca acatgataat caaaatgttg aacaaaaaaa taaaattaaa    8400
gatcataatt taataaccaa gccaaataac aattcatcag aagaatctca tcaaaatgaa    8460
caaatgaaag aacaaaacaa aaatatactt gaaaaacaaa caagaaatat caaaccacat    8520
catgttcata atcataatca taatcataat caaaatcaaa aagattcaac aaaattacag    8580
gaacaagata tatctacaca caaattacat aatactatac atgagcaaca aagtaaagat    8640
aatcatcaag gtaatagaga aaaaaaacaa aaaaatggaa accatgaaag aatgtatttt    8700
gccagtggaa tagttgtatc cattttattt ttatttagtt ttggatttgt tataaatagt    8760
aaaaataata aacaagaata tgataaagag caagaaaaac aacaacaaaa tgattttgta    8820
tgtgataata acaaaatgga tgataaaagc acacaaaaat atggtagaaa tcaagaagag    8880
gtaatggaga tattttttga taatgattat atttaa                              8916
```

<210> SEQ ID NO 28
<211> LENGTH: 22
<212> TYPE: DNA
<213> ORGANISM: Artificial
<220> FEATURE:
<223> OTHER INFORMATION: Oligonucleotide primer

<400> SEQUENCE: 28
caggattaag ttttgaaaat gc    22

<210> SEQ ID NO 29
<211> LENGTH: 21
<212> TYPE: DNA
<213> ORGANISM: Artificial
<220> FEATURE:
<223> OTHER INFORMATION: Oligonucleotide primer

<400> SEQUENCE: 29
ccatgttttg tcatttcatt g    21

<210> SEQ ID NO 30
<211> LENGTH: 18
<212> TYPE: DNA
<213> ORGANISM: Artificial
<220> FEATURE:
<223> OTHER INFORMATION: Oligonucleotide primer

<400> SEQUENCE: 30
gatgatgaaa ccgaagag    18

```
<210> SEQ ID NO 31
<211> LENGTH: 19
<212> TYPE: DNA
<213> ORGANISM: Artificial
<220> FEATURE:
<223> OTHER INFORMATION: Oligonucleotide primer

<400> SEQUENCE: 31
ctgtatcttg tatactatc                                                  19

<210> SEQ ID NO 32
<211> LENGTH: 33
<212> TYPE: DNA
<213> ORGANISM: Artificial
<220> FEATURE:
<223> OTHER INFORMATION: Oligonucleotide primer

<400> SEQUENCE: 32
gatcggatcc aattctatat atcataagtc ctc                                  33

<210> SEQ ID NO 33
<211> LENGTH: 33
<212> TYPE: DNA
<213> ORGANISM: Artificial
<220> FEATURE:
<223> OTHER INFORMATION: Oligonucleotide primer

<400> SEQUENCE: 33
gatcctcgag ttaatgatat cttattccgt ttg                                  33

<210> SEQ ID NO 34
<211> LENGTH: 41
<212> TYPE: DNA
<213> ORGANISM: Artificial
<220> FEATURE:
<223> OTHER INFORMATION: Oligonucleotide primer

<400> SEQUENCE: 34
gatcagatct catgagaatg attttaataa aatatgtatg g                         41

<210> SEQ ID NO 35
<211> LENGTH: 43
<212> TYPE: DNA
<213> ORGANISM: Artificial
<220> FEATURE:
<223> OTHER INFORMATION: Oligonucleotide primer

<400> SEQUENCE: 35
gatcctgcag ttgtgtaagt ggtttatttt ttttatatgt ttg                       43
```